(12) United States Patent
Montenegro et al.

(10) Patent No.: US 12,071,405 B2
(45) Date of Patent: Aug. 27, 2024

(54) MATERIALS FOR ELECTRONIC DEVICES

(71) Applicant: Merck Patent GmbH, Darmstadt (DE)

(72) Inventors: Elvira Montenegro, Weinheim (DE); Teresa Mujica-Fernaud, Darmstadt (DE); Florian Maier-Flaig, Weinheim (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 694 days.

(21) Appl. No.: 16/645,246

(22) PCT Filed: Sep. 5, 2018

(86) PCT No.: PCT/EP2018/073794
§ 371 (c)(1),
(2) Date: Mar. 6, 2020

(87) PCT Pub. No.: WO2019/048443
PCT Pub. Date: Mar. 14, 2019

(65) Prior Publication Data
US 2020/0283386 A1 Sep. 10, 2020

(30) Foreign Application Priority Data
Sep. 8, 2017 (EP) ..................... 17190206

(51) Int. Cl.
| | | |
|---|---|---|
| *C07C 211/54* | (2006.01) | |
| *C07C 211/61* | (2006.01) | |
| *C07D 209/86* | (2006.01) | |
| *C07D 307/91* | (2006.01) | |
| *C07D 333/76* | (2006.01) | |
| *C07D 403/04* | (2006.01) | |
| *C07D 405/12* | (2006.01) | |
| *H10K 85/60* | (2023.01) | |
| *H10K 50/11* | (2023.01) | |
| *H10K 50/15* | (2023.01) | |
| *H10K 50/18* | (2023.01) | |

(52) U.S. Cl.
CPC .......... *C07D 209/86* (2013.01); *C07C 211/54* (2013.01); *C07C 211/61* (2013.01); *C07D 307/91* (2013.01); *C07D 333/76* (2013.01); *C07D 403/04* (2013.01); *C07D 405/12* (2013.01); *H10K 85/624* (2023.02); *H10K 85/633* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/18* (2023.02)

(58) Field of Classification Search
CPC .. C07C 211/61; H10K 85/624; H10K 85/633; H10K 85/654
USPC .................... 428/690, 917; 257/40
See application file for complete search history.

(56) References Cited

U.S. PATENT DOCUMENTS

| | | | |
|---|---|---|---|
| 8,241,763 B2 | 8/2012 | Buesing et al. | |
| 8,334,058 B2 | 12/2012 | Heil et al. | |
| 8,766,001 B2 | 7/2014 | Pflumm et al. | |
| 8,852,756 B2 | 10/2014 | Vestweber et al. | |
| 9,475,792 B2 | 10/2016 | Parham et al. | |
| 9,748,494 B2 | 8/2017 | Ito et al. | |
| 10,312,452 B2 | 6/2019 | Kimura et al. | |
| 2011/0266531 A1 | 11/2011 | Kim et al. | |
| 2012/0305852 A1 | 12/2012 | Anemian et al. | |
| 2016/0111663 A1 | 4/2016 | Kim et al. | |
| 2016/0190472 A1 | 6/2016 | Yen et al. | |
| 2016/0211456 A1 | 7/2016 | Yen et al. | |
| 2016/0240783 A1 | 8/2016 | Yen et al. | |
| 2016/0351817 A1* | 12/2016 | Kim | H10K 85/624 |
| 2018/0269400 A1 | 9/2018 | Jatsch et al. | |
| 2020/0144517 A1 | 5/2020 | Chung et al. | |

FOREIGN PATENT DOCUMENTS

| | | |
|---|---|---|
| CN | 101228250 A | 7/2008 |
| CN | 105358554 A | 2/2016 |
| CN | 105358654 A | 2/2016 |
| CN | 105732594 A | 7/2016 |
| CN | 105884623 A | 8/2016 |
| EP | 3010067 A1 | 4/2016 |
| EP | 3130591 A1 | 2/2017 |
| JP | 2008-545630 A | 12/2008 |
| JP | 2009-542735 A | 12/2009 |
| JP | 2012-028548 A | 2/2012 |
| JP | 2013-519740 A | 5/2013 |
| JP | 2013-251480 A | 12/2013 |
| JP | 2014-051448 A | 3/2014 |
| JP | 2015177137 A | 10/2015 |

(Continued)

OTHER PUBLICATIONS

Huang et al., "Dopant-Free Hole-Transporting Material with a C3h Symmetrical Truxene Core for Highly Efficient Perovskite Solar Cells," Journal of the American Chemical Society, vol. 138, No. 8, Feb. 15, 2016, pp. 2528-2531.
Lai et al., "Synthesis and Characterization of 2,3,7,8,12,13-Hexabromotruxene and Its Hexaaryl Derivatives," Chemistry Letters, vol. 38, No. 3, Feb. 21, 2009, pp. 286-287.
Lin et al., "Synthesis, Structures, Resolution, and Chiroptical Properties of 1,16-Diaryl-Substituted Benzo[5]helicene Derivatives," Chemistry an Asian Journal, vol. 12, Issue 1, Jan. 3, 2017, pp. 86-94.
International Search Report for PCT/EP2018/073794 mailed Nov. 19, 2018.
International Search Report for PCT/EP2018/073827 mailed Nov. 19, 2018.
Shirota, Y., et al., "Charge Carrier Transporting Molecular Materials and Their Applicaitons in Devices", Chemical Reviews, vol. 107, No. 4, (2007), pp. 953-1010.

(Continued)

*Primary Examiner* — Ruiyun Zhang
(74) *Attorney, Agent, or Firm* — Faegre Drinker Biddle & Reath LLP

(57) ABSTRACT

The present application relates to compounds of formula (I) containing a group selected from amino groups, bridged amino groups and carbazole groups, to processes for preparation thereof, and to the use thereof in electronic devices, and in particular OLEDs.

21 Claims, No Drawings

(56) References Cited

FOREIGN PATENT DOCUMENTS

| | | | |
|---|---|---|---|
| JP | 2015177138 A | 10/2015 |
| JP | 2016-516006 A | 6/2016 |
| JP | 2016-153394 A | 8/2016 |
| JP | 2016-155797 A | 9/2016 |
| JP | 2017-039693 A | 2/2017 |
| JP | 2020-533325 A | 11/2020 |
| KR | 10-2012-0116881 A | 10/2012 |
| KR | 10-2014-0134884 A | 11/2014 |
| KR | 10-2015-0012488 A | 2/2015 |
| KR | 10-2015-0114636 A | 10/2015 |
| KR | 10-2017-0041646 A | 4/2017 |
| TW | 201006909 A | 2/2010 |
| WO | WO-2006100896 A1 | 9/2006 |
| WO | WO-2006108497 A1 | 10/2006 |
| WO | WO-2006122630 A1 | 11/2006 |
| WO | WO-2008006449 A1 | 1/2008 |
| WO | WO-2009099060 A1 | 8/2009 |
| WO | WO-2009141026 A1 | 11/2009 |
| WO | 2009/148062 A1 | 12/2009 |
| WO | WO-2010008371 A1 | 1/2010 |
| WO | WO-2010008373 A1 | 1/2010 |
| WO | WO-20100083872 A2 | 7/2010 |
| WO | 2014/171779 A1 | 10/2014 |
| WO | 2015/012618 A1 | 1/2015 |
| WO | WO-2015002208 A1 | 1/2015 |
| WO | WO-2017036573 A1 | 3/2017 |
| WO | WO-2017041874 A1 | 3/2017 |
| WO | 2017/102064 A1 | 6/2017 |
| WO | 2019/048458 A1 | 3/2019 |

OTHER PUBLICATIONS

Written Opinion of the International Searching Authority for PCT/EP2018/073794 mailed Nov. 19, 2018.
Written Opinion of the International Searching Authority for PCT/EP2018/073827 mailed Nov. 19, 2018.

\* cited by examiner

MATERIALS FOR ELECTRONIC DEVICES

CROSS-REFERENCE TO RELATED APPLICATIONS

This application is a national stage application (under 35 U.S.C. § 371) of PCT/EP2018/073794, filed Sep. 5, 2018, which claims benefit of European Application No. 17190206.7, filed Sep. 8, 2017, both of which are incorporated herein by reference in their entirety.

The present application relates to aromatic compounds containing a group selected from amino groups, bridged amino groups and carbazole groups, according to the formula (I) defined below. These compounds are suitable for use in electronic devices.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in an improvement in the performance data, especially lifetime, efficiency and operating voltage. In these aspects, it has not yet been possible to find any entirely satisfactory solution.

There is additionally a search for materials having a high glass transition temperature, a low tendency to crystallization and a high refractive index, especially for use in hole-transporting layers of OLEDs.

A great influence on the performance data of electronic devices is possessed by emission layers and layers having a hole-transporting function. Novel compounds are also being sought for use in these layers, especially hole-transporting compounds and compounds that can serve as matrix material, especially for phosphorescent emitters, in an emitting layer.

A variety of aromatic compounds containing a group selected from amino groups, bridged amino groups and carbazole groups is known in the prior art as hole transport materials and/or matrix materials in electronic devices.

However, there is still a need for alternative compounds suitable for use in electronic devices. There is also a need for improvement with regard to the performance data in use in electronic devices, especially with regard to lifetime, operating voltage and efficiency.

It has now been found that particular compounds from the abovementioned structure class are of excellent suitability for use in electronic devices, especially for use in OLEDs, even more especially for use therein as hole transport materials and for use as matrix materials for phosphorescent emitters. The compounds preferably lead to high lifetime, high efficiency and low operating voltage of the devices. Further preferably, the compounds have a low tendency to crystallization, a high glass transition temperature and a high refractive index.

The compounds conform to the following formula (I):

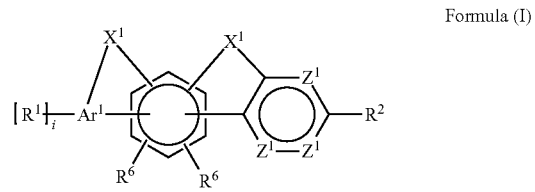

Formula (I)

where the variables that occur are as follows:
$Z^1$ is the same or different at each instance and is selected from $CR^1$ and $CR^3$;
$Ar^1$ is an aryl group which has 6 to 20 aromatic ring atoms and may be substituted by one or more $R^3$ radicals, or a heteroaryl group which has 5 to aromatic ring atoms and may be substituted by one or more $R^3$ radicals;
$X^1$ is the same or different at each instance and is a divalent group selected from $-C(R^4)_2-$, $-C(R^4)_2-C(R^4)_2-$, $-CR^4=CR^4-$ and $-Si(R^4)_2-$;
$R^1$ is the same or different at each instance and is a group of the formula (N)

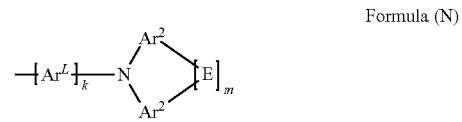

Formula (N)

$Ar^L$ is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;
$Ar^2$ is the same or different at each instance and is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;
E is a single bond or a divalent group selected from $C(R^5)_2$, $Si(R^5)_2$, $N(R^5)$, O, and S;
$R^2$ is selected from H, D, F, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by $-R^7C=CR^7-$, $-C\equiv C-$, $Si(R^7)_2$, $C=O$, $C=NR^7$, $-C(=O)O-$, $-C(=O)NR^7-$, $P(=O)(R^7)$, $-O-$, $-S-$, SO or $SO_2$;
$R^3$, $R^4$, $R^5$ are the same or different at each instance and are selected from H, D, F, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ or $R^4$ or $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by —$R^7C$=$CR^7$—, —C≡C—, $Si(R^7)_2$, C=O, C=$NR^7$, —C(=O)O—, —C(=O)$NR^7$—, $NR^7$, P(=O)($R^7$), —O—, —S—, SO or $SO_2$;

$R^6$ is the same or different at each instance and is selected from H, D, F, C(=O)$R^7$, CN, $Si(R^7)_3$, P(=O)($R^7$)$_2$, $OR^7$, S(=O)$R^7$, S(=O)$_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^6$ radicals may be joined to one another and may form a ring; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by —$R^7C$=$CR^7$—, —C≡C—, $Si(R^7)_2$, C=O, C=$NR^7$, —C(=O)O—, —C(=O)$NR^7$—, $NR^7$, P(=O)($R^7$), —O—, —S—, SO or $SO_2$;

$R^7$ is the same or different at each instance and is selected from H, D, F, C(=O)$R^8$, CN, $Si(R^8)_3$, N($R^8$)$_2$, P(=O)($R^8$)$_2$, $OR^8$, S(=O)$R^8$, S(=O)$_2R^8$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to aromatic ring atoms; where two or more $R^7$ radicals may be joined to one another and may form a ring; where the alkyl, alkoxy, alkenyl and alkynyl groups mentioned and the aromatic ring systems and heteroaromatic ring systems mentioned may each be substituted by one or more $R^8$ radicals; and where one or more $CH_2$ groups in the alkyl, alkoxy, alkenyl and alkynyl groups mentioned may be replaced by —$R^8C$=$CR^8$—, —C≡C—, $Si(R^8)_2$, C=O, C=$NR^8$, —C(=O)O—, —C(=O)$NR^8$—, $NR^8$, P(=O)($R^8$), —O—, —S—, SO or $SO_2$;

$R^8$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^8$ radicals may be joined to one another and may form a ring; and where the alkyl, alkoxy, alkenyl and alkynyl groups, aromatic ring systems and heteroaromatic ring systems mentioned may be substituted by F or CN;

k is 0 or 1, where, in the case that k=0, the $Ar^L$ group is absent and the nitrogen atom of the group of the formula (N) constitutes the attachment position;

m is 0 or 1, where, in the case that m=0, the E group is absent and the Are groups are not bonded to one another;

i is 0 or 1, where, in the case that i=0, the $R^1$ group is absent; and where there is at least one $Z^1$ group that is $CR^1$.

The circles drawn into the six-membered rings of the formula (I) mean that the six-membered rings in question have aromaticity. The bonds drawn into the benzene rings express that the bonds in question may be localized at any position on the benzene ring. More particularly, the $X^1$ bridges may be arranged not just in trans positions but also in cis positions to one another.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

Preferably, an aromatic ring system is understood to mean a chemical group in which the aryl groups present therein are conjugated to one another. This means that the aryl groups present must be bonded to one another via single bonds or via connecting units having a free pi electron pair that can take part in the conjugation. Connecting units here are preferably selected from nitrogen atoms, individual C=C units, individual C≡C units, multiple C=C units conjugated to one another and/or C≡C units, —O—, and —S—.

A heteroaromatic ring system in the context of this invention contains 5 to aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cyclohepty-loxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butyl-thio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenyl-thio, octenylthio, cyclooctenylthio, ethynylthio, propynyl-thio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

The compound of the formula (I) preferably has only a single diarylamino group. It more preferably has only a single amino group.

Preferably, one $Z^1$ group is $CR^1$, and the two other $Z^1$ groups are $CR^3$; or two $Z^1$ groups are $CR^1$, and the other $Z^1$ group is $CR^3$. More preferably, one $Z^1$ group is $CR^1$, and the two other $Z^1$ groups are $CR^3$.

It is preferable that the $Z^1$ group in the meta position to the bond to $X^1$ is $CR^1$.

Preferably, $R^3$ radicals that are constituents of a $Z^1$ group do not form rings with one another.

Preferably, $Ar^1$ is an aryl group which has 6 to 14 aromatic ring atoms and may be substituted by one or more $R^3$ radicals, more preferably a phenyl or naphthyl group that may be substituted by one or more $R^3$ radicals, most preferably a phenyl group that may be substituted by one or more $R^3$ radicals.

$X^1$ is preferably the same or different at each instance and is selected from $C(R^4)_2$ and $Si(R^4)_2$; more preferably, $X^1$ is $C(R^4)_2$.

$Ar^L$ groups are preferably selected from aromatic ring systems which have 6 to 20 aromatic ring atoms and may be substituted by one or more $R^5$ radicals, and heteroaromatic ring systems which have 5 to 20 aromatic ring atoms and may be substituted by one or more $R^5$ radicals. Particularly preferred $Ar^L$ groups are selected from divalent groups derived from benzene, biphenyl, terphenyl, naphthalene, fluorene, indenofluorene, spirobifluorene, dibenzofuran, dibenzothiophene, and carbazole, each of which may be substituted by one or more $R^5$ radicals. Most preferably, $Ar^L$ is a divalent group derived from benzene that may be substituted in each case by one or more $R^5$ radicals. $Ar^L$ groups may be selected identically or differently at each instance.

Preferred $Ar^L$ groups conform to the following formulae:

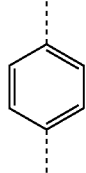

$Ar^L$-1

Ar$^L$-2
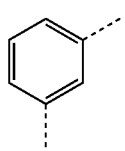
Ar$^L$-3
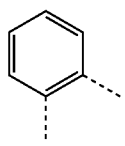
Ar$^L$-4
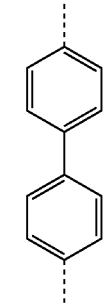
Ar$^L$-5
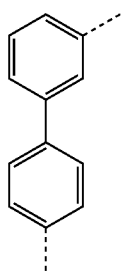
Ar$^L$-6
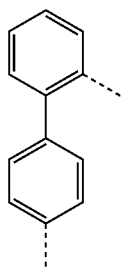
Ar$^L$-7
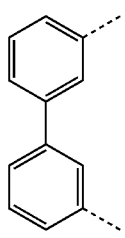
Ar$^L$-8
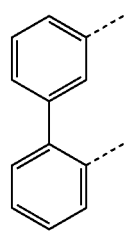
Ar$^L$-9
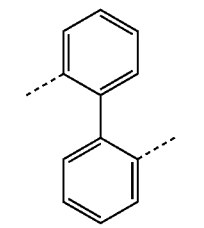
Ar$^L$-10
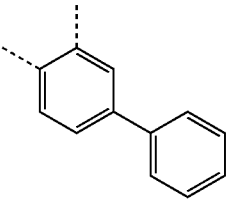
Ar$^L$-11
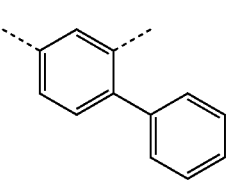
Ar$^L$-12
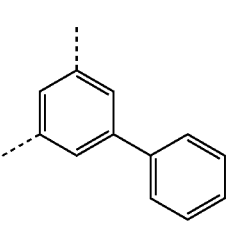
Ar$^L$-13
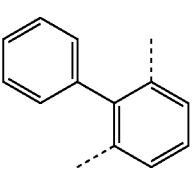
Ar$^L$-14

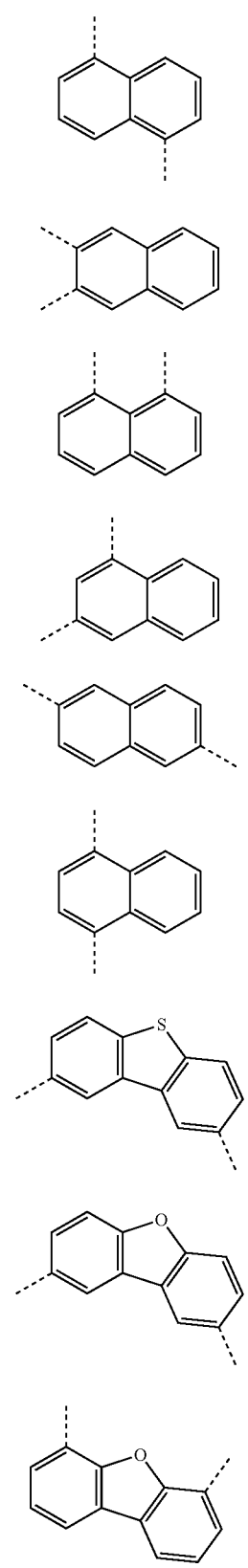
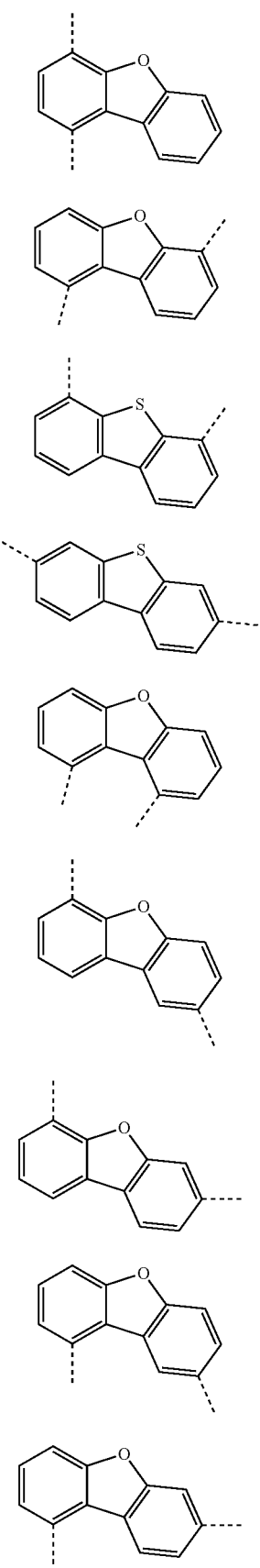

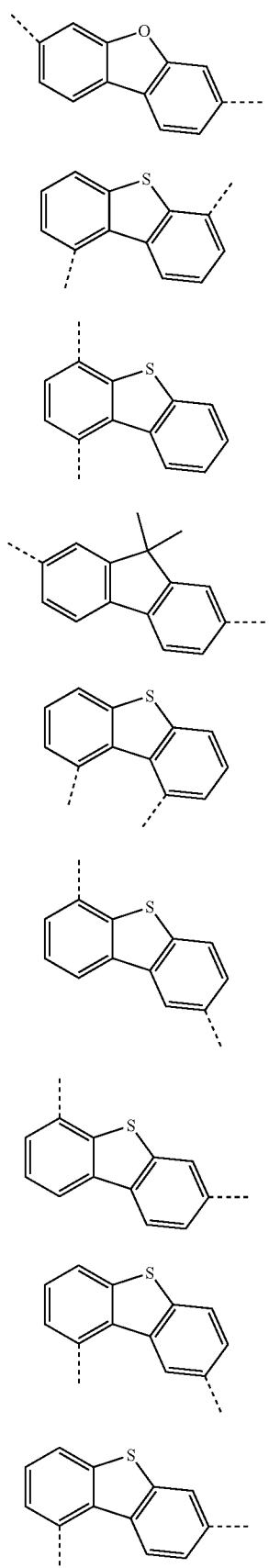
Ar$^L$-33
Ar$^L$-34
Ar$^L$-35
Ar$^L$-36
Ar$^L$-37
Ar$^L$-38
Ar$^L$-39
Ar$^L$-40
Ar$^L$-41
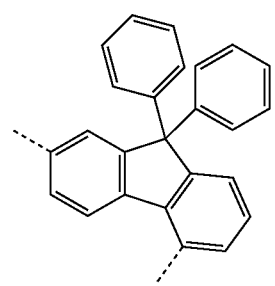
Ar$^L$-42
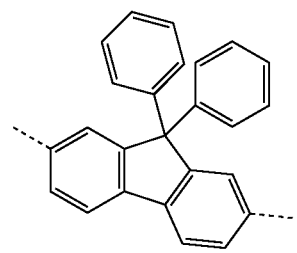
Ar$^L$-43
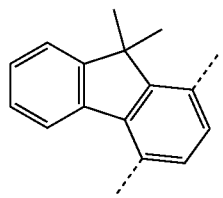
Ar$^L$-44
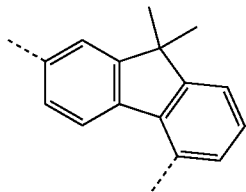
Ar$^L$-45
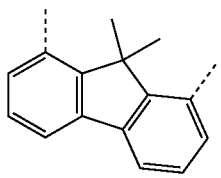
Ar$^L$-46
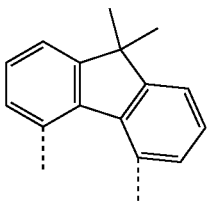
Ar$^L$-47
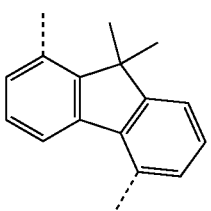
Ar$^L$-48

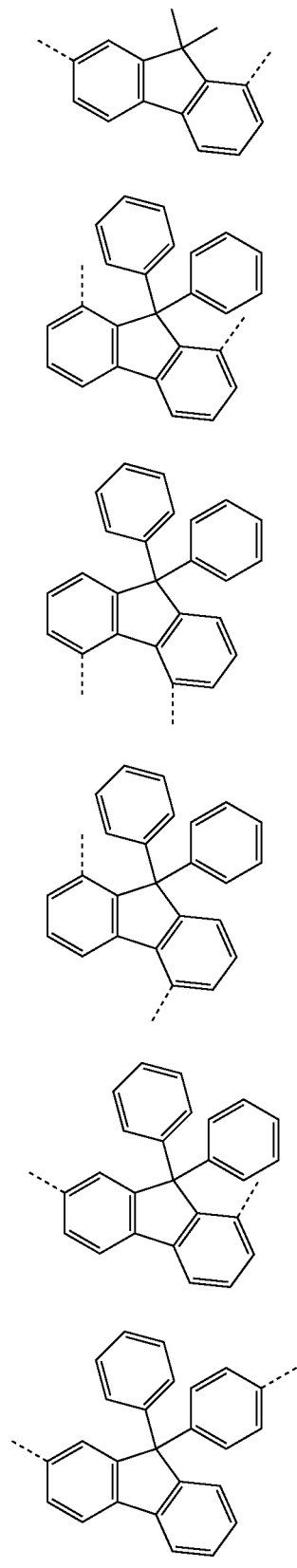
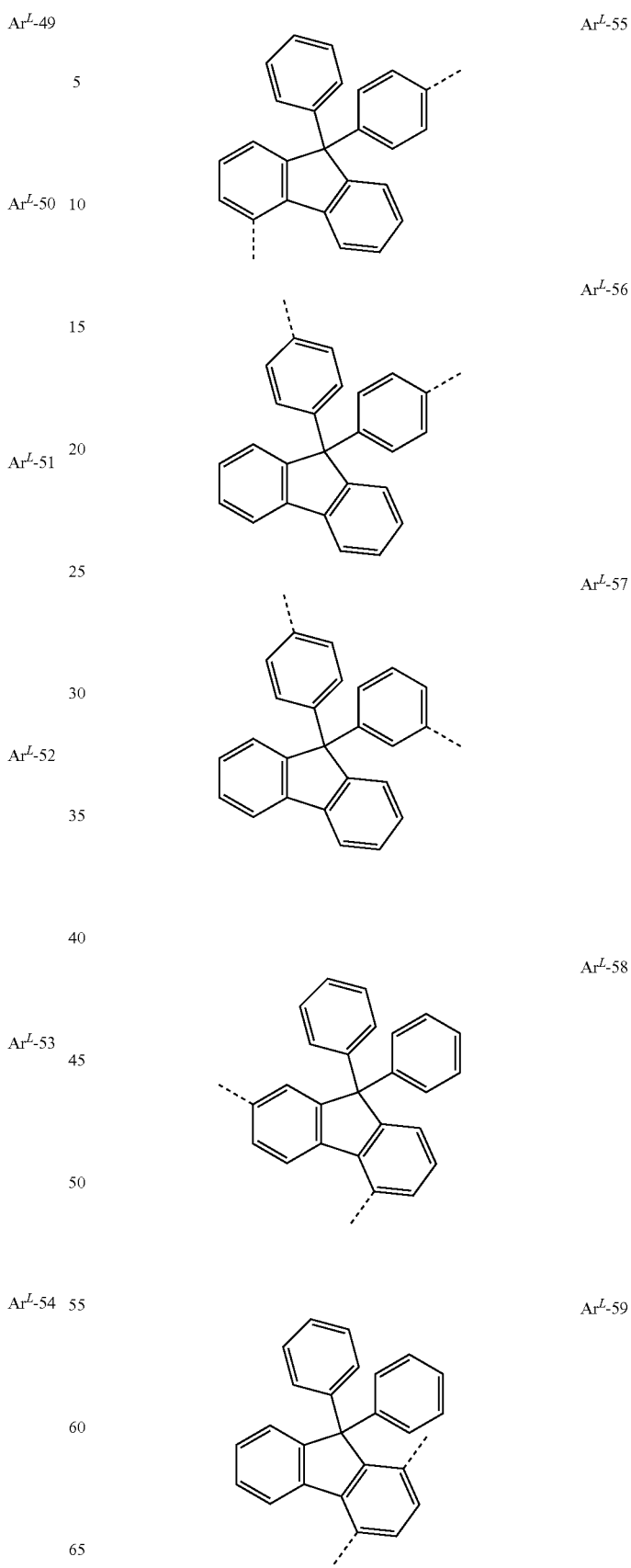

-continued
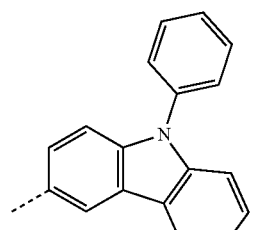
Ar^L-60
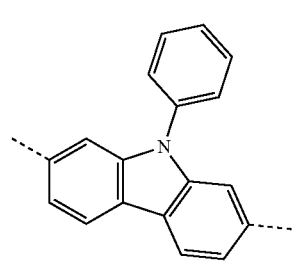
Ar^L-61
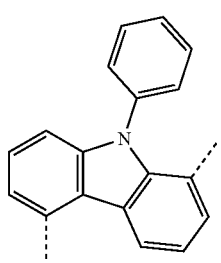
Ar^L-62
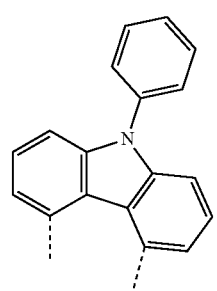
Ar^L-63
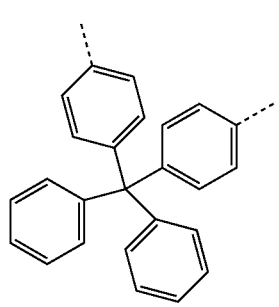
Ar^L-64
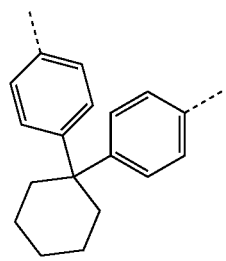
Ar^L-65
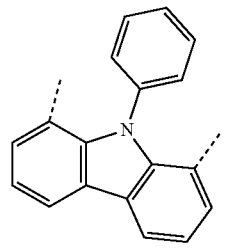
Ar^L-66
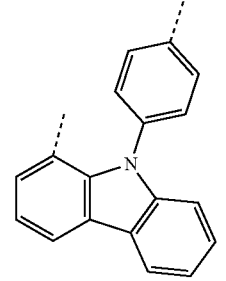
Ar^L-67
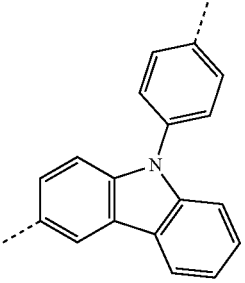
Ar^L-68
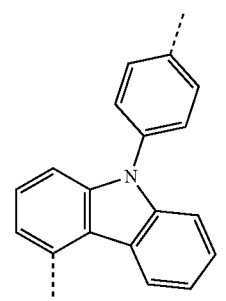
Ar^L-69

Ar$^L$-70 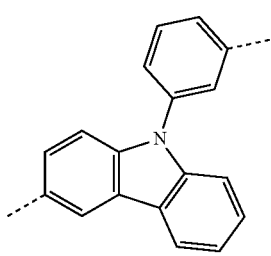

Ar$^L$-71 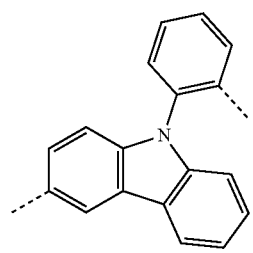

Ar$^L$-72 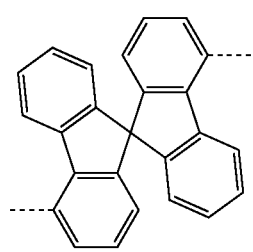

Ar$^L$-73 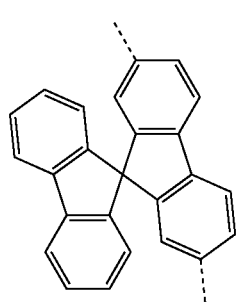

Ar$^L$-74 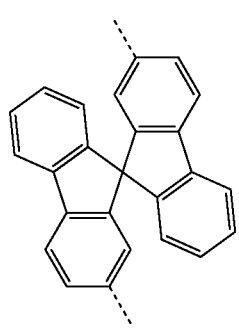

Ar$^L$-75 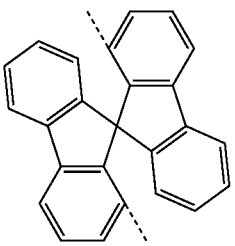

where the dotted lines represent the bonds to the rest of the formula (I).

Preferably, the Ar$^2$ groups are the same or different at each instance and are selected from aromatic ring systems which have 6 to 40 aromatic ring atoms and may be substituted by one or more R$^5$ radicals, and heteroaromatic ring systems which have 5 to 40 aromatic ring atoms and may be substituted by one or more R$^5$ radicals.

It is generally preferable here that the group of Ar$^2$ that binds directly to the nitrogen atom is an aromatic ring system.

Preferably, Ar$^2$ groups are the same or different at each instance and are selected from monovalent groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, dibenzofuran, dibenzothiophene, benzocarbazole, carbazole, benzofuran, benzothiophene, indole, quinoline, pyridine, pyrimidine, pyrazine, pyridazine and triazine, where the monovalent groups may each be substituted by one or more R$^5$ radicals. Alternatively, Ar$^2$ groups may preferably be the same or different at each instance and be selected from combinations of groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, dibenzofuran, dibenzothiophene, carbazole, benzofuran, benzothiophene, indole, quinoline, pyridine, pyrimidine, pyrazine, pyridazine and triazine, where the groups may each be substituted by one or more R$^5$ radicals.

Particularly preferred Ar$^2$ groups are the same or different at each instance and are selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, where the groups mentioned may each be substituted by one or more R$^5$ radicals.

Particularly preferred Ar$^2$ groups are selected from the following formulae,

Ar-1 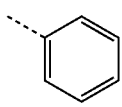

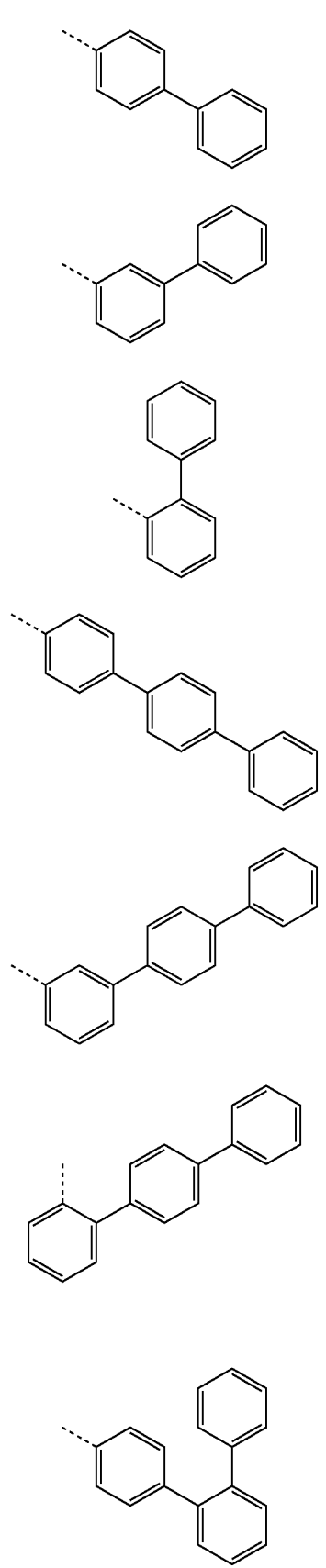
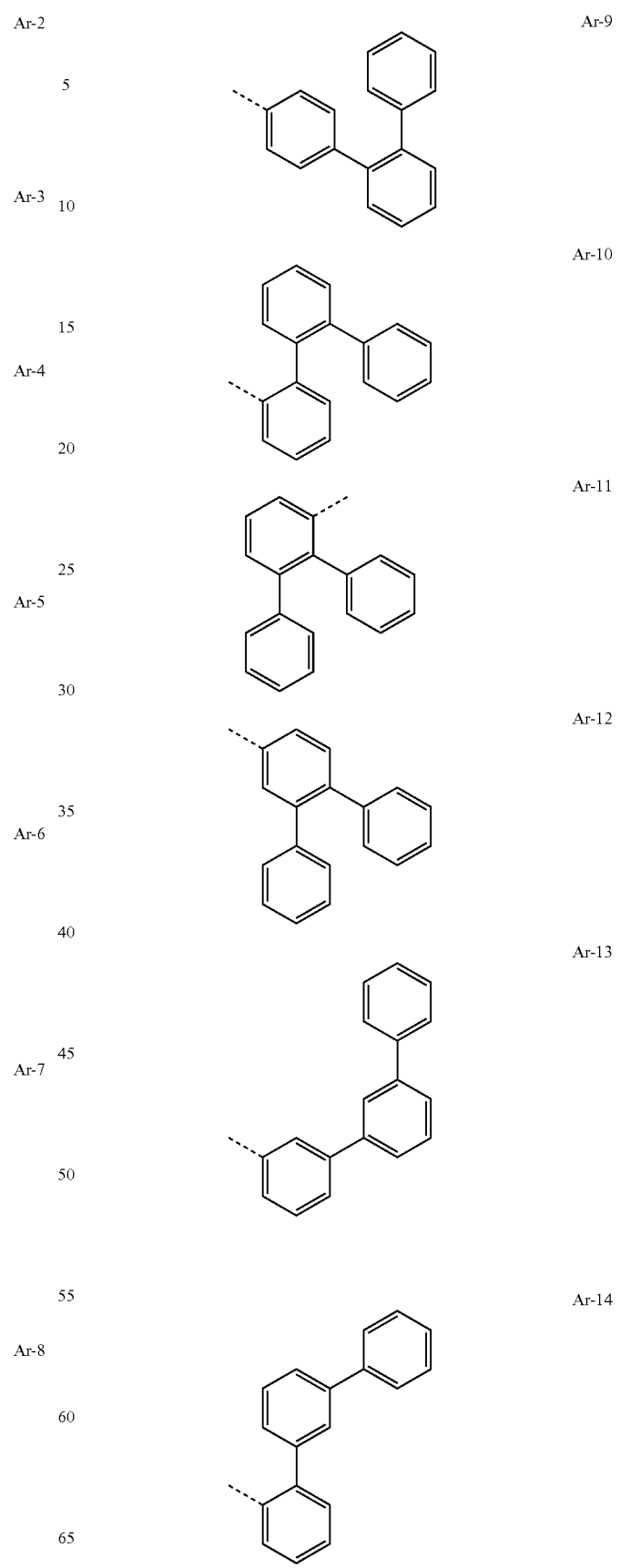

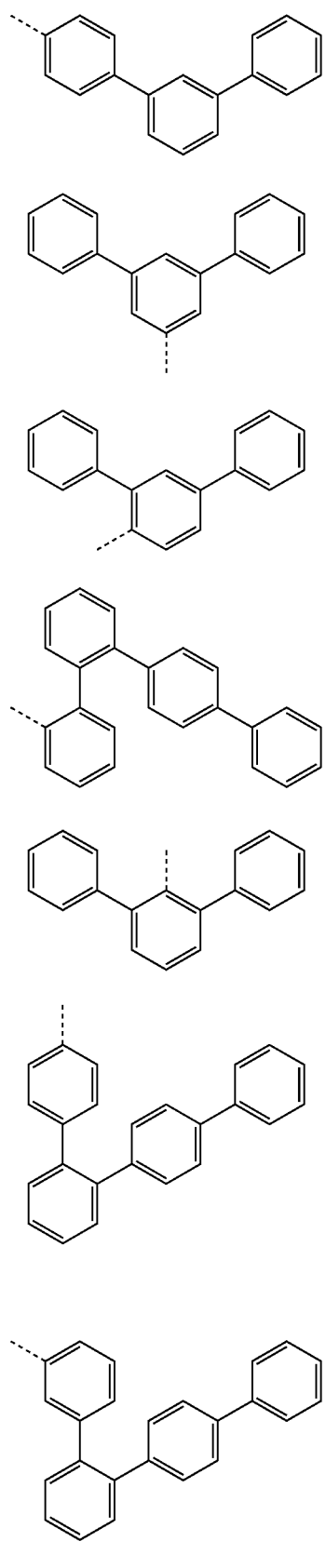
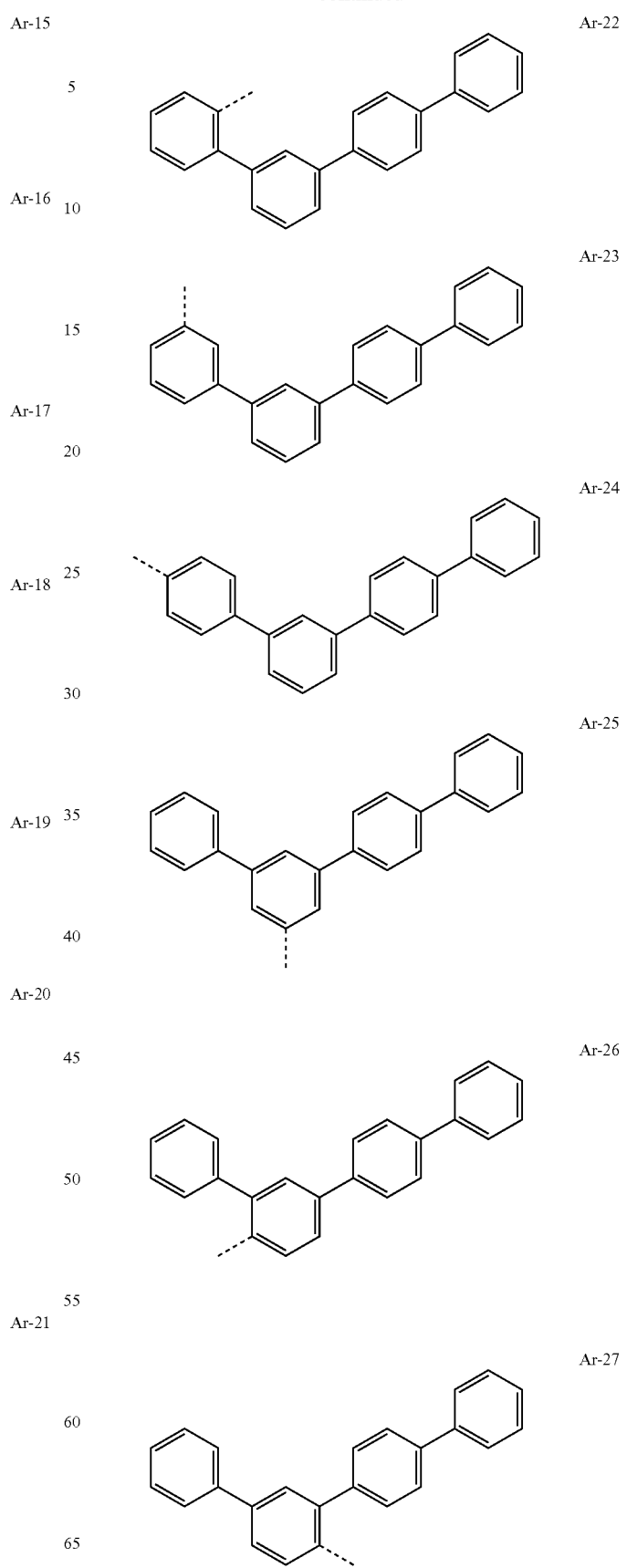

-continued
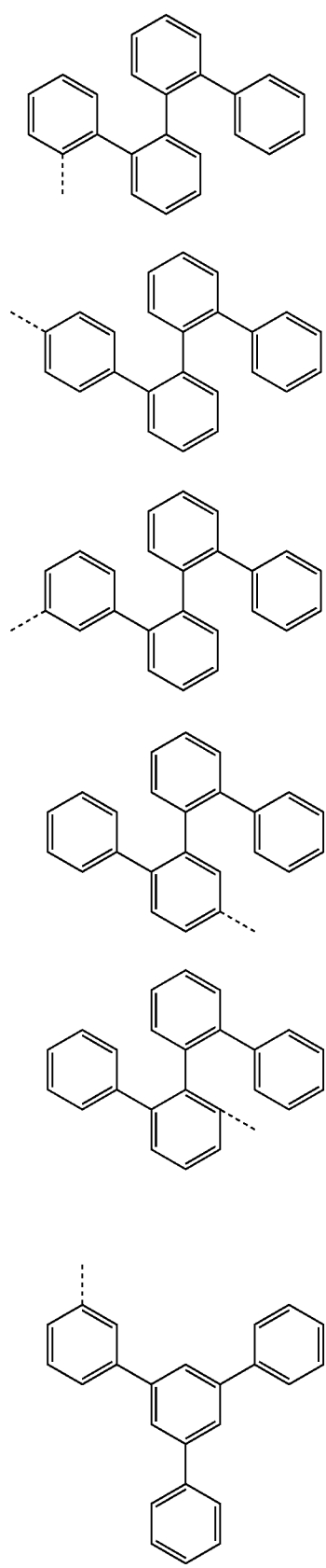
Ar-28
Ar-29
Ar-30
Ar-31
Ar-32
Ar-33
-continued
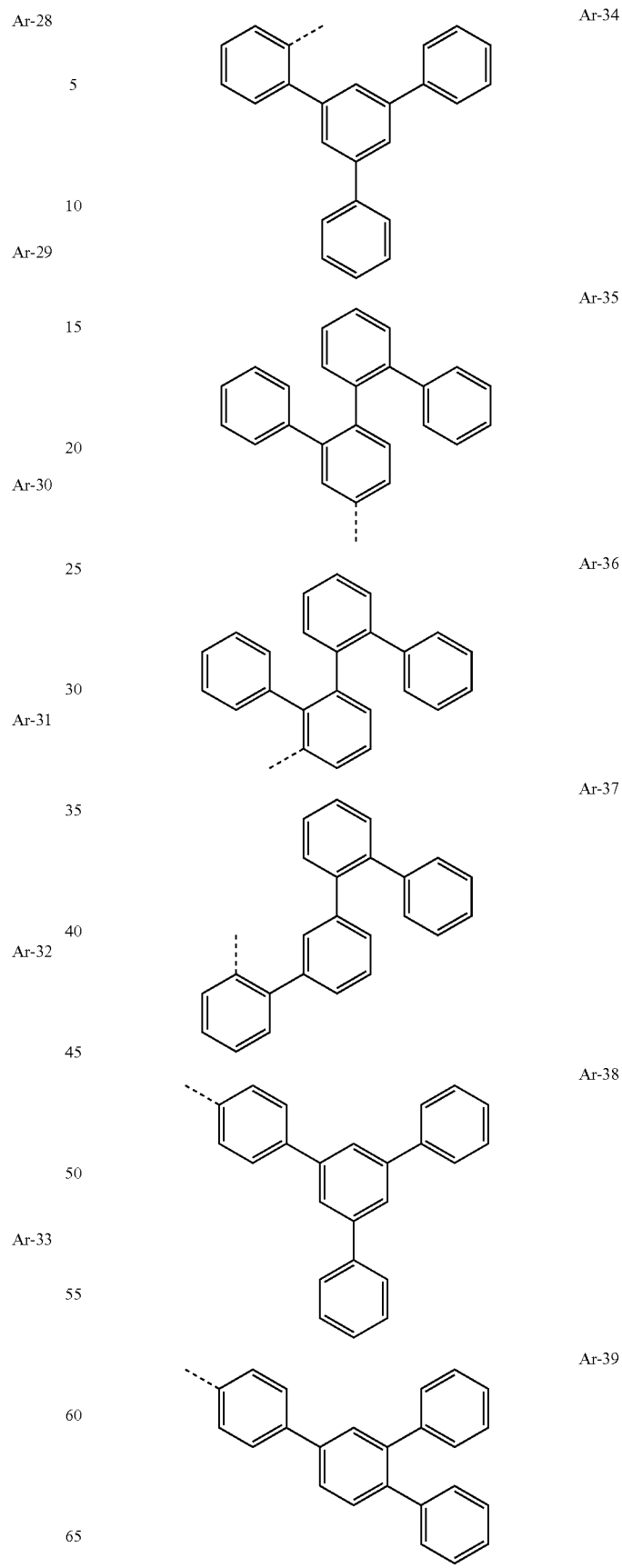
Ar-34
Ar-35
Ar-36
Ar-37
Ar-38
Ar-39

-continued
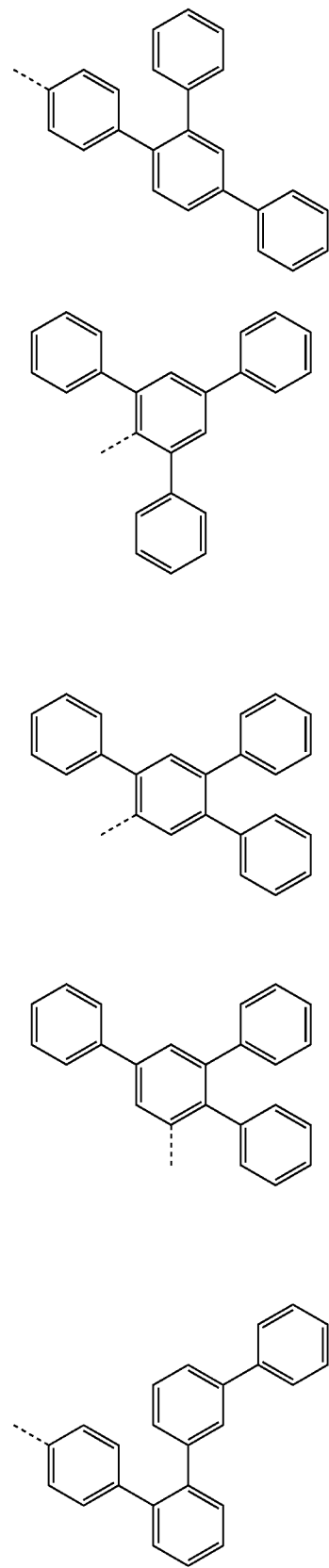
Ar-40
Ar-41
Ar-42
Ar-43
Ar-44
-continued
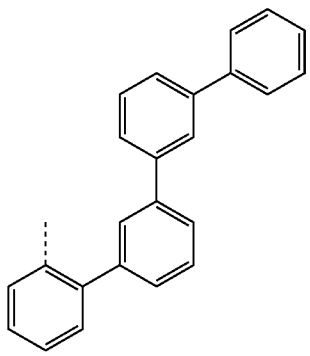
Ar-45
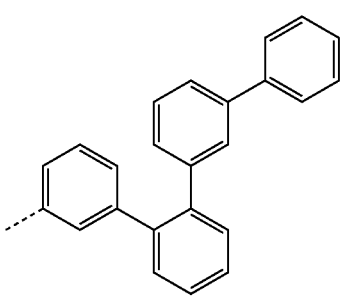
Ar-46
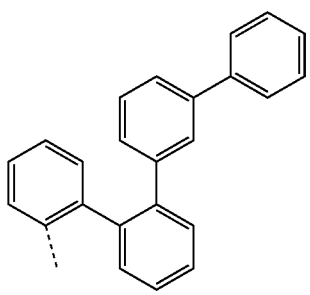
Ar-47
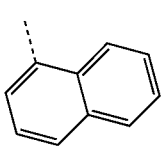
Ar-48
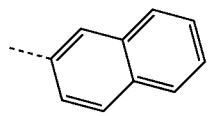
Ar-49
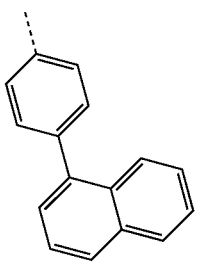
Ar-50

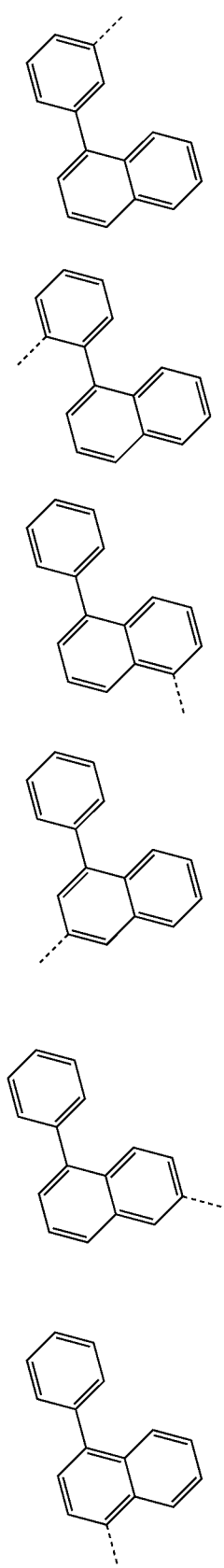
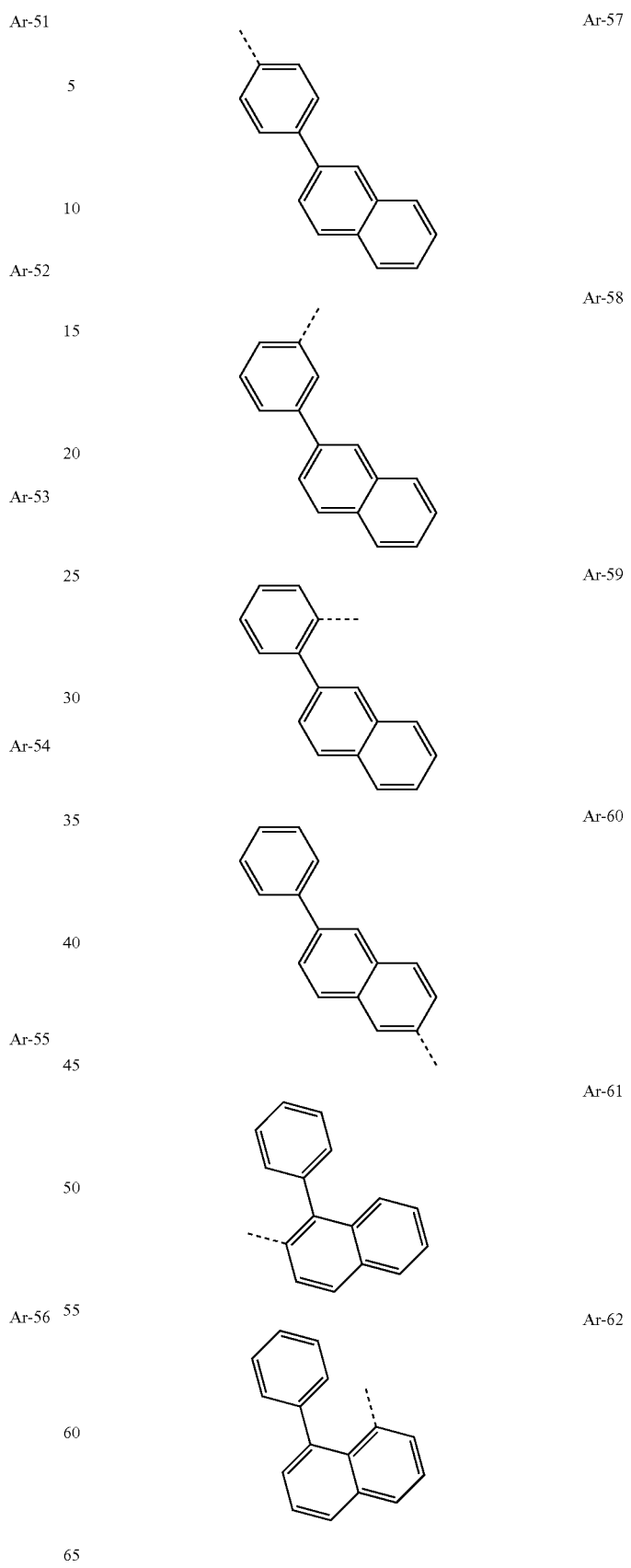

Ar-63
Ar-64
Ar-65
Ar-66
Ar-67
Ar-68
Ar-69
Ar-70
Ar-71
Ar-72
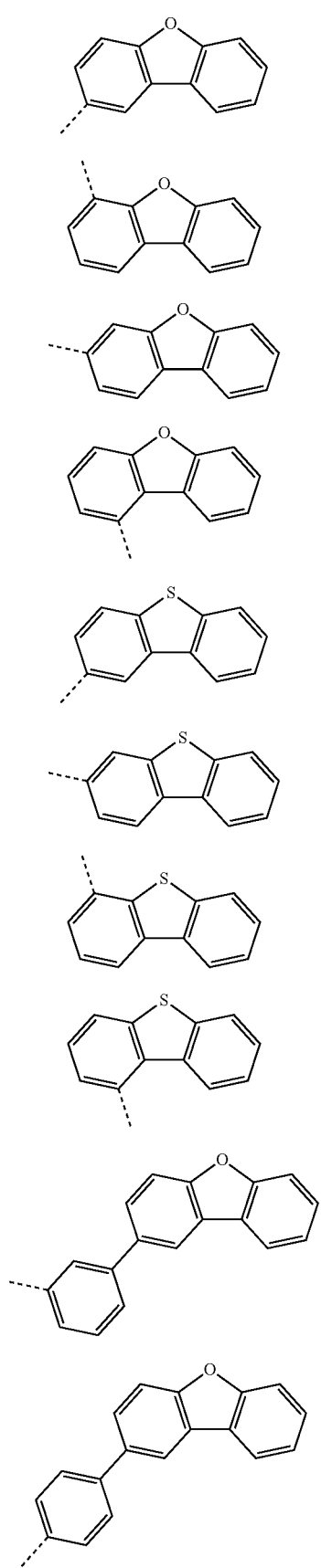
Ar-73
Ar-74
Ar-75
Ar-76
Ar-77
Ar-78
Ar-79
Ar-80
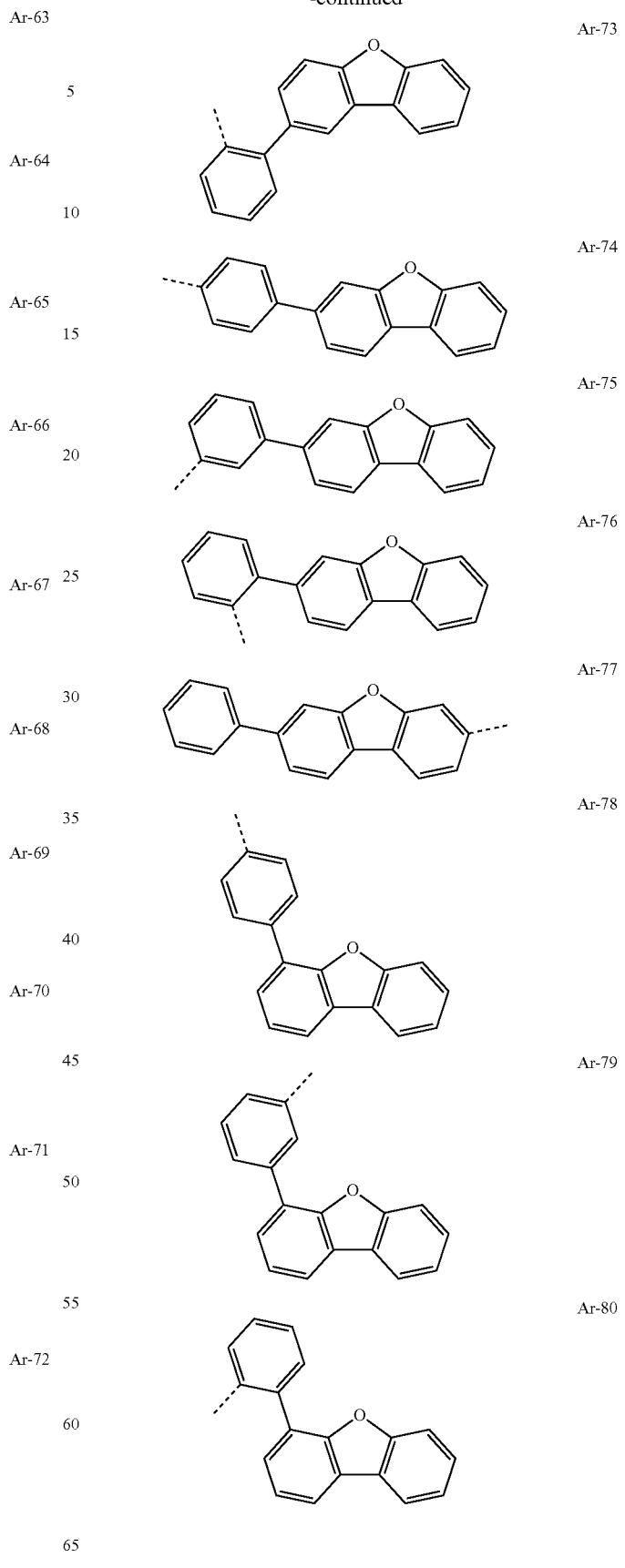

-continued
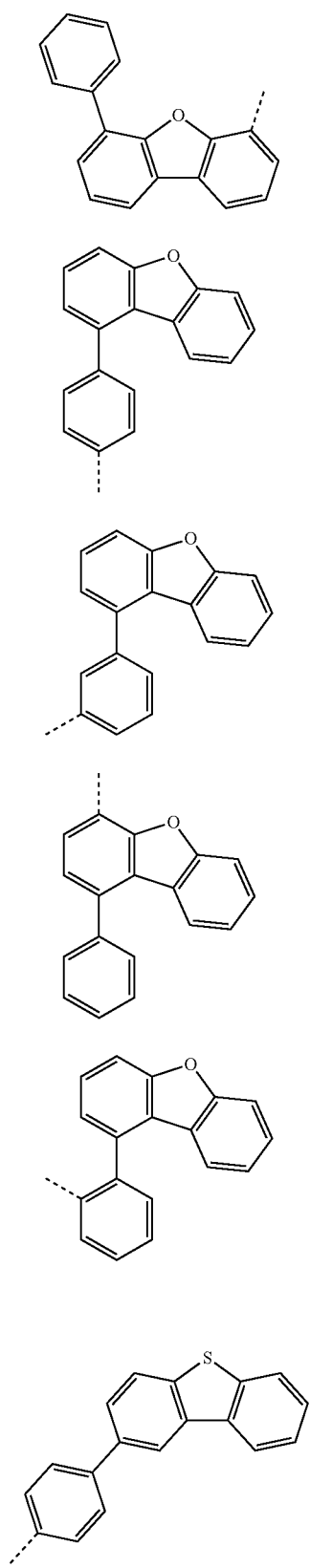
Ar-81
Ar-82
Ar-83
Ar-84
Ar-85
Ar-86
-continued
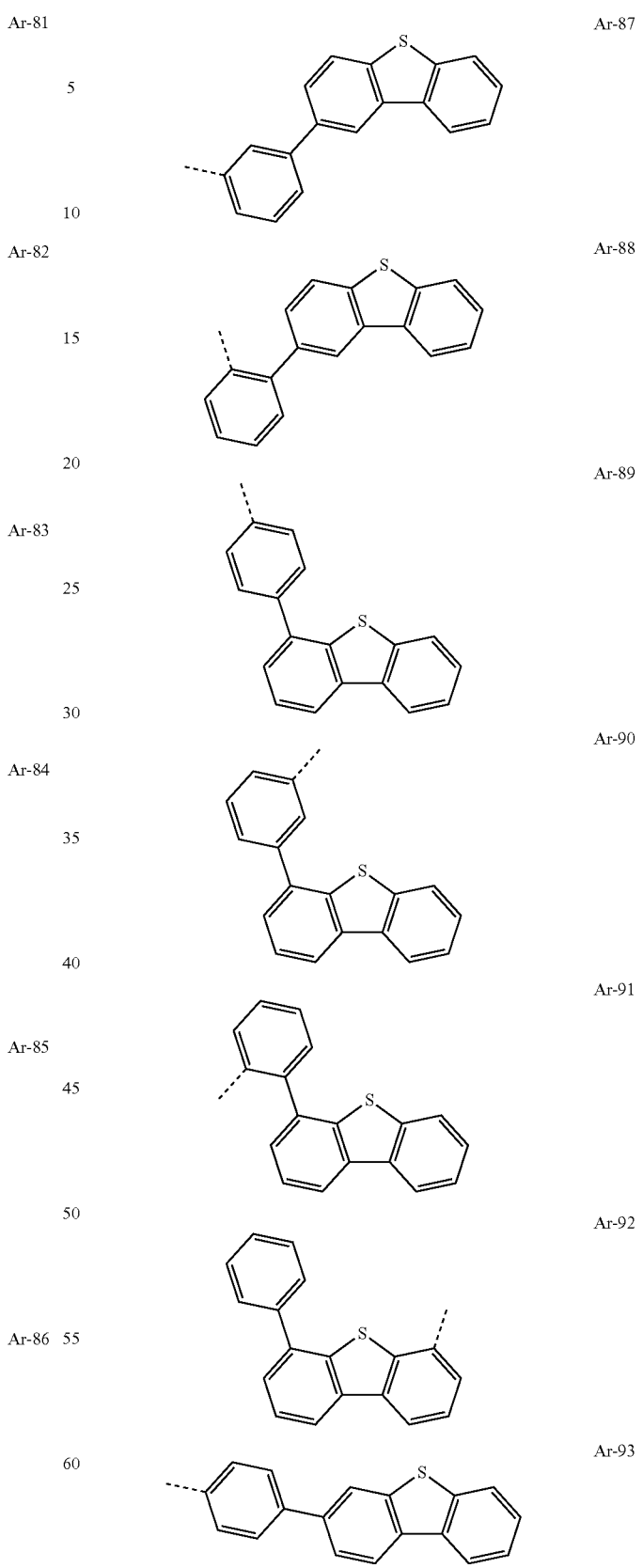
Ar-87
Ar-88
Ar-89
Ar-90
Ar-91
Ar-92
Ar-93

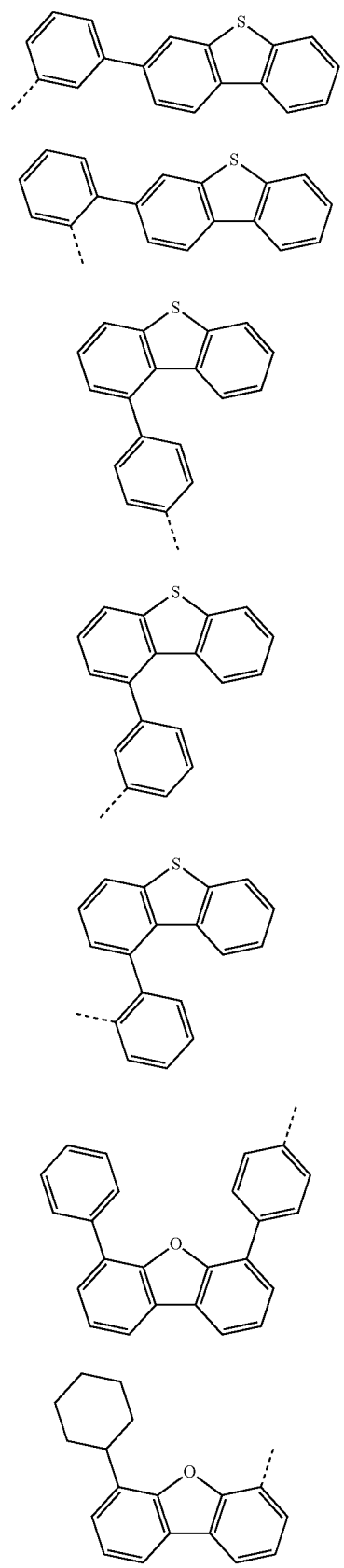
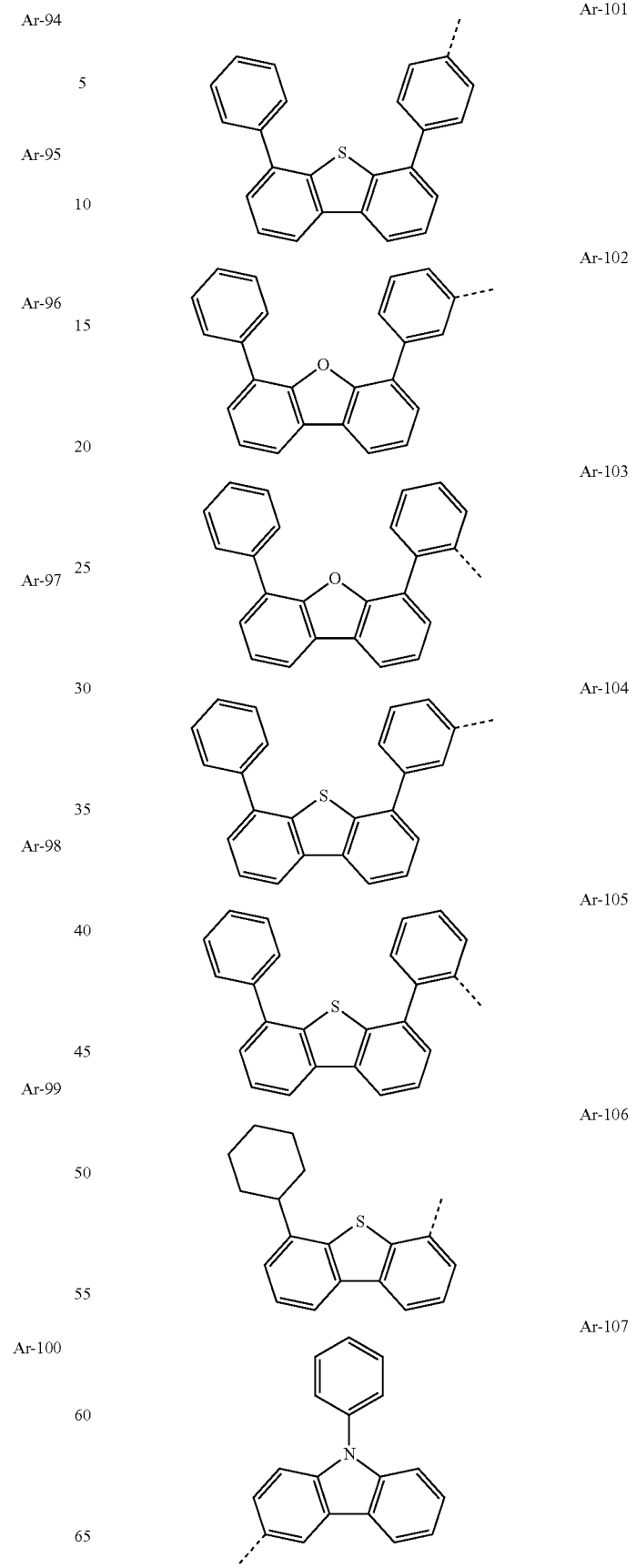

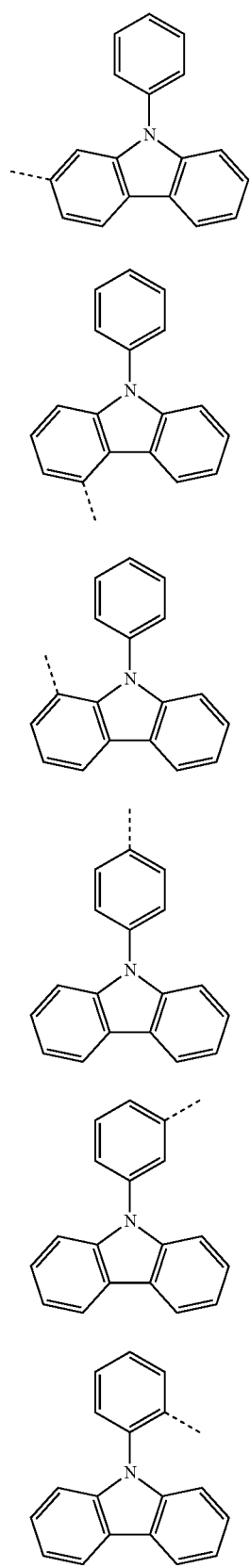
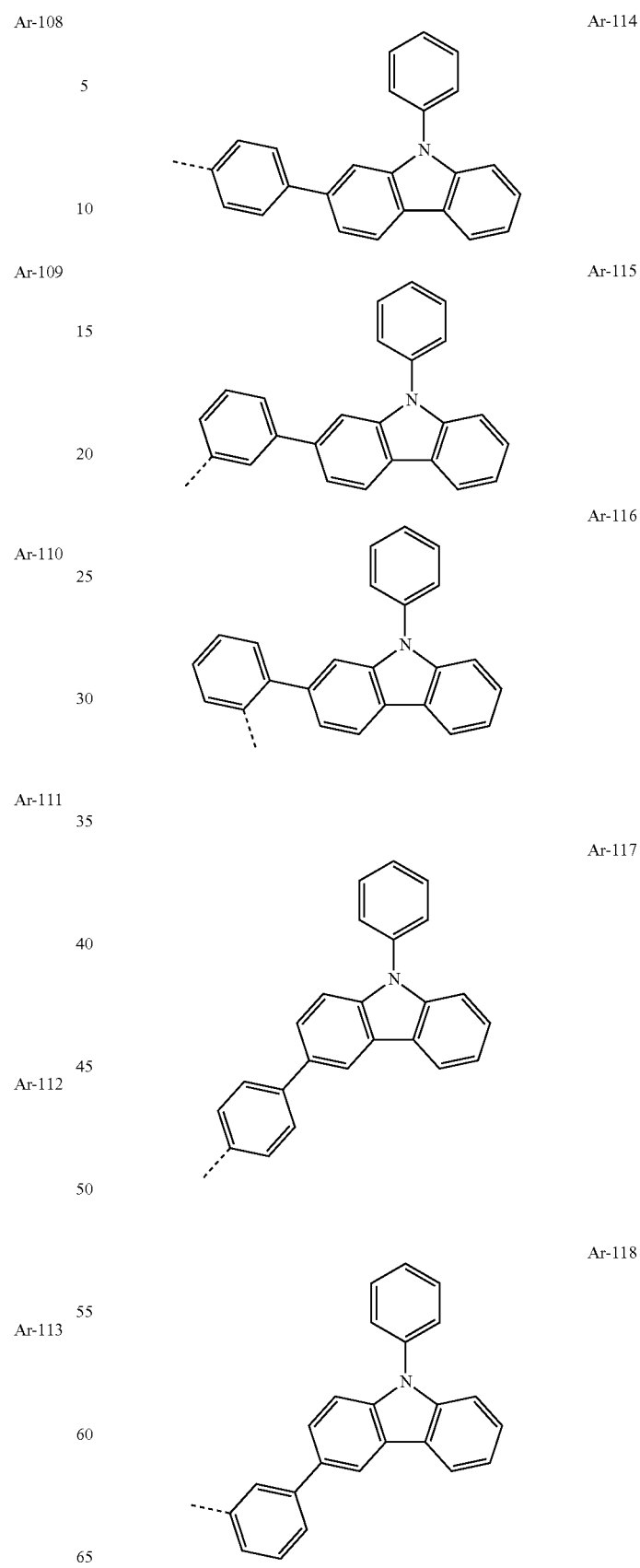

-continued
Ar-119
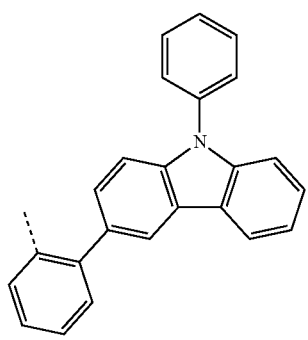
Ar-120
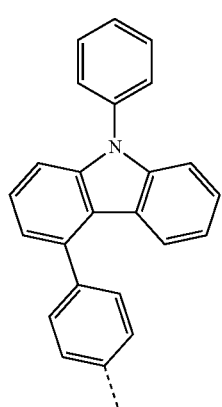
Ar-121
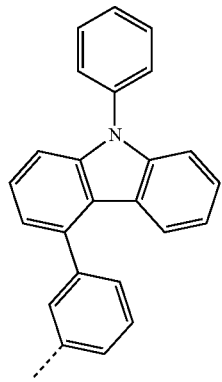
Ar-122
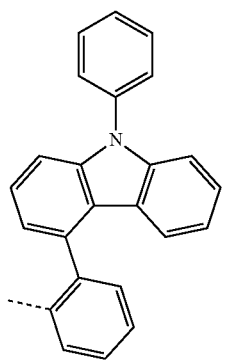
Ar-123
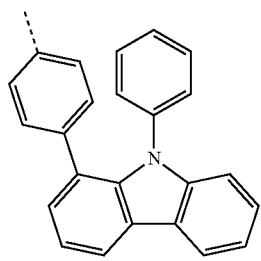
Ar-124
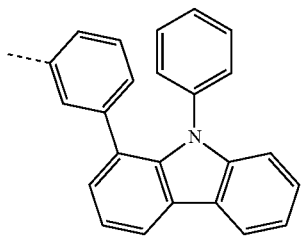
Ar-125
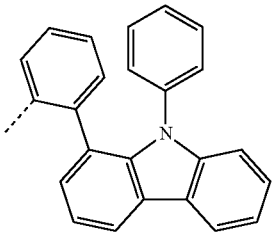
Ar-126
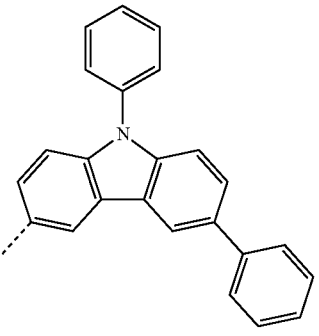
Ar-127
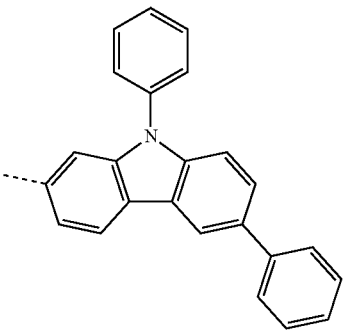

Ar-128
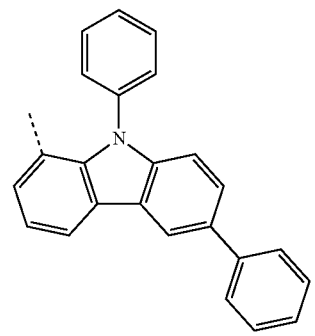
Ar-129
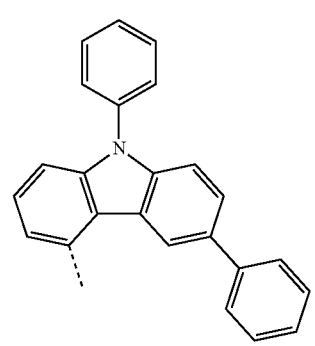
Ar-130
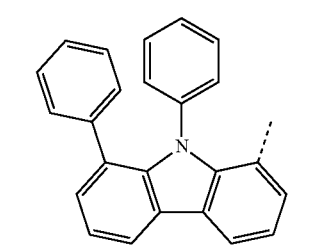
Ar-131
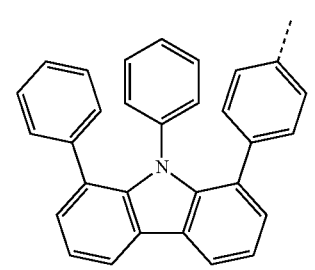
Ar-132
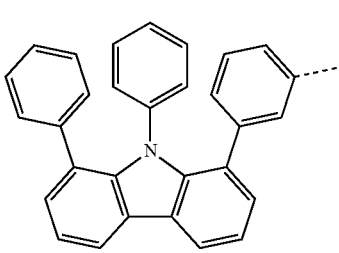
Ar-133
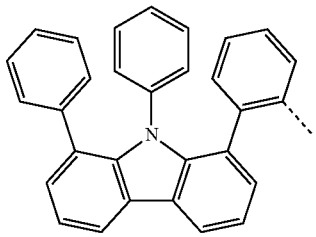
Ar-134
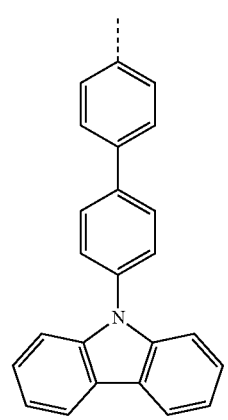
Ar-135
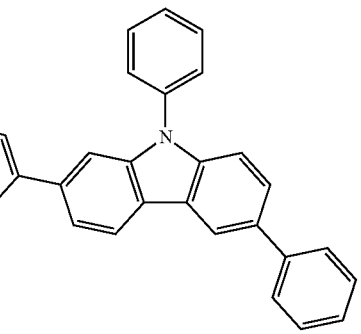
Ar-136
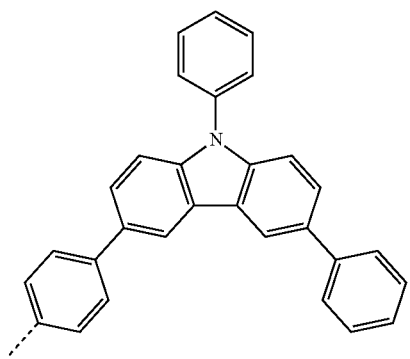

Ar-137
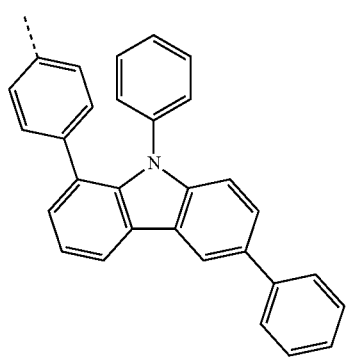
Ar-138
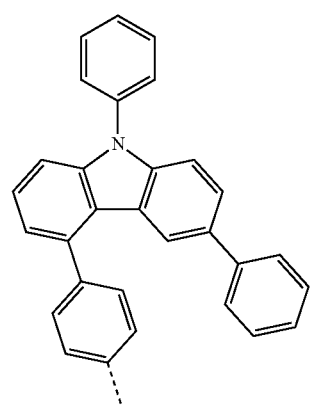
Ar-139
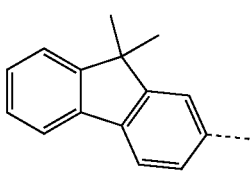
Ar-140
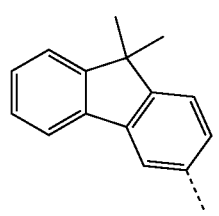
Ar-141
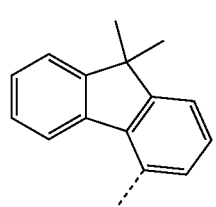
Ar-142
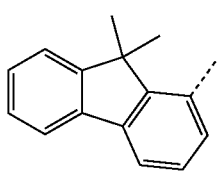
Ar-143
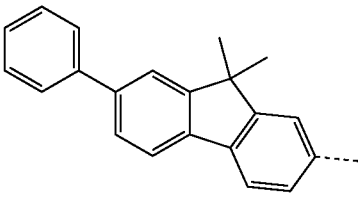
Ar-144
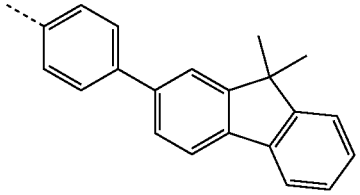
Ar-145
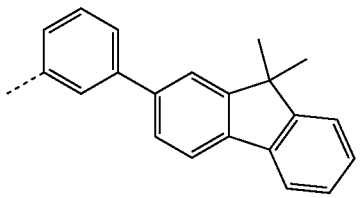
Ar-146
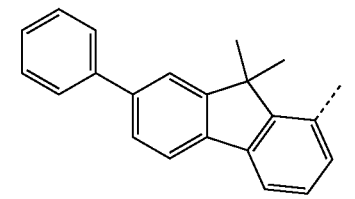
Ar-147
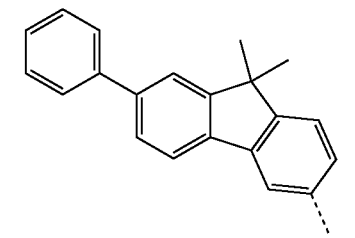
Ar-148
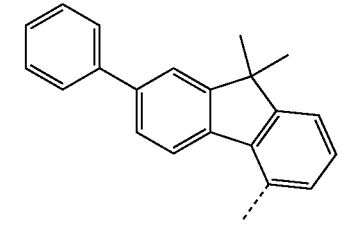
Ar-149
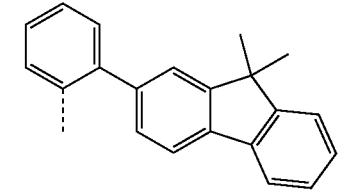

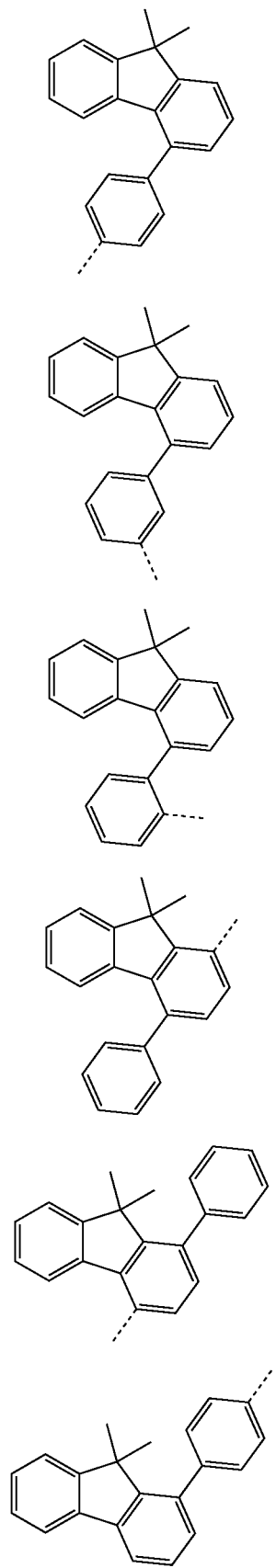
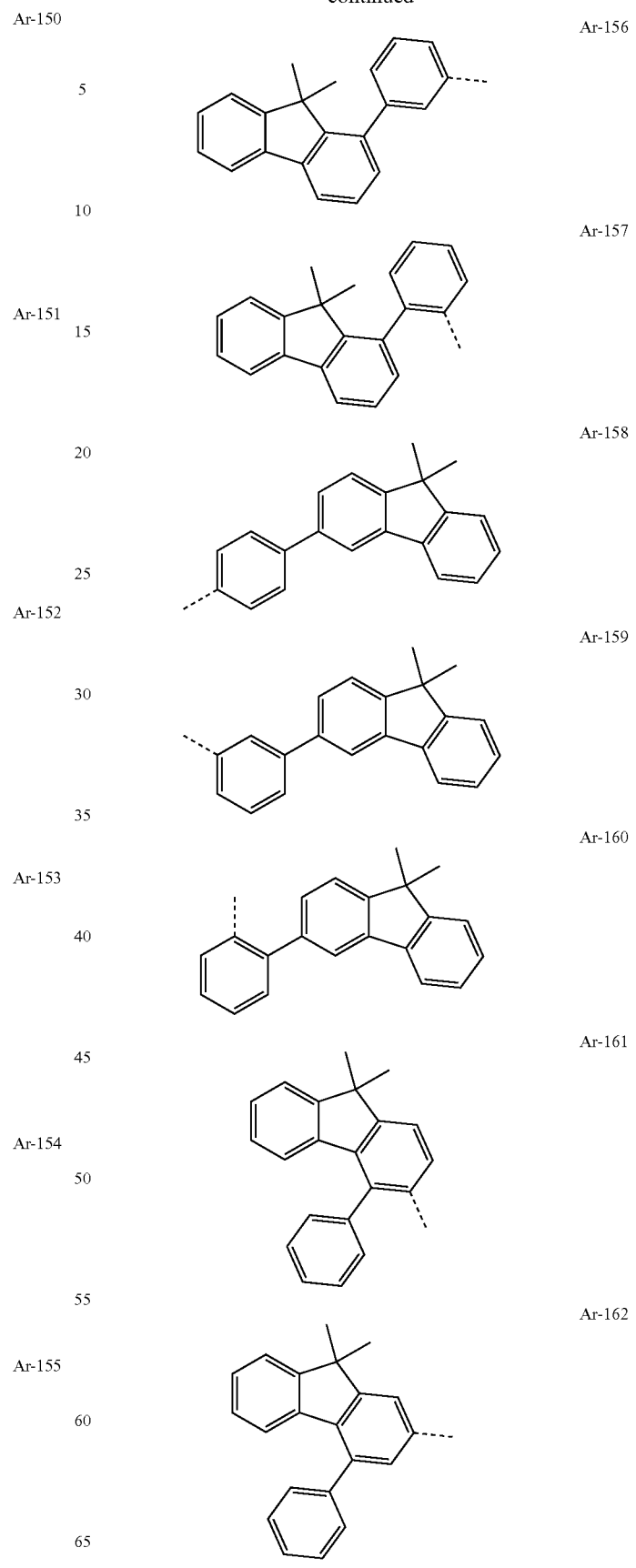

-continued
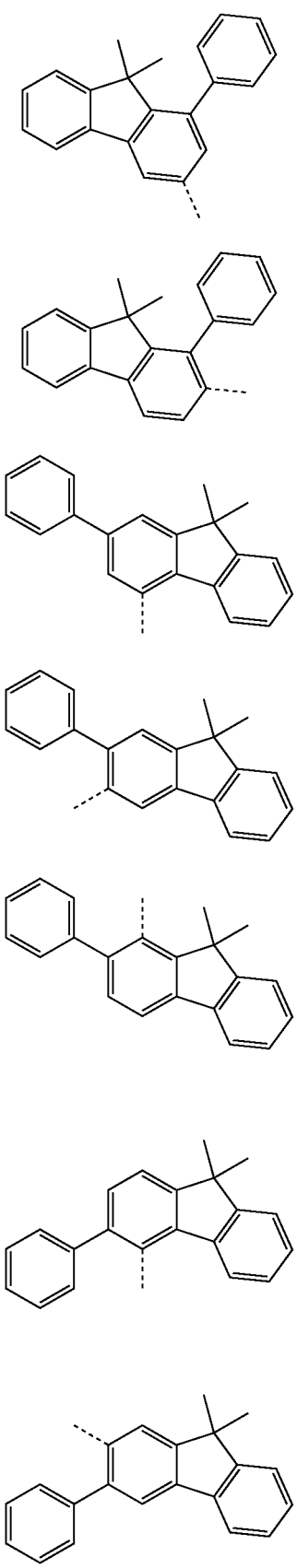
Ar-163
Ar-164
Ar-165
Ar-166
Ar-167
Ar-168
Ar-169
-continued
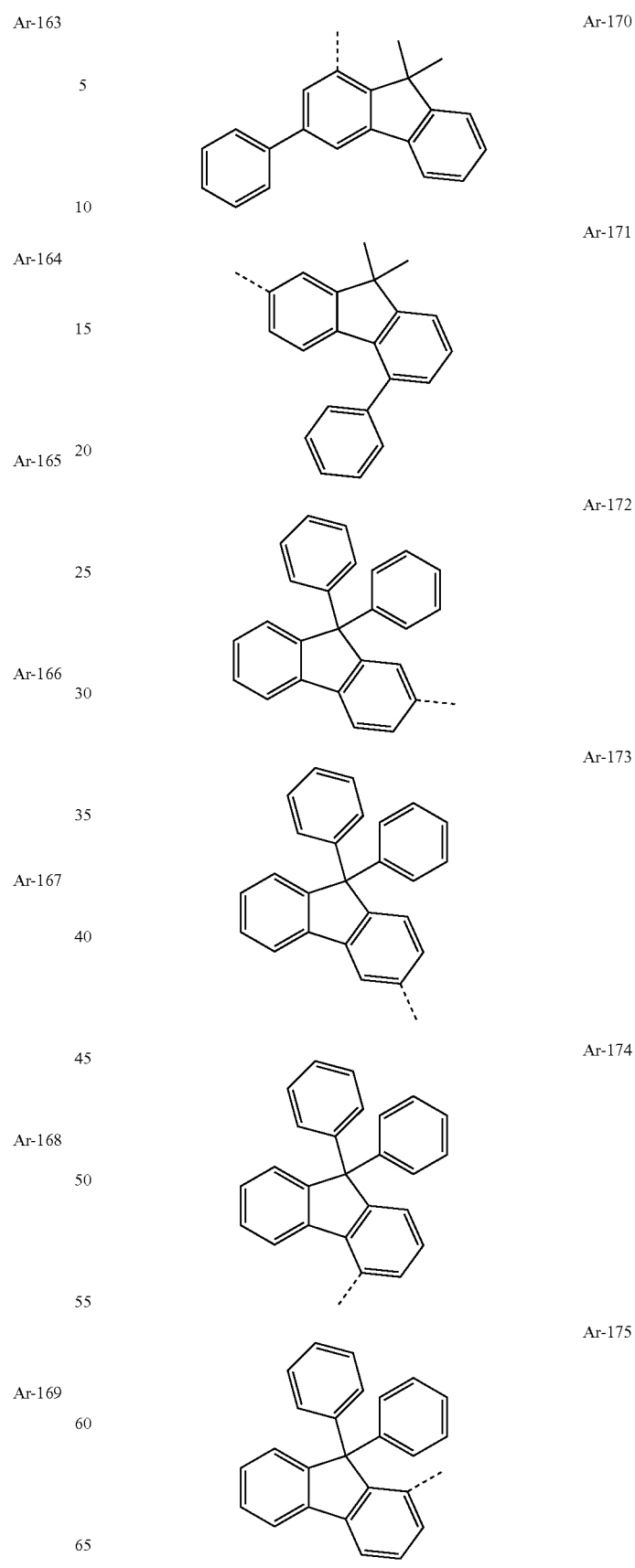
Ar-170
Ar-171
Ar-172
Ar-173
Ar-174
Ar-175

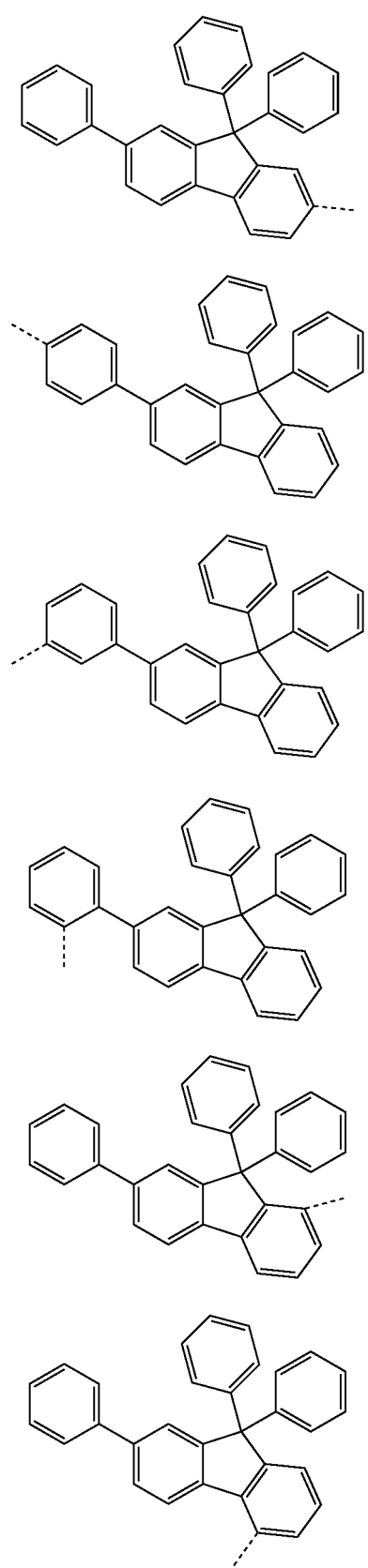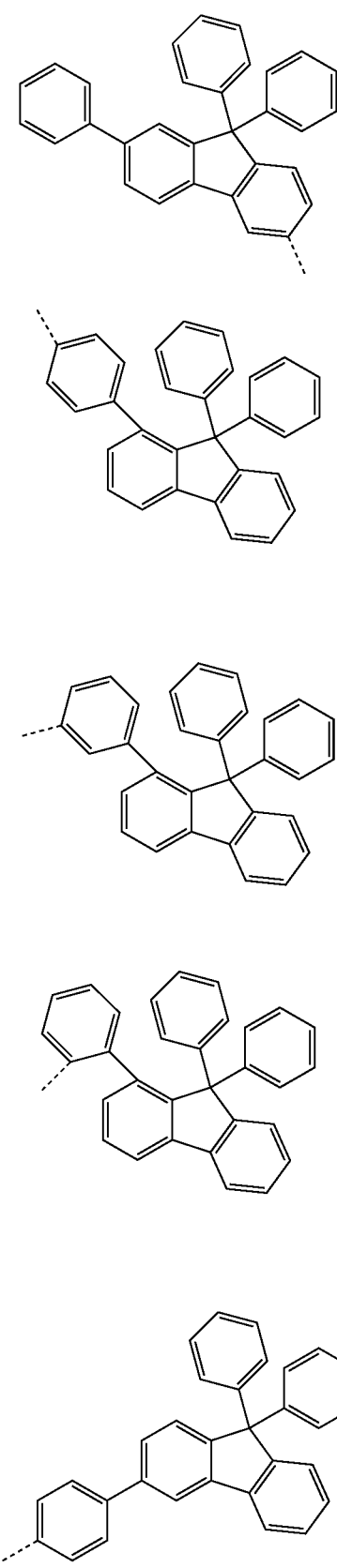

-continued
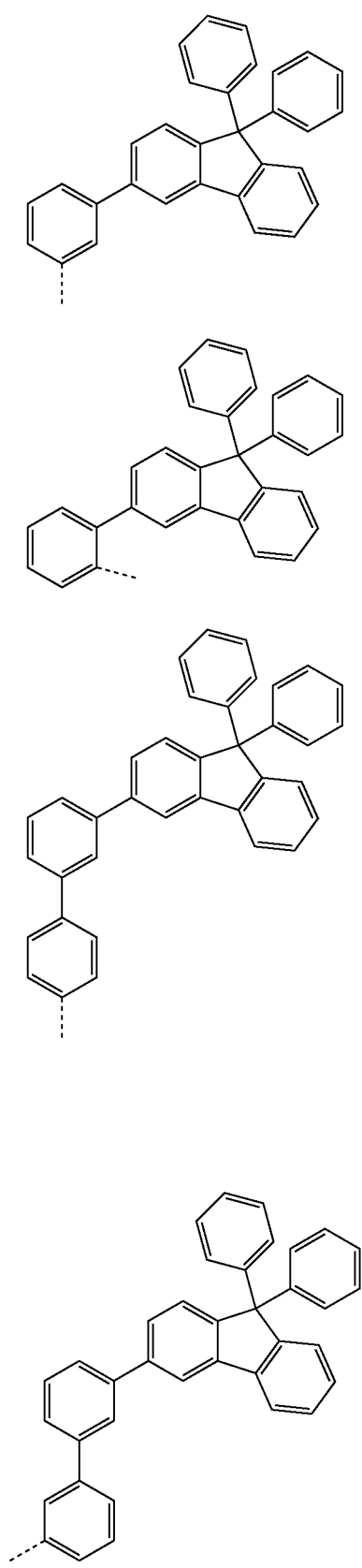
Ar-187
Ar-188
Ar-189
Ar-190
-continued
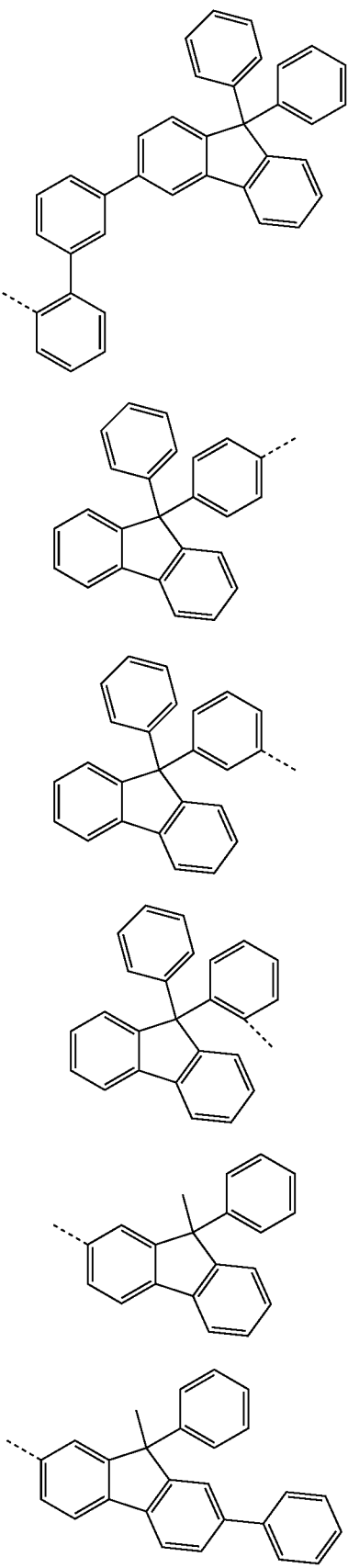
Ar-191
Ar-192
Ar-193
Ar-194
Ar-195
Ar-196

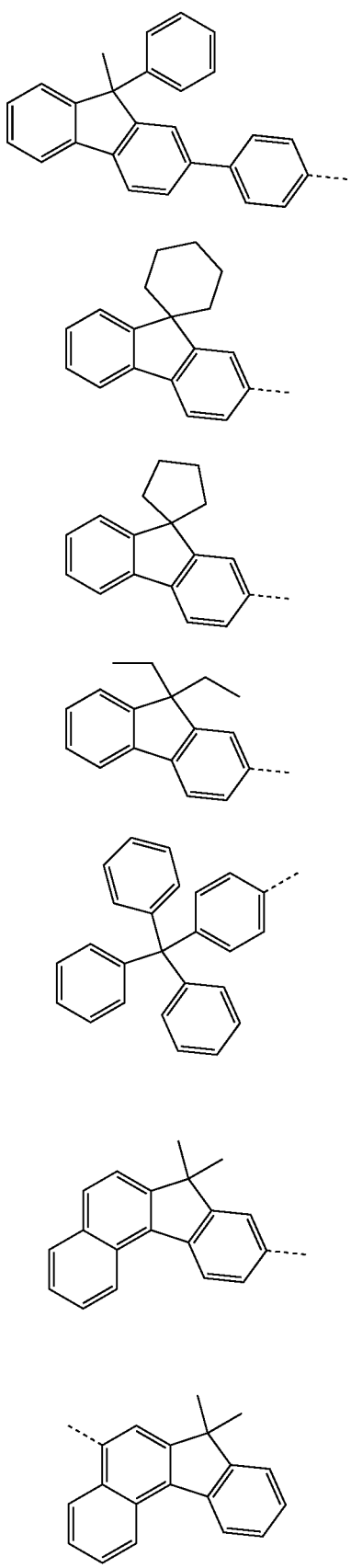

Ar-211
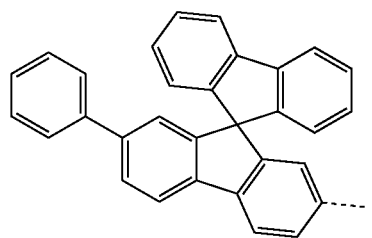
Ar-212
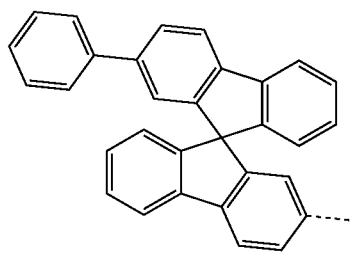
Ar-213
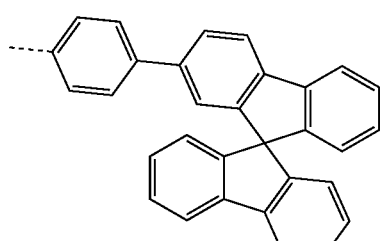
Ar-214
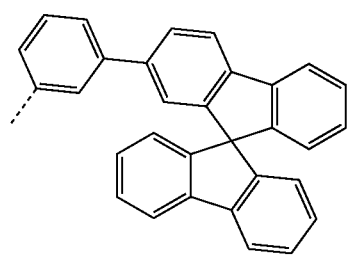
Ar-215
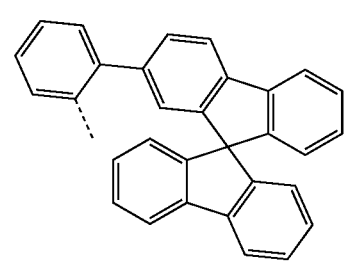
Ar-216
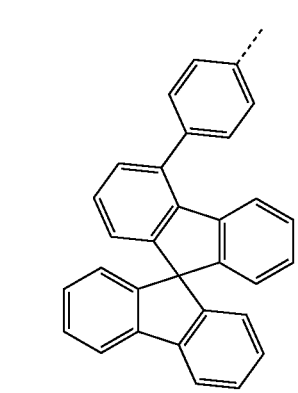
Ar-217
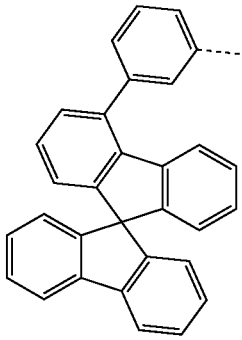
Ar-218
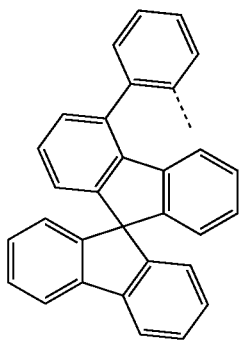
Ar-219
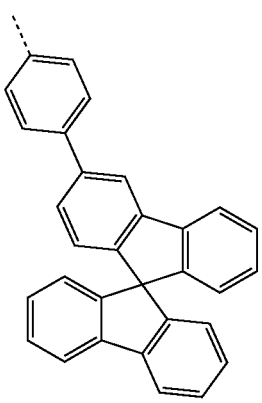
Ar-220
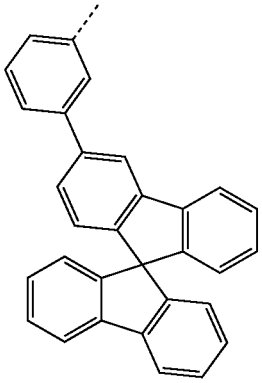

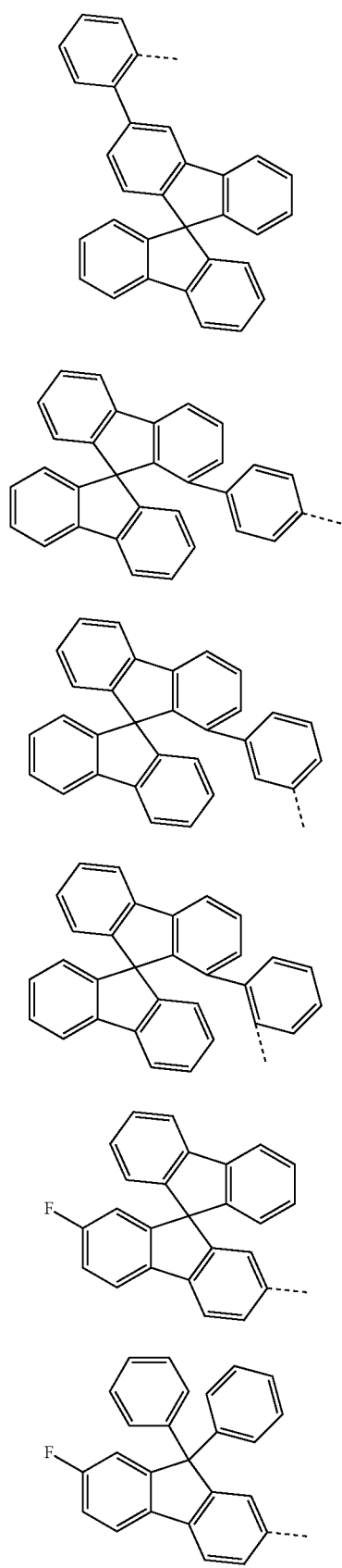

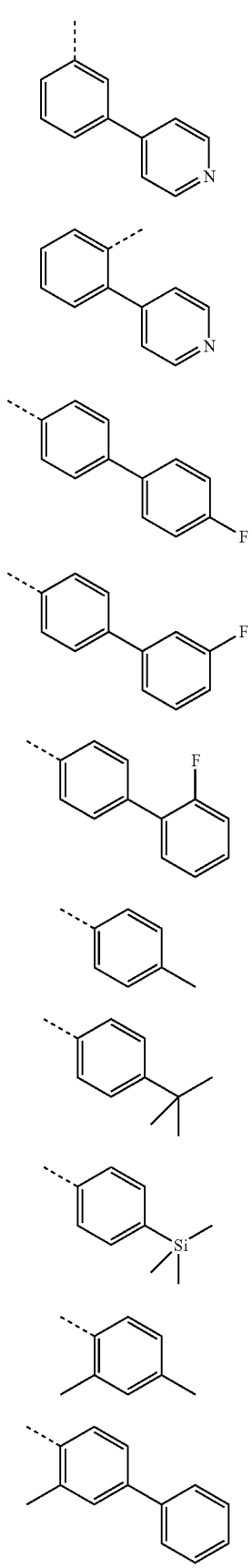 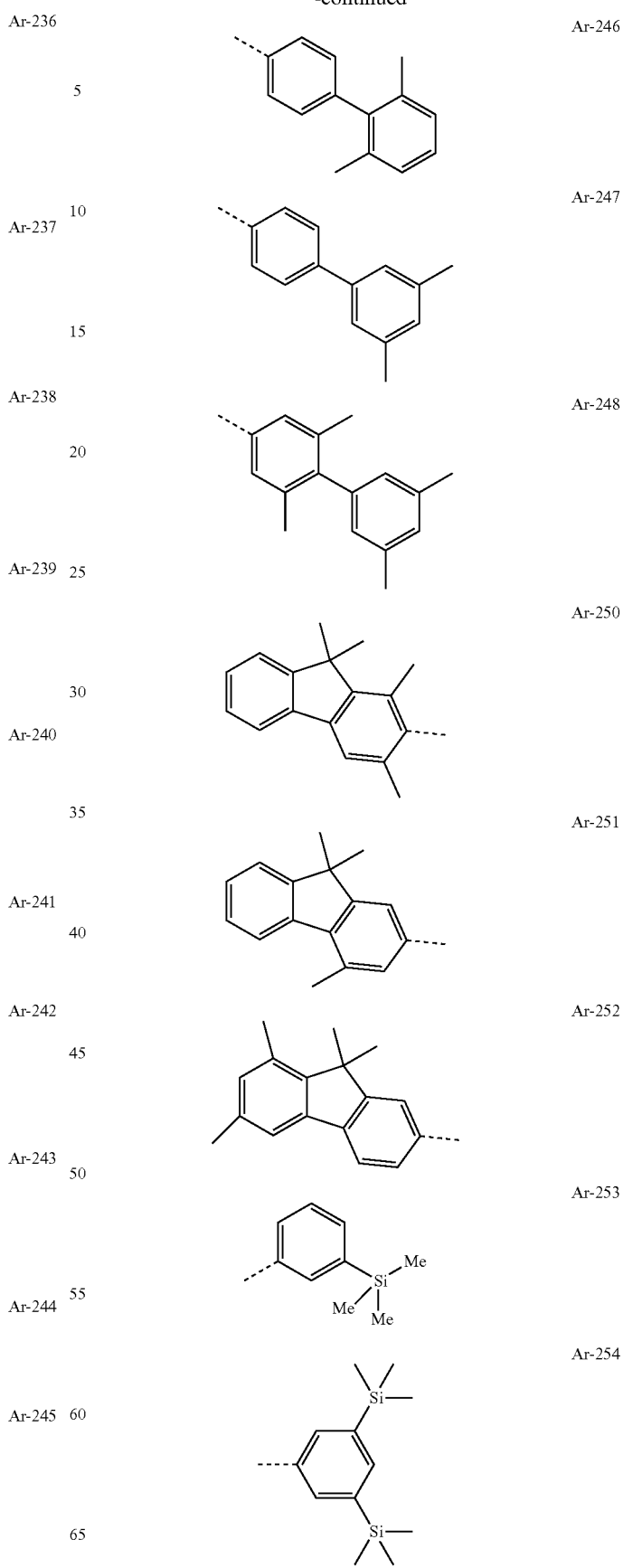

-continued

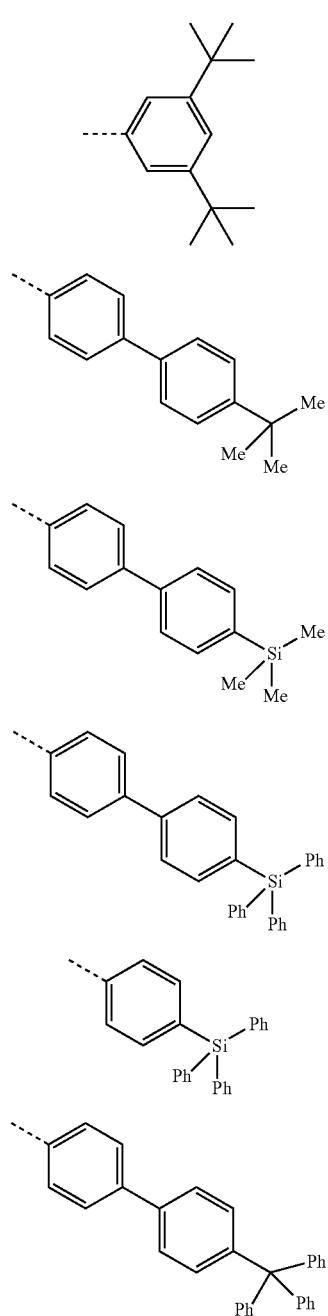

Ar-255

Ar-256

Ar-257

Ar-258

Ar-259

Ar-260 where the groups may each be substituted by an $R^5$ radical at all unoccupied positions and where the dashed bond represents the bond to the nitrogen atom in formula (N).

It is preferable that two different $Ar^2$ groups are bonded to each nitrogen atom in formula (N).

The E group is preferably a single bond.

Preferably, m=0, such that no E group is present.

In an alternative embodiment, which is likewise preferred, m=1, such that the $Ar^2$ groups are bonded to one another via an E group. In this case, is it preferable that the $Ar^2$ groups are selected from phenyl and fluorenyl, each of which may be substituted by one or more $R^5$ radicals. In addition, it is preferable in this case that the E group that joins the two $Ar^2$ groups to one another is bonded to the $Ar^2$ groups in question in the ortho position to the bond of the $Ar^2$ group to the amino group in formula (N). In addition, it is preferable that the E group forms a six-membered ring together with the Are groups if E is selected from $C(R^5)_2$, $Si(R^5)_2$, $NR^5$, O and S; and a five-membered ring if E is a single bond.

Preferred embodiments of the unit

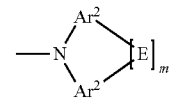

from the group of the formula (N) when m=1 are the groups depicted below:

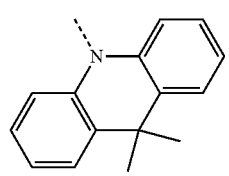

N-1

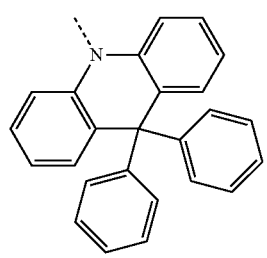

N-2

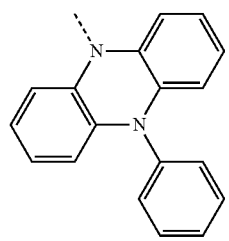

N-3

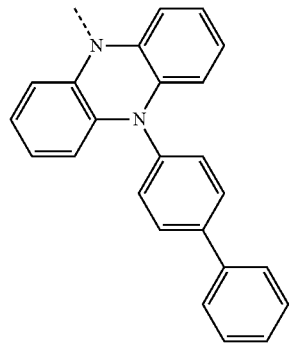

N-4

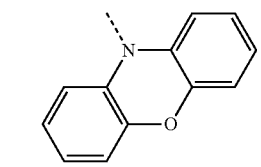

N-5

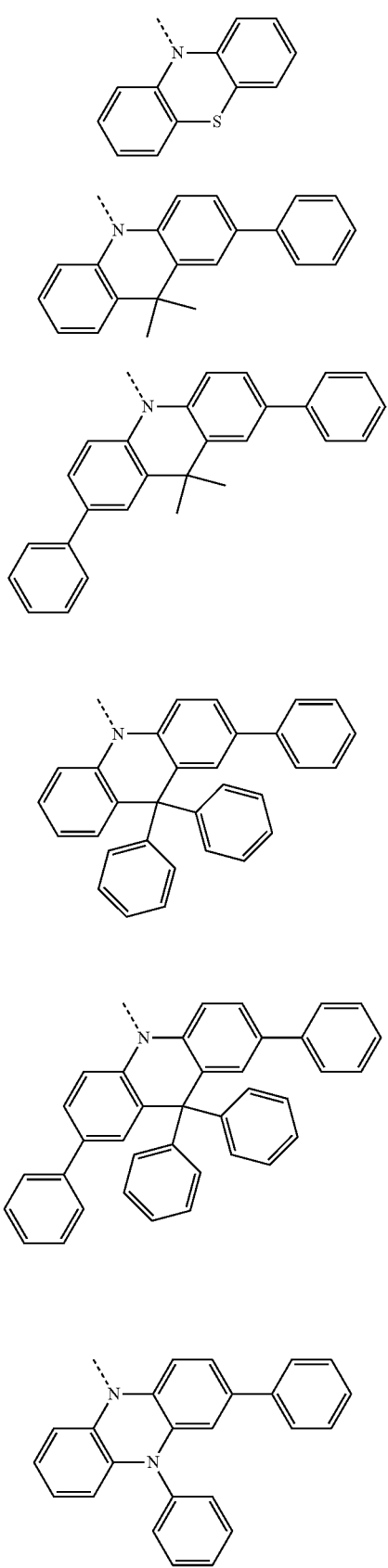
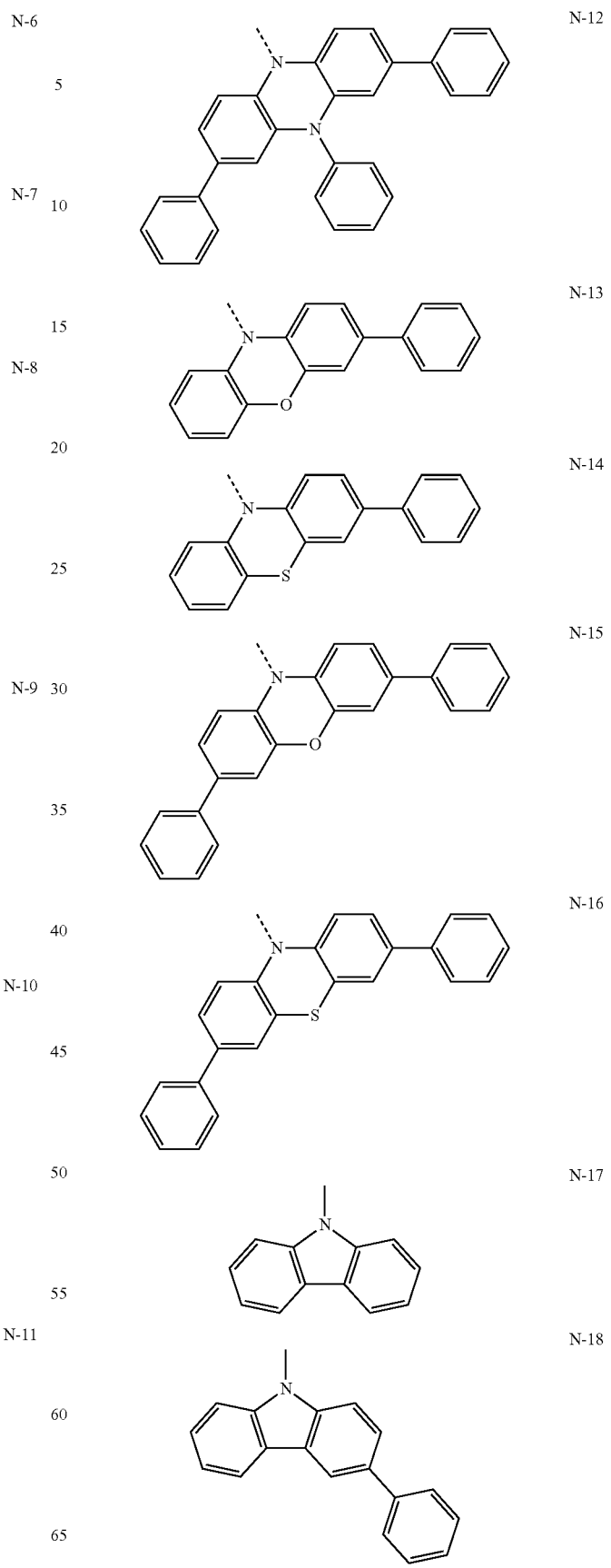

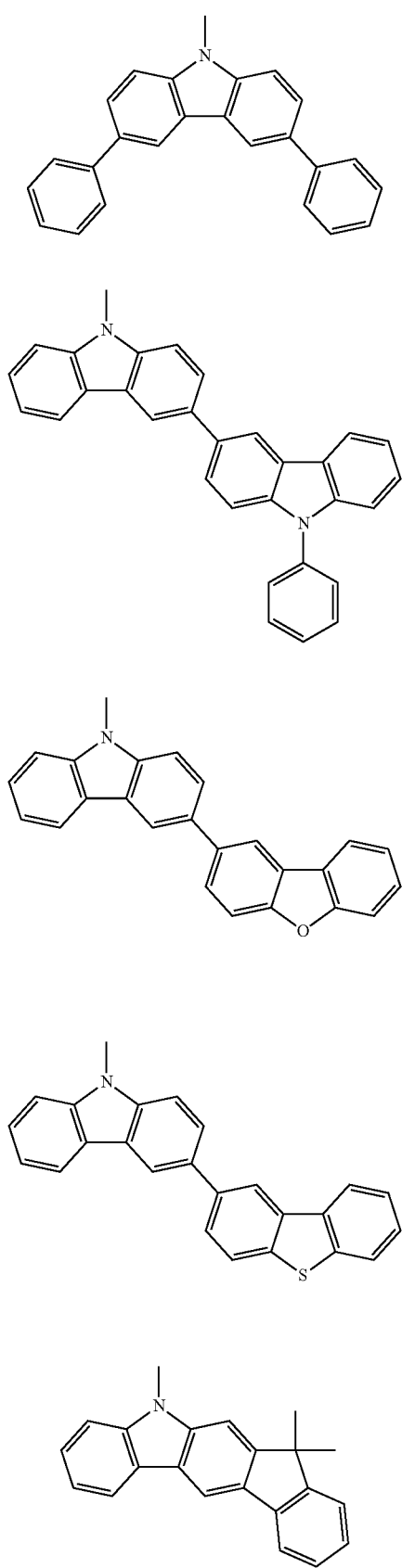

N-29
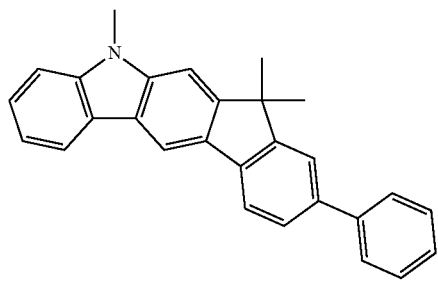
N-30
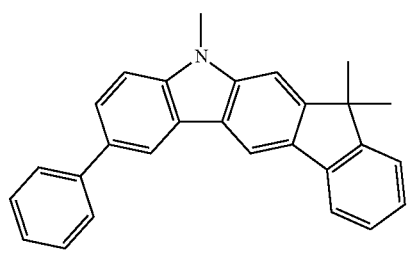
N-31
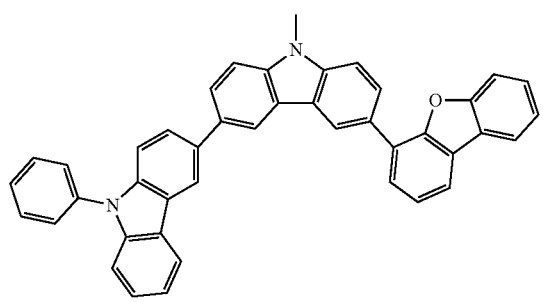
N-32
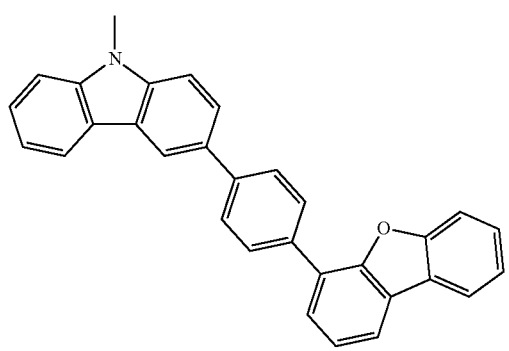
where the groups may each be substituted by an $R^5$ radical at their unoccupied positions, and are preferably unsubstituted in the unoccupied positions, and where the dashed bonds represent the bonds to the rest of the formula.
Preferred embodiments from the group of the formula (N) when m=0 are the groups depicted below:
A-1
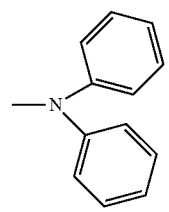
A-2
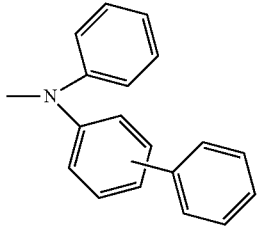
A-3
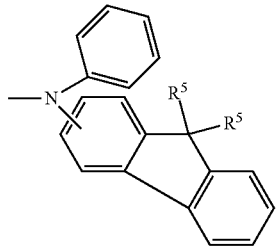
A-4
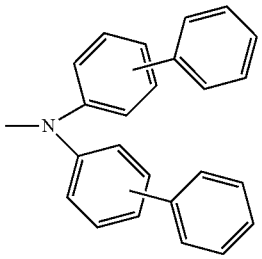
A-5
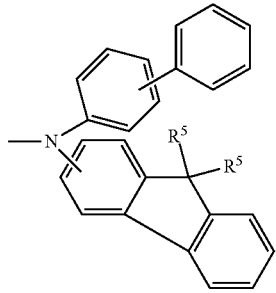
A-6
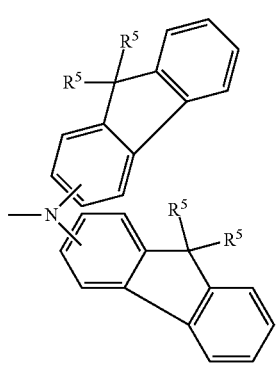

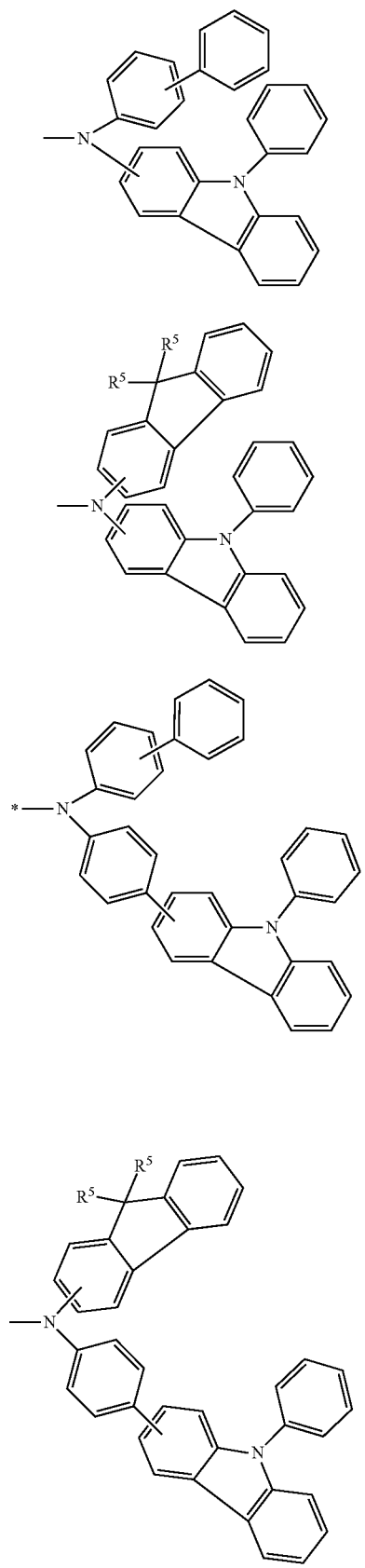
A-7
A-8
A-9
A-10
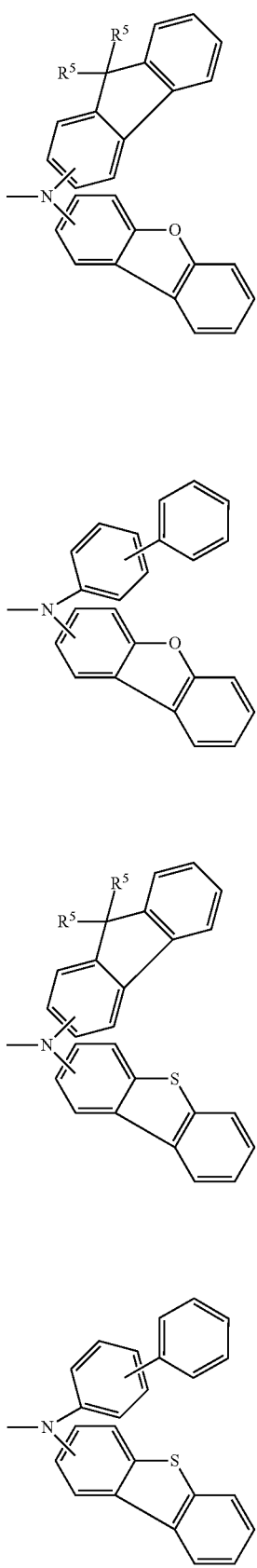
A-11
A-12
A-13
A-14

A-15
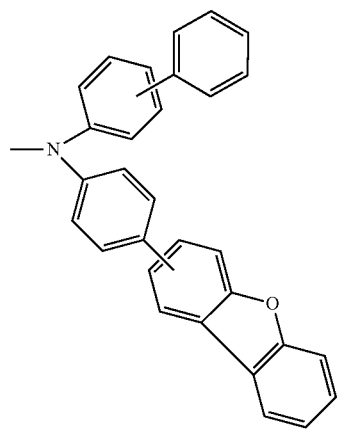
A-16
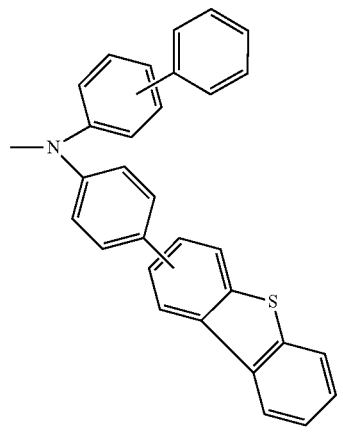
A-17
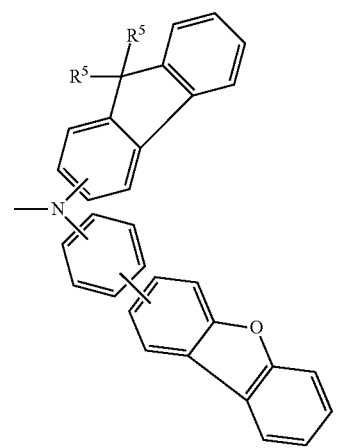
A-18
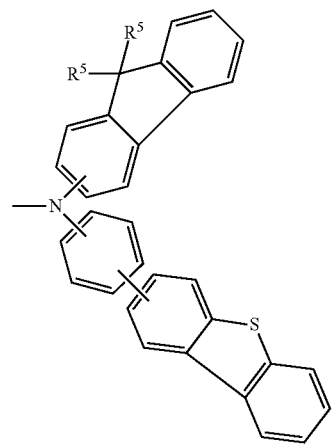
A-19
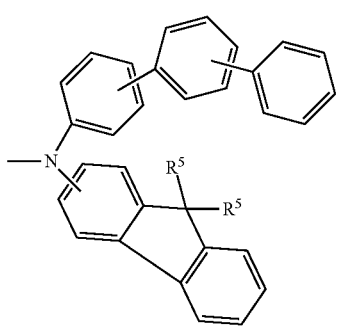
A-20
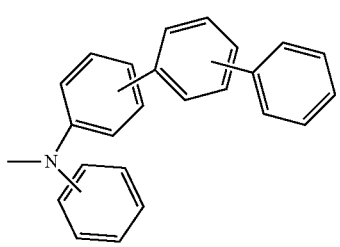
A-21
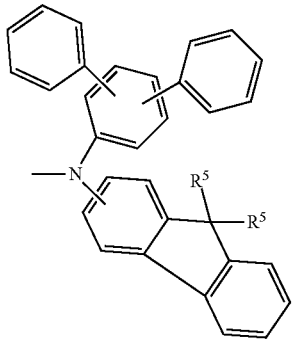
A-22
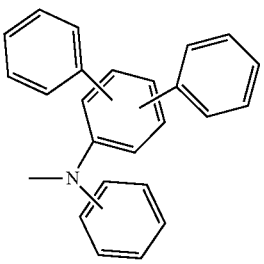

A-23
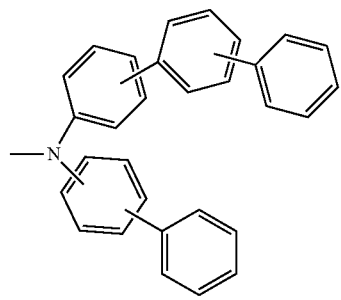
A-24
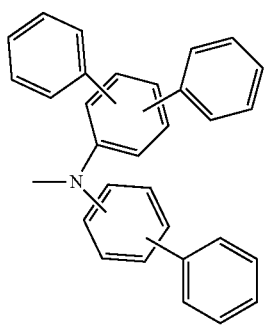
A-25
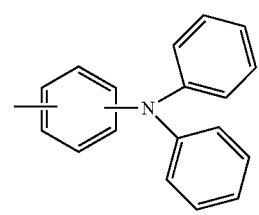
A-26
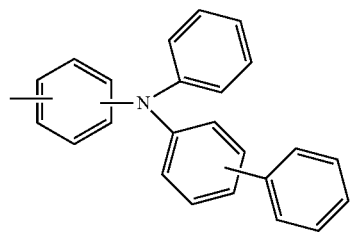
A-27
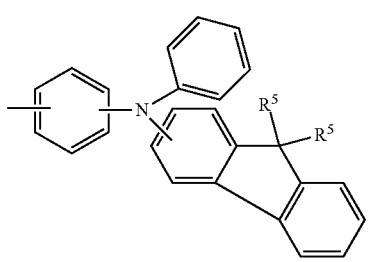
A-28
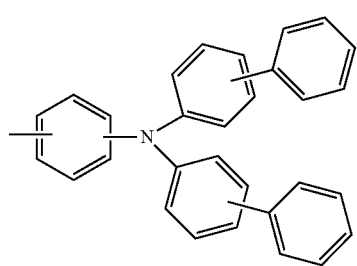
A-29
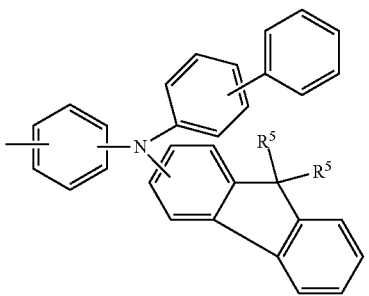
A-30
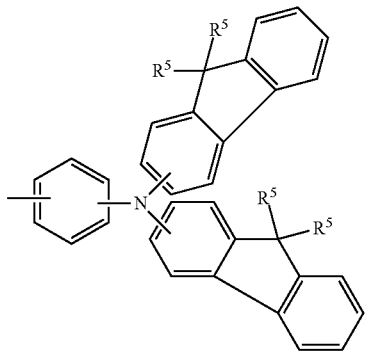
A-31
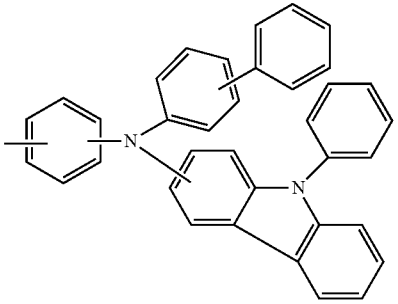
A-32
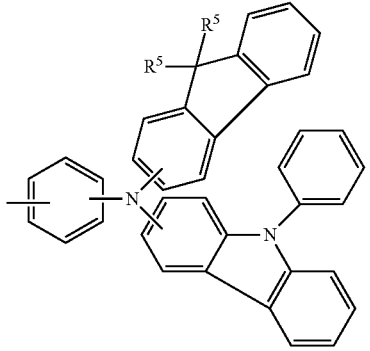

A-33
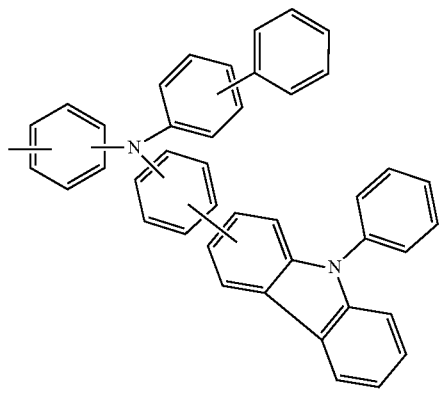
A-34
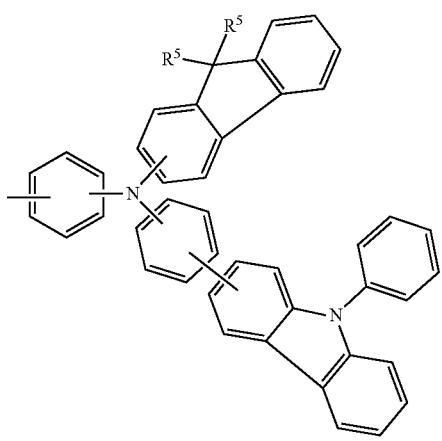
A-35
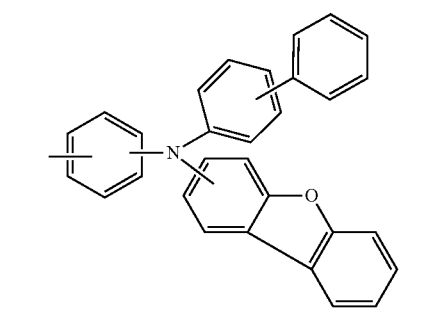
A-36
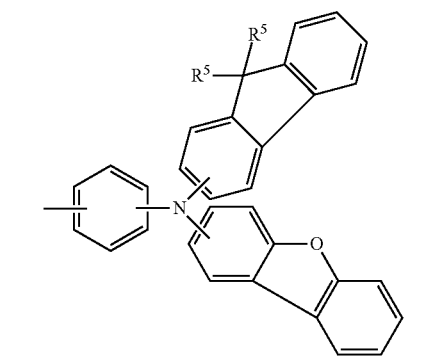
A-37
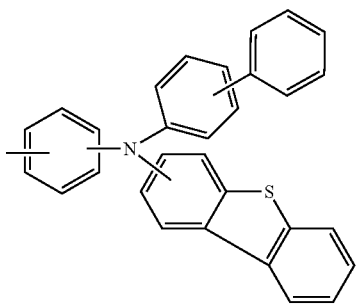
A-38
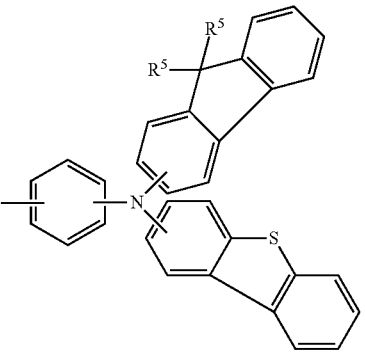
A-39
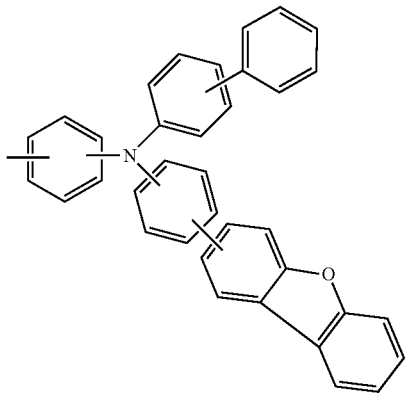
A-40

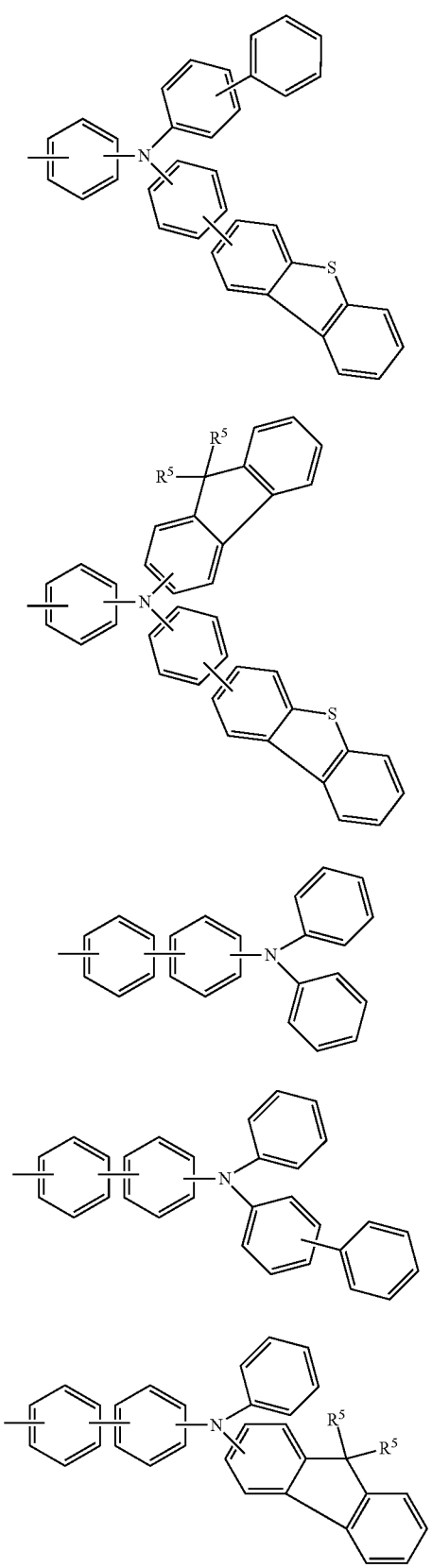

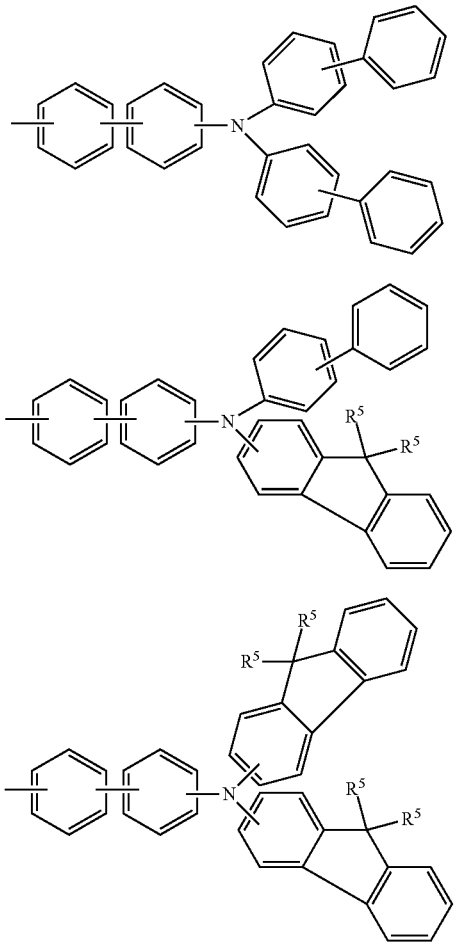

where the groups may each be substituted by an R⁵ radical at their unoccupied positions, and are preferably unsubstituted in the unoccupied positions, and where the dashed bonds represent the bonds to the rest of the formula.

R² is preferably selected from H, D, F, CN, straight-chain alkyl or alkoxy groups having 1 to 10 carbon atoms, branched or cyclic alkyl or alkoxy groups having 3 to 10 carbon atoms, alkenyl or alkynyl groups having 2 to carbon atoms, aromatic ring systems having 6 to 40 aromatic ring atoms and heteroaromatic ring systems having 5 to 40 aromatic ring atoms, where said alkyl, alkoxy, alkenyl and alkynyl groups and said aromatic ring systems and heteroaromatic ring systems may each be substituted by one or more R⁷ radicals. More preferably, R² is selected from H, F, CN, straight-chain alkyl groups having 1 to 10 carbon atoms, branched or cyclic alkyl groups having 3 to 10 carbon atoms, aromatic ring systems having 6 to 40 aromatic ring atoms and heteroaromatic ring systems having 5 to 40 aromatic ring atoms; where said alkyl groups and said aromatic ring systems and heteroaromatic ring systems may each be substituted by one or more R⁷ radicals. Most preferably, R² is H.

R³ is preferably the same or different at each instance and is selected from H, D, F, CN, Si(R⁷)₃, N(R⁷)₂, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^7$ radicals.

$R^4$ is preferably the same or different at each instance and is selected from H, D, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^7$ radicals. More preferably, $R^4$ is the same or different at each instance and is selected from straight-chain alkyl groups having 1 to 20 carbon atoms, branched or cyclic alkyl groups having 3 to 20 carbon atoms and aromatic ring systems having 6 to 40 aromatic ring atoms, where the alkyl groups mentioned and the aromatic ring systems mentioned may each be substituted by one or more $R^7$ radicals.

$R^5$ is preferably the same or different at each instance and is selected from H, D, F, CN, $Si(R^7)_3$, $N(R^7)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^7$ radicals.

$R^6$ is preferably the same or different at each instance and is selected from H, D, F, CN, $Si(R^7)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^7$ radicals. More preferably, $R^6$ is H.

$R^7$ is preferably the same or different at each instance and is selected from H, D, F, CN, $Si(R^8)_3$, $N(R^8)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^8$ radicals.

Index i is preferably 0.

Preferred embodiments of the formula (I) correspond to one of the following formulae (I-1) to (I-9):

Formula (I-1)
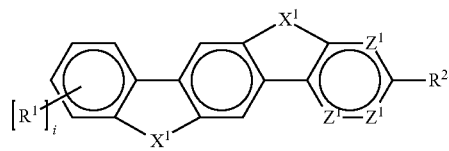

Formula (I-2)
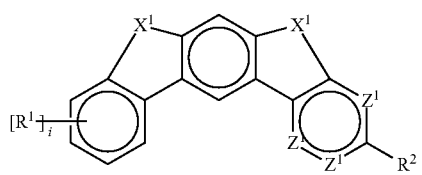

Formula (I-3)
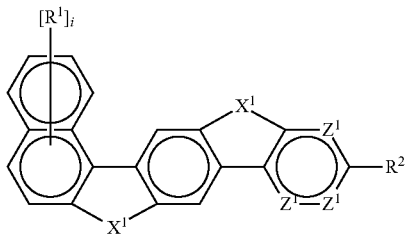

Formula (I-4)
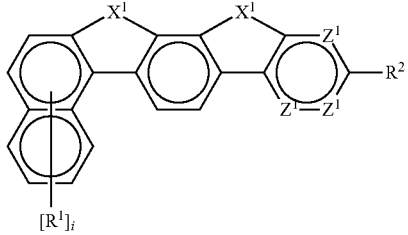

Formula (I-5)
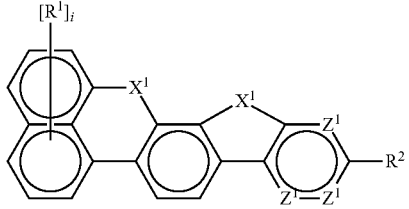

Formula (I-6)
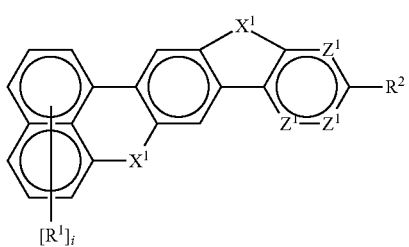

Formula (I-7)
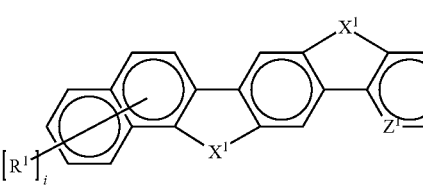

Formula (I-8)
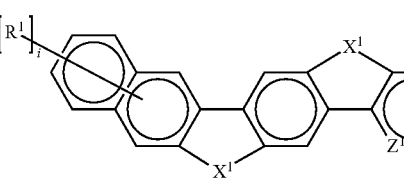

Formula (I-9)
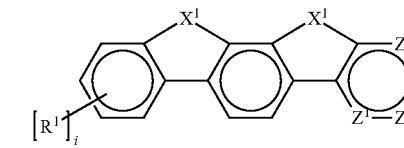

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.
Preferred embodiments of the formulae (I-1) to (I-9) conform to the formulae shown below:
Formula (I-1-A)
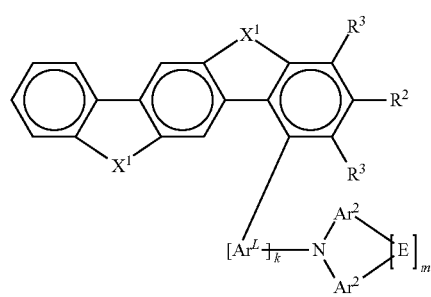
Formula (I-1-B)
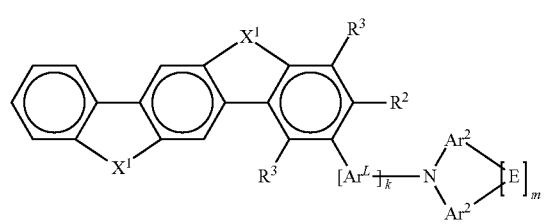
Formula (I-1-C)
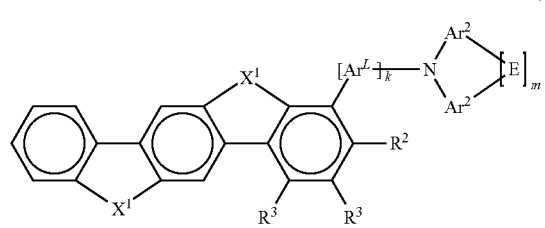
Formula (I-2-A)
Formula (I-2-B)
Formula (I-2-C)
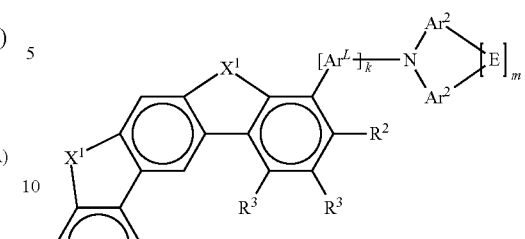
Formula (I-3-A)
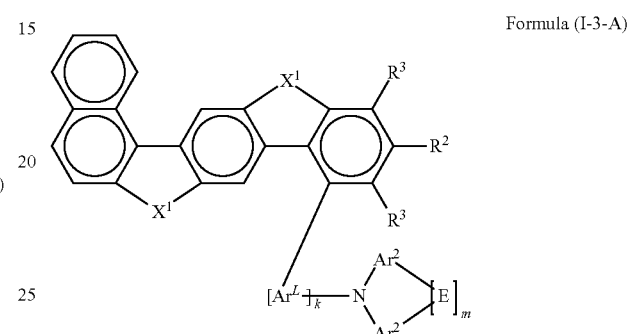
Formula (I-3-B)
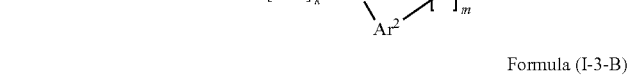
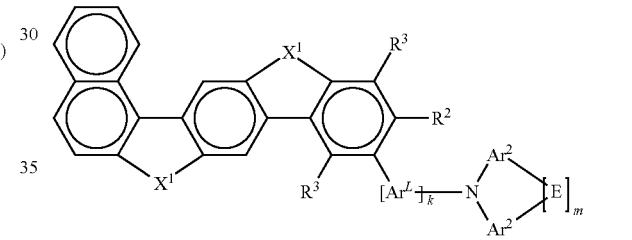
Formula (I-3-C)
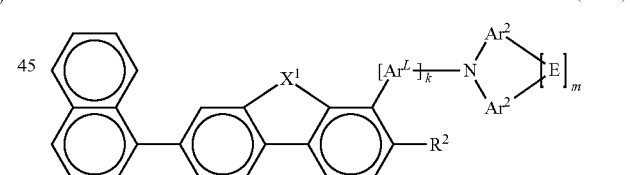
Formula (I-4-A)
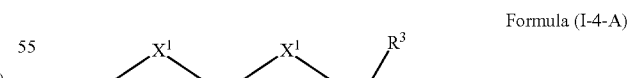
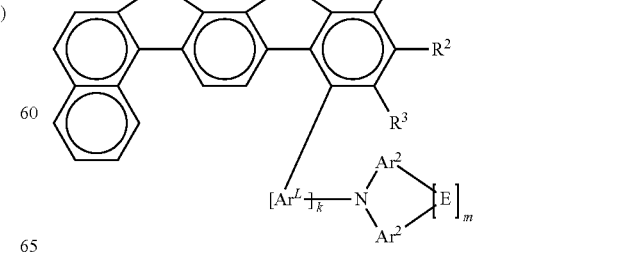

Formula (I-4-B)
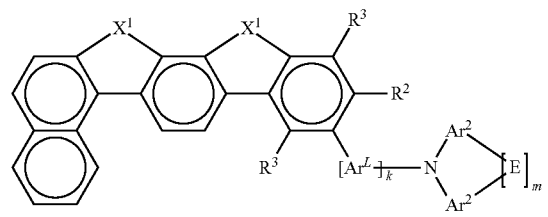
Formula (I-4-C)
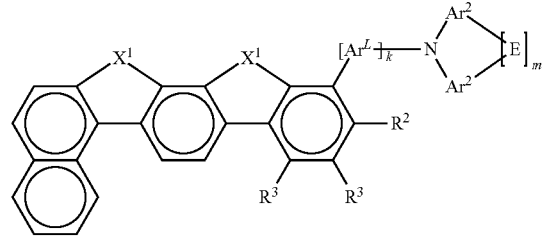
Formula (I-5-A)
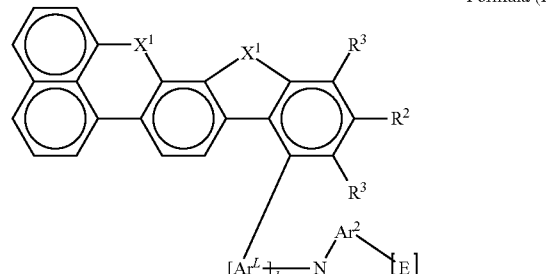
Formula (I-5-B)
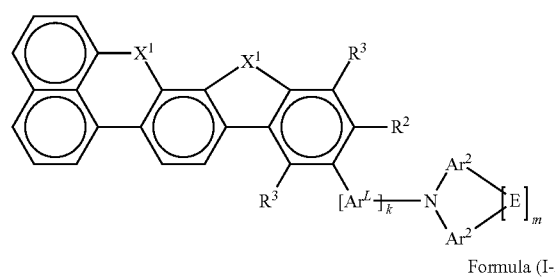
Formula (I-5-C)
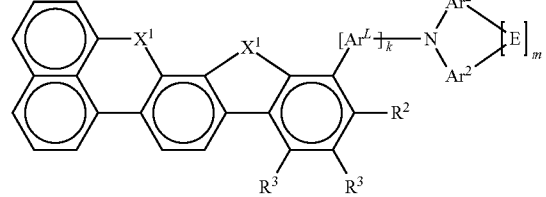
Formula (I-6-A)
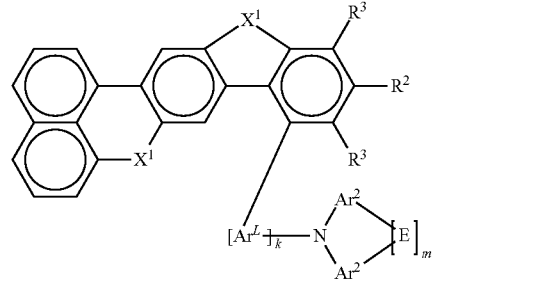
Formula (I-6-B)
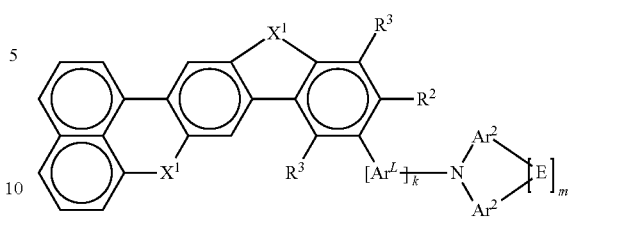
Formula (I-6-C)
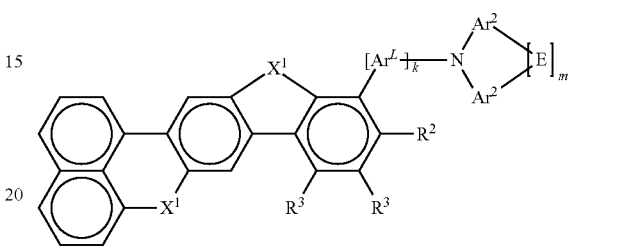
Formula (I-7-A)
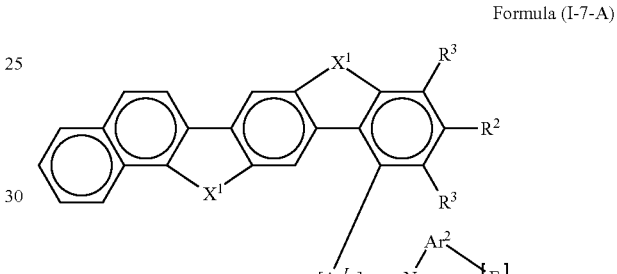
Formula (I-7-B)
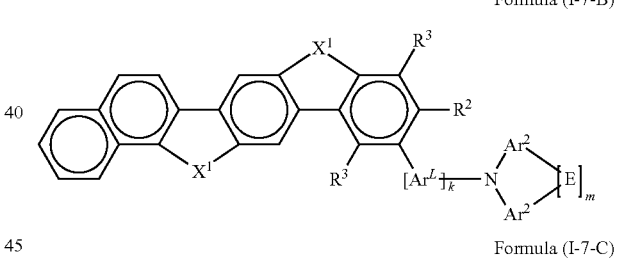
Formula (I-7-C)
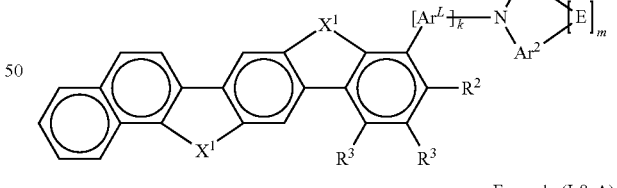
Formula (I-8-A)
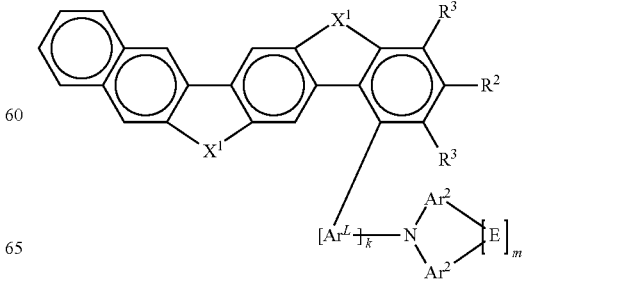

Formula (I-8-B)

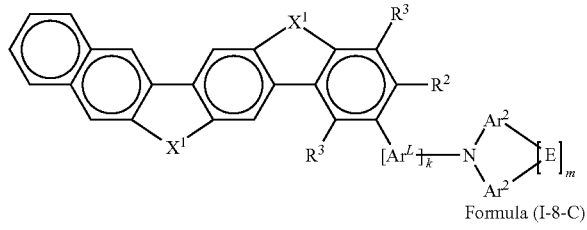

Formula (I-8-C)

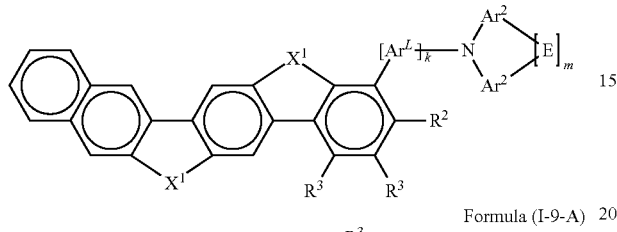

Formula (I-9-A)

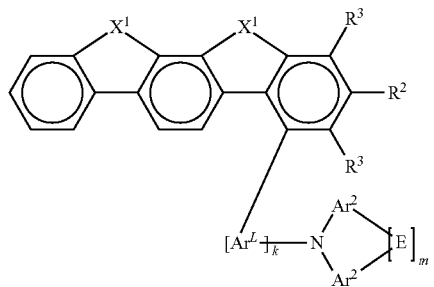

Formula (I-9-B)

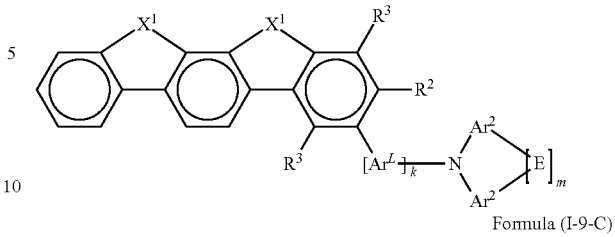

Formula (I-9-C)

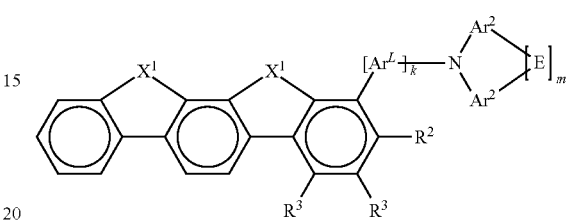

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.

Among the abovementioned formulae, preference is given to the formulae (I-1-A), (I-2-A), (I-3-A), (I-4-A), (I-5-A), (I-6-A), (I-7-A), (I-8-A) and (I-9-A). Particular preference is given to the formula (I-1-A).

Further preferred embodiments of the compounds of the formula (I) correspond to the following formulae:

Formula (I-1-D)

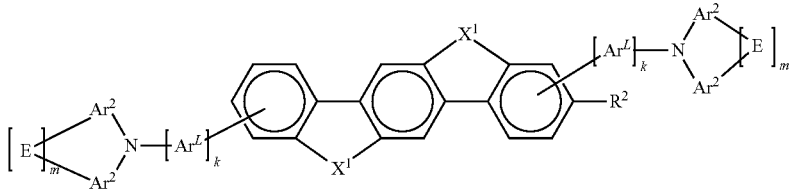

Formula (I-2-D)

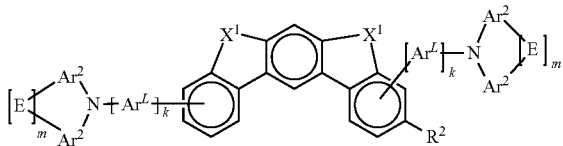

Formula (I-3-D)

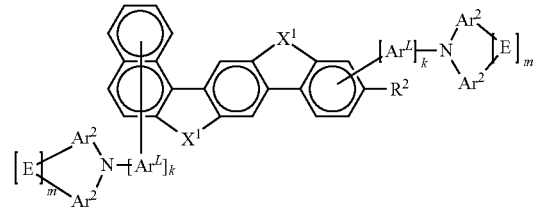

Formula (I-4-D)

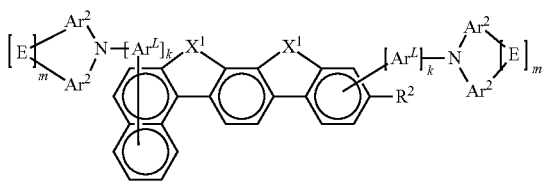

Formula (I-5-D)

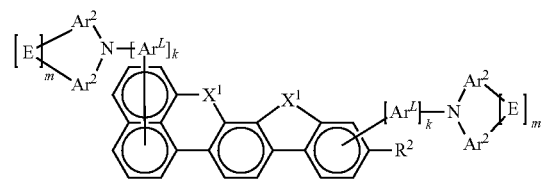

-continued

Formula (I-6-D)

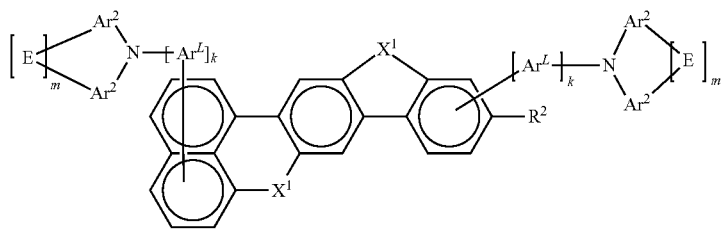

Formula (I-7-D)

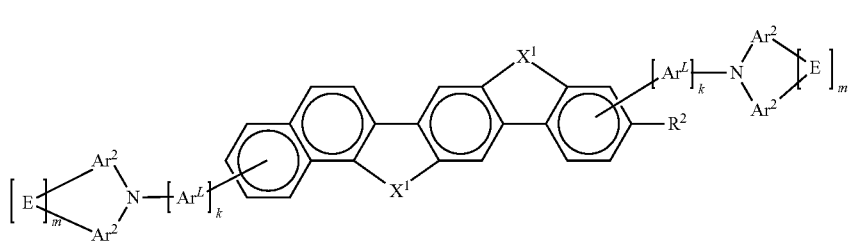

Formula (I-8-D)

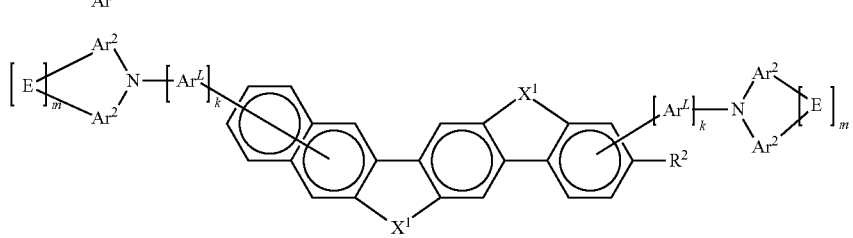

Formula (I-9-D)

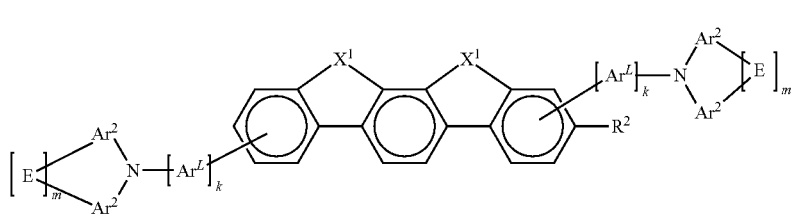

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.

Preferred embodiments of the formula (I-1-D) correspond to the following formulae:

Formula (I-1-D-1)

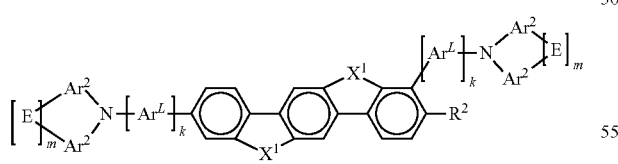

Formula (I-1-D-2)

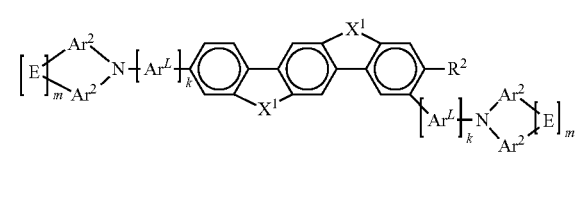

-continued

Formula (I-1-D-3)

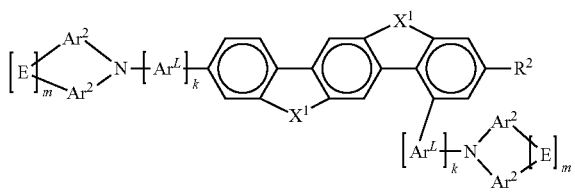

Formula (I-1-D-4)

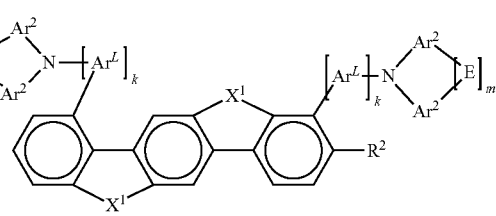

Formula (I-1-D-5)

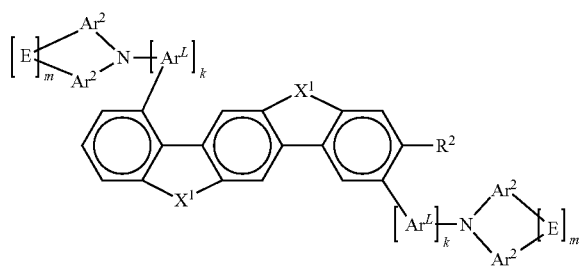

Formula (I-1-D-6)

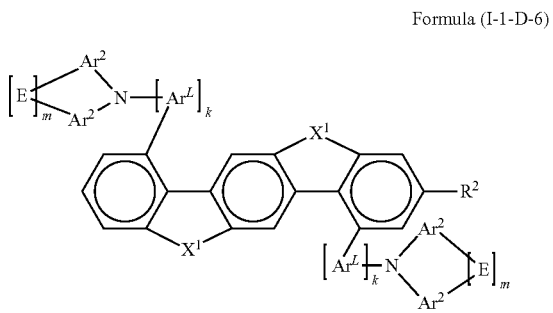

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.

Further preferred embodiments of the compounds of the formulae (I-1) to (I-8) correspond to the following formulae:

Formula (I-1-E)

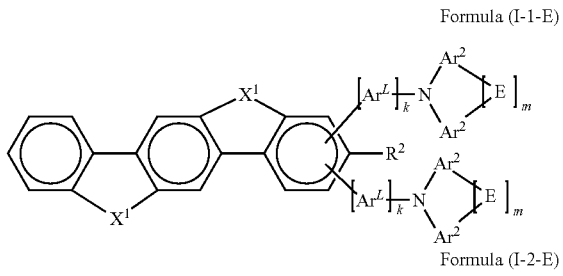

Formula (I-2-E)

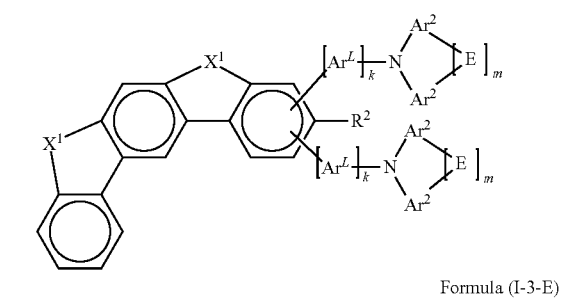

Formula (I-3-E)

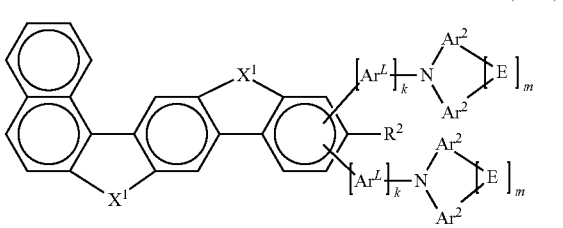

Formula (I-4-E)

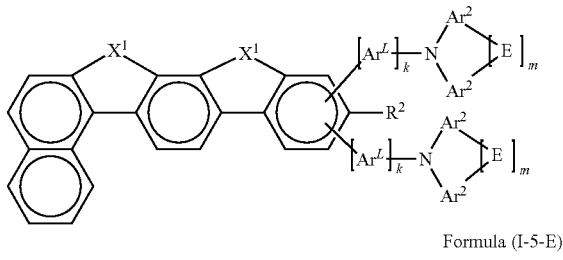

Formula (I-5-E)

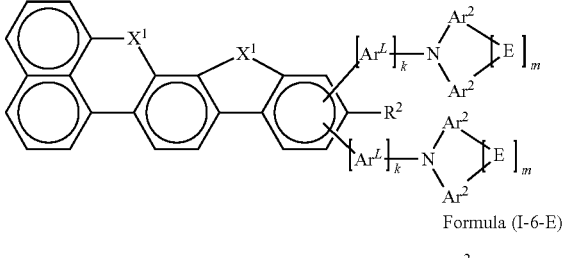

Formula (I-6-E)

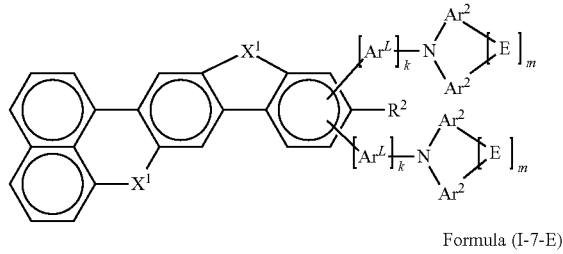

Formula (I-7-E)

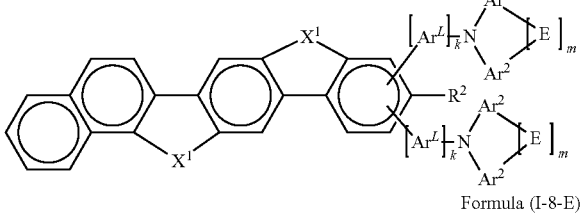

Formula (I-8-E)

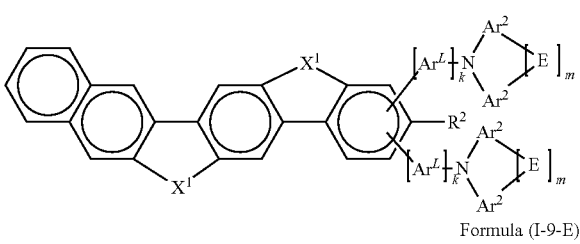

Formula (I-9-E)

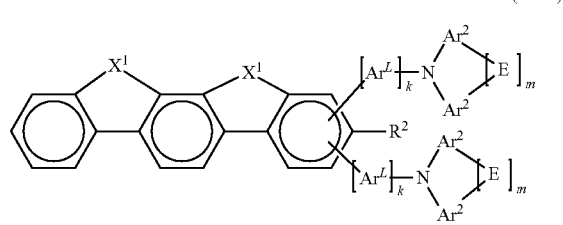

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.

Among these formulae, particular preference is given to the formula (I-1-E).

Preferred embodiments of the formulae (I-1-E) to (I-9-E) conform to the formulae shown below:
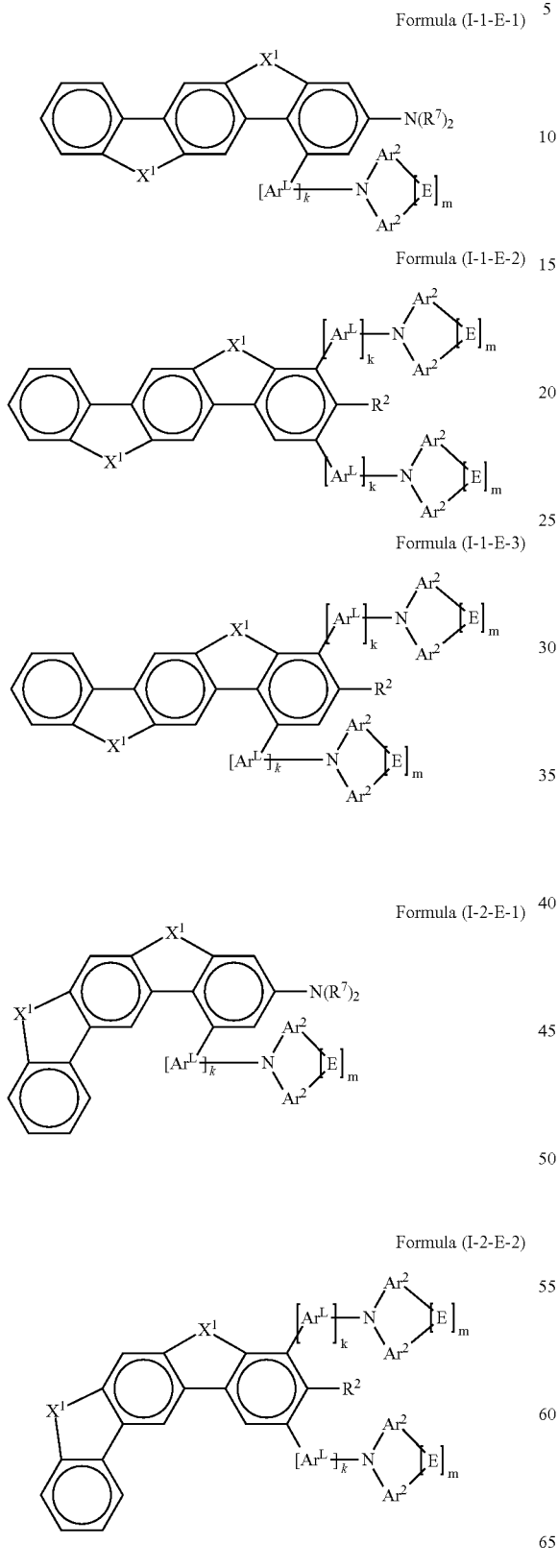
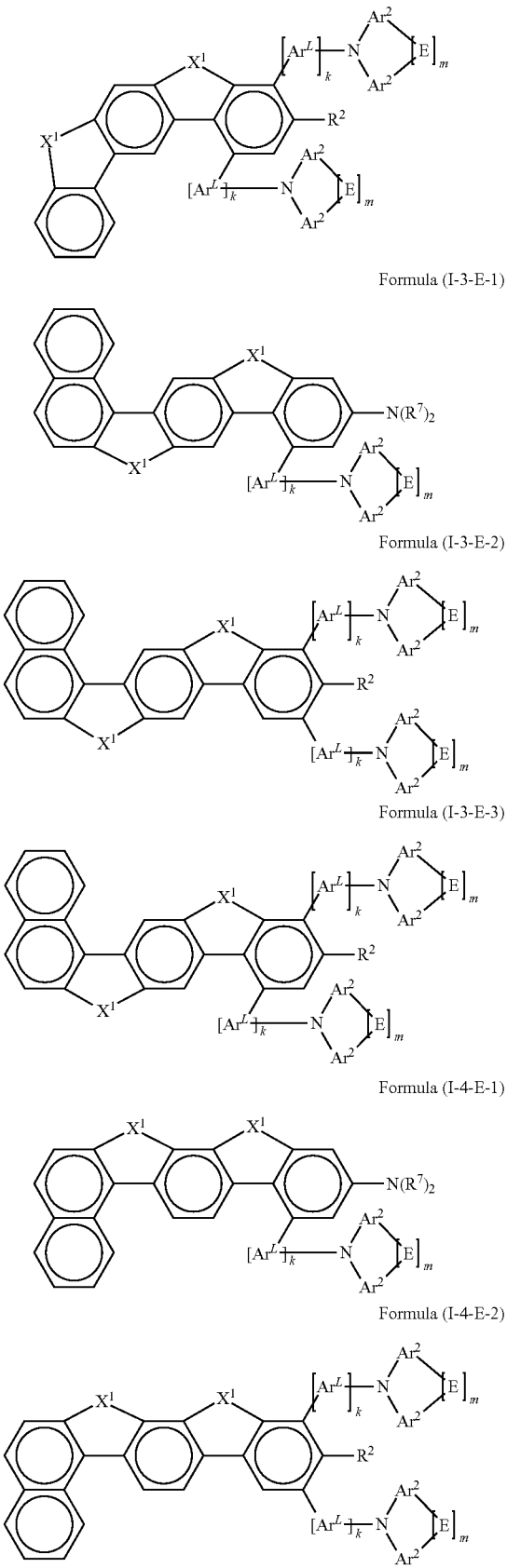

Formula (I-4-E-3)
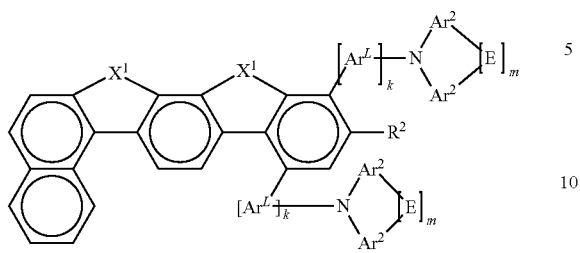
Formula (I-5-E-1)
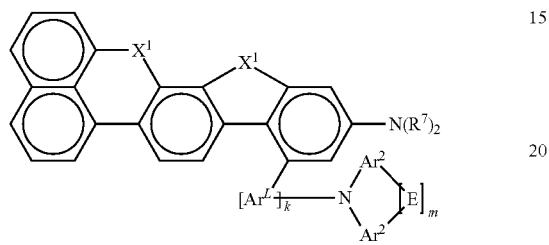
Formula (I-5-E-2)
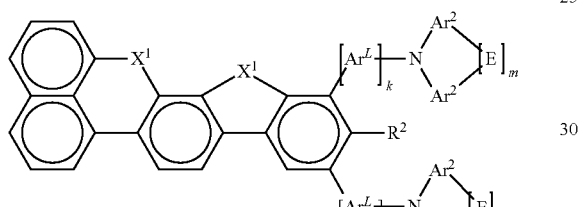
Formula I-5-E-3)
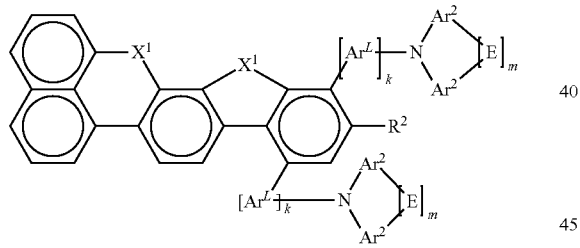
Formula (I-6-E-1)
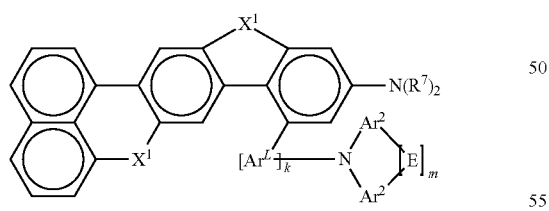
Formula (I-6-E-2)
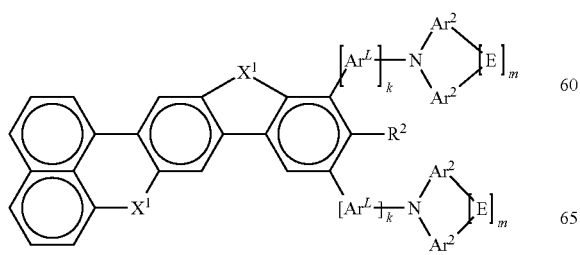
Formula (I-6-E-3)
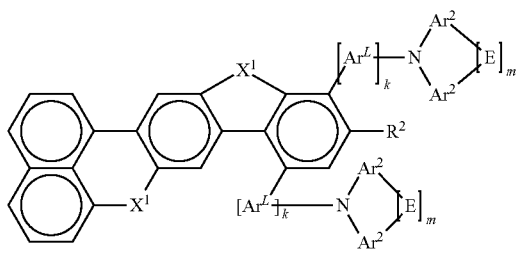
Formula (I-7-E-1)
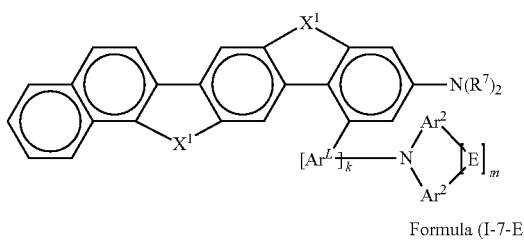
Formula (I-7-E-2)
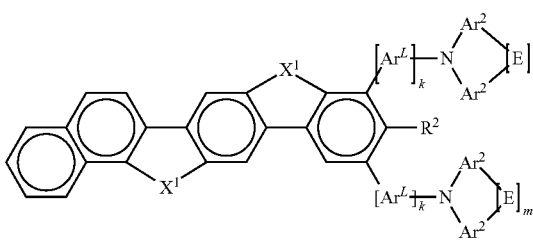
Formula (I-7-E-3)
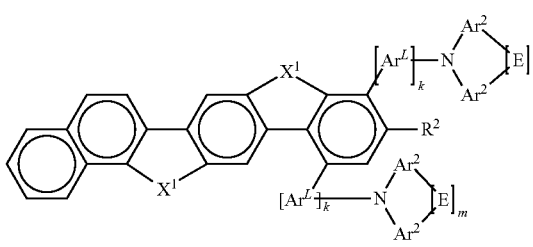
Formula (I-8-E-1)
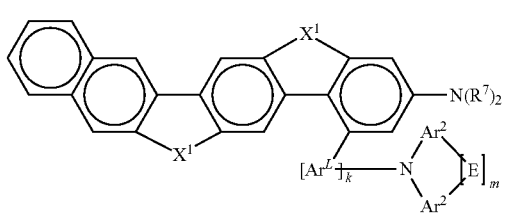
Formula (I-8-E-2)
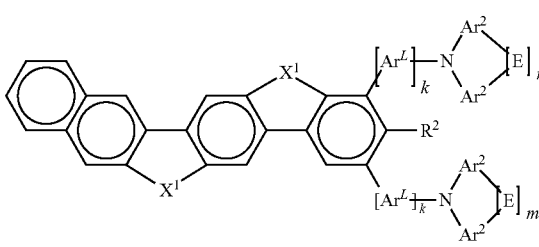

Formula (I-8-E-3)

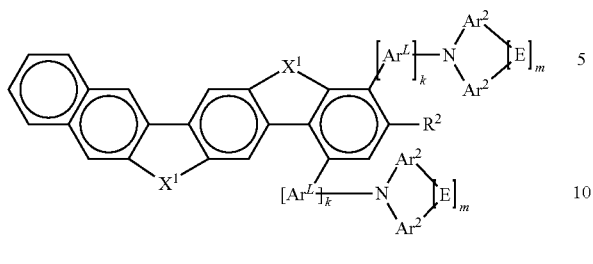

Formula (I-1-A-1)

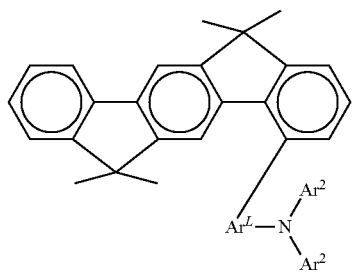

Formula (I-9-E-1)

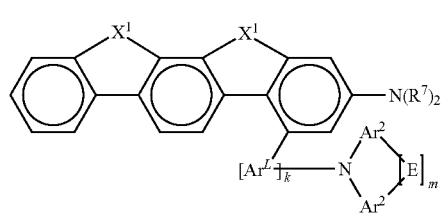

Formula (I-9-E-2)

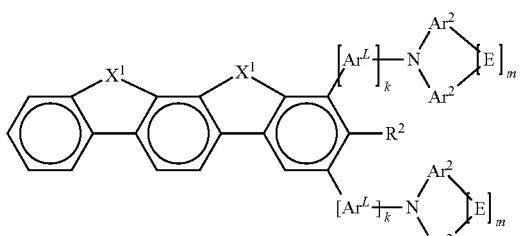

Formula (I-9-E-3)

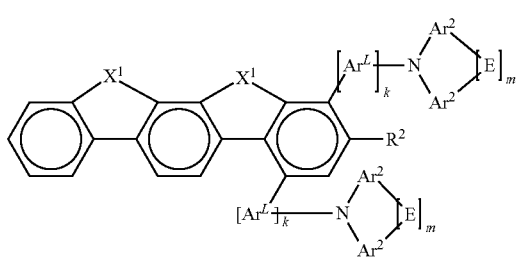

where the variables that occur are as defined above, and $X^1$ is preferably $C(R^4)_2$, and where the compounds may each be substituted at the unoccupied positions on the aromatic rings by an $R^3$ or $R^6$ radical, and are preferably unsubstituted at these positions.

Among these formulae, particular preference is given to the formulae (I-1-E-1), (I-1-E-2) and (I-1-E-3).

For the abovementioned preferred base structures, the abovementioned preferred embodiments of the variables are preferably applicable.

Particularly preferred specific compounds conform to the following formula:

where the variables $Ar^L$ and Are that occur are selected as follows:

| Compound | $Ar^L$ group | One $Ar^2$ group | Other $Ar^2$ group |
|---|---|---|---|
| C-1 | $Ar^L$-1 | Ar-1 | Ar-1 |
| C-2 | " | " | Ar-2 |
| C-3 | " | " | Ar-4 |
| C-4 | " | " | Ar-5 |
| C-5 | " | " | Ar-74 |
| C-6 | " | " | Ar-78 |
| C-7 | " | " | Ar-82 |
| C-8 | " | " | Ar-108 |
| C-9 | " | " | Ar-117 |
| C-10 | " | " | Ar-139 |
| C-11 | " | " | Ar-150 |
| C-12 | " | " | Ar-172 |
| C-13 | " | " | Ar-207 |
| C-14 | " | Ar-2 | Ar-2 |
| C-15 | " | " | Ar-4 |
| C-16 | " | " | Ar-5 |
| C-17 | " | " | Ar-74 |
| C-18 | " | " | Ar-78 |
| C-19 | " | " | Ar-82 |
| C-20 | " | " | Ar-108 |
| C-21 | " | " | Ar-117 |
| C-22 | " | " | Ar-139 |
| C-23 | " | " | Ar-150 |
| C-24 | " | " | Ar-172 |
| C-25 | " | " | Ar-207 |
| C-26 | " | Ar-4 | Ar-4 |
| C-27 | " | " | Ar-5 |
| C-28 | " | " | Ar-74 |
| C-29 | " | " | Ar-78 |
| C-30 | " | " | Ar-82 |
| C-31 | " | " | Ar-108 |
| C-32 | " | " | Ar-117 |
| C-33 | " | " | Ar-139 |
| C-34 | " | " | Ar-150 |
| C-35 | " | " | Ar-172 |
| C-36 | " | " | Ar-207 |
| C-37 | " | Ar-5 | Ar-5 |
| C-38 | " | " | Ar-74 |
| C-39 | " | " | Ar-78 |
| C-40 | " | " | Ar-82 |
| C-41 | " | " | Ar-108 |
| C-42 | " | " | Ar-117 |
| C-43 | " | " | Ar-139 |
| C-44 | " | " | Ar-150 |
| C-45 | " | " | Ar-172 |
| C-46 | " | " | Ar-207 |
| C-47 | " | Ar-74 | Ar-74 |
| C-48 | " | " | Ar-78 |
| C-49 | " | " | Ar-82 |
| C-50 | " | " | Ar-108 |
| C-51 | " | " | Ar-117 |
| C-52 | " | " | Ar-139 |
| C-53 | " | " | Ar-150 |
| C-54 | " | " | Ar-172 |
| C-55 | " | " | Ar-207 |
| C-56 | " | Ar-78 | Ar-78 |
| C-57 | " | " | Ar-82 |
| C-58 | " | " | Ar-108 |

-continued

| Compound | Ar^L group | One Ar^2 group | Other Ar^2 group |
| --- | --- | --- | --- |
| C-59 | " | " | Ar-117 |
| C-60 | " | " | Ar-139 |
| C-61 | " | " | Ar-150 |
| C-62 | " | " | Ar-172 |
| C-63 | " | " | Ar-207 |
| C-64 | " | Ar-82 | Ar-82 |
| C-65 | " | " | Ar-108 |
| C-66 | " | " | Ar-117 |
| C-67 | " | " | Ar-139 |
| C-68 | " | " | Ar-150 |
| C-69 | " | " | Ar-172 |
| C-70 | " | " | Ar-207 |
| C-71 | " | Ar-108 | Ar-108 |
| C-72 | " | " | Ar-117 |
| C-73 | " | " | Ar-139 |
| C-74 | " | " | Ar-150 |
| C-75 | " | " | Ar-172 |
| C-76 | " | " | Ar-207 |
| C-77 | " | Ar-117 | Ar-117 |
| C-78 | " | " | Ar-139 |
| C-79 | " | " | Ar-150 |
| C-80 | " | " | Ar-172 |
| C-81 | " | " | Ar-207 |
| C-82 | " | Ar-139 | Ar-139 |
| C-83 | " | " | Ar-150 |
| C-84 | " | " | Ar-172 |
| C-85 | " | " | Ar-207 |
| C-86 | " | Ar-150 | Ar-150 |
| C-87 | " | " | Ar-172 |
| C-88 | " | " | Ar-207 |
| C-89 | " | Ar-172 | Ar-172 |
| C-90 | " | " | Ar-207 |
| C-91 | " | Ar-207 | Ar-207 |
| C-92 | Ar^L-2 | Ar-1 | Ar-1 |
| C-93 | " | " | Ar-2 |
| C-94 | " | " | Ar-4 |
| C-95 | " | " | Ar-5 |
| C-96 | " | " | Ar-74 |
| C-97 | " | " | Ar-78 |
| C-98 | " | " | Ar-82 |
| C-99 | " | " | Ar-108 |
| C-100 | " | " | Ar-117 |
| C-101 | " | " | Ar-139 |
| C-102 | " | " | Ar-150 |
| C-103 | " | " | Ar-172 |
| C-104 | " | " | Ar-207 |
| C-105 | " | Ar-2 | Ar-2 |
| C-106 | " | " | Ar-4 |
| C-107 | " | " | Ar-5 |
| C-108 | " | " | Ar-74 |
| C-109 | " | " | Ar-78 |
| C-110 | " | " | Ar-82 |
| C-111 | " | " | Ar-108 |
| C-112 | " | " | Ar-117 |
| C-113 | " | " | Ar-139 |
| C-114 | " | " | Ar-150 |
| C-115 | " | " | Ar-172 |
| C-116 | " | " | Ar-207 |
| C-117 | " | Ar-4 | Ar-4 |
| C-118 | " | " | Ar-5 |
| C-119 | " | " | Ar-74 |
| C-120 | " | " | Ar-78 |
| C-121 | " | " | Ar-82 |
| C-122 | " | " | Ar-108 |
| C-123 | " | " | Ar-117 |
| C-124 | " | " | Ar-139 |
| C-125 | " | " | Ar-150 |
| C-126 | " | " | Ar-172 |
| C-127 | " | " | Ar-207 |
| C-128 | " | Ar-5 | Ar-5 |
| C-129 | " | " | Ar-74 |
| C-130 | " | " | Ar-78 |
| C-131 | " | " | Ar-82 |
| C-132 | " | " | Ar-108 |
| C-133 | " | " | Ar-117 |
| C-134 | " | " | Ar-139 |
| C-135 | " | " | Ar-150 |
| C-136 | " | " | Ar-172 |
| C-137 | " | " | Ar-207 |
| C-138 | " | Ar-74 | Ar-74 |
| C-139 | " | " | Ar-78 |
| C-140 | " | " | Ar-82 |
| C-141 | " | " | Ar-108 |
| C-142 | " | " | Ar-117 |
| C-143 | " | " | Ar-139 |
| C-144 | " | " | Ar-150 |
| C-145 | " | " | Ar-172 |
| C-146 | " | " | Ar-207 |
| C-147 | " | Ar-78 | Ar-78 |
| C-148 | " | " | Ar-82 |
| C-149 | " | " | Ar-108 |
| C-150 | " | " | Ar-117 |
| C-151 | " | " | Ar-139 |
| C-152 | " | " | Ar-150 |
| C-153 | " | " | Ar-172 |
| C-154 | " | " | Ar-207 |
| C-155 | " | Ar-82 | Ar-82 |
| C-156 | " | " | Ar-108 |
| C-157 | " | " | Ar-117 |
| C-158 | " | " | Ar-139 |
| C-159 | " | " | Ar-150 |
| C-160 | " | " | Ar-172 |
| C-161 | " | " | Ar-207 |
| C-162 | " | Ar-108 | Ar-108 |
| C-163 | " | " | Ar-117 |
| C-164 | " | " | Ar-139 |
| C-165 | " | " | Ar-150 |
| C-166 | " | " | Ar-172 |
| C-167 | " | " | Ar-207 |
| C-168 | " | Ar-117 | Ar-117 |
| C-169 | " | " | Ar-139 |
| C-170 | " | " | Ar-150 |
| C-171 | " | " | Ar-172 |
| C-172 | " | " | Ar-207 |
| C-173 | " | Ar-139 | Ar-139 |
| C-174 | " | " | Ar-150 |
| C-175 | " | " | Ar-172 |
| C-176 | " | " | Ar-207 |
| C-177 | " | Ar-150 | Ar-150 |
| C-178 | " | " | Ar-172 |
| C-179 | " | " | Ar-207 |
| C-180 | " | Ar-172 | Ar-172 |
| C-181 | " | " | Ar-207 |
| C-182 | " | Ar-207 | Ar-207 |
| C-183 | Ar^L-3 | Ar-1 | Ar-1 |
| C-184 | " | " | Ar-2 |
| C-185 | " | " | Ar-4 |
| C-186 | " | " | Ar-5 |
| C-187 | " | " | Ar-74 |
| C-188 | " | " | Ar-78 |
| C-189 | " | " | Ar-82 |
| C-190 | " | " | Ar-108 |
| C-191 | " | " | Ar-117 |
| C-192 | " | " | Ar-139 |
| C-193 | " | " | Ar-150 |
| C-194 | " | " | Ar-172 |
| C-195 | " | " | Ar-207 |
| C-196 | " | Ar-2 | Ar-2 |
| C-197 | " | " | Ar-4 |
| C-198 | " | " | Ar-5 |
| C-199 | " | " | Ar-74 |
| C-200 | " | " | Ar-78 |
| C-201 | " | " | Ar-82 |
| C-202 | " | " | Ar-108 |
| C-203 | " | " | Ar-117 |
| C-204 | " | " | Ar-139 |
| C-205 | " | " | Ar-150 |
| C-206 | " | " | Ar-172 |
| C-207 | " | " | Ar-207 |
| C-208 | " | Ar-4 | Ar-4 |
| C-209 | " | " | Ar-5 |
| C-210 | " | " | Ar-74 |
| C-211 | " | " | Ar-78 |
| C-212 | " | " | Ar-82 |

| Compound | Ar$^L$ group | One Ar$^2$ group | Other Ar$^2$ group |
|---|---|---|---|
| C-213 | " | " | Ar-108 |
| C-214 | " | " | Ar-117 |
| C-215 | " | " | Ar-139 |
| C-216 | " | " | Ar-150 |
| C-217 | " | " | Ar-172 |
| C-218 | " | " | Ar-207 |
| C-219 | " | Ar-5 | Ar-5 |
| C-220 | " | " | Ar-74 |
| C-221 | " | " | Ar-78 |
| C-222 | " | " | Ar-82 |
| C-223 | " | " | Ar-108 |
| C-224 | " | " | Ar-117 |
| C-225 | " | " | Ar-139 |
| C-226 | " | " | Ar-150 |
| C-227 | " | " | Ar-172 |
| C-228 | " | " | Ar-207 |
| C-229 | " | Ar-74 | Ar-74 |
| C-230 | " | " | Ar-78 |
| C-231 | " | " | Ar-82 |
| C-232 | " | " | Ar-108 |
| C-233 | " | " | Ar-117 |
| C-234 | " | " | Ar-139 |
| C-235 | " | " | Ar-150 |
| C-236 | " | " | Ar-172 |
| C-237 | " | " | Ar-207 |
| C-238 | " | Ar-78 | Ar-78 |
| C-239 | " | " | Ar-82 |
| C-240 | " | " | Ar-108 |
| C-241 | " | " | Ar-117 |
| C-242 | " | " | Ar-139 |
| C-243 | " | " | Ar-150 |
| C-244 | " | " | Ar-172 |
| C-245 | " | " | Ar-207 |
| C-246 | " | Ar-82 | Ar-82 |
| C-247 | " | " | Ar-108 |
| C-248 | " | " | Ar-117 |
| C-249 | " | " | Ar-139 |
| C-250 | " | " | Ar-150 |
| C-251 | " | " | Ar-172 |
| C-252 | " | " | Ar-207 |
| C-253 | " | Ar-108 | Ar-108 |
| C-254 | " | " | Ar-117 |
| C-255 | " | " | Ar-139 |
| C-256 | " | " | Ar-150 |
| C-257 | " | " | Ar-172 |
| C-258 | " | " | Ar-207 |
| C-259 | " | Ar-117 | Ar-117 |
| C-260 | " | " | Ar-139 |
| C-261 | " | " | Ar-150 |
| C-262 | " | " | Ar-172 |
| C-263 | " | " | Ar-207 |
| C-264 | " | Ar-139 | Ar-139 |
| C-265 | " | " | Ar-150 |
| C-266 | " | " | Ar-172 |
| C-267 | " | " | Ar-207 |
| C-268 | " | Ar-150 | Ar-150 |
| C-269 | " | " | Ar-172 |
| C-270 | " | " | Ar-207 |
| C-271 | " | Ar-172 | Ar-172 |
| C-272 | " | " | Ar-207 |
| C-273 | " | Ar-207 | Ar-207 |
| C-274 | Ar$^L$-4 | Ar-1 | Ar-1 |
| C-275 | " | " | Ar-2 |
| C-276 | " | " | Ar-4 |
| C-277 | " | " | Ar-5 |
| C-278 | " | " | Ar-74 |
| C-279 | " | " | Ar-78 |
| C-280 | " | " | Ar-82 |
| C-281 | " | " | Ar-108 |
| C-282 | " | " | Ar-117 |
| C-283 | " | " | Ar-139 |
| C-284 | " | " | Ar-150 |
| C-285 | " | " | Ar-172 |
| C-286 | " | " | Ar-207 |
| C-287 | " | Ar-2 | Ar-2 |
| C-288 | " | " | Ar-4 |
| C-289 | " | " | Ar-5 |
| C-290 | " | " | Ar-74 |
| C-291 | " | " | Ar-78 |
| C-292 | " | " | Ar-82 |
| C-293 | " | " | Ar-108 |
| C-294 | " | " | Ar-117 |
| C-295 | " | " | Ar-139 |
| C-296 | " | " | Ar-150 |
| C-297 | " | " | Ar-172 |
| C-298 | " | " | Ar-207 |
| C-299 | " | Ar-4 | Ar-4 |
| C-300 | " | " | Ar-5 |
| C-301 | " | " | Ar-74 |
| C-302 | " | " | Ar-78 |
| C-303 | " | " | Ar-82 |
| C-304 | " | " | Ar-108 |
| C-305 | " | " | Ar-117 |
| C-306 | " | " | Ar-139 |
| C-307 | " | " | Ar-150 |
| C-308 | " | " | Ar-172 |
| C-309 | " | " | Ar-207 |
| C-310 | " | Ar-5 | Ar-5 |
| C-311 | " | " | Ar-74 |
| C-312 | " | " | Ar-78 |
| C-313 | " | " | Ar-82 |
| C-314 | " | " | Ar-108 |
| C-315 | " | " | Ar-117 |
| C-316 | " | " | Ar-139 |
| C-317 | " | " | Ar-150 |
| C-318 | " | " | Ar-172 |
| C-319 | " | " | Ar-207 |
| C-320 | " | Ar-74 | Ar-74 |
| C-321 | " | " | Ar-78 |
| C-322 | " | " | Ar-82 |
| C-323 | " | " | Ar-108 |
| C-324 | " | " | Ar-117 |
| C-325 | " | " | Ar-139 |
| C-326 | " | " | Ar-150 |
| C-327 | " | " | Ar-172 |
| C-328 | " | " | Ar-207 |
| C-329 | " | Ar-78 | Ar-78 |
| C-330 | " | " | Ar-82 |
| C-331 | " | " | Ar-108 |
| C-332 | " | " | Ar-117 |
| C-333 | " | " | Ar-139 |
| C-334 | " | " | Ar-150 |
| C-335 | " | " | Ar-172 |
| C-336 | " | " | Ar-207 |
| C-337 | " | Ar-82 | Ar-82 |
| C-338 | " | " | Ar-108 |
| C-339 | " | " | Ar-117 |
| C-340 | " | " | Ar-139 |
| C-341 | " | " | Ar-150 |
| C-342 | " | " | Ar-172 |
| C-343 | " | " | Ar-207 |
| C-344 | " | Ar-108 | Ar-108 |
| C-345 | " | " | Ar-117 |
| C-346 | " | " | Ar-139 |
| C-347 | " | " | Ar-150 |
| C-348 | " | " | Ar-172 |
| C-349 | " | " | Ar-207 |
| C-350 | " | Ar-117 | Ar-117 |
| C-351 | " | " | Ar-139 |
| C-352 | " | " | Ar-150 |
| C-353 | " | " | Ar-172 |
| C-354 | " | " | Ar-207 |
| C-355 | " | Ar-139 | Ar-139 |
| C-356 | " | " | Ar-150 |
| C-357 | " | " | Ar-172 |
| C-358 | " | " | Ar-207 |
| C-359 | " | Ar-150 | Ar-150 |
| C-360 | " | " | Ar-172 |
| C-361 | " | " | Ar-207 |
| C-362 | " | Ar-172 | Ar-172 |
| C-363 | " | " | Ar-207 |
| C-364 | " | Ar-207 | Ar-207 |
| C-365 | Ar$^L$-7 | Ar-1 | Ar-1 |
| C-366 | " | " | Ar-2 |

-continued

| Compound | Ar$^L$ group | One Ar$^2$ group | Other Ar$^2$ group |
|---|---|---|---|
| C-367 | " | " | Ar-4 |
| C-368 | " | " | Ar-5 |
| C-369 | " | " | Ar-74 |
| C-370 | " | " | Ar-78 |
| C-371 | " | " | Ar-82 |
| C-372 | " | " | Ar-108 |
| C-373 | " | " | Ar-117 |
| C-374 | " | " | Ar-139 |
| C-375 | " | " | Ar-150 |
| C-376 | " | " | Ar-172 |
| C-377 | " | " | Ar-207 |
| C-378 | " | Ar-2 | Ar-2 |
| C-379 | " | " | Ar-4 |
| C-380 | " | " | Ar-5 |
| C-381 | " | " | Ar-74 |
| C-382 | " | " | Ar-78 |
| C-383 | " | " | Ar-82 |
| C-384 | " | " | Ar-108 |
| C-385 | " | " | Ar-117 |
| C-386 | " | " | Ar-139 |
| C-387 | " | " | Ar-150 |
| C-388 | " | " | Ar-172 |
| C-389 | " | " | Ar-207 |
| C-390 | " | Ar-4 | Ar-4 |
| C-391 | " | " | Ar-5 |
| C-392 | " | " | Ar-74 |
| C-393 | " | " | Ar-78 |
| C-394 | " | " | Ar-82 |
| C-395 | " | " | Ar-108 |
| C-396 | " | " | Ar-117 |
| C-397 | " | " | Ar-139 |
| C-398 | " | " | Ar-150 |
| C-399 | " | " | Ar-172 |
| C-400 | " | " | Ar-207 |
| C-401 | " | Ar-5 | Ar-5 |
| C-402 | " | " | Ar-74 |
| C-403 | " | " | Ar-78 |
| C-404 | " | " | Ar-82 |
| C-405 | " | " | Ar-108 |
| C-406 | " | " | Ar-117 |
| C-407 | " | " | Ar-139 |
| C-408 | " | " | Ar-150 |
| C-409 | " | " | Ar-172 |
| C-410 | " | " | Ar-207 |
| C-411 | " | Ar-74 | Ar-74 |
| C-412 | " | " | Ar-78 |
| C-413 | " | " | Ar-82 |
| C-414 | " | " | Ar-108 |
| C-415 | " | " | Ar-117 |
| C-416 | " | " | Ar-139 |
| C-417 | " | " | Ar-150 |
| C-418 | " | " | Ar-172 |
| C-419 | " | " | Ar-207 |
| C-420 | " | Ar-78 | Ar-78 |
| C-421 | " | " | Ar-82 |
| C-422 | " | " | Ar-108 |
| C-423 | " | " | Ar-117 |
| C-424 | " | " | Ar-139 |
| C-425 | " | " | Ar-150 |
| C-426 | " | " | Ar-172 |
| C-427 | " | " | Ar-207 |
| C-428 | " | Ar-82 | A-82 |
| C-429 | " | " | Ar-108 |
| C-430 | " | " | Ar-117 |
| C-431 | " | " | Ar-139 |
| C-432 | " | " | Ar-150 |
| C-433 | " | " | Ar-172 |
| C-434 | " | " | Ar-207 |
| C-435 | " | Ar-108 | Ar-108 |
| C-436 | " | " | Ar-117 |
| C-437 | " | " | Ar-139 |
| C-438 | " | " | Ar-150 |
| C-439 | " | " | Ar-172 |
| C-440 | " | " | Ar-207 |
| C-441 | " | Ar-117 | Ar-117 |
| C-442 | " | " | Ar-139 |
| C-443 | " | " | Ar-150 |
| C-444 | " | " | Ar-172 |
| C-445 | " | " | Ar-207 |
| C-446 | " | Ar-139 | Ar-139 |
| C-447 | " | " | Ar-150 |
| C-448 | " | " | Ar-172 |
| C-449 | " | " | Ar-207 |
| C-450 | " | Ar-150 | Ar-150 |
| C-451 | " | " | Ar-172 |
| C-452 | " | " | Ar-207 |
| C-453 | " | Ar-172 | Ar-172 |
| C-454 | " | " | Ar-207 |
| C-455 | " | Ar-207 | Ar-207 |
| C-456 | Ar$^L$-19 | Ar-1 | Ar-1 |
| C-457 | " | " | Ar-2 |
| C-458 | " | " | Ar-4 |
| C-459 | " | " | Ar-5 |
| C-460 | " | " | Ar-74 |
| C-461 | " | " | Ar-78 |
| C-462 | " | " | Ar-82 |
| C-463 | " | " | Ar-108 |
| C-464 | " | " | Ar-117 |
| C-465 | " | " | Ar-139 |
| C-466 | " | " | Ar-150 |
| C-467 | " | " | Ar-172 |
| C-468 | " | " | Ar-207 |
| C-469 | " | Ar-2 | Ar-2 |
| C-470 | " | " | Ar-4 |
| C-471 | " | " | Ar-5 |
| C-472 | " | " | Ar-74 |
| C-473 | " | " | Ar-78 |
| C-474 | " | " | Ar-82 |
| C-475 | " | " | Ar-108 |
| C-476 | " | " | Ar-117 |
| C-477 | " | " | Ar-139 |
| C-478 | " | " | Ar-150 |
| C-479 | " | " | Ar-172 |
| C-480 | " | " | Ar-207 |
| C-481 | " | Ar-4 | Ar-4 |
| C-482 | " | " | Ar-5 |
| C-483 | " | " | Ar-74 |
| C-484 | " | " | Ar-78 |
| C-485 | " | " | Ar-82 |
| C-486 | " | " | Ar-108 |
| C-487 | " | " | Ar-117 |
| C-488 | " | " | Ar-139 |
| C-489 | " | " | Ar-150 |
| C-490 | " | " | Ar-172 |
| C-491 | " | " | Ar-207 |
| C-492 | " | Ar-5 | Ar-5 |
| C-493 | " | " | Ar-74 |
| C-494 | " | " | Ar-78 |
| C-495 | " | " | Ar-82 |
| C-496 | " | " | Ar-108 |
| C-497 | " | " | Ar-117 |
| C-498 | " | " | Ar-139 |
| C-499 | " | " | Ar-150 |
| C-500 | " | " | Ar-172 |
| C-501 | " | " | Ar-207 |
| C-502 | " | Ar-74 | Ar-74 |
| C-503 | " | " | Ar-78 |
| C-504 | " | " | Ar-82 |
| C-505 | " | " | Ar-108 |
| C-506 | " | " | Ar-117 |
| C-507 | " | " | Ar-139 |
| C-508 | " | " | Ar-150 |
| C-509 | " | " | Ar-172 |
| C-510 | " | " | Ar-207 |
| C-511 | " | Ar-78 | Ar-78 |
| C-512 | " | " | Ar-82 |
| C-513 | " | " | Ar-108 |
| C-514 | " | " | Ar-117 |
| C-515 | " | " | Ar-139 |
| C-516 | " | " | Ar-150 |
| C-517 | " | " | Ar-172 |
| C-518 | " | " | Ar-207 |
| C-519 | " | Ar-82 | Ar-82 |
| C-520 | " | " | Ar-108 |

-continued

| Compound | Ar$^L$ group | One Ar$^2$ group | Other Ar$^2$ group |
|---|---|---|---|
| C-521 | " | " | Ar-117 |
| C-522 | " | " | Ar-139 |
| C-523 | " | " | Ar-150 |
| C-524 | " | " | Ar-172 |
| C-525 | " | " | Ar-207 |
| C-526 | " | Ar-108 | Ar-108 |
| C-527 | " | " | Ar-117 |
| C-528 | " | " | Ar-139 |
| C-529 | " | " | Ar-150 |
| C-530 | " | " | Ar-172 |
| C-531 | " | " | Ar-207 |
| C-532 | " | Ar-117 | Ar-117 |
| C-533 | " | " | Ar-139 |
| C-534 | " | " | Ar-150 |
| C-535 | " | " | Ar-172 |
| C-536 | " | " | Ar-207 |
| C-537 | " | Ar-139 | Ar-139 |
| C-538 | " | " | Ar-150 |
| C-539 | " | " | Ar-172 |
| C-540 | " | " | Ar-207 |
| C-541 | " | Ar-150 | Ar-150 |
| C-542 | " | " | Ar-172 |
| C-543 | " | " | Ar-207 |
| C-544 | " | Ar-172 | Ar-172 |
| C-545 | " | " | Ar-207 |
| C-546 | " | Ar-207 | Ar-207 |
| C-547 | Ar$^L$-36 | Ar-1 | Ar-1 |
| C-548 | " | " | Ar-2 |
| C-549 | " | " | Ar-4 |
| C-550 | " | " | Ar-5 |
| C-551 | " | " | Ar-74 |
| C-552 | " | " | Ar-78 |
| C-553 | " | " | Ar-82 |
| C-554 | " | " | Ar-108 |
| C-555 | " | " | Ar-117 |
| C-556 | " | " | Ar-139 |
| C-557 | " | " | Ar-150 |
| C-558 | " | " | Ar-172 |
| C-559 | " | " | Ar-207 |
| C-560 | " | Ar-2 | Ar-2 |
| C-561 | " | " | Ar-4 |
| C-562 | " | " | Ar-5 |
| C-563 | " | " | Ar-74 |
| C-564 | " | " | Ar-78 |
| C-565 | " | " | Ar-82 |
| C-566 | " | " | Ar-108 |
| C-567 | " | " | Ar-117 |
| C-568 | " | " | Ar-139 |
| C-569 | " | " | Ar-150 |
| C-570 | " | " | Ar-172 |
| C-571 | " | " | Ar-207 |
| C-572 | " | Ar-4 | Ar-4 |
| C-573 | " | " | Ar-5 |
| C-574 | " | " | Ar-74 |
| C-575 | " | " | Ar-78 |
| C-576 | " | " | Ar-82 |
| C-577 | " | " | Ar-108 |
| C-578 | " | " | Ar-117 |
| C-579 | " | " | Ar-139 |
| C-580 | " | " | Ar-150 |
| C-581 | " | " | Ar-172 |
| C-582 | " | " | Ar-207 |
| C-583 | " | Ar-5 | Ar-5 |
| C-584 | " | " | Ar-74 |
| C-585 | " | " | Ar-78 |
| C-586 | " | " | Ar-82 |
| C-587 | " | " | Ar-108 |
| C-588 | " | " | Ar-117 |
| C-589 | " | " | Ar-139 |
| C-590 | " | " | Ar-150 |
| C-591 | " | " | Ar-172 |
| C-592 | " | " | Ar-207 |
| C-593 | " | Ar-74 | Ar-74 |
| C-594 | " | " | Ar-78 |
| C-595 | " | " | Ar-82 |
| C-596 | " | " | Ar-108 |
| C-597 | " | " | Ar-117 |

-continued

| Compound | Ar$^L$ group | One Ar$^2$ group | Other Ar$^2$ group |
|---|---|---|---|
| C-598 | " | " | Ar-139 |
| C-599 | " | " | Ar-150 |
| C-600 | " | " | Ar-172 |
| C-601 | " | " | Ar-207 |
| C-602 | " | Ar-78 | Ar-78 |
| C-603 | " | " | Ar-82 |
| C-604 | " | " | Ar-108 |
| C-605 | " | " | Ar-117 |
| C-606 | " | " | Ar-139 |
| C-607 | " | " | Ar-150 |
| C-608 | " | " | Ar-172 |
| C-609 | " | " | Ar-207 |
| C-610 | " | Ar-82 | Ar-82 |
| C-611 | " | " | Ar-108 |
| C-612 | " | " | Ar-117 |
| C-613 | " | " | Ar-139 |
| C-614 | " | " | Ar-150 |
| C-615 | " | " | Ar-172 |
| C-616 | " | " | Ar-207 |
| C-617 | " | Ar-108 | Ar-108 |
| C-618 | " | " | Ar-117 |
| C-619 | " | " | Ar-139 |
| C-620 | " | " | Ar-150 |
| C-621 | " | " | Ar-172 |
| C-622 | " | " | Ar-207 |
| C-623 | " | Ar-117 | Ar-117 |
| C-624 | " | " | Ar-139 |
| C-625 | " | " | Ar-150 |
| C-626 | " | " | Ar-172 |
| C-627 | " | " | Ar-207 |
| C-628 | " | Ar-139 | Ar-139 |
| C-629 | " | " | Ar-150 |
| C-630 | " | " | Ar-172 |
| C-631 | " | " | Ar-207 |
| C-632 | " | Ar-150 | Ar-150 |
| C-633 | " | " | Ar-172 |
| C-634 | " | " | Ar-207 |
| C-635 | " | Ar-172 | Ar-172 |
| C-636 | " | " | Ar-207 |
| C-637 | " | Ar-207 | Ar-207 |

Further particularly preferred specific compounds conform to the following formula:

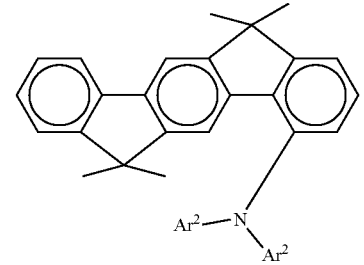

Formula (I-1-A-2)

where the variables Are that occur are selected as follows:

| Compound | One Ar$^2$ group | Other Ar$^2$ group |
|---|---|---|
| C-638 | Ar-1 | Ar-1 |
| C-639 | " | Ar-2 |
| C-640 | " | Ar-4 |
| C-641 | " | Ar-5 |
| C-642 | " | Ar-74 |
| C-643 | " | Ar-78 |
| C-644 | " | Ar-82 |
| C-645 | " | Ar-108 |
| C-646 | " | Ar-117 |
| C-647 | " | Ar-139 |

| Compound | One Ar² group | Other Ar² group |
|---|---|---|
| C-648 | " | Ar-150 |
| C-649 | " | Ar-172 |
| C-650 | " | Ar-207 |
| C-651 | Ar-2 | Ar-2 |
| C-652 | " | Ar-4 |
| C-653 | " | Ar-5 |
| C-654 | " | Ar-74 |
| C-655 | " | Ar-78 |
| C-656 | " | Ar-82 |
| C-657 | " | Ar-108 |
| C-658 | " | Ar-117 |
| C-659 | " | Ar-139 |
| C-660 | " | Ar-150 |
| C-661 | " | Ar-172 |
| C-662 | " | Ar-207 |
| C-663 | Ar-4 | Ar-4 |
| C-664 | " | Ar-5 |
| C-665 | " | Ar-74 |
| C-666 | " | Ar-78 |
| C-667 | " | Ar-82 |
| C-668 | " | Ar-108 |
| C-669 | " | Ar-117 |
| C-670 | " | Ar-139 |
| C-671 | " | Ar-150 |
| C-672 | " | Ar-172 |
| C-673 | " | Ar-207 |
| C-674 | Ar-5 | Ar-5 |
| C-675 | " | Ar-74 |
| C-676 | " | Ar-78 |
| C-677 | " | Ar-82 |
| C-678 | " | Ar-108 |
| C-679 | " | Ar-117 |
| C-680 | " | Ar-139 |
| C-681 | " | Ar-150 |
| C-682 | " | Ar-172 |
| C-683 | " | Ar-207 |
| C-684 | Ar-74 | Ar-74 |
| C-685 | " | Ar-78 |
| C-686 | " | Ar-82 |
| C-687 | " | Ar-108 |
| C-688 | " | Ar-117 |
| C-689 | " | Ar-139 |
| C-690 | " | Ar-150 |
| C 691 | " | Ar-172 |
| C-692 | " | Ar-207 |
| C-693 | Ar-78 | Ar-78 |
| C-694 | " | Ar-82 |
| C-695 | " | Ar-108 |
| C-696 | " | Ar-117 |
| C-697 | " | Ar-139 |
| C-698 | " | Ar-150 |
| C-699 | " | Ar-172 |
| C-700 | " | Ar-207 |
| C-701 | Ar-82 | Ar-82 |
| C-702 | " | Ar-108 |
| C-703 | " | Ar-117 |
| C-704 | " | Ar-139 |
| C-705 | " | Ar-150 |
| C-706 | " | Ar-172 |
| C-707 | " | Ar-207 |
| C-708 | Ar-108 | Ar-108 |
| C-709 | " | Ar-117 |
| C-710 | " | Ar-139 |
| C-711 | " | Ar-150 |
| C-712 | " | Ar-172 |
| C-713 | " | Ar-207 |
| C-714 | Ar-117 | Ar-117 |
| C-715 | " | Ar-139 |
| C-716 | " | Ar-150 |
| C-717 | " | Ar-172 |
| C-718 | " | Ar-207 |
| C-719 | Ar-139 | Ar-139 |
| C-720 | " | Ar-150 |
| C-721 | " | Ar-172 |
| C-722 | " | Ar-207 |
| C-723 | Ar-150 | Ar-150 |
| C-724 | " | Ar-172 |
| C-725 | " | Ar-207 |
| C-726 | Ar-172 | Ar-172 |
| C-727 | " | Ar-207 |
| C-728 | Ar-207 | Ar-207 |

Further particularly preferred specific compounds conform to the following formula:

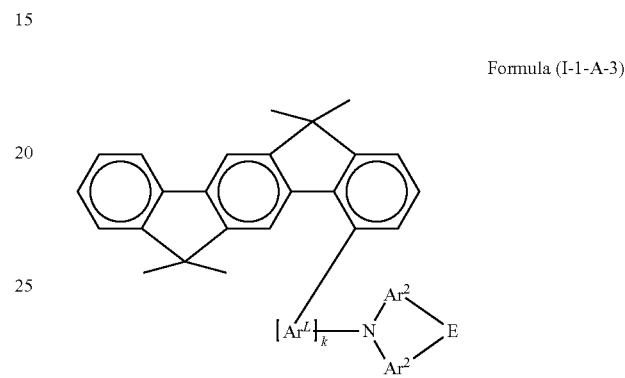

Formula (I-1-A-3)

where the variable k that occurs, the $Ar^L$ group and the unit

are selected as follows:

| Compound | k | $Ar^L$ | Unit |
|---|---|---|---|
| C-729 | 0 | — | N-17 |
| C-730 | 0 | — | N-20 |
| C-731 | 1 | $Ar^L$-1 | N-17 |
| C-732 | 1 | $Ar^L$-1 | N-20 |
| C-733 | 1 | $Ar^L$-2 | N-17 |
| C-734 | 1 | $Ar^L$-2 | N-20 |
| C-735 | 1 | $Ar^L$-3 | N-17 |
| C-736 | 1 | $Ar^L$-3 | N-20 |
| C-737 | 1 | $Ar^L$-4 | N-17 |
| C-738 | 1 | $Ar^L$-4 | N-20 |
| C-739 | 1 | $Ar^L$-7 | N-17 |
| C-740 | 1 | $Ar^L$-7 | N-20 |
| C-741 | 1 | $Ar^L$-19 | N-17 |
| C-742 | 1 | $Ar^L$-19 | N-20 |
| C-743 | 1 | $Ar^L$-36 | N-17 |
| C-744 | 1 | $Ar^L$-36 | N-20 |

Preferred specific compounds of formula (I) are depicted in the following table:

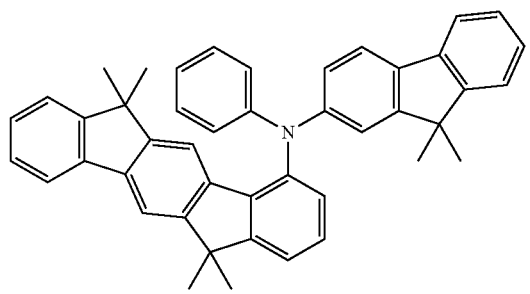 [SMILES: CC1(C)c2ccccc2-c2ccc(N(c3ccccc3)c3cccc4c3-c3cc5c(cc3C4(C)C)-c3ccccc3C5(C)C)cc21]
(1)
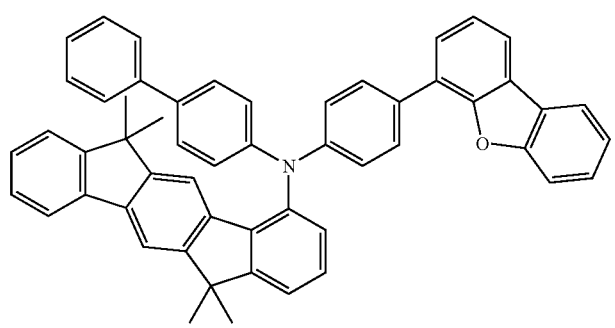 [SMILES: CC1(C)c2ccccc2-c2cc3c(cc21)-c1c(N(c2ccc(-c4ccccc4)cc2)c2ccc(-c4cccc5c4oc4ccccc45)cc2)cccc1C3(C)C]
(2)
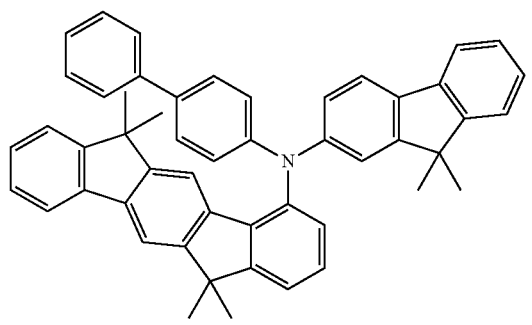 [SMILES: CC1(C)c2ccccc2-c2ccc(N(c3ccc(-c4ccccc4)cc3)c3cccc4c3-c3cc5c(cc3C4(C)C)-c3ccccc3C5(C)C)cc21]
(3)
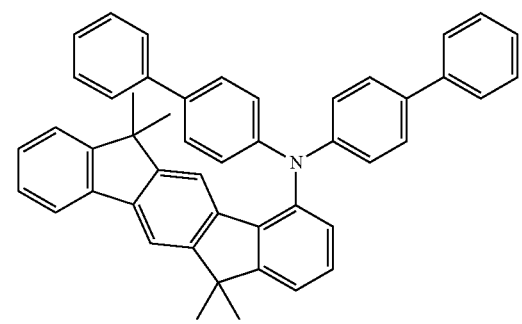 [SMILES: CC1(C)c2ccccc2-c2cc3c(cc21)-c1c(N(c2ccc(-c4ccccc4)cc2)c2ccc(-c4ccccc4)cc2)cccc1C3(C)C]
(4)

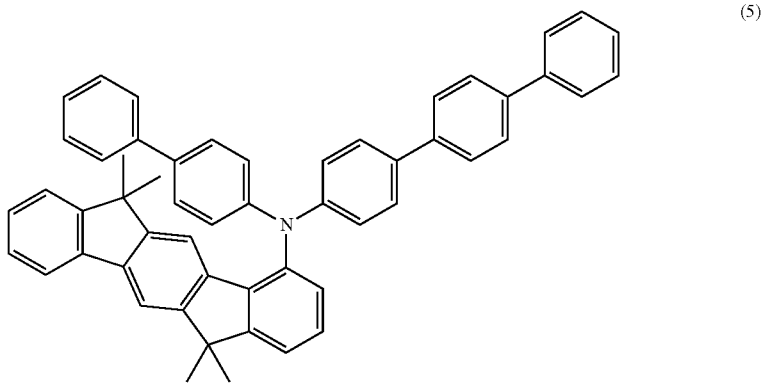
(5)
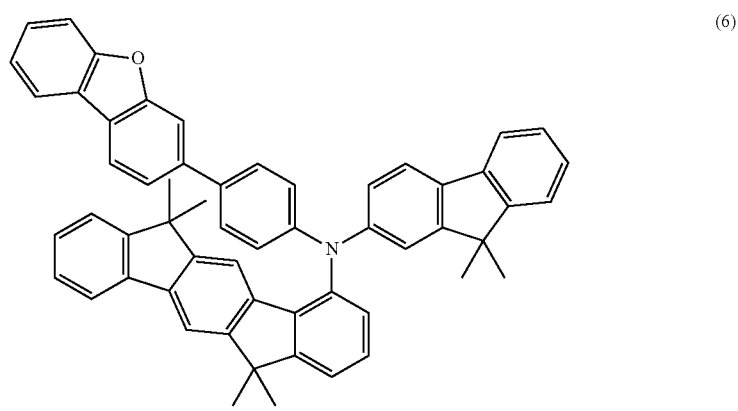
(6)
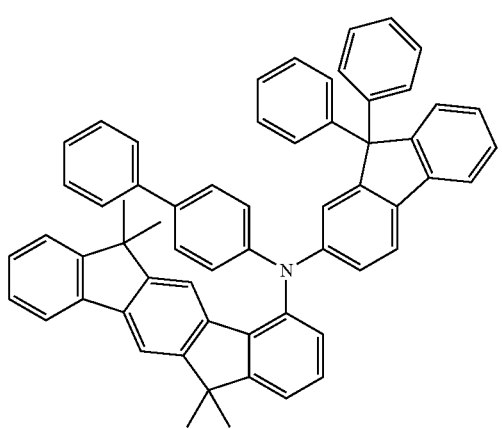 [SMILES: CC1(C)c2ccccc2-c2cc3c(cc21)-c1c(N(c2ccc(-c4ccccc4)cc2)c2ccc4c(c2)C(c2ccccc2)(c2ccccc2)c2ccccc2-4)cccc1C3(C)C]
(7)

(8)
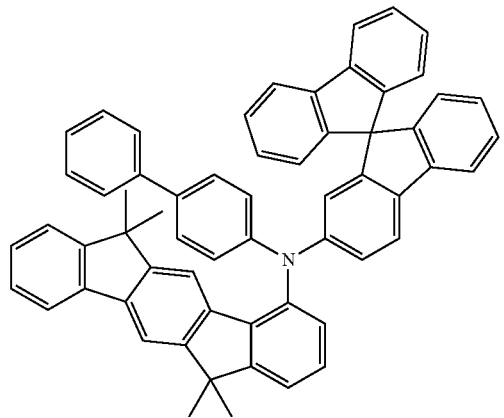 [SMILES: CC1(C)c2ccccc2-c2cc3c(cc21)-c1c(N(c2ccc(-c4ccccc4)cc2)c2ccc4c(c2)C2(c5ccccc5-c5ccccc52)c2ccccc2-4)cccc1C3(C)C]
(9)
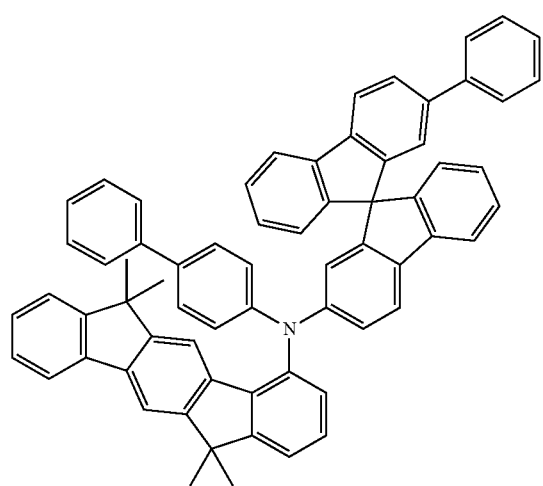 [SMILES: CC1(C)c2ccccc2-c2cc3c(cc21)-c1c(N(c2ccc(-c4ccccc4)cc2)c2ccc4c(c2)C2(c5ccccc5-c5ccc(-c6ccccc6)cc52)c2ccccc2-4)cccc1C3(C)C]
(10)
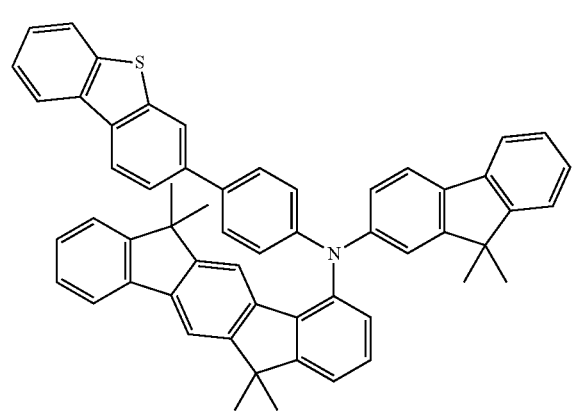 [SMILES: CC1(C)c2ccccc2-c2ccc(N(c3ccc(-c4ccc5c(c4)sc4ccccc45)cc3)c3cccc4c3-c3cc5c(cc3C4(C)C)-c3ccccc3C5(C)C)cc21]

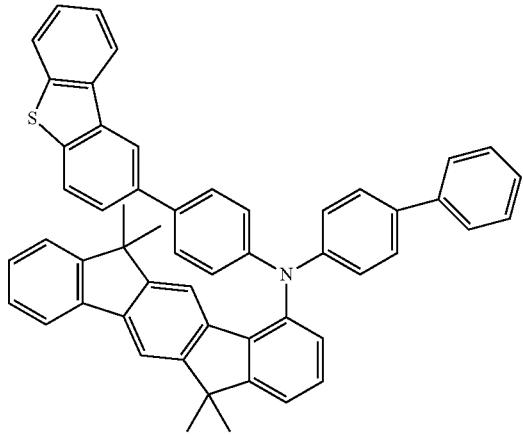 [SMILES: CC1(C)c2ccccc2-c2cc3c(cc21)-c1c(N(c2ccc(-c4ccccc4)cc2)c2ccc(-c4ccc5sc6ccccc6c5c4)cc2)cccc1C3(C)C]
(11)
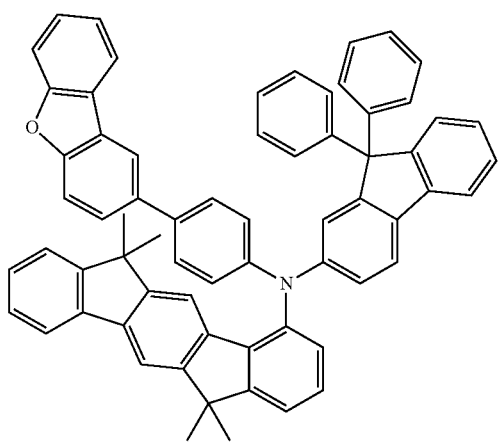 [SMILES: CC1(C)c2ccccc2-c2cc3c(cc21)-c1c(N(c2ccc(-c4ccc5oc6ccccc6c5c4)cc2)c2ccc4c(c2)C(c2ccccc2)(c2ccccc2)c2ccccc2-4)cccc1C3(C)C]
(12)
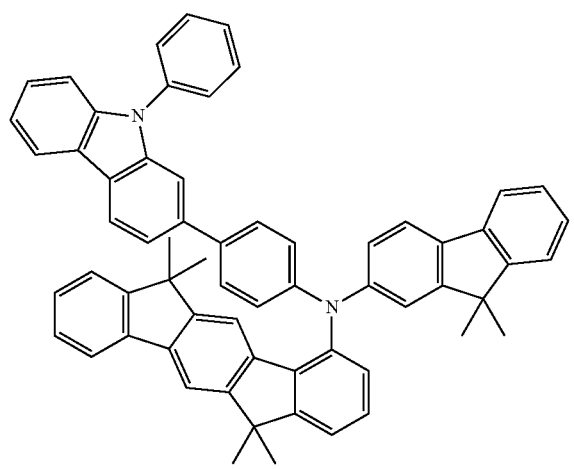 [SMILES: CC1(C)c2ccccc2-c2ccc(N(c3ccc(-c4ccc5c6ccccc6n(-c6ccccc6)c5c4)cc3)c3cccc4c3-c3cc5c(cc3C4(C)C)-c3ccccc3C5(C)C)cc21]
(13)

-continued
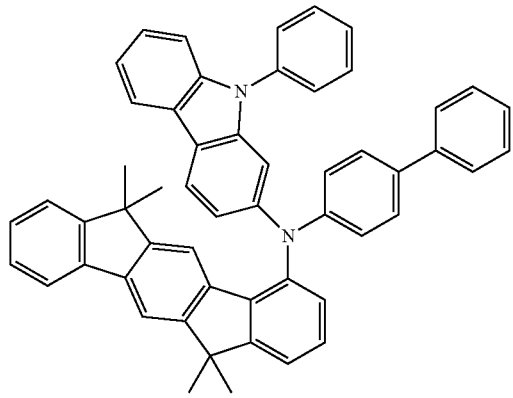 [SMILES: CC1(C)c2ccccc2-c2cc3c(cc21)-c1c(N(c2ccc(-c4ccccc4)cc2)c2ccc4c5ccccc5n(-c5ccccc5)c4c2)cccc1C3(C)C]
(14)
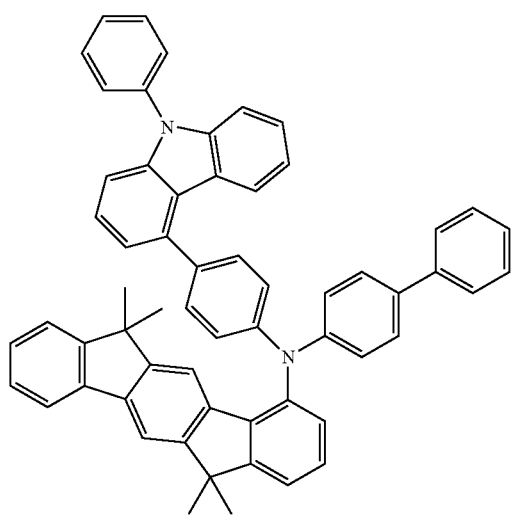 [SMILES: CC1(C)c2ccccc2-c2cc3c(cc21)-c1c(N(c2ccc(-c4ccccc4)cc2)c2ccc(-c4cccc5c4c4ccccc4n5-c4ccccc4)cc2)cccc1C3(C)C]
(15)
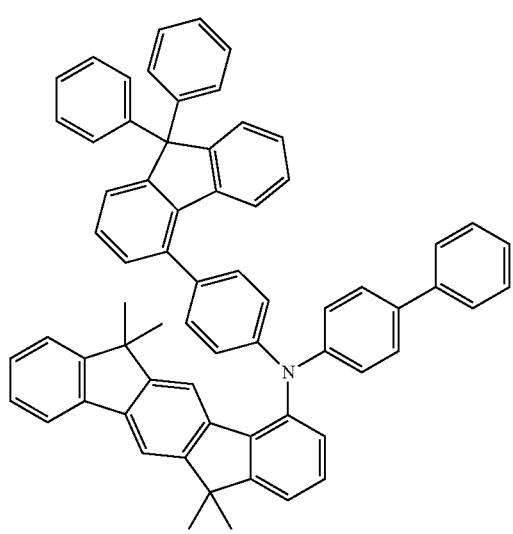 [SMILES: CC1(C)c2ccccc2-c2cc3c(cc21)-c1c(N(c2ccc(-c4ccccc4)cc2)c2ccc(-c4cccc5c4-c4ccccc4C5(c4ccccc4)c4ccccc4)cc2)cccc1C3(C)C]
(16)

(17)
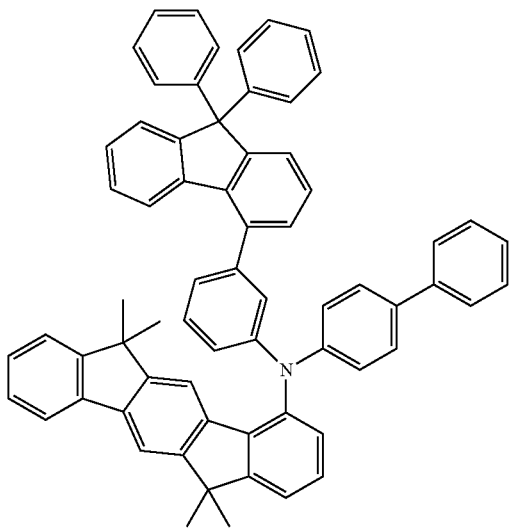 [SMILES: CC1(C)c2ccccc2-c2cc3c(cc21)-c1c(N(c2ccc(-c4ccccc4)cc2)c2cccc(-c4cccc5c4-c4ccccc4C5(c4ccccc4)c4ccccc4)c2)cccc1C3(C)C]
(18)
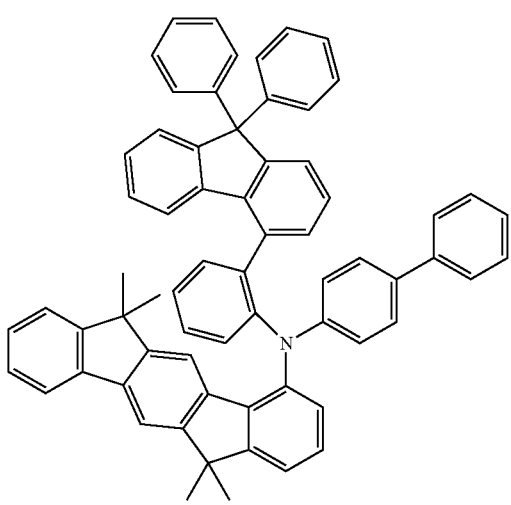 [SMILES: CC1(C)c2ccccc2-c2cc3c(cc21)-c1c(N(c2ccc(-c4ccccc4)cc2)c2ccccc2-c2cccc4c2-c2ccccc2C4(c2ccccc2)c2ccccc2)cccc1C3(C)C]
(19)
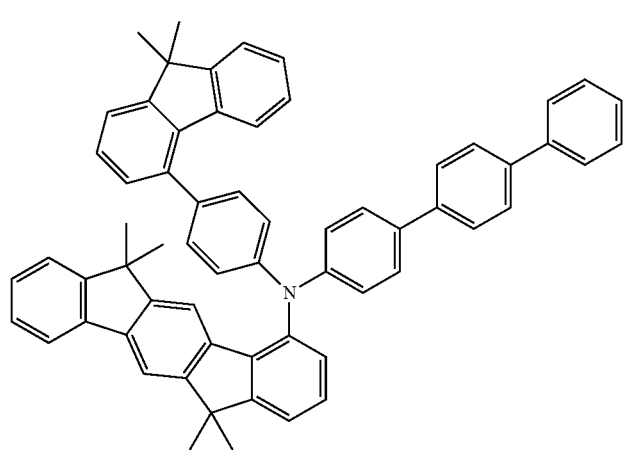 [SMILES: CC1(C)c2ccccc2-c2cc3c(cc21)-c1c(N(c2ccc(-c4ccc(-c5ccccc5)cc4)cc2)c2ccc(-c4cccc5c4-c4ccccc4C5(C)C)cc2)cccc1C3(C)C]

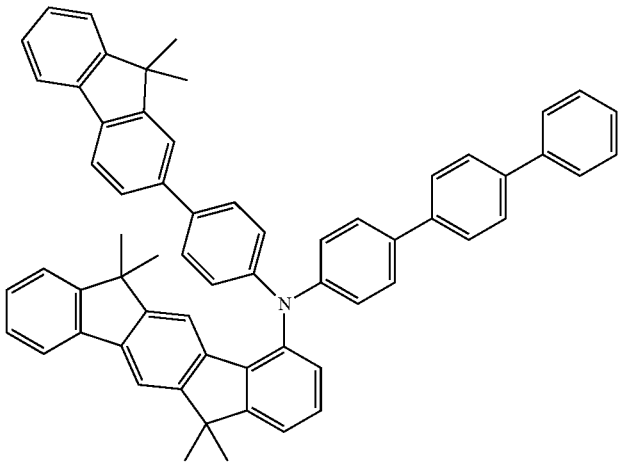 [SMILES: CC1(C)c2ccccc2-c2ccc(-c3ccc(N(c4ccc(-c5ccc(-c6ccccc6)cc5)cc4)c4cccc5c4-c4cc6c(cc4C5(C)C)-c4ccccc4C6(C)C)cc3)cc21]
(20)
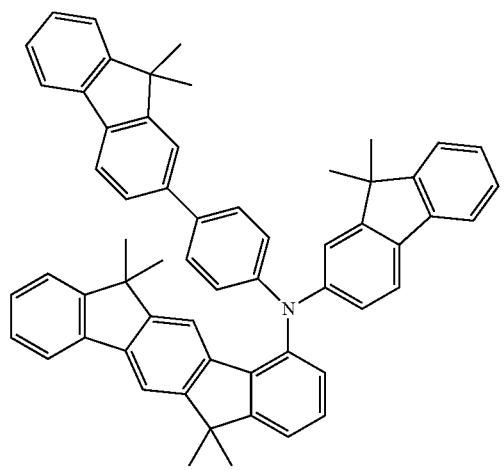 [SMILES: CC1(C)c2ccccc2-c2ccc(-c3ccc(N(c4ccc5c(c4)C(C)(C)c4ccccc4-5)c4cccc5c4-c4cc6c(cc4C5(C)C)-c4ccccc4C6(C)C)cc3)cc21]
(21)
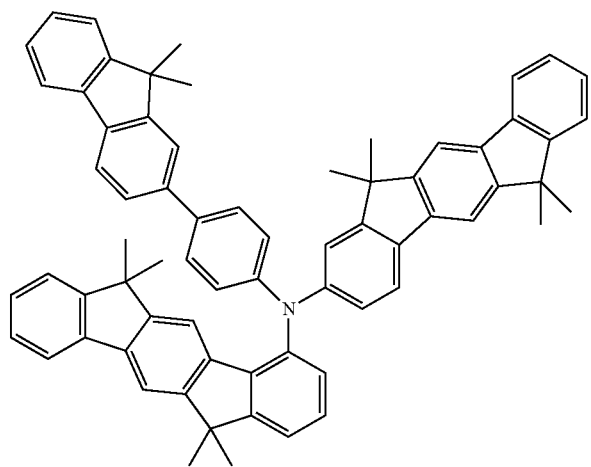 [SMILES: CC1(C)c2ccccc2-c2ccc(-c3ccc(N(c4ccc5c(c4)C(C)(C)c4cc6c(cc4-5)C(C)(C)c4ccccc4-6)c4cccc5c4-c4cc6c(cc4C5(C)C)-c4ccccc4C6(C)C)cc3)cc21]
(22)

-continued
(23)
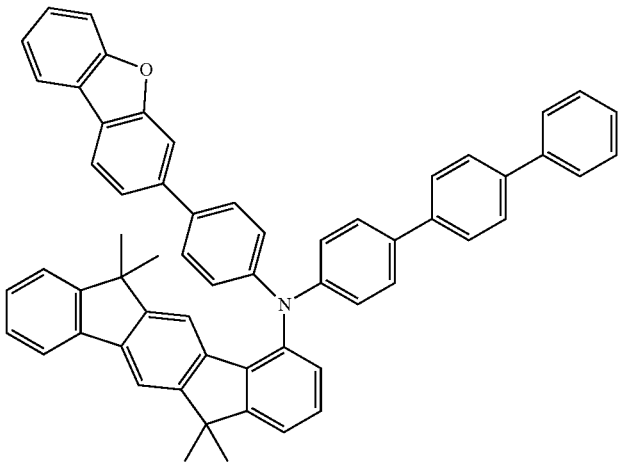 [SMILES: CC1(C)c2ccccc2-c2cc3c(cc21)-c1c(N(c2ccc(-c4ccc(-c5ccccc5)cc4)cc2)c2ccc(-c4ccc5c(c4)oc4ccccc45)cc2)cccc1C3(C)C]
(24)
(25)

(26)
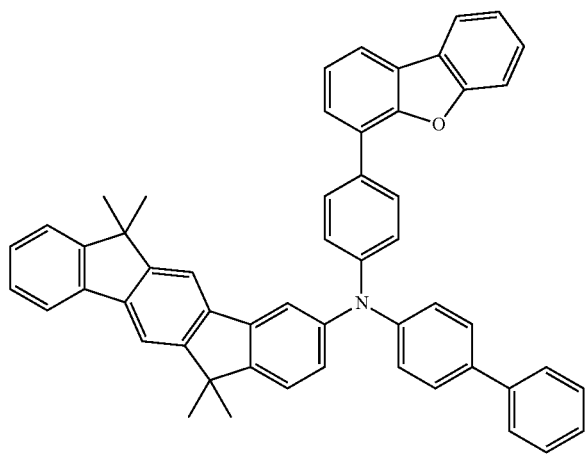 [SMILES: CC1(C)c2ccccc2-c2cc3c(cc21)-c1cc(N(c2ccc(-c4ccccc4)cc2)c2ccc(-c4cccc5c4oc4ccccc45)cc2)ccc1C3(C)C]
(27)
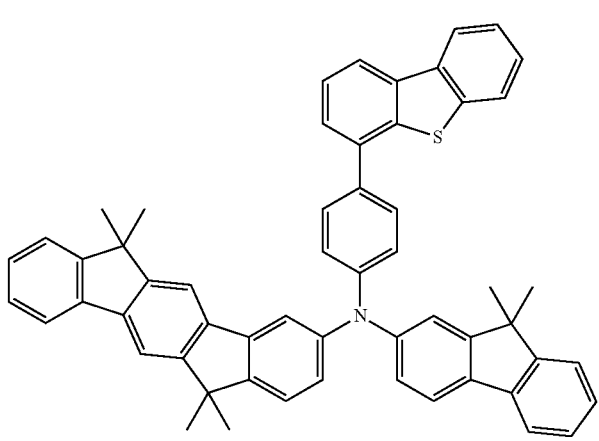 [SMILES: CC1(C)c2ccccc2-c2ccc(N(c3ccc(-c4cccc5c4sc4ccccc45)cc3)c3ccc4c(c3)-c3cc5c(cc3C4(C)C)-c3ccccc3C5(C)C)cc21]
(28)
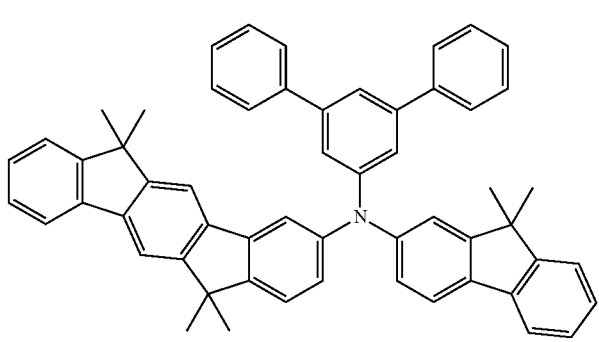 [SMILES: CC1(C)c2ccccc2-c2ccc(N(c3cc(-c4ccccc4)cc(-c4ccccc4)c3)c3ccc4c(c3)-c3cc5c(cc3C4(C)C)-c3ccccc3C5(C)C)cc21]
(29)
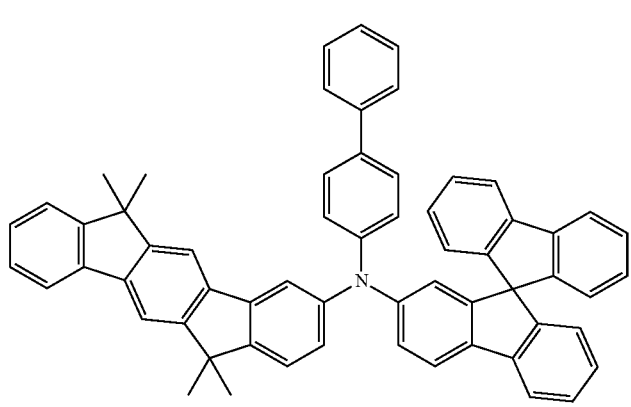 [SMILES: CC1(C)c2ccccc2-c2cc3c(cc21)-c1cc(N(c2ccc(-c4ccccc4)cc2)c2ccc4c(c2)C2(c5ccccc5-c5ccccc52)c2ccccc2-4)ccc1C3(C)C]

(30)
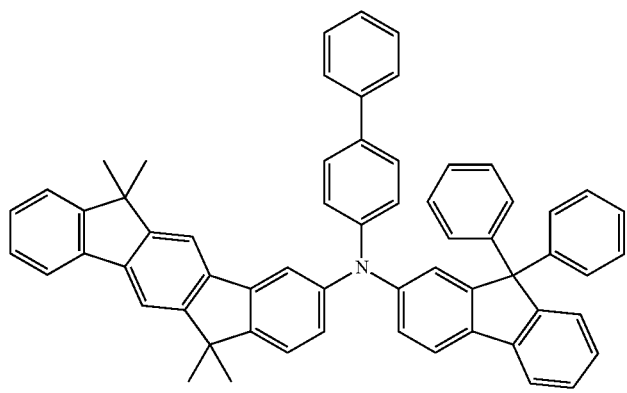 [SMILES: CC1(C)c2ccccc2-c2cc3c(cc21)-c1cc(N(c2ccc(-c4ccccc4)cc2)c2ccc4c(c2)C(c2ccccc2)(c2ccccc2)c2ccccc2-4)ccc1C3(C)C]
(31)
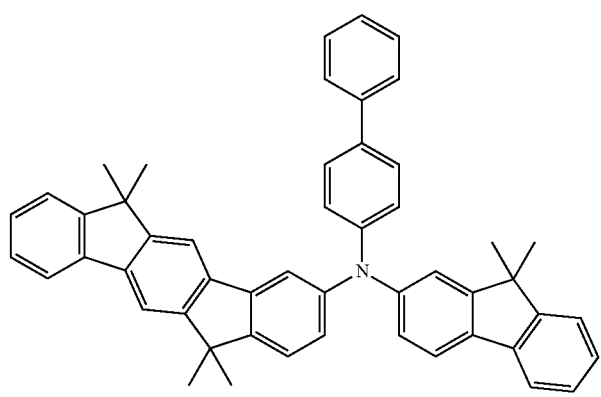 [SMILES: CC1(C)c2ccccc2-c2ccc(N(c3ccc(-c4ccccc4)cc3)c3ccc4c(c3)-c3cc5c(cc3C4(C)C)-c3ccccc3C5(C)C)cc21]
(32)
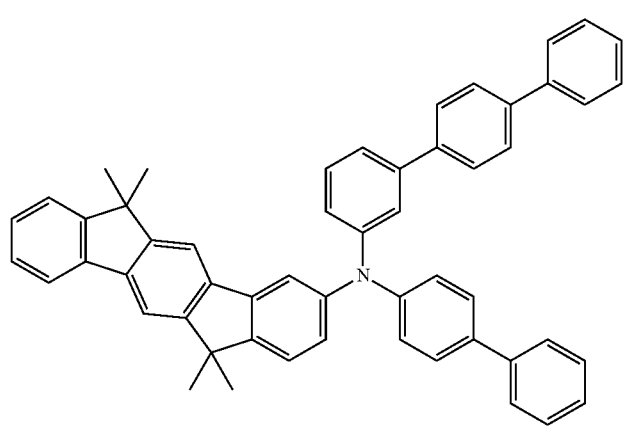 [SMILES: CC1(C)c2ccccc2-c2cc3c(cc21)-c1cc(N(c2ccc(-c4ccccc4)cc2)c2cccc(-c4ccc(-c5ccccc5)cc4)c2)ccc1C3(C)C]

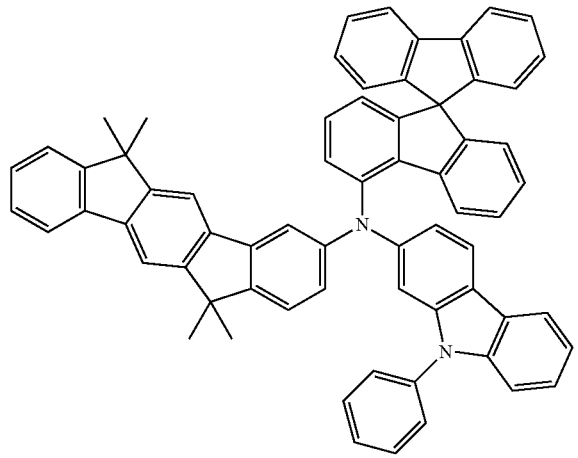 [SMILES: CC1(C)c2ccccc2-c2cc3c(cc21)-c1cc(N(c2ccc4c5ccccc5n(-c5ccccc5)c4c2)c2cccc4c2-c2ccccc2C42c4ccccc4-c4ccccc42)ccc1C3(C)C]
(33)
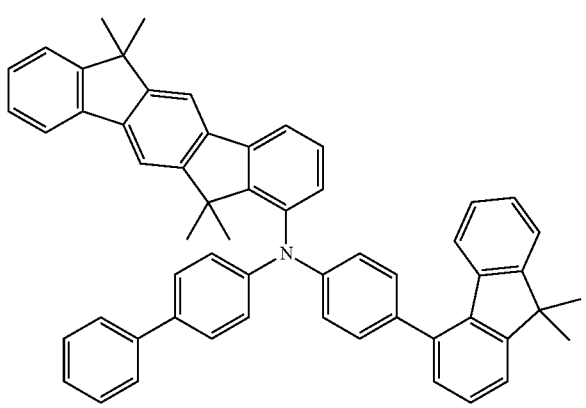 [SMILES: CC1(C)c2ccccc2-c2cc3c(cc21)-c1cccc(N(c2ccc(-c4ccccc4)cc2)c2ccc(-c4cccc5c4-c4ccccc4C5(C)C)cc2)c1C3(C)C]
(34)
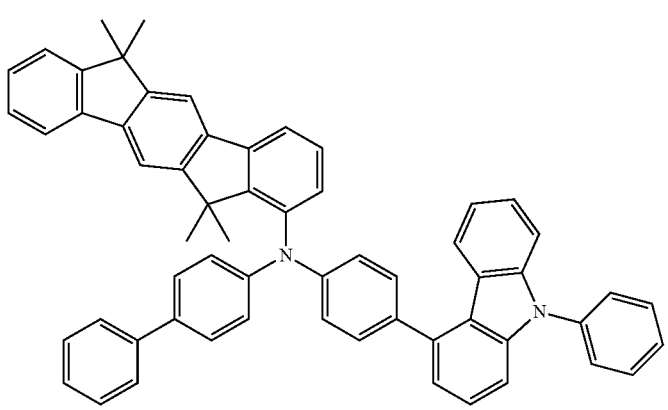 [SMILES: CC1(C)c2ccccc2-c2cc3c(cc21)-c1cccc(N(c2ccc(-c4ccccc4)cc2)c2ccc(-c4cccc5c4c4ccccc4n5-c4ccccc4)cc2)c1C3(C)C]
(35)

-continued
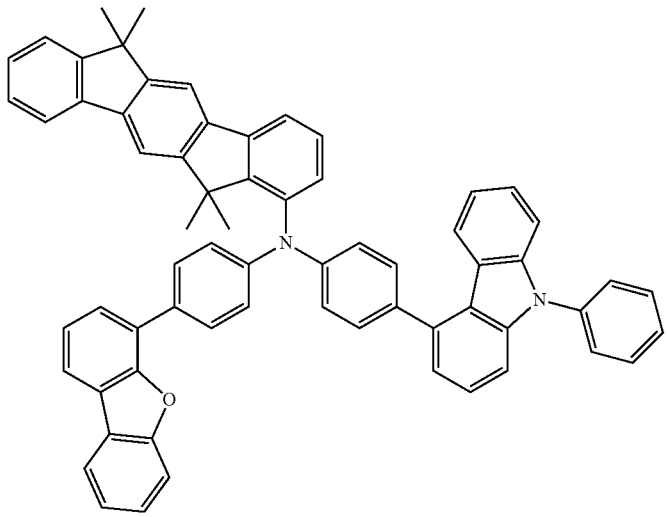 [SMILES: CC1(C)c2ccccc2-c2cc3c(cc21)-c1cccc(N(c2ccc(-c4cccc5c4oc4ccccc45)cc2)c2ccc(-c4cccc5c4c4ccccc4n5-c4ccccc4)cc2)c1C3(C)C]
(36)
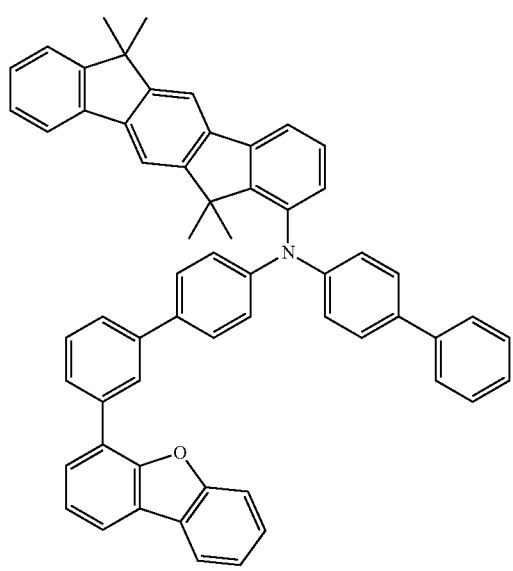 [SMILES: CC1(C)c2ccccc2-c2cc3c(cc21)-c1cccc(N(c2ccc(-c4ccccc4)cc2)c2ccc(-c4cccc(-c5cccc6c5oc5ccccc56)c4)cc2)c1C3(C)C]
(37)
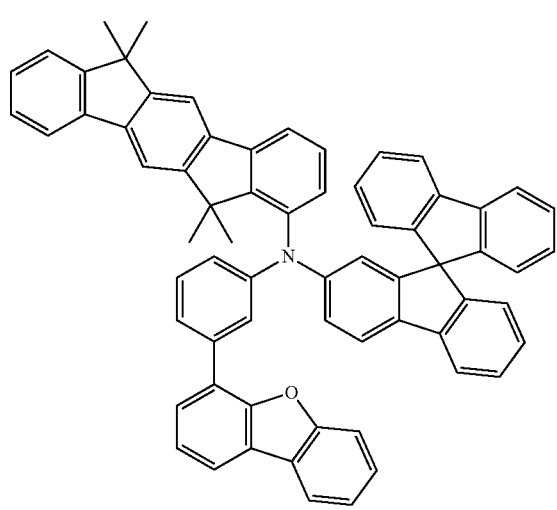 [SMILES: CC1(C)c2ccccc2-c2cc3c(cc21)-c1cccc(N(c2cccc(-c4cccc5c4oc4ccccc45)c2)c2ccc4c(c2)C2(c5ccccc5-c5ccccc52)c2ccccc2-4)c1C3(C)C]
(38)

(39)
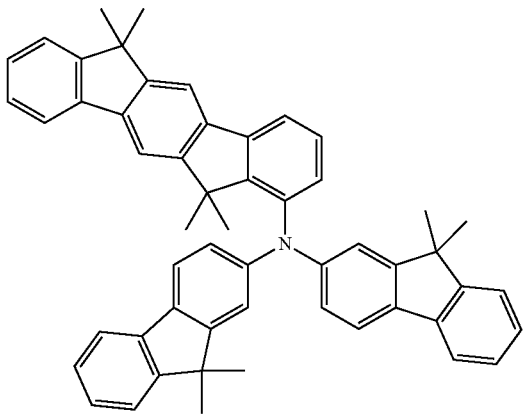 [SMILES: CC1(C)c2ccccc2-c2ccc(N(c3ccc4c(c3)C(C)(C)c3ccccc3-4)c3cccc4c3C(C)(C)c3cc5c(cc3-4)C(C)(C)c3ccccc3-5)cc21]
(40)
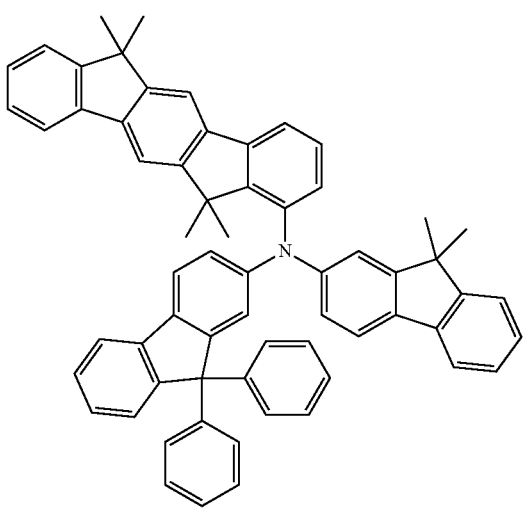 [SMILES: CC1(C)c2ccccc2-c2ccc(N(c3ccc4c(c3)C(c3ccccc3)(c3ccccc3)c3ccccc3-4)c3cccc4c3C(C)(C)c3cc5c(cc3-4)C(C)(C)c3ccccc3-5)cc21]
(41)
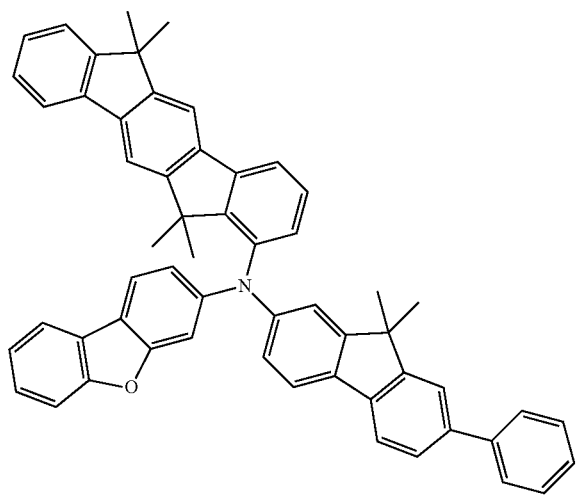 [SMILES: CC1(C)c2cc(-c3ccccc3)ccc2-c2ccc(N(c3ccc4c(c3)oc3ccccc34)c3cccc4c3C(C)(C)c3cc5c(cc3-4)C(C)(C)c3ccccc3-5)cc21]

(42)
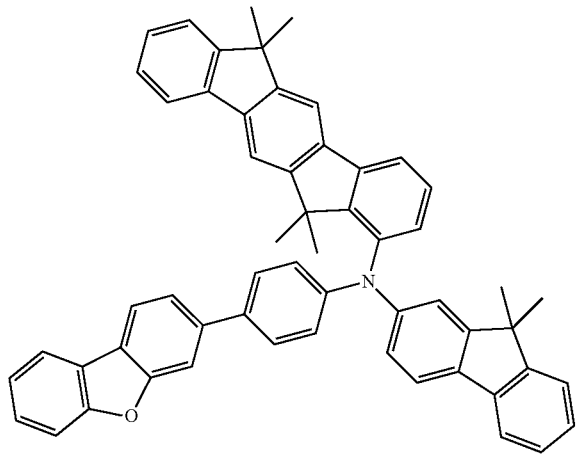 [SMILES: CC1(C)c2ccccc2-c2ccc(N(c3ccc(-c4ccc5c(c4)oc4ccccc45)cc3)c3cccc4c3C(C)(C)c3cc5c(cc3-4)C(C)(C)c3ccccc3-5)cc21]
(43)
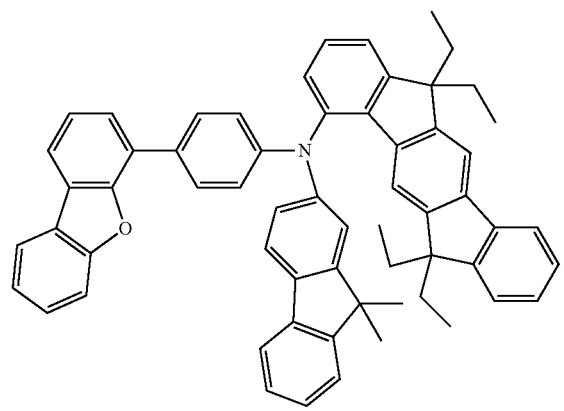 [SMILES: CCC1(CC)c2ccccc2-c2cc3c(cc21)-c1c(N(c2ccc(-c4cccc5c4oc4ccccc45)cc2)c2ccc4c(c2)C(C)(C)c2ccccc2-4)cccc1C3(CC)CC]
(44)
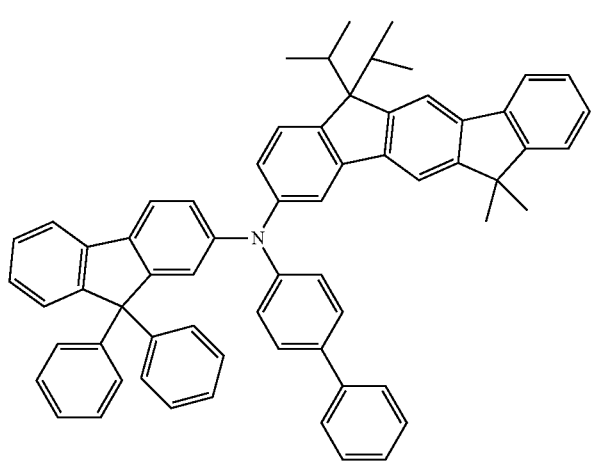 [SMILES: CC(C)C1(C(C)C)c2ccc(N(c3ccc(-c4ccccc4)cc3)c3ccc4c(c3)C(c3ccccc3)(c3ccccc3)c3ccccc3-4)cc2-c2cc3c(cc21)-c1ccccc1C3(C)C]

-continued
(45)
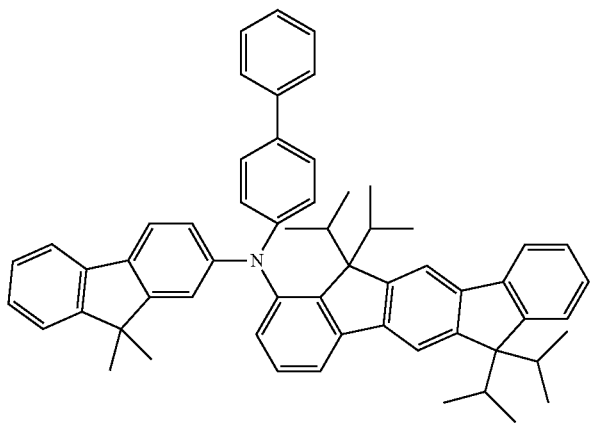 [SMILES: CC(C)C1(C(C)C)c2ccccc2-c2cc3c(cc21)-c1cccc(N(c2ccc(-c4ccccc4)cc2)c2ccc4c(c2)C(C)(C)c2ccccc2-4)c1C3(C(C)C)C(C)C]
(46)
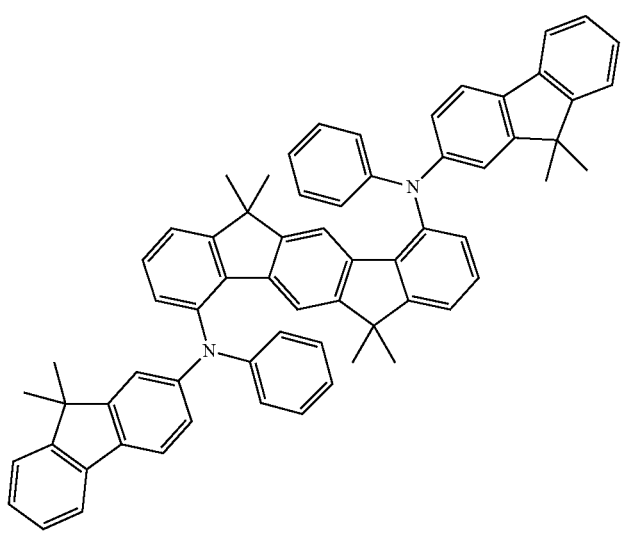 [SMILES: CC1(C)c2ccccc2-c2ccc(N(c3ccccc3)c3cccc4c3-c3cc5c(cc3C4(C)C)-c3c(N(c4ccccc4)c4ccc6c(c4)C(C)(C)c4ccccc4-6)cccc3C5(C)C)cc21]
(47)
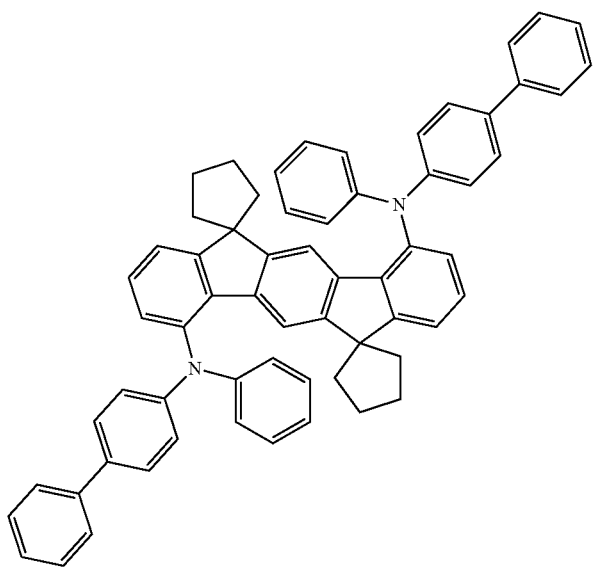 [SMILES: c1ccc(-c2ccc(N(c3ccccc3)c3cccc4c3-c3cc5c(cc3C43CCCC3)-c3c(N(c4ccccc4)c4ccc(-c6ccccc6)cc4)cccc3C53CCCC3)cc2)cc1]

(48)
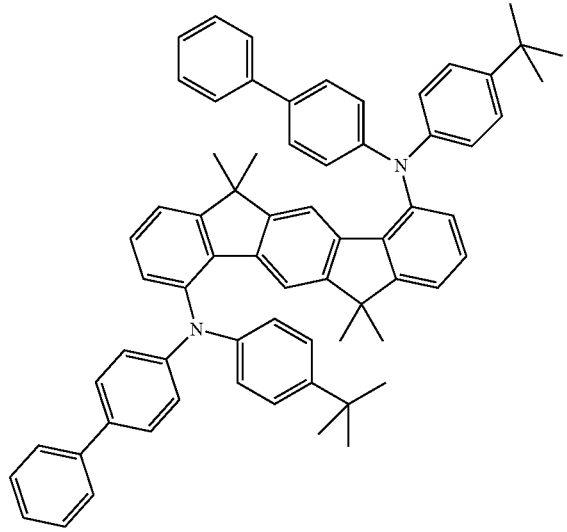 [SMILES: CC(C)(C)c1ccc(N(c2ccc(-c3ccccc3)cc2)c2cccc3c2-c2cc4c(cc2C3(C)C)-c2c(N(c3ccc(-c5ccccc5)cc3)c3ccc(C(C)(C)C)cc3)cccc2C4(C)C)cc1]
(49)
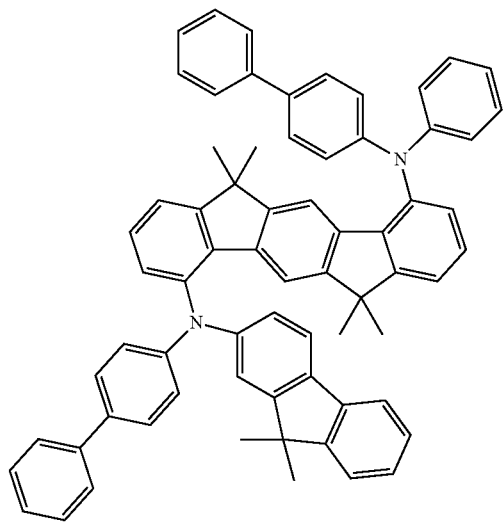 [SMILES: CC1(C)c2ccccc2-c2ccc(N(c3ccc(-c4ccccc4)cc3)c3cccc4c3-c3cc5c(cc3C4(C)C)-c3c(N(c4ccccc4)c4ccc(-c6ccccc6)cc4)cccc3C5(C)C)cc21]

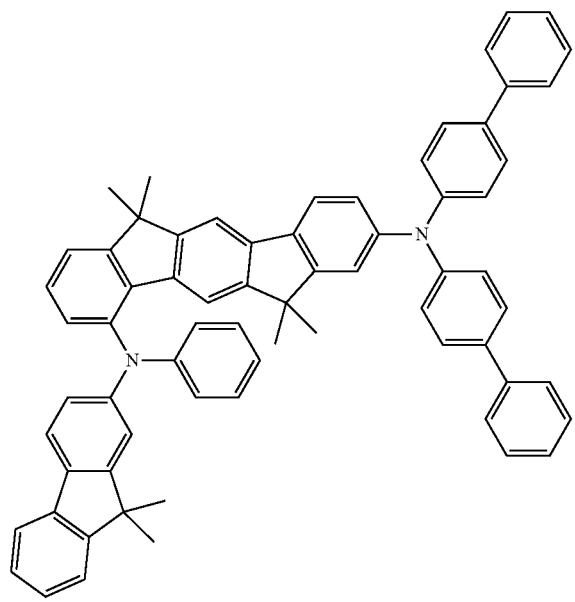 [SMILES: CC1(C)c2ccccc2-c2ccc(N(c3ccccc3)c3cccc4c3-c3cc5c(cc3C4(C)C)-c3ccc(N(c4ccc(-c6ccccc6)cc4)c4ccc(-c6ccccc6)cc4)cc3C5(C)C)cc21]
(50)
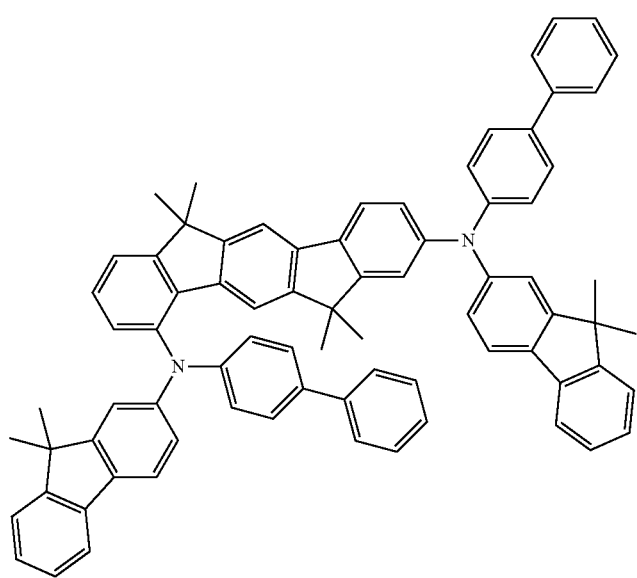
(51)

-continued
(52)
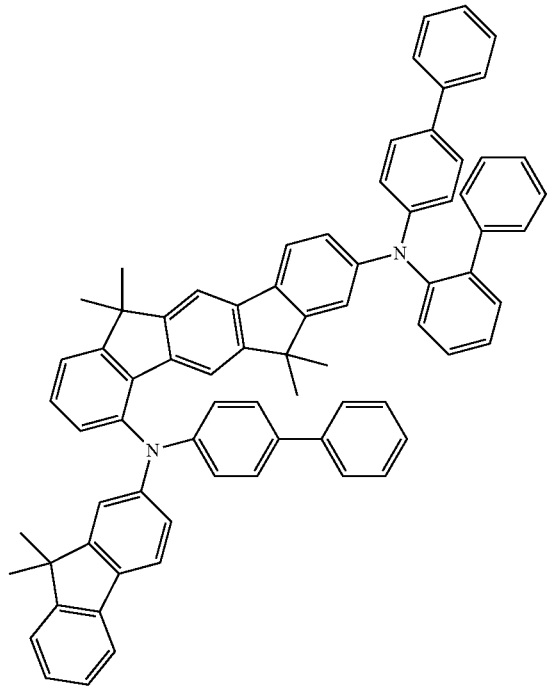 [SMILES: CC1(C)c2ccccc2-c2ccc(N(c3ccc(-c4ccccc4)cc3)c3cccc4c3-c3cc5c(cc3C4(C)C)-c3ccc(N(c4ccc(-c6ccccc6)cc4)c4ccccc4-c4ccccc4)cc3C5(C)C)cc21]
(53)
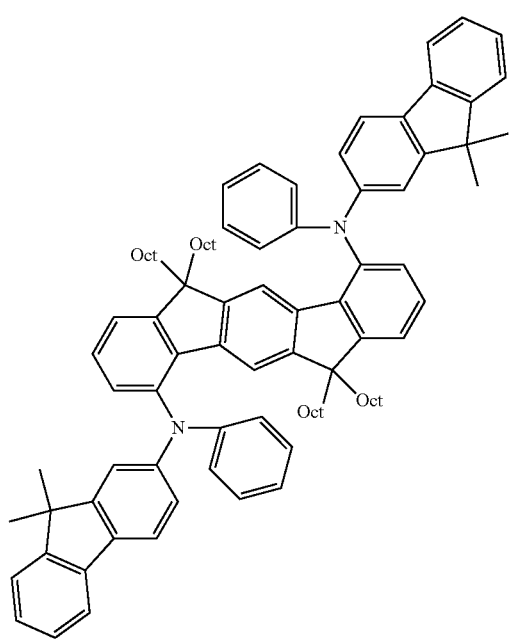

-continued
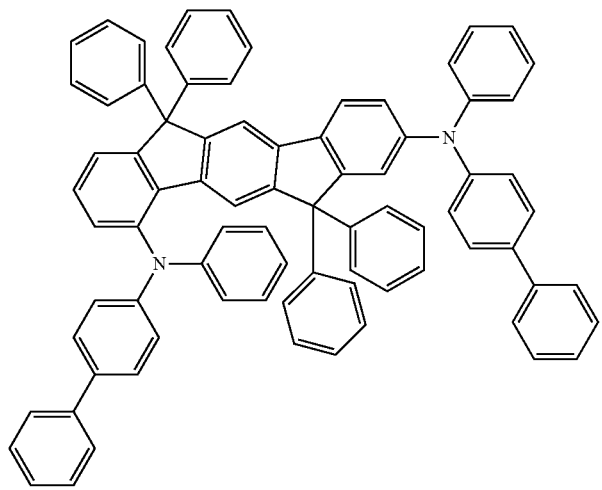 [SMILES: c1ccc(-c2ccc(N(c3ccccc3)c3ccc4c(c3)C(c3ccccc3)(c3ccccc3)c3cc5c(cc3-4)C(c3ccccc3)(c3ccccc3)c3cccc(N(c4ccccc4)c4ccc(-c6ccccc6)cc4)c3-5)cc2)cc1]
(54)
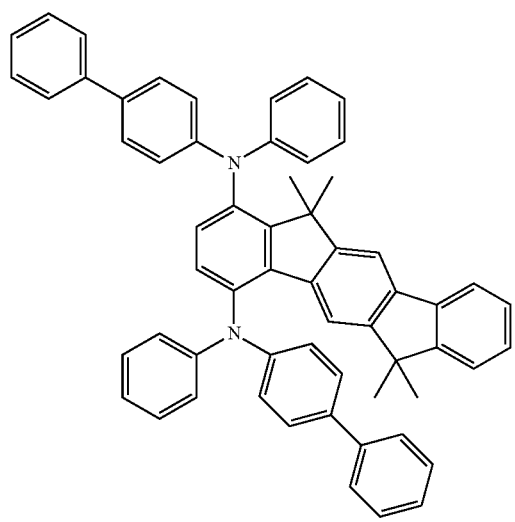 [SMILES: CC1(C)c2ccccc2-c2cc3c(cc21)-c1c(N(c2ccccc2)c2ccc(-c4ccccc4)cc2)ccc(N(c2ccccc2)c2ccc(-c4ccccc4)cc2)c1C3(C)C]
(55)

(56)
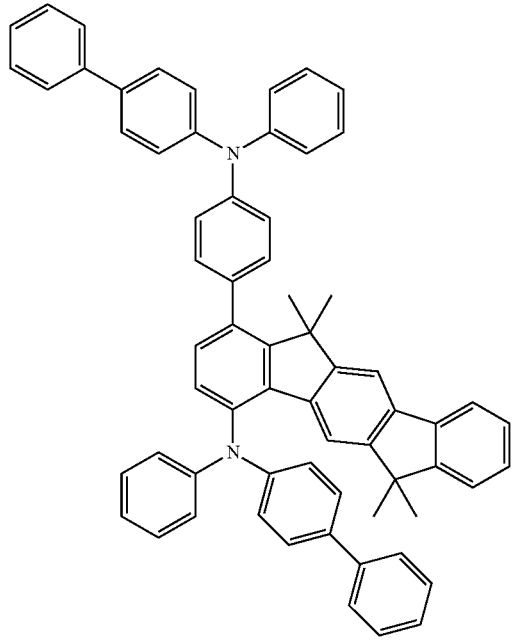 [SMILES: CC1(C)c2ccccc2-c2cc3c(cc21)-c1c(N(c2ccccc2)c2ccc(-c4ccccc4)cc2)ccc(-c2ccc(N(c4ccccc4)c4ccc(-c5ccccc5)cc4)cc2)c1C3(C)C]
(57)
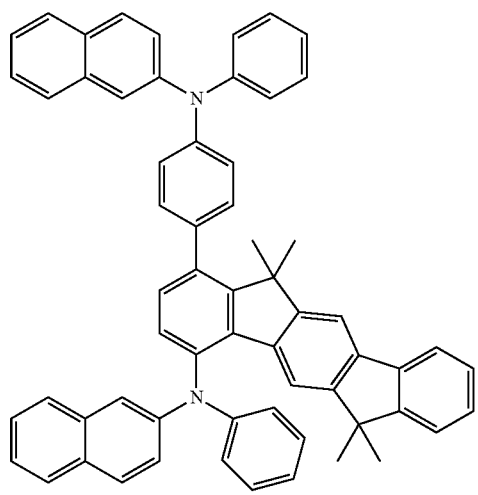 [SMILES: CC1(C)c2ccccc2-c2cc3c(cc21)-c1c(N(c2ccccc2)c2ccc4ccccc4c2)ccc(-c2ccc(N(c4ccccc4)c4ccc5ccccc5c4)cc2)c1C3(C)C]

(58)
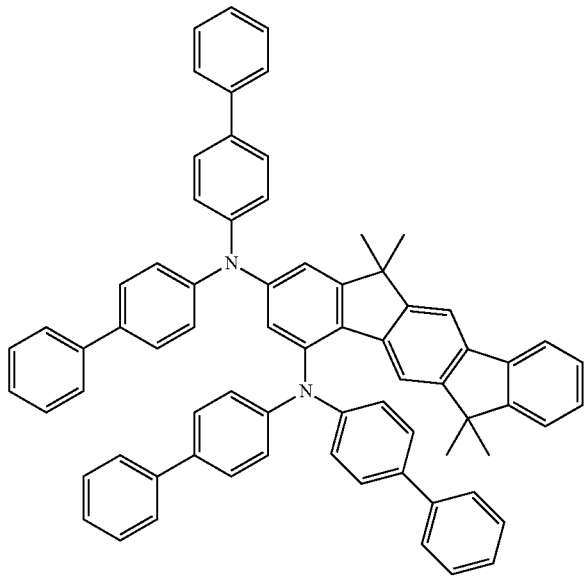 [SMILES: CC1(C)c2ccccc2-c2cc3c(cc21)-c1c(N(c2ccc(-c4ccccc4)cc2)c2ccc(-c4ccccc4)cc2)cc(N(c2ccc(-c4ccccc4)cc2)c2ccc(-c4ccccc4)cc2)cc1C3(C)C]
(59)
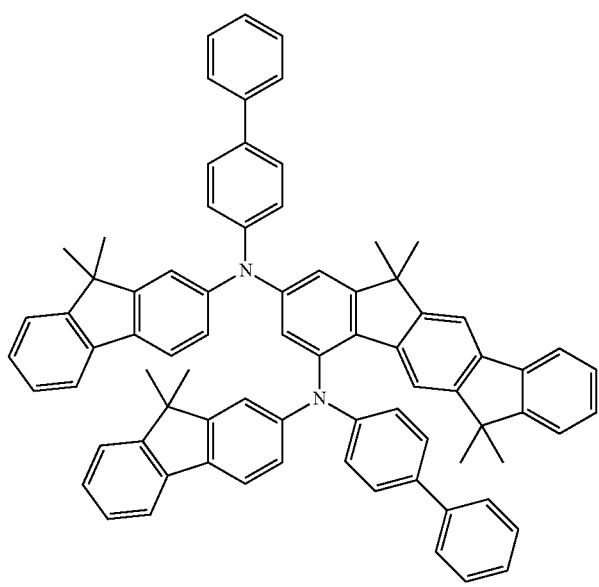 [SMILES: CC1(C)c2ccccc2-c2ccc(N(c3ccc(-c4ccccc4)cc3)c3cc(N(c4ccc(-c5ccccc5)cc4)c4ccc5c(c4)C(C)(C)c4ccccc4-5)c4c(c3)C(C)(C)c3cc5c(cc3-4)C(C)(C)c3ccccc3-5)cc21]
(60)
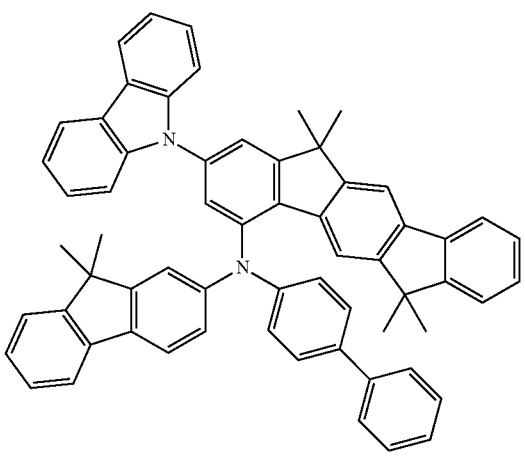 [SMILES: CC1(C)c2ccccc2-c2ccc(N(c3ccc(-c4ccccc4)cc3)c3cc(-n4c5ccccc5c5ccccc54)cc4c3-c3cc5c(cc3C4(C)C)-c3ccccc3C5(C)C)cc21]

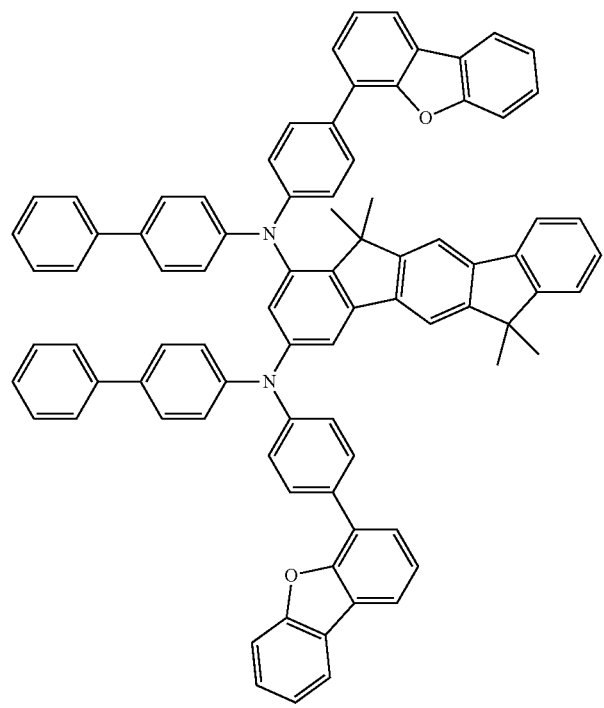 [SMILES: CC1(C)c2ccccc2-c2cc3c(cc21)-c1cc(N(c2ccc(-c4ccccc4)cc2)c2ccc(-c4cccc5c4oc4ccccc45)cc2)cc(N(c2ccc(-c4ccccc4)cc2)c2ccc(-c4cccc5c4oc4ccccc45)cc2)c1C3(C)C]
(61)
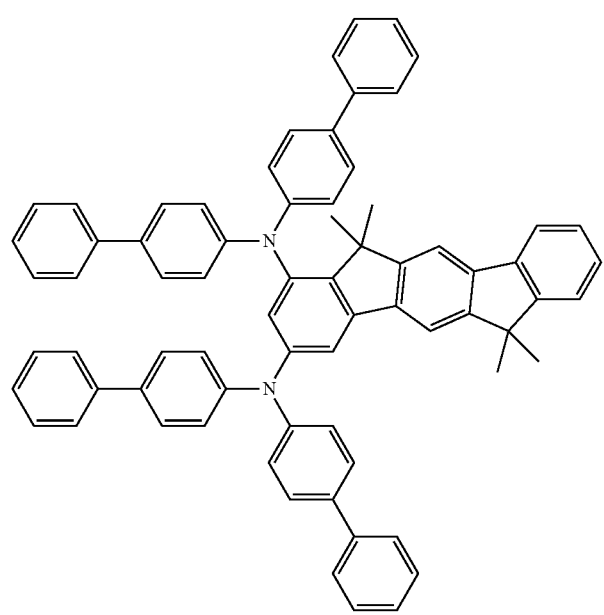 [SMILES: CC1(C)c2ccccc2-c2cc3c(cc21)-c1cc(N(c2ccc(-c4ccccc4)cc2)c2ccc(-c4ccccc4)cc2)cc(N(c2ccc(-c4ccccc4)cc2)c2ccc(-c4ccccc4)cc2)c1C3(C)C]
(62)

(63)
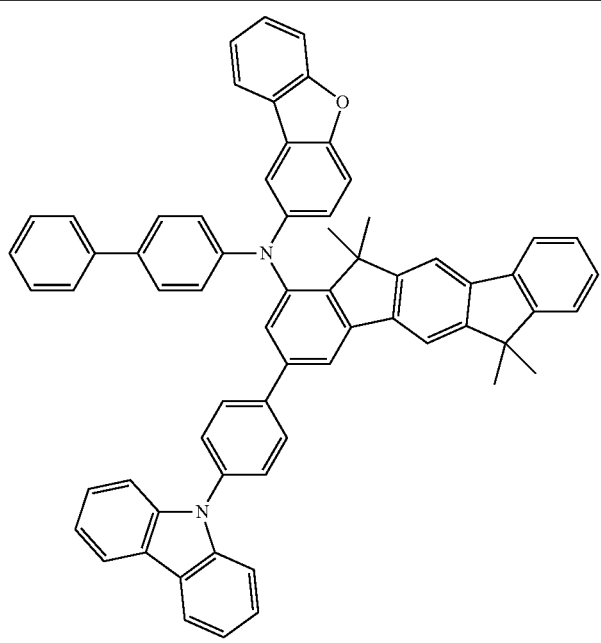
(64)
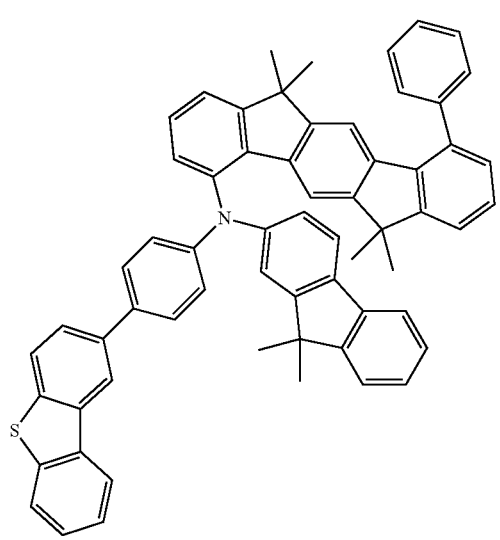 [SMILES: CC1(C)c2ccccc2-c2ccc(N(c3ccc(-c4ccc5sc6ccccc6c5c4)cc3)c3cccc4c3-c3cc5c(cc3C4(C)C)-c3c(-c4ccccc4)cccc3C5(C)C)cc21]
(65)
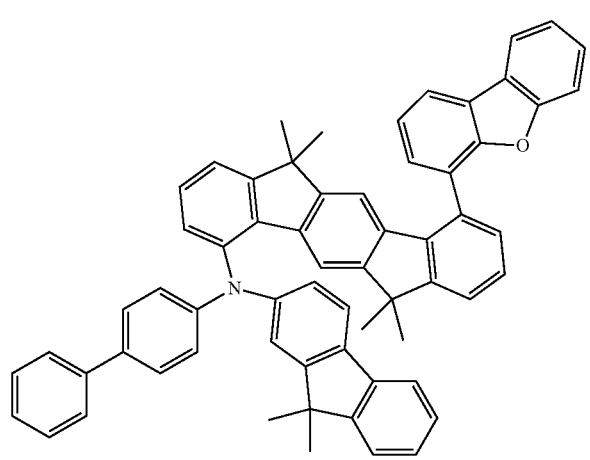 [SMILES: CC1(C)c2ccccc2-c2ccc(N(c3ccc(-c4ccccc4)cc3)c3cccc4c3-c3cc5c(cc3C4(C)C)-c3c(-c4cccc6c4oc4ccccc46)cccc3C5(C)C)cc21]

(66)
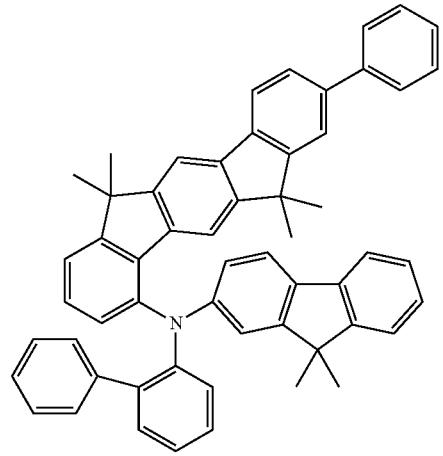 [SMILES: CC1(C)c2ccccc2-c2ccc(N(c3ccccc3-c3ccccc3)c3cccc4c3-c3cc5c(cc3C4(C)C)-c3ccc(-c4ccccc4)cc3C5(C)C)cc21]
(67)
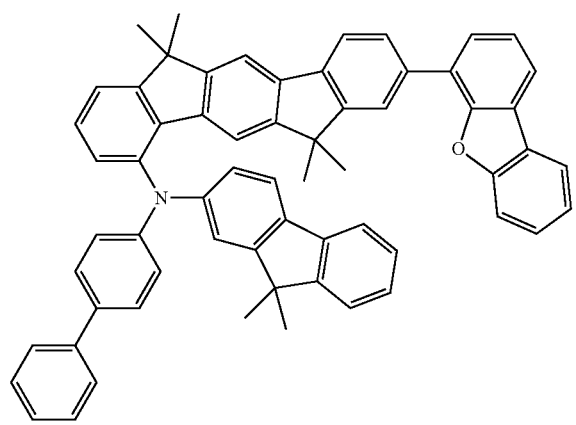 [SMILES: CC1(C)c2ccccc2-c2ccc(N(c3ccc(-c4ccccc4)cc3)c3cccc4c3-c3cc5c(cc3C4(C)C)-c3ccc(-c4cccc6c4oc4ccccc46)cc3C5(C)C)cc21]
(68)
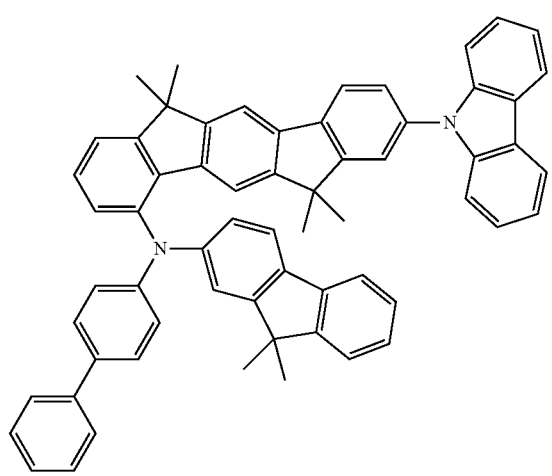 [SMILES: CC1(C)c2ccccc2-c2ccc(N(c3ccc(-c4ccccc4)cc3)c3cccc4c3-c3cc5c(cc3C4(C)C)-c3ccc(-n4c6ccccc6c6ccccc64)cc3C5(C)C)cc21]

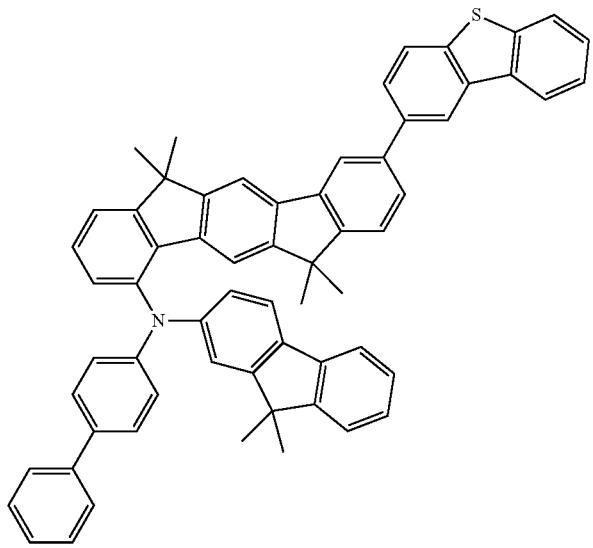 [SMILES: CC1(C)c2ccccc2-c2ccc(N(c3ccc(-c4ccccc4)cc3)c3cccc4c3-c3cc5c(cc3C4(C)C)-c3cc(-c4ccc6sc7ccccc7c6c4)ccc3C5(C)C)cc21]
(69)
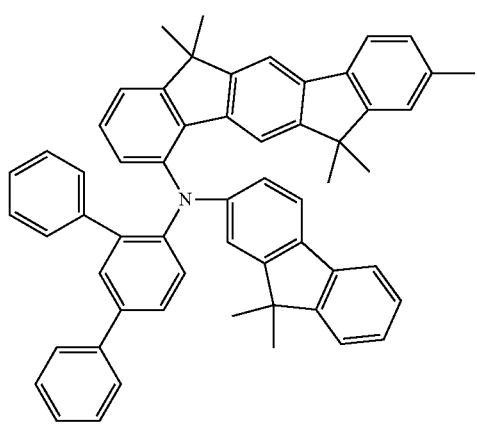 [SMILES: Cc1ccc2c(c1)C(C)(C)c1cc3c(cc1-2)C(C)(C)c1cccc(N(c2ccc4c(c2)C(C)(C)c2ccccc2-4)c2ccc(-c4ccccc4)cc2-c2ccccc2)c1-3]
(70)
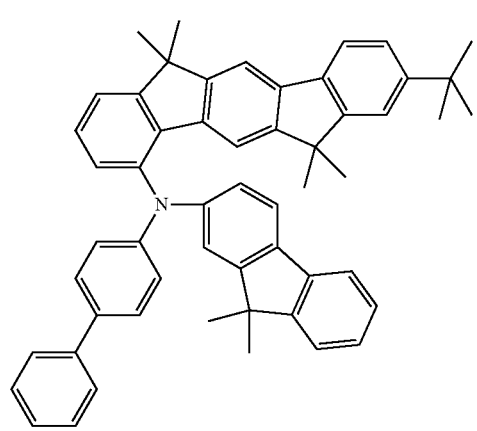 [SMILES: CC(C)(C)c1ccc2c(c1)C(C)(C)c1cc3c(cc1-2)C(C)(C)c1cccc(N(c2ccc(-c4ccccc4)cc2)c2ccc4c(c2)C(C)(C)c2ccccc2-4)c1-3]
(71)

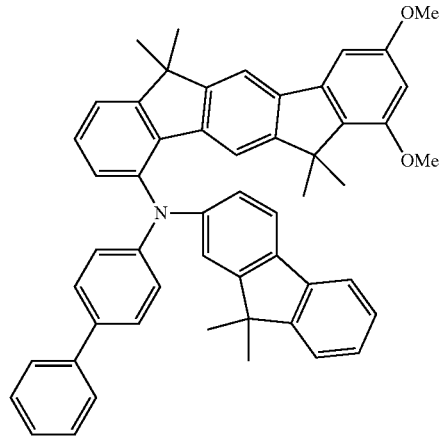 [SMILES: COc1cc(OC)c2c(c1)-c1cc3c(cc1C2(C)C)-c1c(N(c2ccc(-c4ccccc4)cc2)c2ccc4c(c2)C(C)(C)c2ccccc2-4)cccc1C3(C)C]
(72)
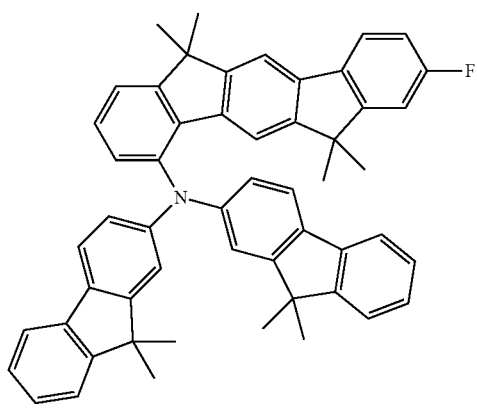 [SMILES: CC1(C)c2ccccc2-c2ccc(N(c3ccc4c(c3)C(C)(C)c3ccccc3-4)c3cccc4c3-c3cc5c(cc3C4(C)C)-c3ccc(F)cc3C5(C)C)cc21]
(73)
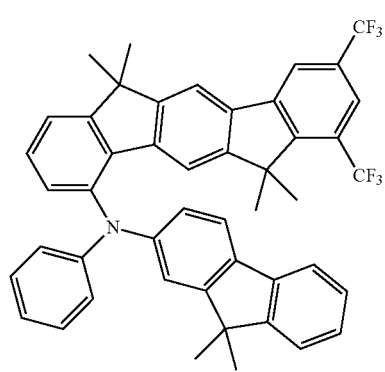 [SMILES: CC1(C)c2ccccc2-c2ccc(N(c3ccccc3)c3cccc4c3-c3cc5c(cc3C4(C)C)-c3cc(C(F)(F)F)cc(C(F)(F)F)c3C5(C)C)cc21]
(74)

-continued
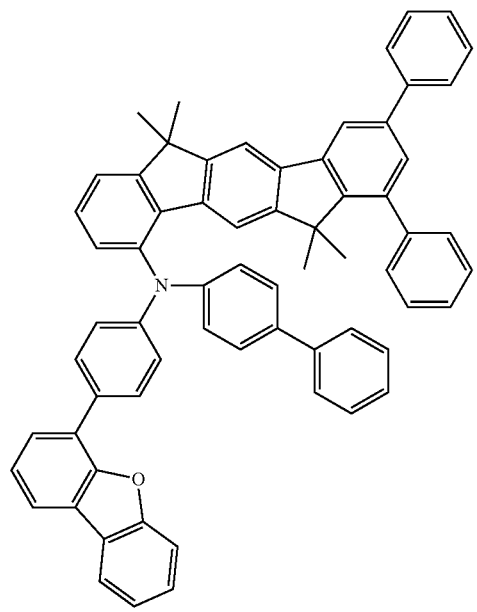 [SMILES: CC1(C)c2cc3c(cc2-c2c(N(c4ccc(-c5ccccc5)cc4)c4ccc(-c5cccc6c5oc5ccccc56)cc4)cccc21)C(C)(C)c1c(-c2ccccc2)cc(-c2ccccc2)cc1-3]
(75)
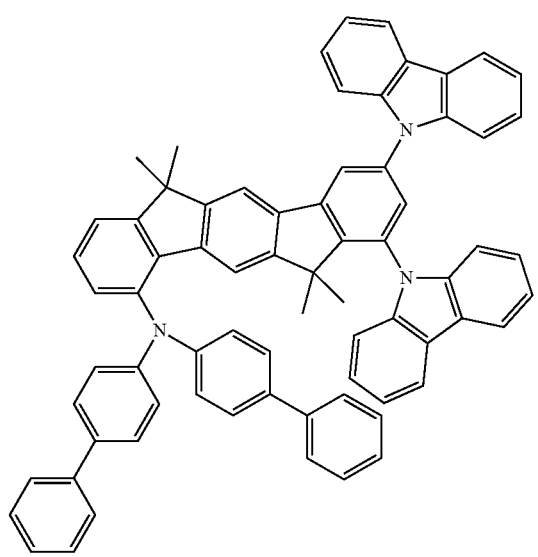 [SMILES: CC1(C)c2cc3c(cc2-c2c(N(c4ccc(-c5ccccc5)cc4)c4ccc(-c5ccccc5)cc4)cccc21)C(C)(C)c1c-3cc(-n2c3ccccc3c3ccccc32)cc1-n1c2ccccc2c2ccccc21]
(76)
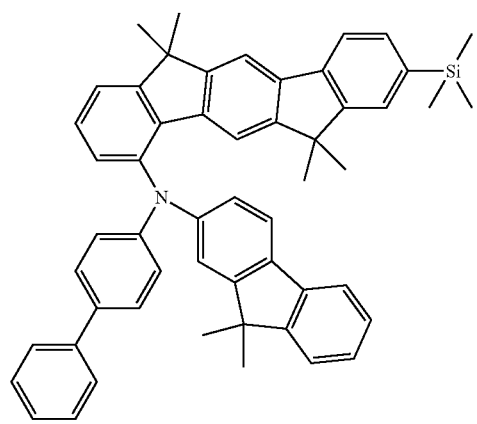 [SMILES: CC1(C)c2ccccc2-c2ccc(N(c3ccc(-c4ccccc4)cc3)c3cccc4c3-c3cc5c(cc3C4(C)C)-c3ccc([Si](C)(C)C)cc3C5(C)C)cc21]
(77)

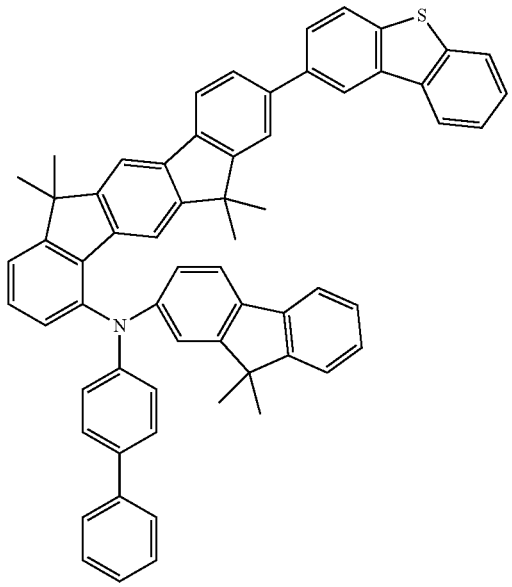 [SMILES: CC1(C)c2ccccc2-c2ccc(N(c3ccc(-c4ccccc4)cc3)c3cccc4c3-c3cc5c(cc3C4(C)C)-c3ccc(-c4ccc6sc7ccccc7c6c4)cc3C5(C)C)cc21]
(78)
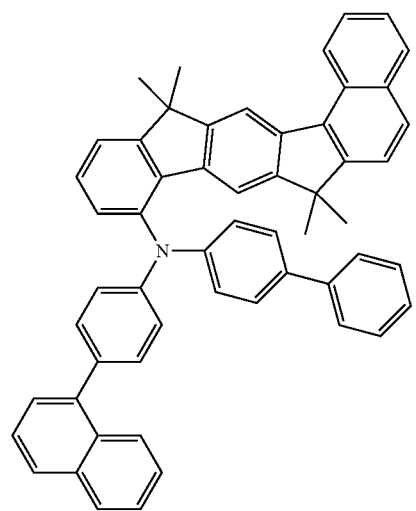 [SMILES: CC1(C)c2cc3c(cc2-c2c(N(c4ccc(-c5ccccc5)cc4)c4ccc(-c5cccc6ccccc56)cc4)cccc21)C(C)(C)c1ccc2ccccc2c1-3]
(79)

(80)
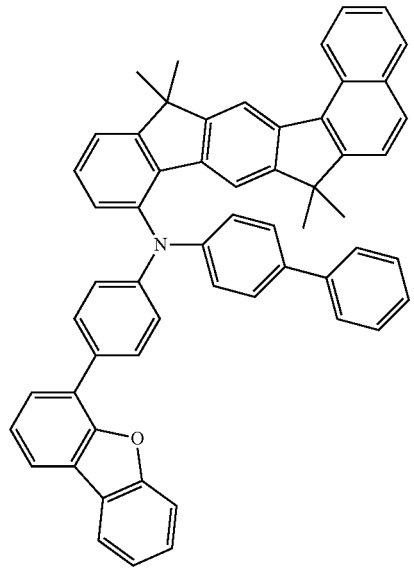 [SMILES: CC1(C)c2cc3c(cc2-c2c(N(c4ccc(-c5ccccc5)cc4)c4ccc(-c5cccc6c5oc5ccccc56)cc4)cccc21)C(C)(C)c1ccc2ccccc2c1-3]
(81)
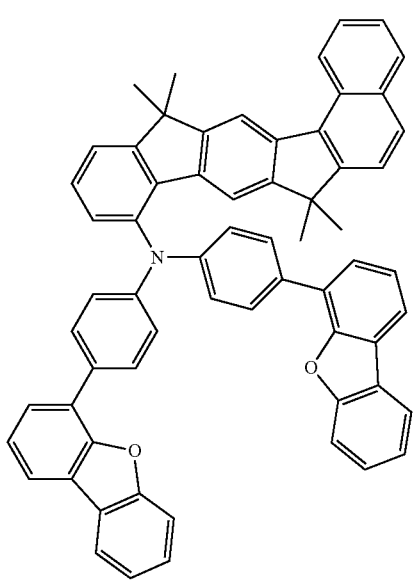 [SMILES: CC1(C)c2cc3c(cc2-c2c(N(c4ccc(-c5cccc6c5oc5ccccc56)cc4)c4ccc(-c5cccc6c5oc5ccccc56)cc4)cccc21)C(C)(C)c1ccc2ccccc2c1-3]

(82)
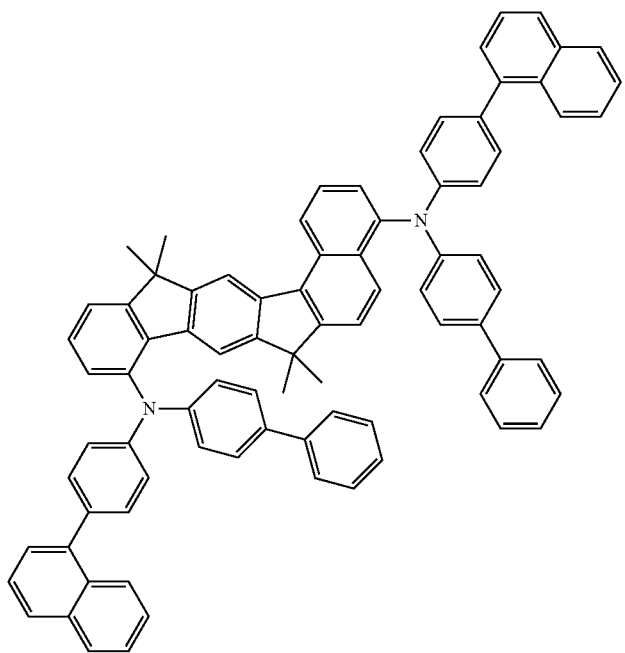 [SMILES: CC1(C)c2cc3c(cc2-c2c(N(c4ccc(-c5ccccc5)cc4)c4ccc(-c5cccc6ccccc56)cc4)cccc21)C(C)(C)c1ccc2c(N(c4ccc(-c5ccccc5)cc4)c4ccc(-c5cccc6ccccc56)cc4)cccc2c1-3]
(83)
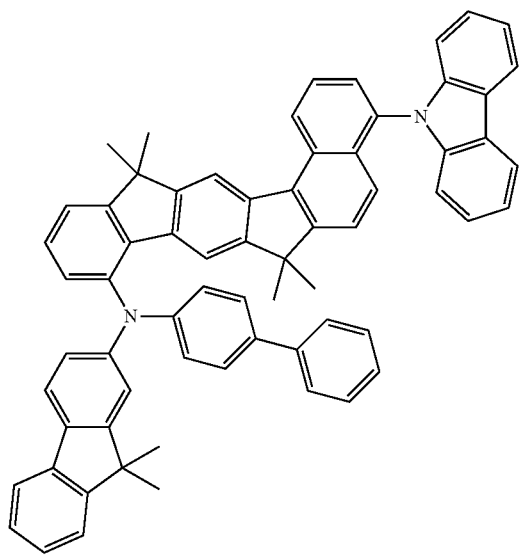 [SMILES: CC1(C)c2ccccc2-c2ccc(N(c3ccc(-c4ccccc4)cc3)c3cccc4c3-c3cc5c(cc3C4(C)C)-c3c(ccc4c(-n6c7ccccc7c7ccccc76)cccc34)C5(C)C)cc21]

-continued
(84)
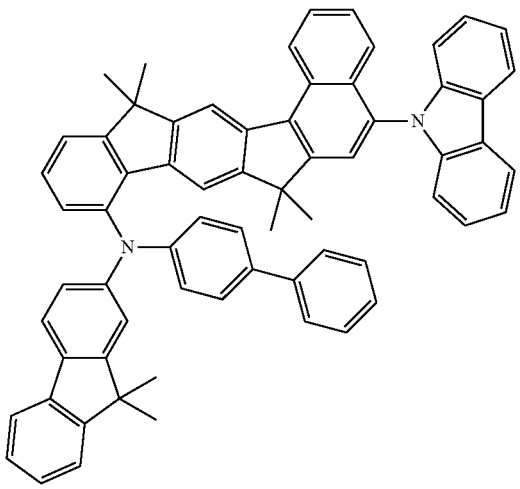 [SMILES: CC1(C)c2ccccc2-c2ccc(N(c3ccc(-c4ccccc4)cc3)c3cccc4c3-c3cc5c(cc3C4(C)C)-c3c(cc(-n4c6ccccc6c6ccccc64)c4ccccc34)C5(C)C)cc21]
(85)
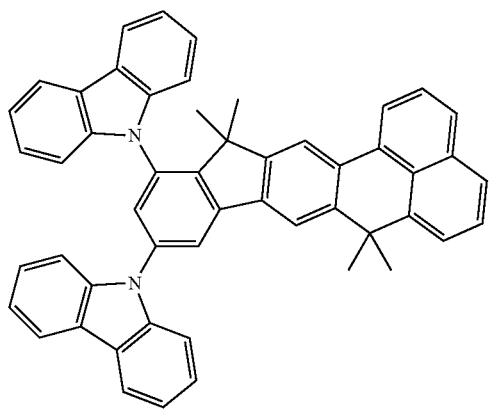 [SMILES: CC1(C)c2cc3c(cc2-c2cc(-n4c5ccccc5c5ccccc54)cc(-n4c5ccccc5c5ccccc54)c21)C(C)(C)c1cccc2cccc-3c12]
(86)
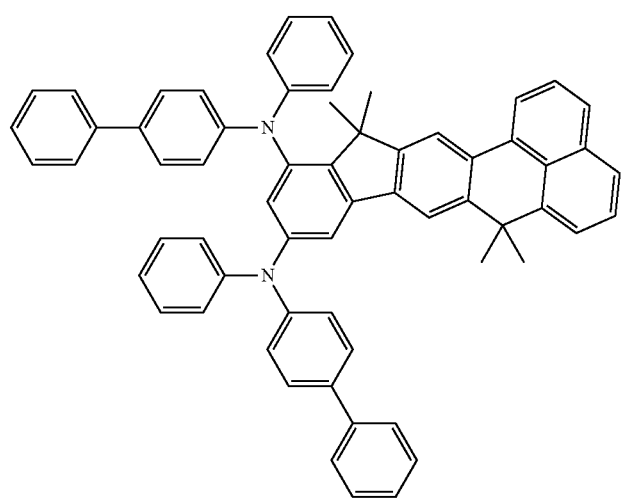 [SMILES: CC1(C)c2cc3c(cc2-c2cc(N(c4ccccc4)c4ccc(-c5ccccc5)cc4)cc(N(c4ccccc4)c4ccc(-c5ccccc5)cc4)c21)C(C)(C)c1cccc2cccc-3c12]

(87)
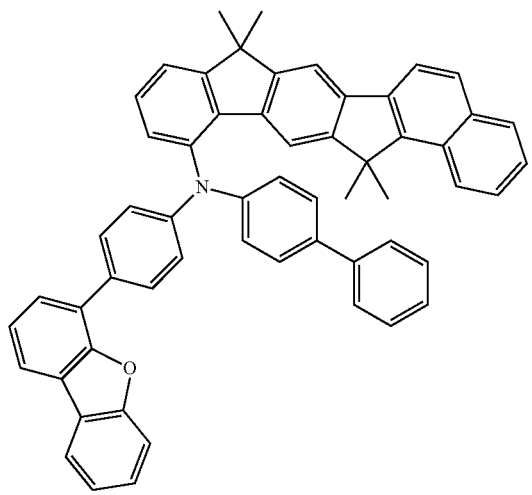 [SMILES: CC1(C)c2cc3c(cc2-c2c(N(c4ccc(-c5ccccc5)cc4)c4ccc(-c5cccc6c5oc5ccccc56)cc4)cccc21)C(C)(C)c1c-3ccc2ccccc12]
(88)
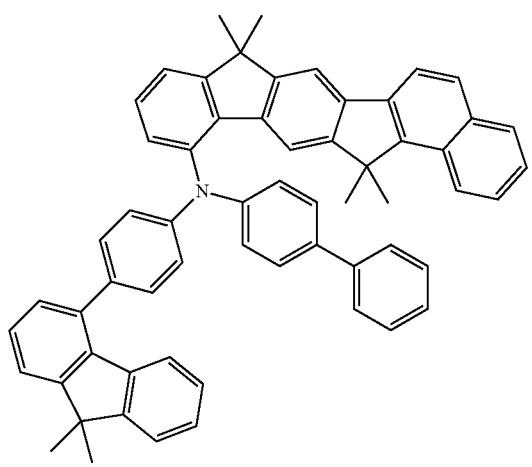 [SMILES: CC1(C)c2ccccc2-c2c(-c3ccc(N(c4ccc(-c5ccccc5)cc4)c4cccc5c4-c4cc6c(cc4C5(C)C)-c4ccc5ccccc5c4C6(C)C)cc3)cccc21]
(89)
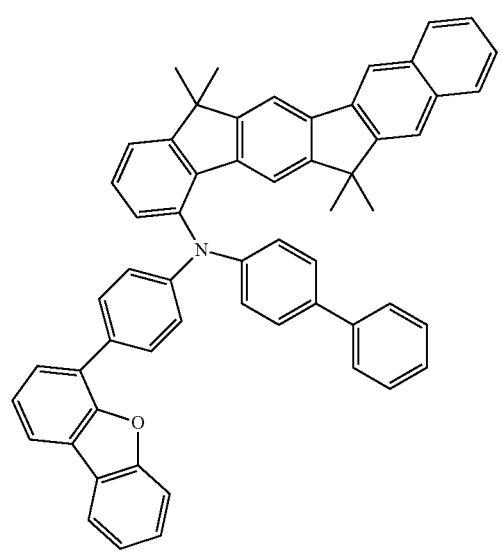 [SMILES: CC1(C)c2cc3c(cc2-c2cc4ccccc4cc21)C(C)(C)c1cccc(N(c2ccc(-c4ccccc4)cc2)c2ccc(-c4cccc5c4oc4ccccc45)cc2)c1-3]

-continued
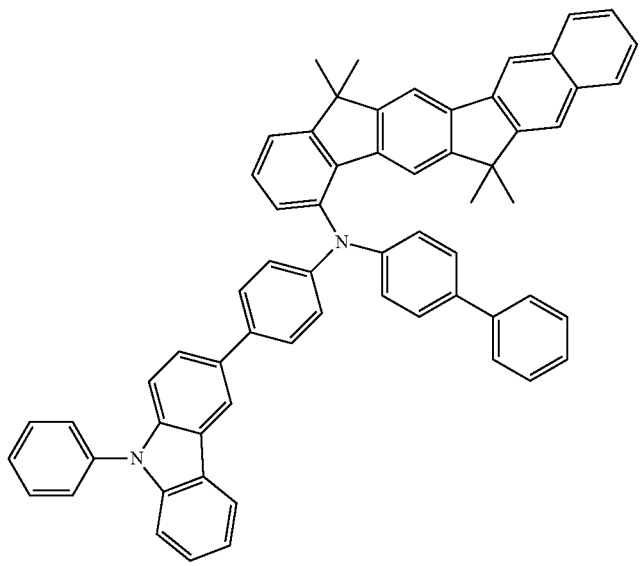 [SMILES: CC1(C)c2cc3c(cc2-c2cc4ccccc4cc21)C(C)(C)c1cccc(N(c2ccc(-c4ccccc4)cc2)c2ccc(-c4ccc5c(c4)c4ccccc4n5-c4ccccc4)cc2)c1-3]
(90)
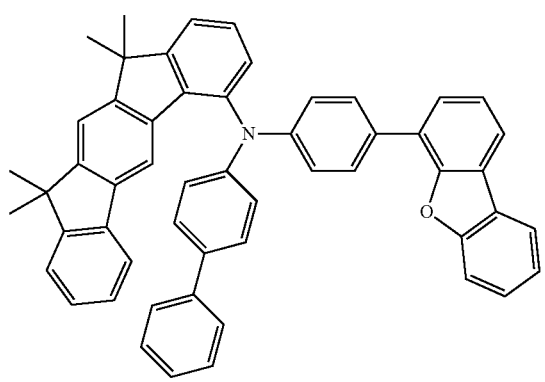 [SMILES: CC1(C)c2ccccc2-c2cc3c(cc21)C(C)(C)c1cccc(N(c2ccc(-c4ccccc4)cc2)c2ccc(-c4cccc5c4oc4ccccc45)cc2)c1-3]
(91)
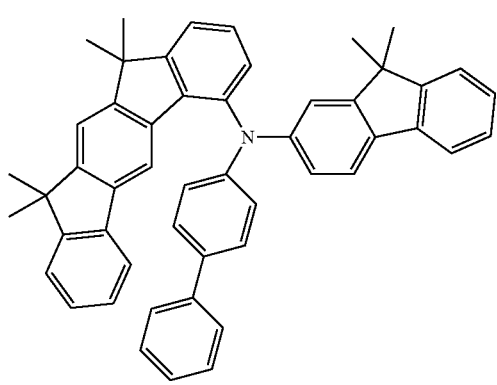 [SMILES: CC1(C)c2ccccc2-c2ccc(N(c3ccc(-c4ccccc4)cc3)c3cccc4c3-c3cc5c(cc3C4(C)C)C(C)(C)c3ccccc3-5)cc21]
(92)

-continued
(93)
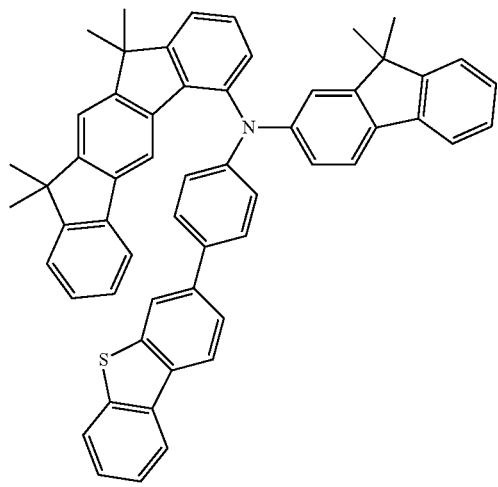 [SMILES: CC1(C)c2ccccc2-c2ccc(N(c3ccc(-c4ccc5c(c4)sc4ccccc45)cc3)c3cccc4c3-c3cc5c(cc3C4(C)C)C(C)(C)c3ccccc3-5)cc21]
(94)
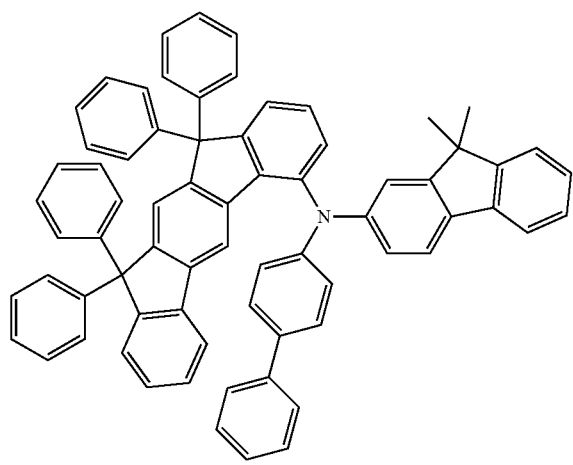 [SMILES: CC1(C)c2ccccc2-c2ccc(N(c3ccc(-c4ccccc4)cc3)c3cccc4c3-c3cc5c(cc3C4(c3ccccc3)c3ccccc3)C(c3ccccc3)(c3ccccc3)c3ccccc3-5)cc21]
(95)
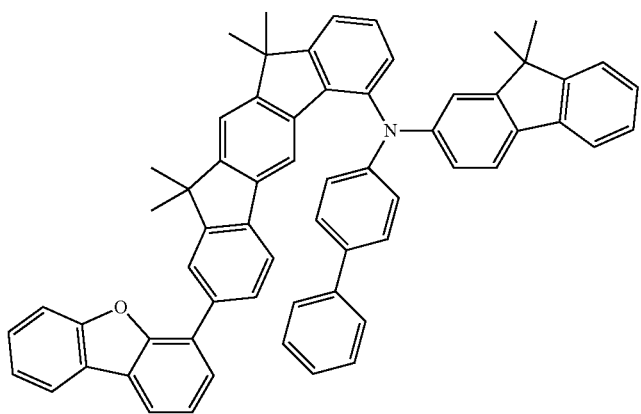 [SMILES: CC1(C)c2ccccc2-c2ccc(N(c3ccc(-c4ccccc4)cc3)c3cccc4c3-c3cc5c(cc3C4(C)C)C(C)(C)c3cc(-c4cccc6c4oc4ccccc46)ccc3-5)cc21]

-continued
(96)
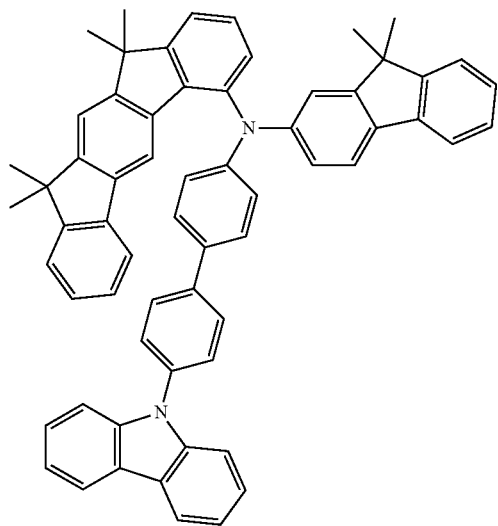 [SMILES: CC1(C)c2ccccc2-c2ccc(N(c3ccc(-c4ccc(-n5c6ccccc6c6ccccc65)cc4)cc3)c3cccc4c3-c3cc5c(cc3C4(C)C)C(C)(C)c3ccccc3-5)cc21]
(97)
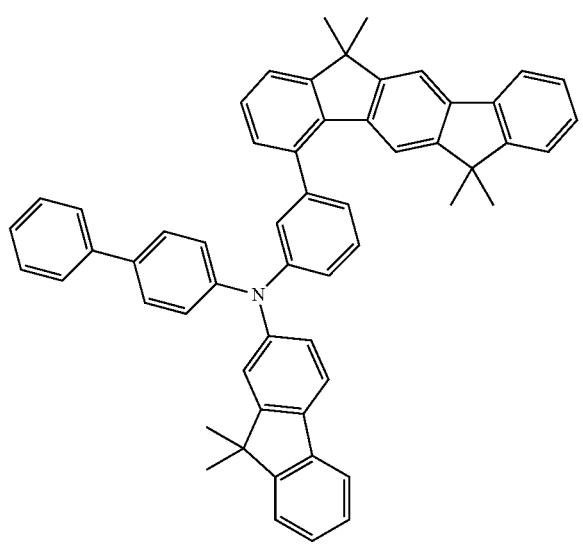 [SMILES: CC1(C)c2ccccc2-c2ccc(N(c3ccc(-c4ccccc4)cc3)c3cccc(-c4cccc5c4-c4cc6c(cc4C5(C)C)-c4ccccc4C6(C)C)c3)cc21]
(98)
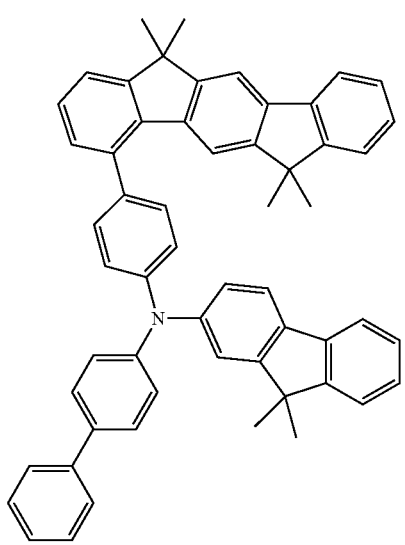 [SMILES: CC1(C)c2ccccc2-c2ccc(N(c3ccc(-c4ccccc4)cc3)c3ccc(-c4cccc5c4-c4cc6c(cc4C5(C)C)-c4ccccc4C6(C)C)cc3)cc21]

-continued
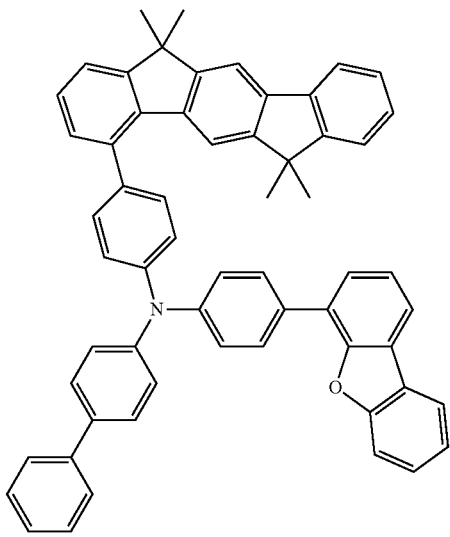 [SMILES: CC1(C)c2ccccc2-c2cc3c(cc21)-c1c(-c2ccc(N(c4ccc(-c5ccccc5)cc4)c4ccc(-c5cccc6c5oc5ccccc56)cc4)cc2)cccc1C3(C)C]
(99)
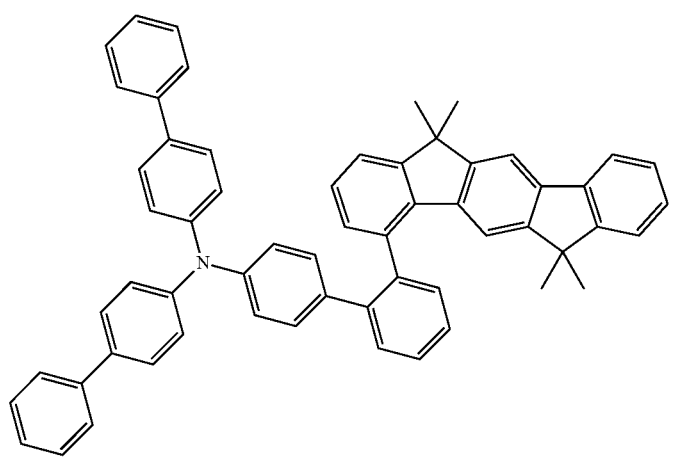 [SMILES: CC1(C)c2ccccc2-c2cc3c(cc21)-c1c(-c2ccccc2-c2ccc(N(c4ccc(-c5ccccc5)cc4)c4ccc(-c5ccccc5)cc4)cc2)cccc1C3(C)C]
(100)
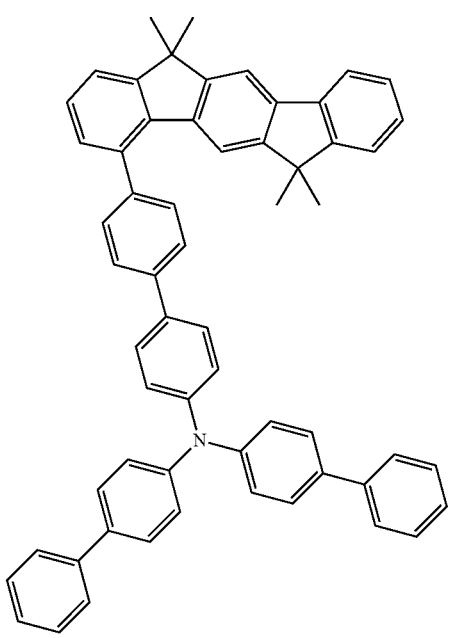 [SMILES: CC1(C)c2ccccc2-c2cc3c(cc21)-c1c(-c2ccc(-c4ccc(N(c5ccc(-c6ccccc6)cc5)c5ccc(-c6ccccc6)cc5)cc4)cc2)cccc1C3(C)C]
(101)

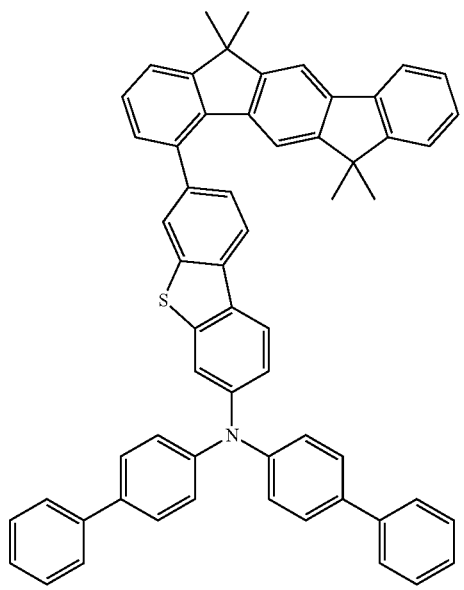 [SMILES: CC1(C)c2ccccc2-c2cc3c(cc21)-c1c(-c2ccc4c(c2)sc2cc(N(c5ccc(-c6ccccc6)cc5)c5ccc(-c6ccccc6)cc5)ccc24)cccc1C3(C)C]
(102)
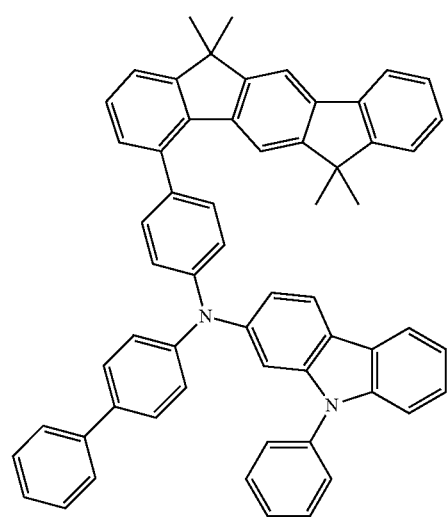 [SMILES: CC1(C)c2ccccc2-c2cc3c(cc21)-c1c(-c2ccc(N(c4ccc(-c5ccccc5)cc4)c4ccc5c6ccccc6n(-c6ccccc6)c5c4)cc2)cccc1C3(C)C]
(103)

-continued
(104)
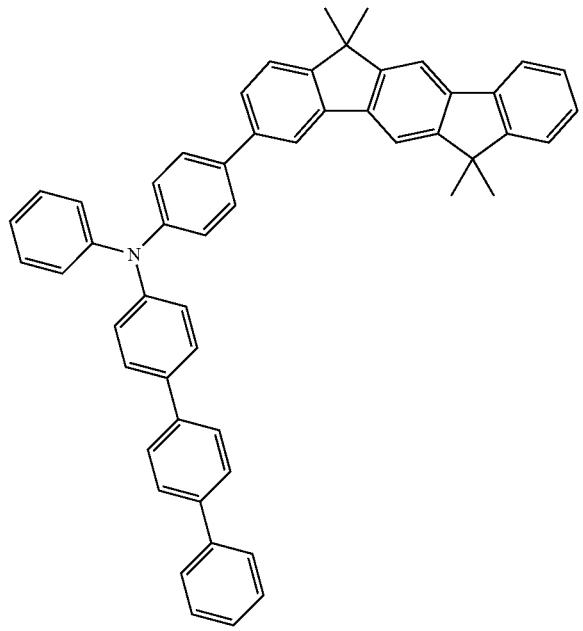 [SMILES: CC1(C)c2ccccc2-c2cc3c(cc21)-c1cc(-c2ccc(N(c4ccccc4)c4ccc(-c5ccc(-c6ccccc6)cc5)cc4)cc2)ccc1C3(C)C]
(105)
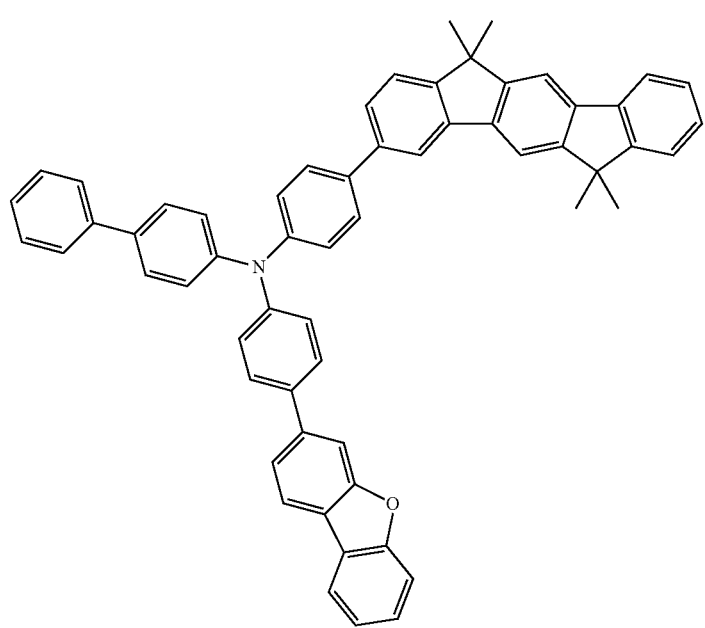 [SMILES: CC1(C)c2ccccc2-c2cc3c(cc21)-c1cc(-c2ccc(N(c4ccc(-c5ccccc5)cc4)c4ccc(-c5ccc6c(c5)oc5ccccc56)cc4)cc2)ccc1C3(C)C]

(106)
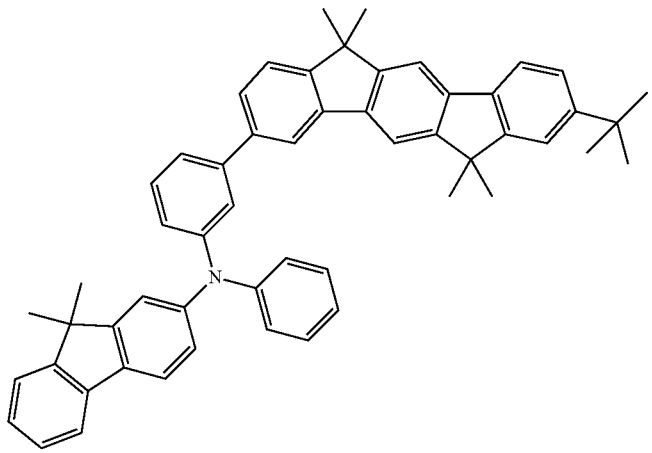 [SMILES: CC(C)(C)c1ccc2c(c1)C(C)(C)c1cc3c(cc1-2)C(C)(C)c1ccc(-c2cccc(N(c4ccccc4)c4ccc5c(c4)C(C)(C)c4ccccc4-5)c2)cc1-3]
(107)
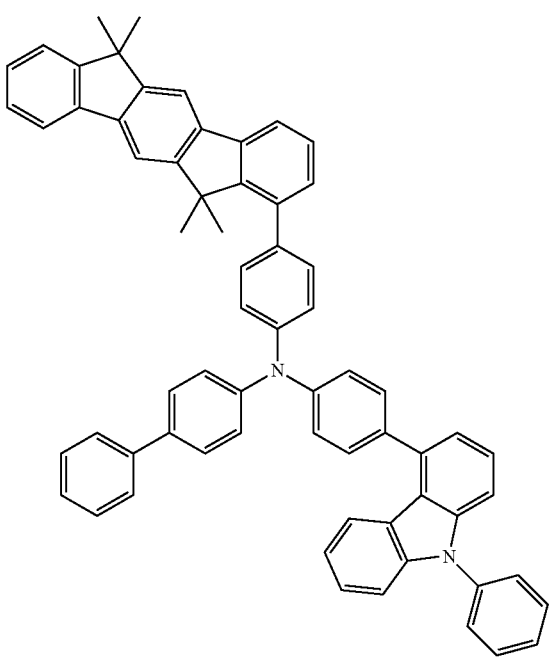 [SMILES: CC1(C)c2ccccc2-c2cc3c(cc21)-c1cccc(-c2ccc(N(c4ccc(-c5ccccc5)cc4)c4ccc(-c5cccc6c5c5ccccc5n6-c5ccccc5)cc4)cc2)c1C3(C)C]
(108)
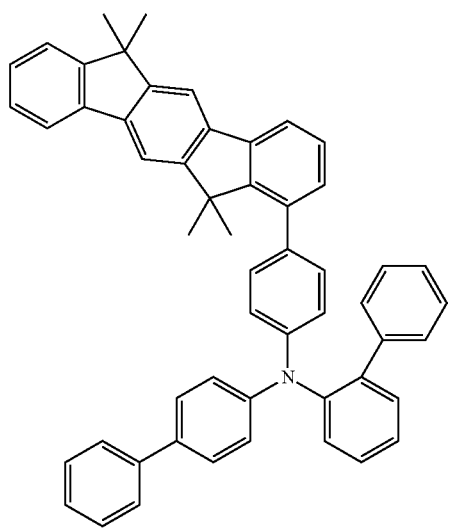 [SMILES: CC1(C)c2ccccc2-c2cc3c(cc21)-c1cccc(-c2ccc(N(c4ccc(-c5ccccc5)cc4)c4ccccc4-c4ccccc4)cc2)c1C3(C)C]

-continued
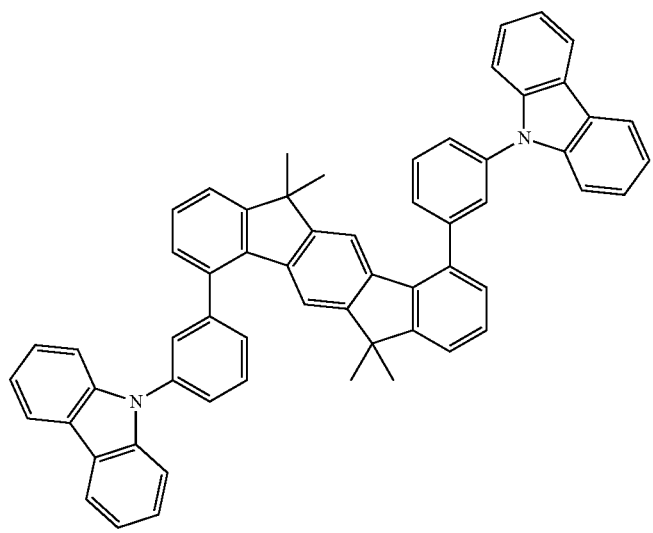 [SMILES: CC1(C)c2cc3c(cc2-c2c(-c4cccc(-n5c6ccccc6c6ccccc65)c4)cccc21)C(C)(C)c1cccc(-c2cccc(-n4c5ccccc5c5ccccc54)c2)c1-3]
(109)
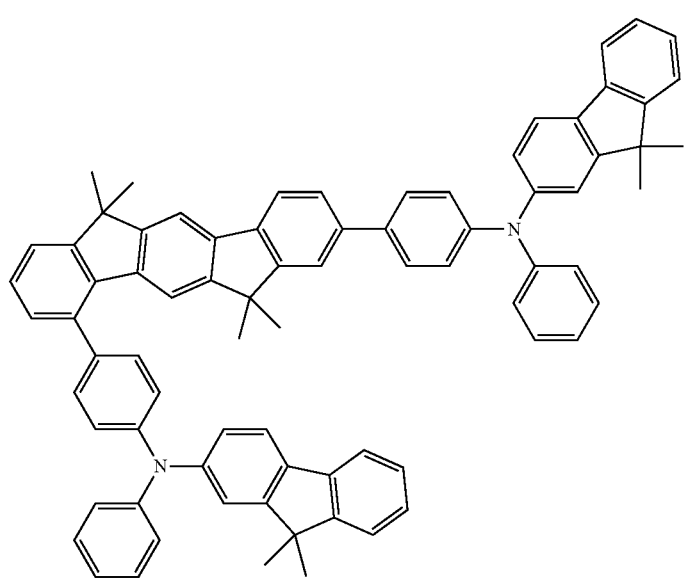 [SMILES: CC1(C)c2ccccc2-c2ccc(N(c3ccccc3)c3ccc(-c4ccc5c(c4)C(C)(C)c4cc6c(cc4-5)C(C)(C)c4cccc(-c5ccc(N(c7ccccc7)c7ccc8c(c7)C(C)(C)c7ccccc7-8)cc5)c4-6)cc3)cc21]
(110)
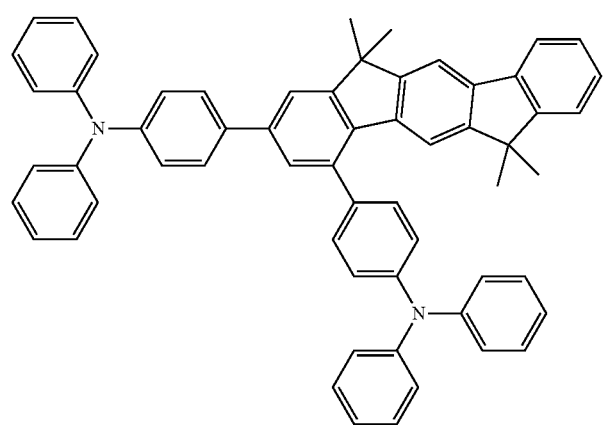 [SMILES: CC1(C)c2ccccc2-c2cc3c(cc21)-c1c(-c2ccc(N(c4ccccc4)c4ccccc4)cc2)cc(-c2ccc(N(c4ccccc4)c4ccccc4)cc2)cc1C3(C)C]
(111)

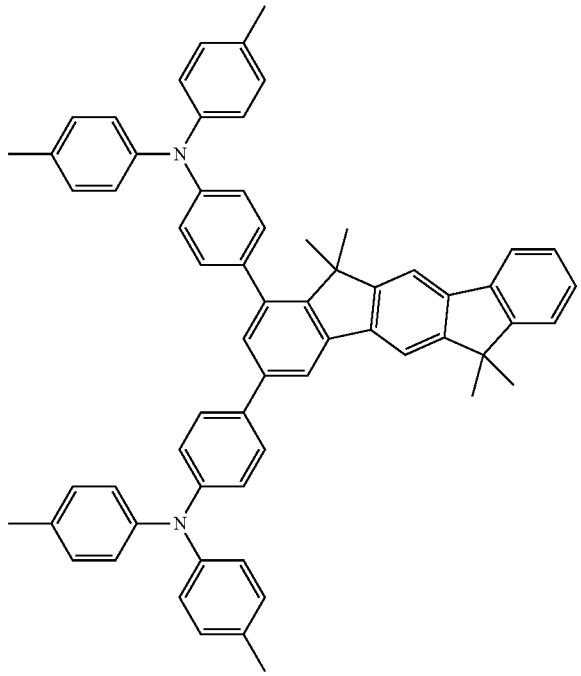 [SMILES: Cc1ccc(N(c2ccc(C)cc2)c2ccc(-c3cc(-c4ccc(N(c5ccc(C)cc5)c5ccc(C)cc5)cc4)c4c(c3)-c3cc5c(cc3C4(C)C)-c3ccccc3C5(C)C)cc2)cc1]
(112)
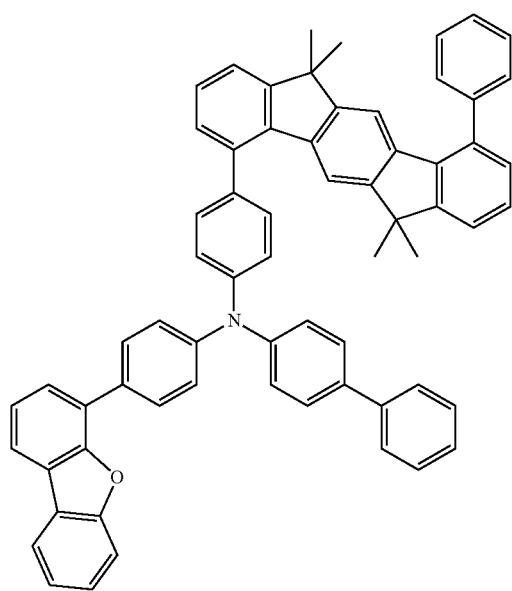 [SMILES: CC1(C)c2cc3c(cc2-c2c(-c4ccccc4)cccc21)C(C)(C)c1cccc(-c2ccc(N(c4ccc(-c5ccccc5)cc4)c4ccc(-c5cccc6c5oc5ccccc56)cc4)cc2)c1-3]
(113)

(114)
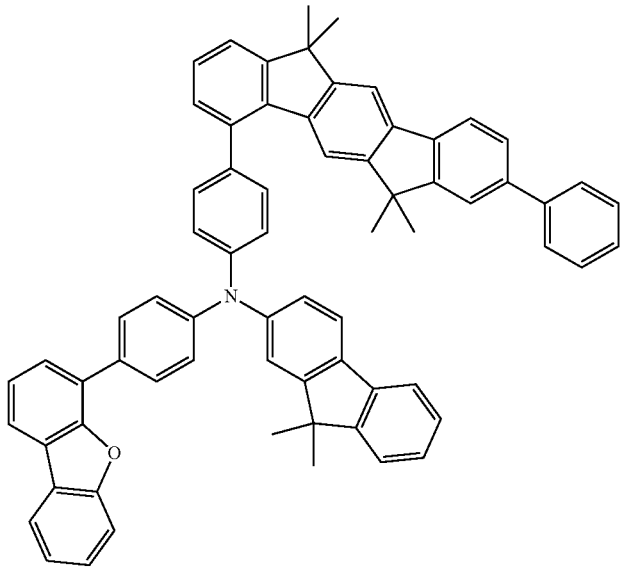 [SMILES: CC1(C)c2ccccc2-c2ccc(N(c3ccc(-c4cccc5c4-c4cc6c(cc4C5(C)C)-c4ccc(-c5ccccc5)cc4C6(C)C)cc3)c3ccc(-c4cccc5c4oc4ccccc45)cc3)cc21]
(115)
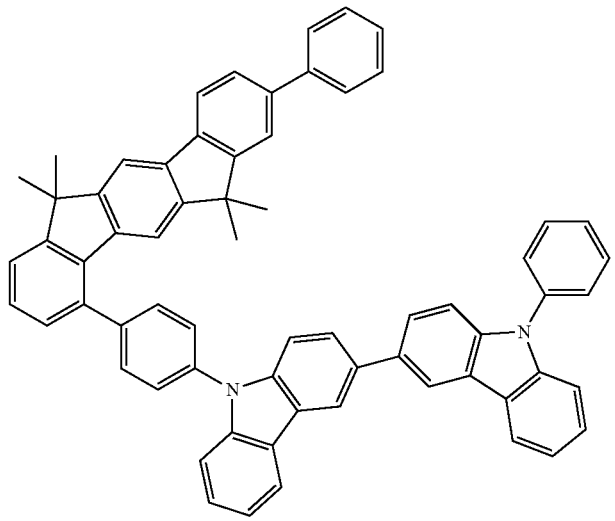 [SMILES: CC1(C)c2cc(-c3ccccc3)ccc2-c2cc3c(cc21)-c1c(-c2ccc(-n4c5ccccc5c5cc(-c6ccc7c(c6)c6ccccc6n7-c6ccccc6)ccc54)cc2)cccc1C3(C)C]

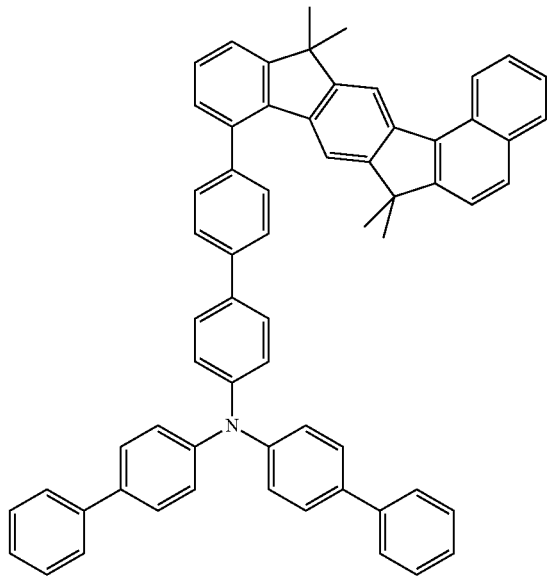 [SMILES: CC1(C)c2cc3c(cc2-c2c(-c4ccc(-c5ccc(N(c6ccc(-c7ccccc7)cc6)c6ccc(-c7ccccc7)cc6)cc5)cc4)cccc21)C(C)(C)c1ccc2ccccc2c1-3]
(116)
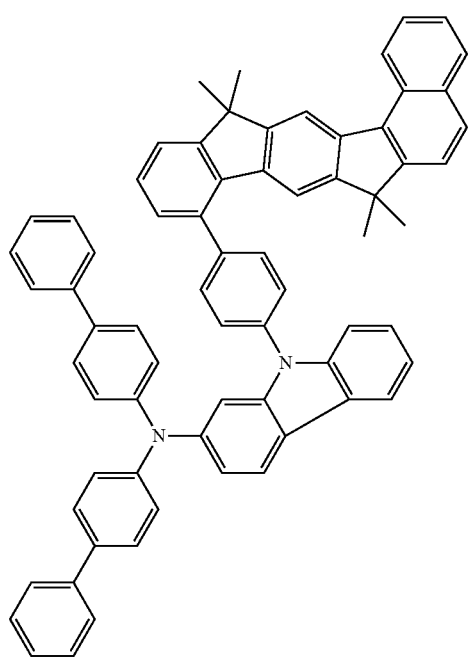 [SMILES: CC1(C)c2cc3c(cc2-c2c(-c4ccc(-n5c6ccccc6c6ccc(N(c7ccc(-c8ccccc8)cc7)c7ccc(-c8ccccc8)cc7)cc65)cc4)cccc21)C(C)(C)c1ccc2ccccc2c1-3]
(117)

-continued
(118)
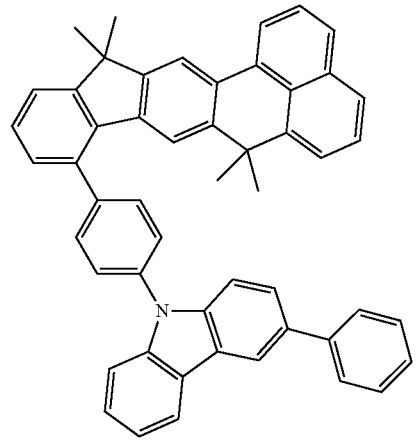 [SMILES: CC1(C)c2cc3c(cc2-c2c(-c4ccc(-n5c6ccccc6c6cc(-c7ccccc7)ccc65)cc4)cccc21)C(C)(C)c1cccc2cccc-3c12]
(119)
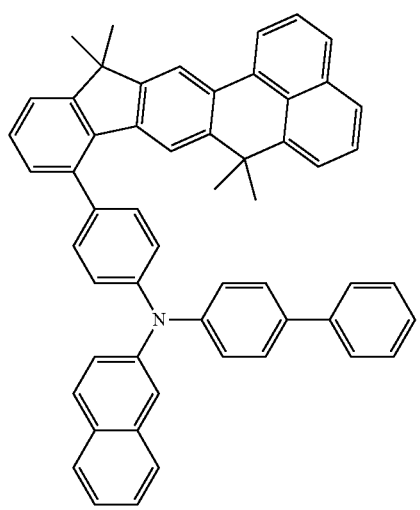 [SMILES: CC1(C)c2cc3c(cc2-c2c(-c4ccc(N(c5ccc(-c6ccccc6)cc5)c5ccc6ccccc6c5)cc4)cccc21)C(C)(C)c1cccc2cccc-3c12]
(120)
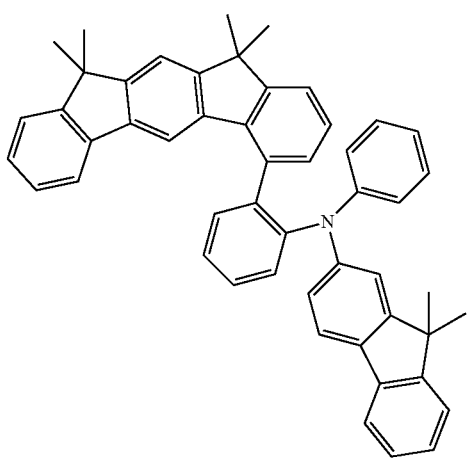 [SMILES: CC1(C)c2ccccc2-c2ccc(N(c3ccccc3)c3ccccc3-c3cccc4c3-c3cc5c(cc3C4(C)C)C(C)(C)c3ccccc3-5)cc21]

(121)
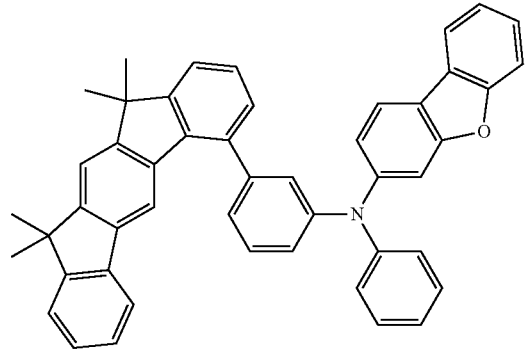 [SMILES: CC1(C)c2ccccc2-c2cc3c(cc21)C(C)(C)c1cccc(-c2cccc(N(c4ccccc4)c4ccc5c(c4)oc4ccccc45)c2)c1-3]
(122)
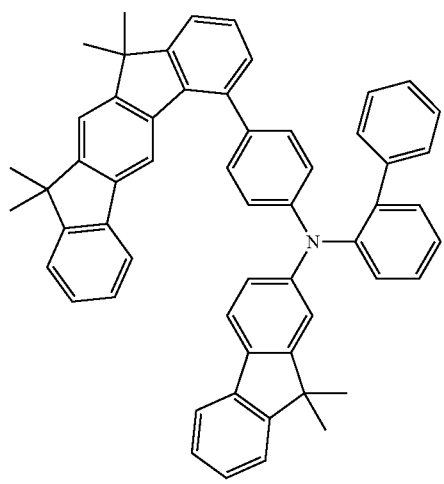 [SMILES: CC1(C)c2ccccc2-c2ccc(N(c3ccc(-c4cccc5c4-c4cc6c(cc4C5(C)C)C(C)(C)c4ccccc4-6)cc3)c3ccccc3-c3ccccc3)cc21]
(123)
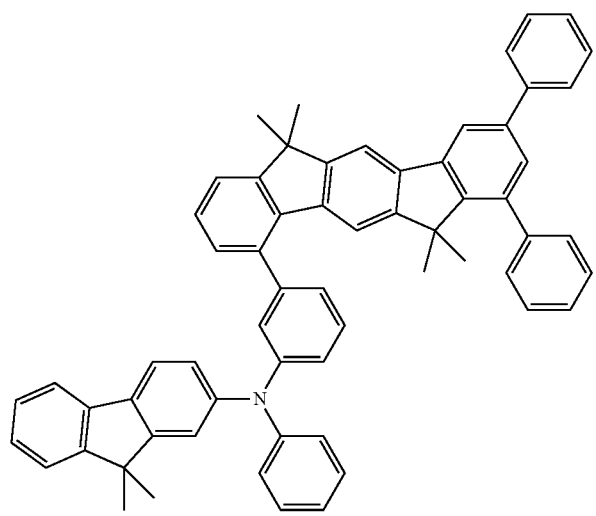 [SMILES: CC1(C)c2ccccc2-c2ccc(N(c3ccccc3)c3cccc(-c4cccc5c4-c4cc6c(cc4C5(C)C)-c4cc(-c5ccccc5)cc(-c5ccccc5)c4C6(C)C)c3)cc21]

(124)
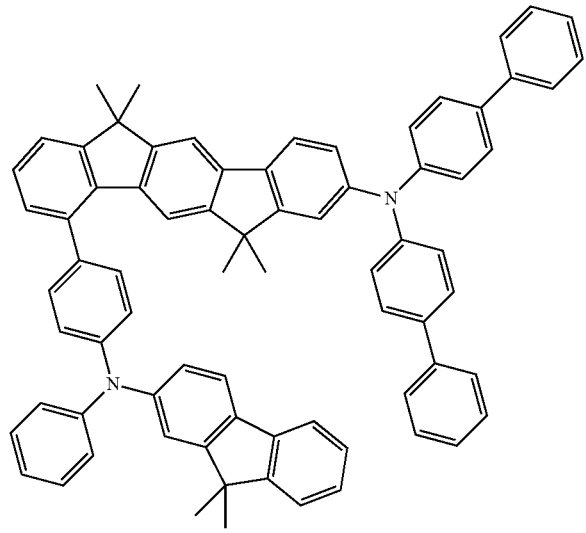 [SMILES: CC1(C)c2ccccc2-c2ccc(N(c3ccccc3)c3ccc(-c4cccc5c4-c4cc6c(cc4C5(C)C)-c4ccc(N(c5ccc(-c7ccccc7)cc5)c5ccc(-c7ccccc7)cc5)cc4C6(C)C)cc3)cc21]
(125)
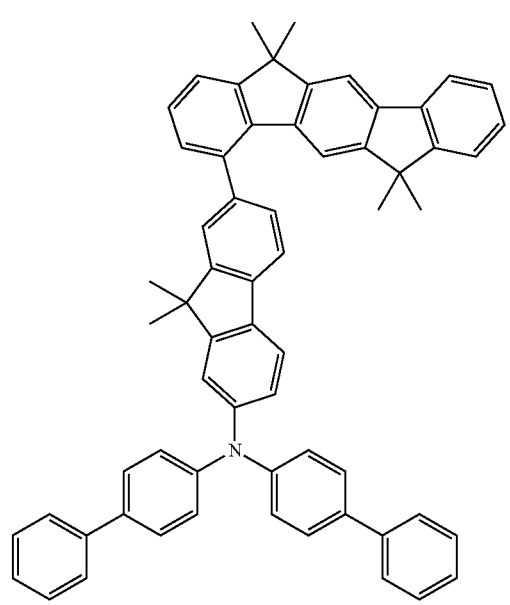 [SMILES: CC1(C)c2cc(-c3cccc4c3-c3cc5c(cc3C4(C)C)-c3ccccc3C5(C)C)ccc2-c2ccc(N(c3ccc(-c4ccccc4)cc3)c3ccc(-c4ccccc4)cc3)cc21]

(126)
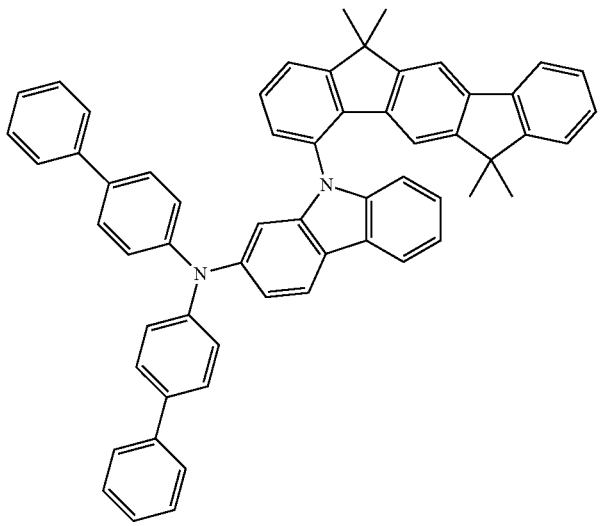 [SMILES: CC1(C)c2ccccc2-c2cc3c(cc21)-c1c(-n2c4ccccc4c4ccc(N(c5ccc(-c6ccccc6)cc5)c5ccc(-c6ccccc6)cc5)cc42)cccc1C3(C)C]
(127)
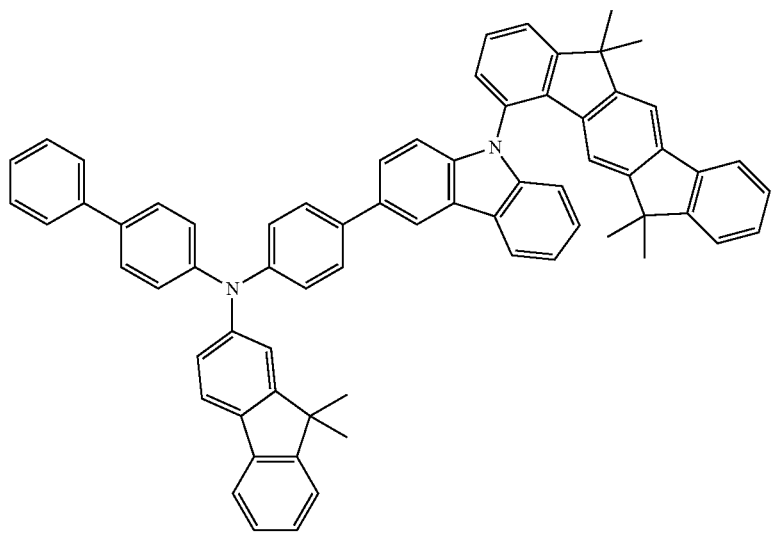 [SMILES: CC1(C)c2ccccc2-c2ccc(N(c3ccc(-c4ccccc4)cc3)c3ccc(-c4ccc5c(c4)c4ccccc4n5-c4cccc5c4-c4cc6c(cc4C5(C)C)-c4ccccc4C6(C)C)cc3)cc21]
(128)
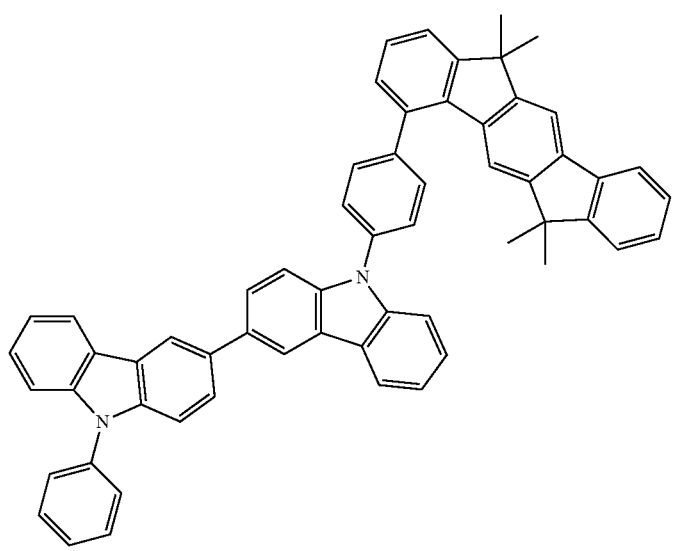 [SMILES: CC1(C)c2ccccc2-c2cc3c(cc21)-c1c(-c2ccc(-n4c5ccccc5c5cc(-c6ccc7c(c6)c6ccccc6n7-c6ccccc6)ccc54)cc2)cccc1C3(C)C]

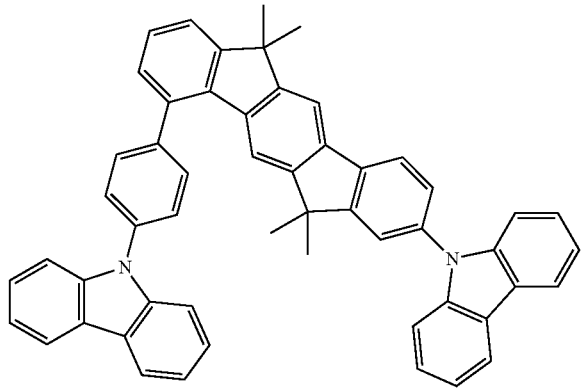 [SMILES: CC1(C)c2cc(-n3c4ccccc4c4ccccc43)ccc2-c2cc3c(cc21)-c1c(-c2ccc(-n4c5ccccc5c5ccccc54)cc2)cccc1C3(C)C]
(129)
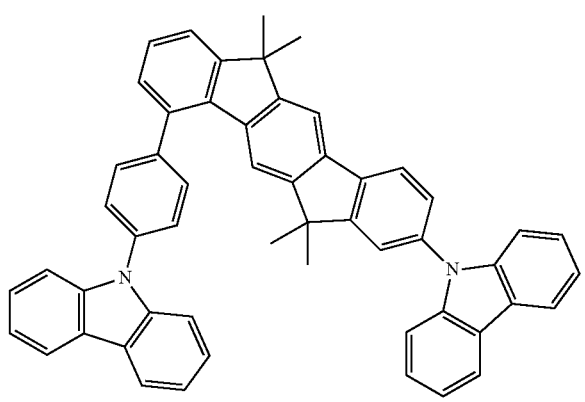 [SMILES: CC1(C)c2cc(-n3c4ccccc4c4ccccc43)ccc2-c2cc3c(cc21)-c1c(-c2ccc(-n4c5ccccc5c5ccccc54)cc2)cccc1C3(C)C]
(130)
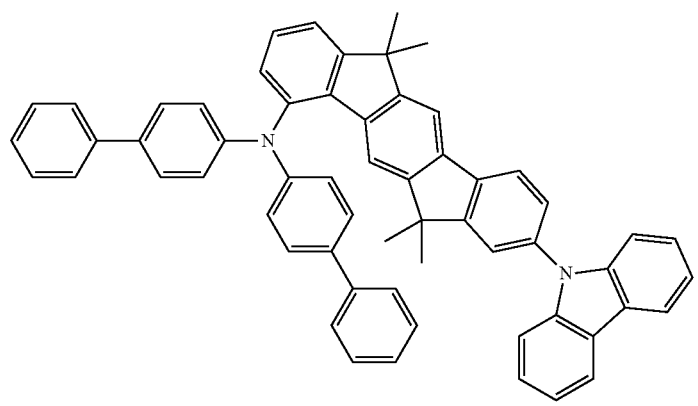 [SMILES: CC1(C)c2cc(-n3c4ccccc4c4ccccc43)ccc2-c2cc3c(cc21)-c1c(N(c2ccc(-c4ccccc4)cc2)c2ccc(-c4ccccc4)cc2)cccc1C3(C)C]
(131)

-continued
(132)
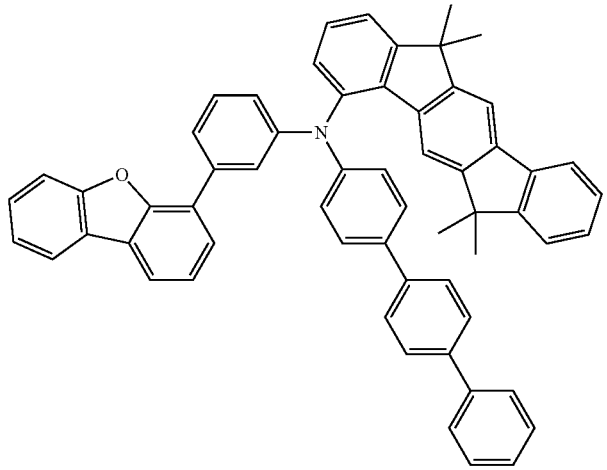 [SMILES: CC1(C)c2ccccc2-c2cc3c(cc21)-c1c(N(c2ccc(-c4ccc(-c5ccccc5)cc4)cc2)c2cccc(-c4cccc5c4oc4ccccc45)c2)cccc1C3(C)C]
(133)
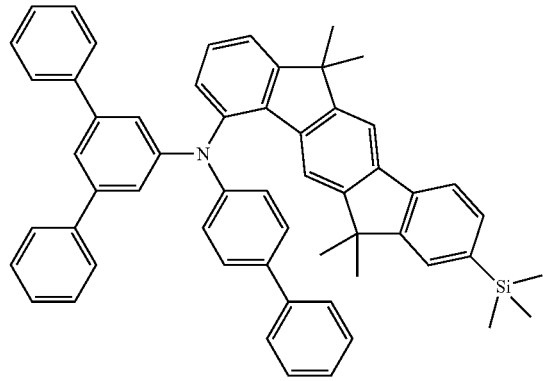 [SMILES: CC1(C)c2cc([Si](C)(C)C)ccc2-c2cc3c(cc21)-c1c(N(c2ccc(-c4ccccc4)cc2)c2cc(-c4ccccc4)cc(-c4ccccc4)c2)cccc1C3(C)C]
(134)
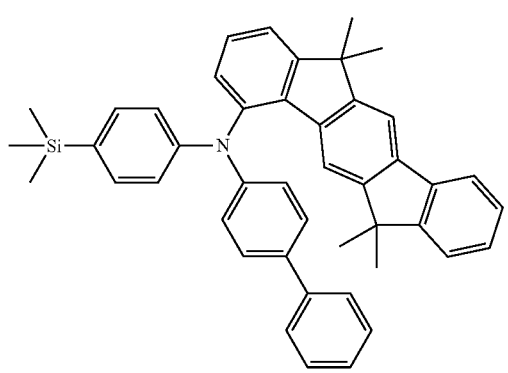 [SMILES: CC1(C)c2ccccc2-c2cc3c(cc21)-c1c(N(c2ccc(-c4ccccc4)cc2)c2ccc([Si](C)(C)C)cc2)cccc1C3(C)C]
(135)
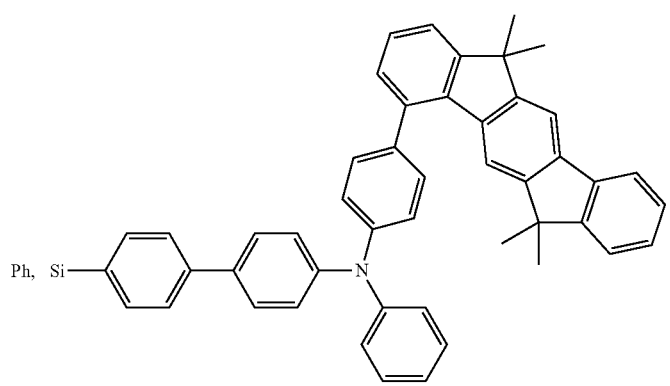

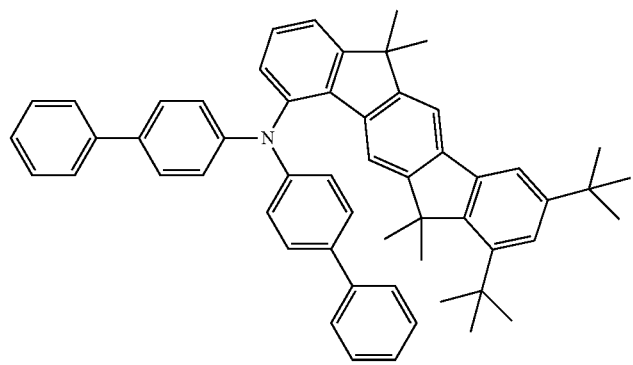 [SMILES: CC(C)(C)c1cc2c(c(C(C)(C)C)c1)C(C)(C)c1cc3c(cc1-2)C(C)(C)c1cccc(N(c2ccc(-c4ccccc4)cc2)c2ccc(-c4ccccc4)cc2)c1-3]
(136)
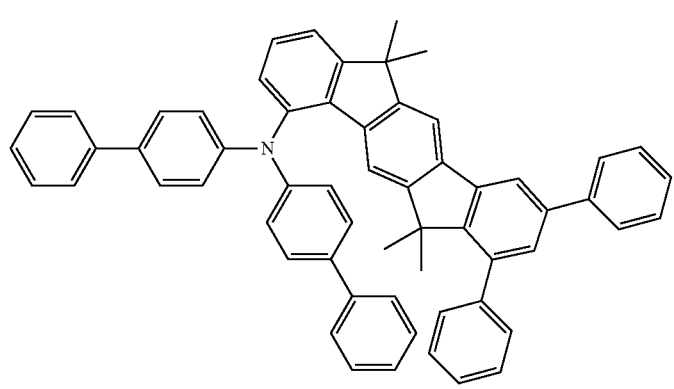 [SMILES: CC1(C)c2cc3c(cc2-c2c(N(c4ccc(-c5ccccc5)cc4)c4ccc(-c5ccccc5)cc4)cccc21)C(C)(C)c1c(-c2ccccc2)cc(-c2ccccc2)cc1-3]
(137)
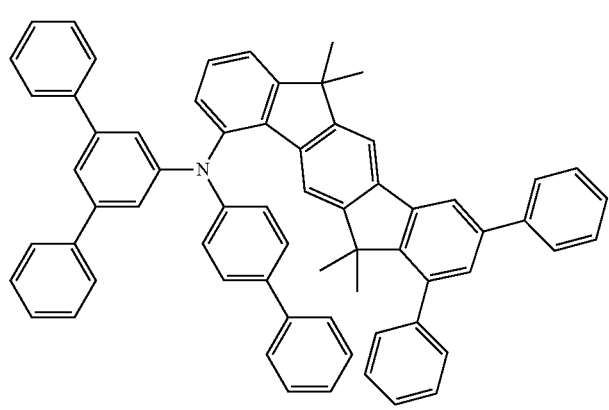 [SMILES: CC1(C)c2cc3c(cc2-c2c(N(c4ccc(-c5ccccc5)cc4)c4cc(-c5ccccc5)cc(-c5ccccc5)c4)cccc21)C(C)(C)c1c(-c2ccccc2)cc(-c2ccccc2)cc1-3]
(138)

-continued
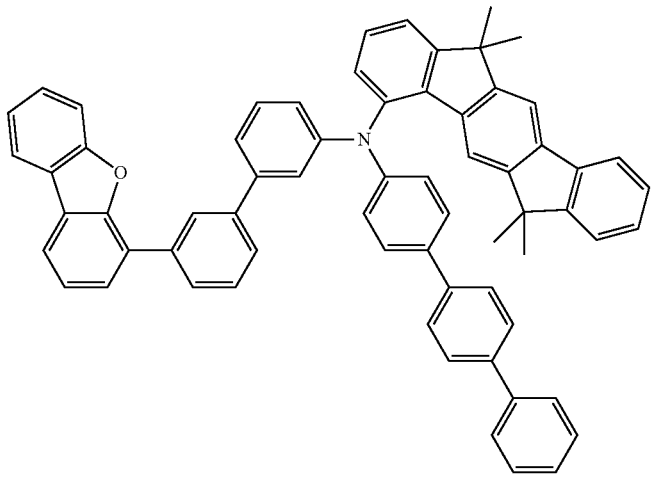 [SMILES: CC1(C)c2ccccc2-c2cc3c(cc21)-c1c(N(c2ccc(-c4ccc(-c5ccccc5)cc4)cc2)c2cccc(-c4cccc(-c5cccc6c5oc5ccccc56)c4)c2)cccc1C3(C)C]
(139)
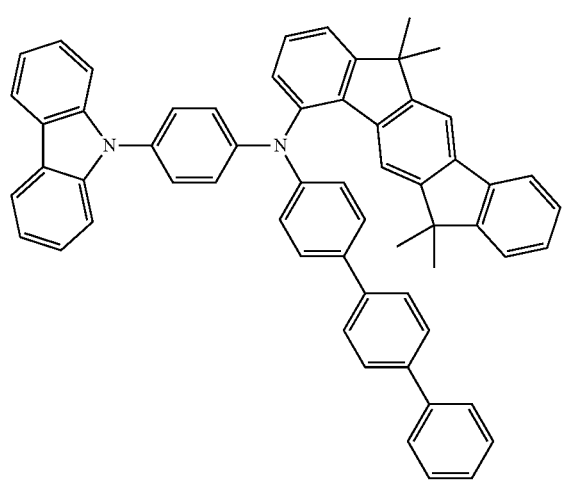 [SMILES: CC1(C)c2ccccc2-c2cc3c(cc21)-c1c(N(c2ccc(-c4ccc(-c5ccccc5)cc4)cc2)c2ccc(-n4c5ccccc5c5ccccc54)cc2)cccc1C3(C)C]
(140)
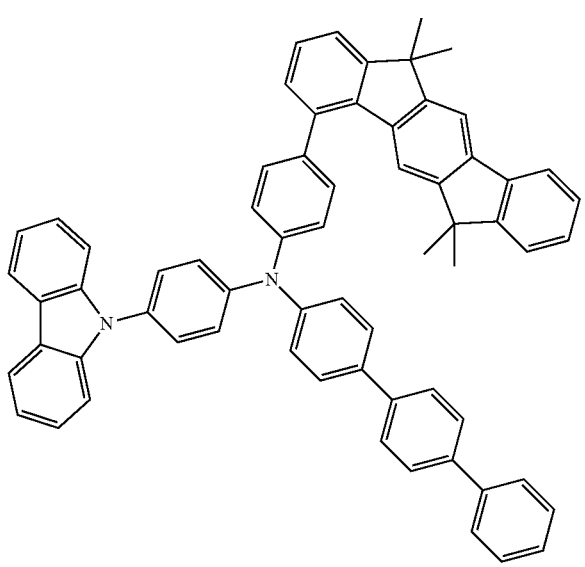 [SMILES: CC1(C)c2ccccc2-c2cc3c(cc21)-c1c(-c2ccc(N(c4ccc(-c5ccc(-c6ccccc6)cc5)cc4)c4ccc(-n5c6ccccc6c6ccccc65)cc4)cc2)cccc1C3(C)C]
(141)

(142)
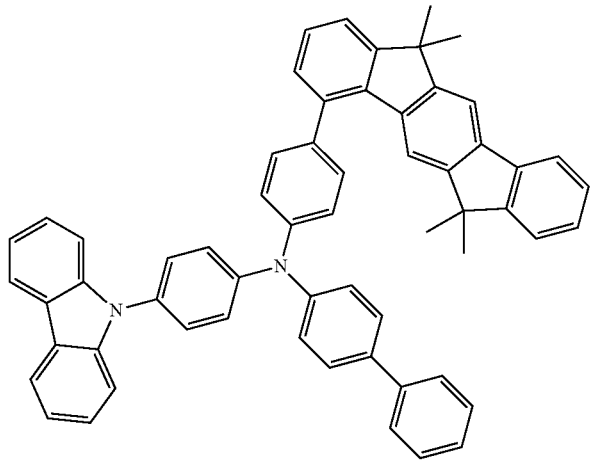 [SMILES: CC1(C)c2ccccc2-c2cc3c(cc21)-c1c(-c2ccc(N(c4ccc(-c5ccccc5)cc4)c4ccc(-n5c6ccccc6c6ccccc65)cc4)cc2)cccc1C3(C)C]
(143)
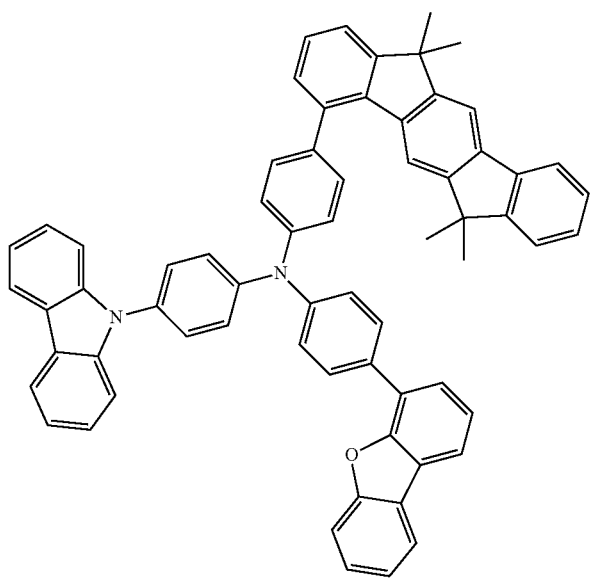 [SMILES: CC1(C)c2ccccc2-c2cc3c(cc21)-c1c(-c2ccc(N(c4ccc(-c5cccc6c5oc5ccccc56)cc4)c4ccc(-n5c6ccccc6c6ccccc65)cc4)cc2)cccc1C3(C)C]

-continued
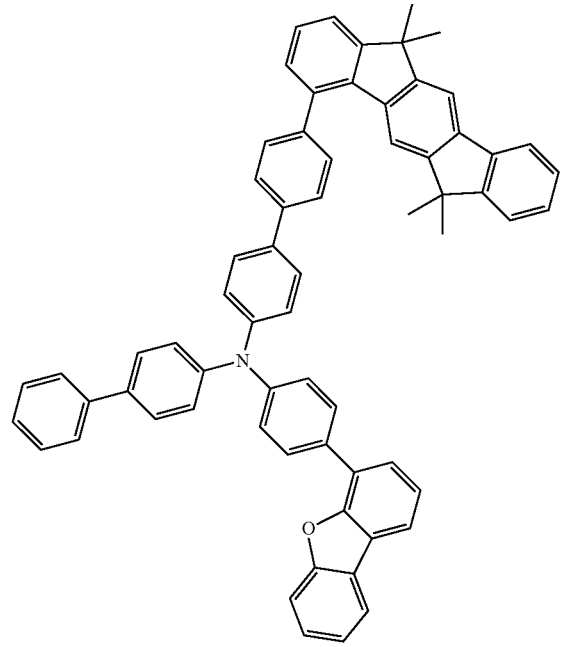 [SMILES: CC1(C)c2ccccc2-c2cc3c(cc21)-c1c(-c2ccc(-c4ccc(N(c5ccc(-c6ccccc6)cc5)c5ccc(-c6cccc7c6oc6ccccc67)cc5)cc4)cc2)cccc1C3(C)C]
(144)
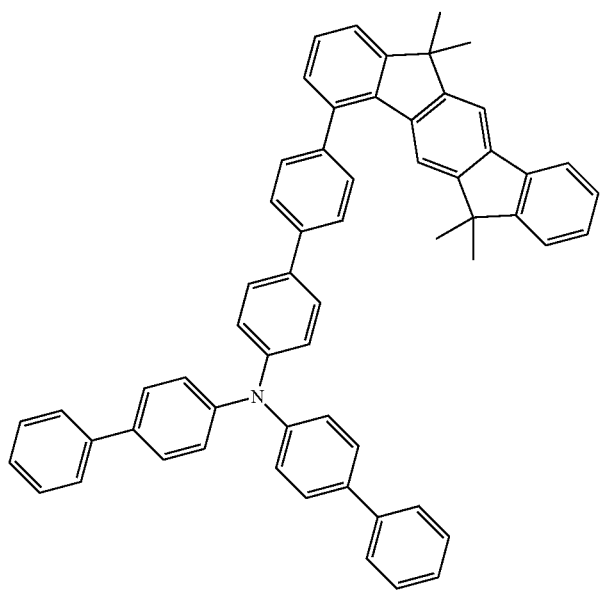 [SMILES: CC1(C)c2ccccc2-c2cc3c(cc21)-c1c(-c2ccc(-c4ccc(N(c5ccc(-c6ccccc6)cc5)c5ccc(-c6ccccc6)cc5)cc4)cc2)cccc1C3(C)C]
(145)

-continued
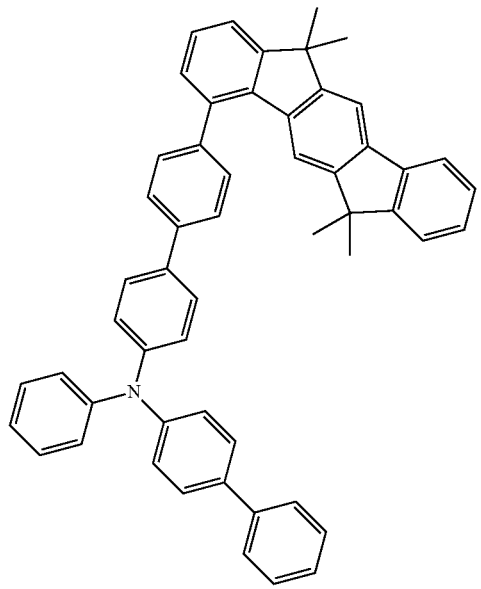 [SMILES: CC1(C)c2ccccc2-c2cc3c(cc21)-c1c(-c2ccc(-c4ccc(N(c5ccccc5)c5ccc(-c6ccccc6)cc5)cc4)cc2)cccc1C3(C)C]
(146)
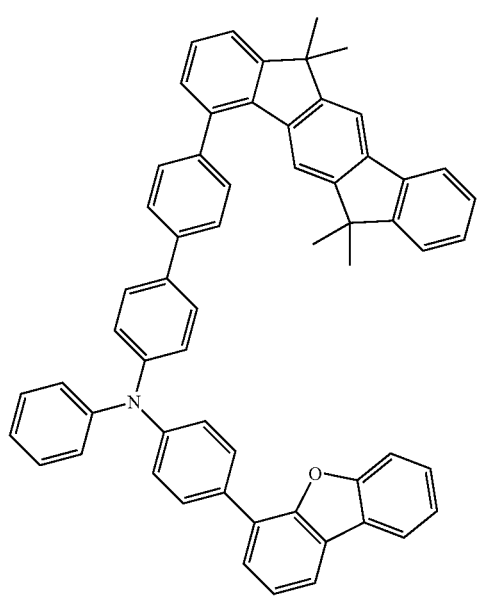 [SMILES: CC1(C)c2ccccc2-c2cc3c(cc21)-c1c(-c2ccc(-c4ccc(N(c5ccccc5)c5ccc(-c6cccc7c6oc6ccccc67)cc5)cc4)cc2)cccc1C3(C)C]
(147)

-continued
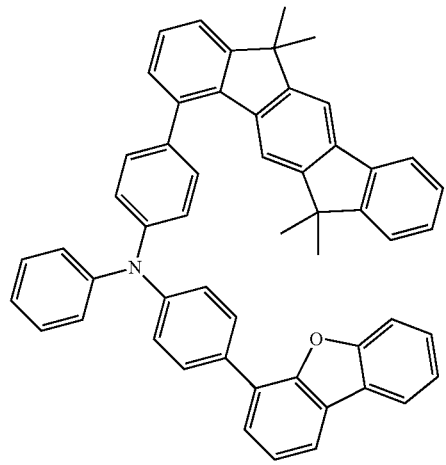 [SMILES: CC1(C)c2ccccc2-c2cc3c(cc21)-c1c(-c2ccc(N(c4ccccc4)c4ccc(-c5cccc6c5oc5ccccc56)cc4)cc2)cccc1C3(C)C]
(148)
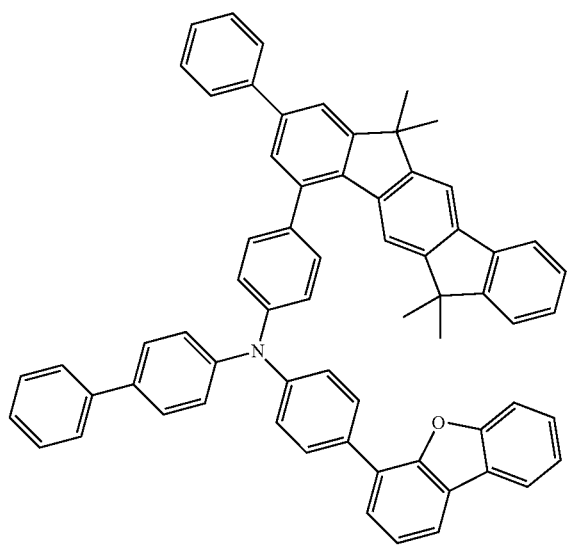 [SMILES: CC1(C)c2ccccc2-c2cc3c(cc21)-c1c(-c2ccc(N(c4ccc(-c5ccccc5)cc4)c4ccc(-c5cccc6c5oc5ccccc56)cc4)cc2)cc(-c2ccccc2)cc1C3(C)C]
(149)
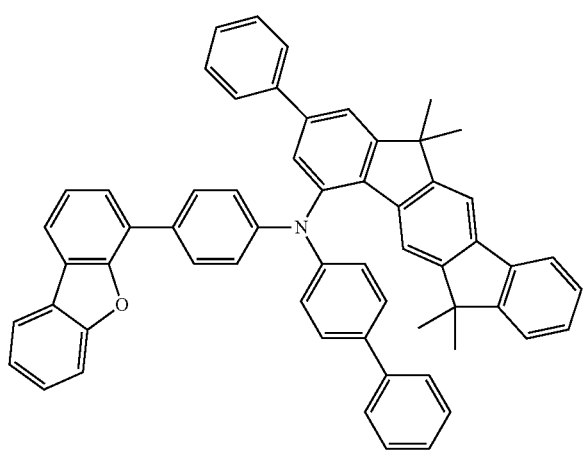 [SMILES: CC1(C)c2ccccc2-c2cc3c(cc21)-c1c(N(c2ccc(-c4ccccc4)cc2)c2ccc(-c4cccc5c4oc4ccccc45)cc2)cc(-c2ccccc2)cc1C3(C)C]
(150)

(151)
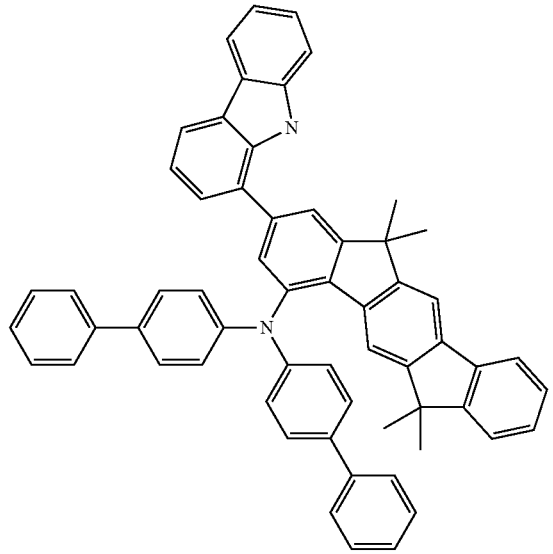 [SMILES: CC1(C)c2ccccc2-c2cc3c(cc21)-c1c(N(c2ccc(-c4ccccc4)cc2)c2ccc(-c4ccccc4)cc2)cc(-c2cccc4c2[nH]c2ccccc24)cc1C3(C)C]
(152)
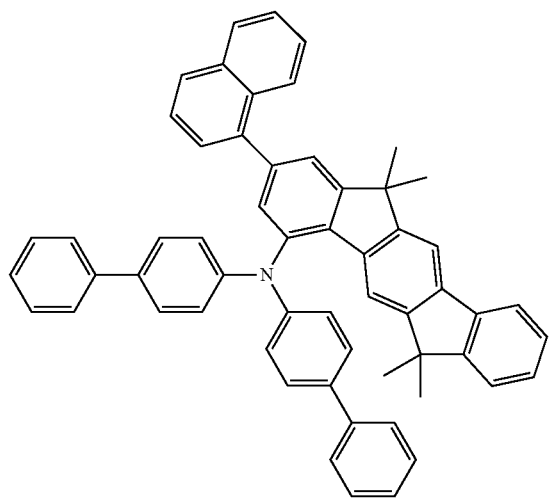 [SMILES: CC1(C)c2ccccc2-c2cc3c(cc21)-c1c(N(c2ccc(-c4ccccc4)cc2)c2ccc(-c4ccccc4)cc2)cc(-c2cccc4ccccc24)cc1C3(C)C]
(153)
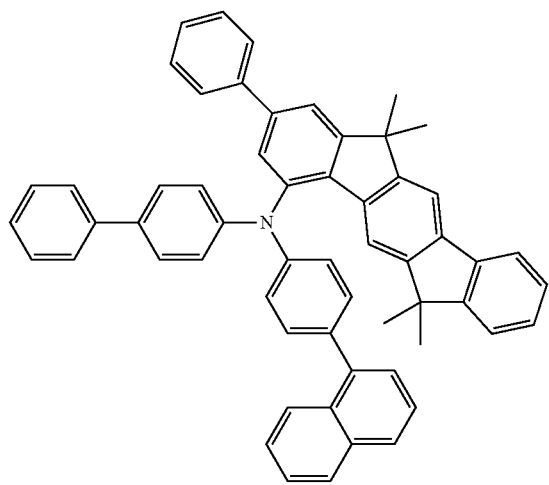 [SMILES: CC1(C)c2ccccc2-c2cc3c(cc21)-c1c(N(c2ccc(-c4ccccc4)cc2)c2ccc(-c4cccc5ccccc45)cc2)cc(-c2ccccc2)cc1C3(C)C]

-continued
(154)
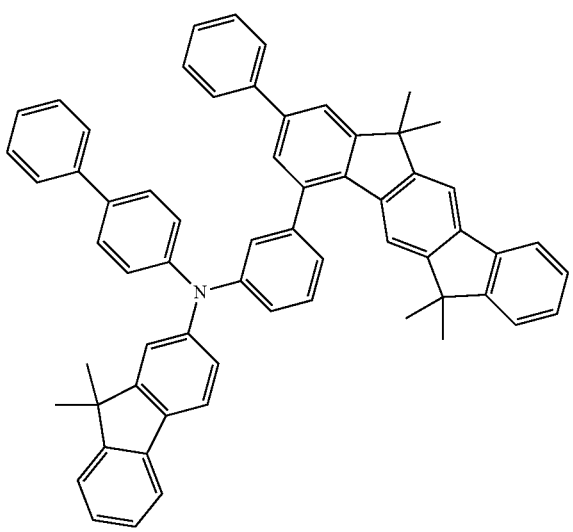 [SMILES: CC1(C)c2ccccc2-c2ccc(N(c3ccc(-c4ccccc4)cc3)c3cccc(-c4cc(-c5ccccc5)cc5c4-c4cc6c(cc4C5(C)C)-c4ccccc4C6(C)C)c3)cc21]
(155)
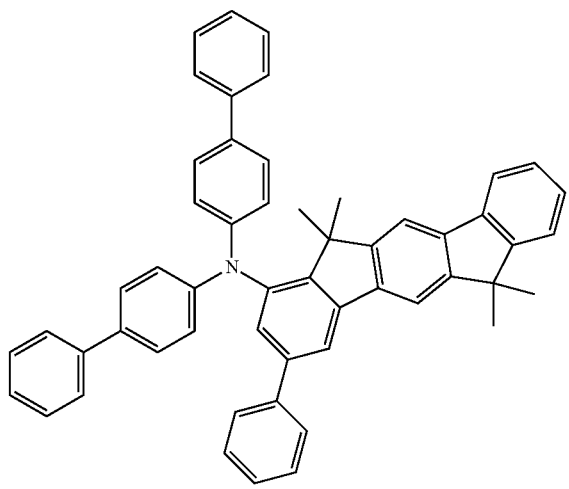 [SMILES: CC1(C)c2ccccc2-c2cc3c(cc21)-c1cc(-c2ccccc2)cc(N(c2ccc(-c4ccccc4)cc2)c2ccc(-c4ccccc4)cc2)c1C3(C)C]
(156)
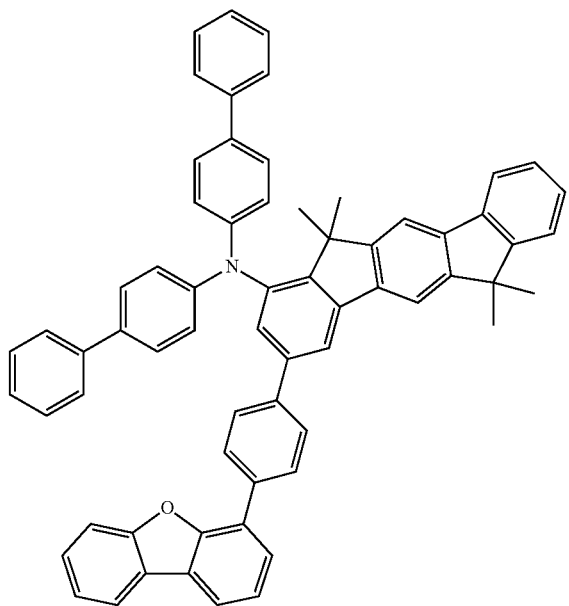 [SMILES: CC1(C)c2ccccc2-c2cc3c(cc21)-c1cc(-c2ccc(-c4cccc5c4oc4ccccc45)cc2)cc(N(c2ccc(-c4ccccc4)cc2)c2ccc(-c4ccccc4)cc2)c1C3(C)C]

(157)
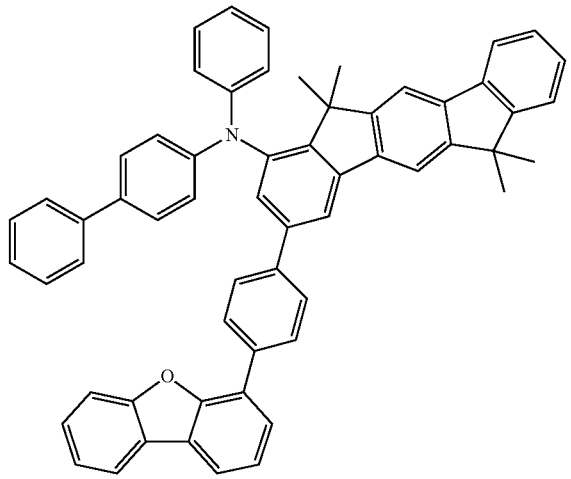 [SMILES: CC1(C)c2ccccc2-c2cc3c(cc21)-c1cc(-c2ccc(-c4cccc5c4oc4ccccc45)cc2)cc(N(c2ccccc2)c2ccc(-c4ccccc4)cc2)c1C3(C)C]
(158)
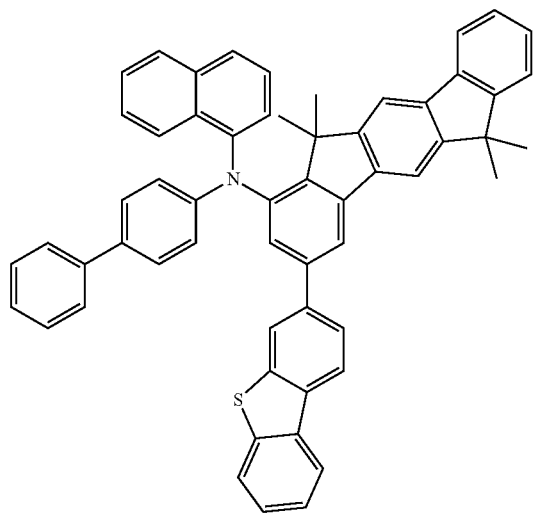 [SMILES: CC1(C)c2ccccc2-c2cc3c(cc21)-c1cc(-c2ccc4c(c2)sc2ccccc24)cc(N(c2ccc(-c4ccccc4)cc2)c2cccc4ccccc24)c1C3(C)C]

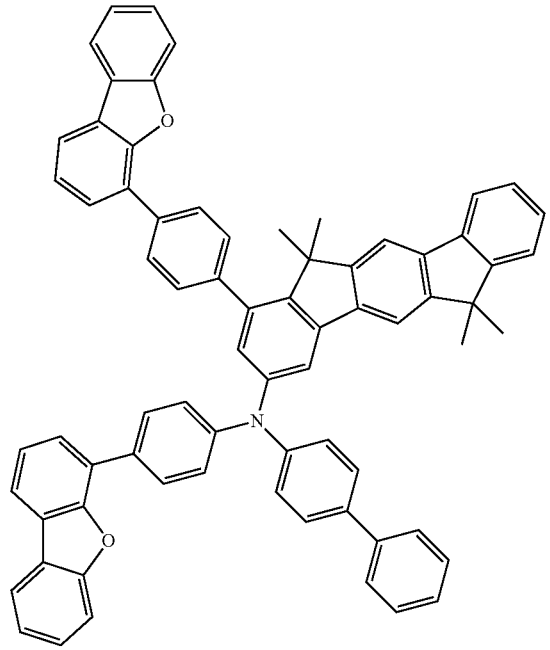 [SMILES: CC1(C)c2ccccc2-c2cc3c(cc21)-c1cc(N(c2ccc(-c4ccccc4)cc2)c2ccc(-c4cccc5c4oc4ccccc45)cc2)cc(-c2ccc(-c4cccc5c4oc4ccccc45)cc2)c1C3(C)C]
(159)
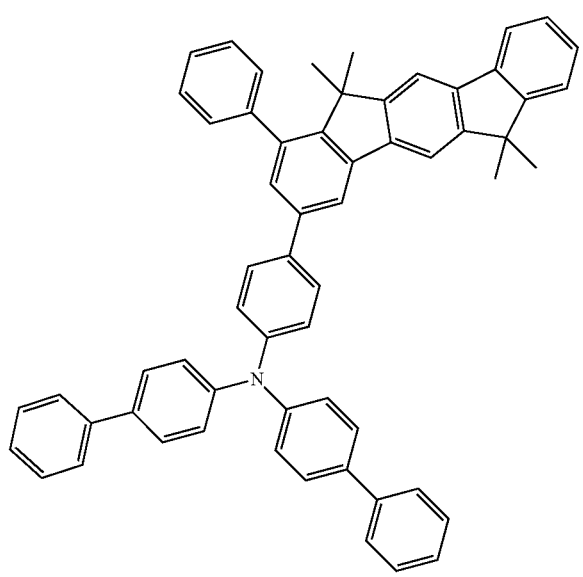 [SMILES: CC1(C)c2ccccc2-c2cc3c(cc21)-c1cc(-c2ccc(N(c4ccc(-c5ccccc5)cc4)c4ccc(-c5ccccc5)cc4)cc2)cc(-c2ccccc2)c1C3(C)C]
(160)

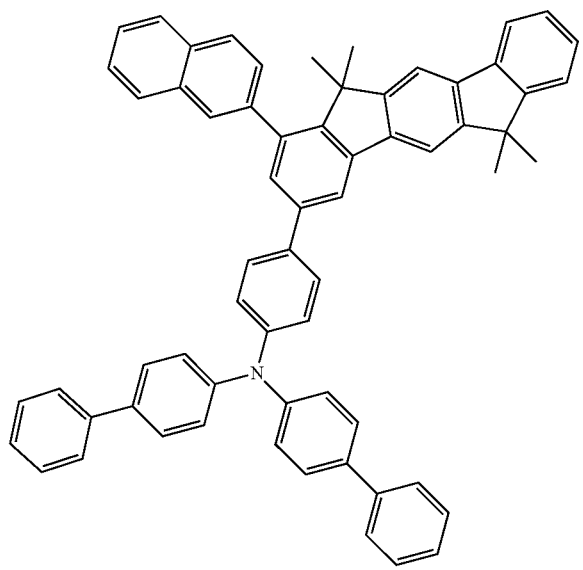 [SMILES: CC1(C)c2ccccc2-c2cc3c(cc21)-c1cc(-c2ccc(N(c4ccc(-c5ccccc5)cc4)c4ccc(-c5ccccc5)cc4)cc2)cc(-c2ccc4ccccc4c2)c1C3(C)C]
(161)
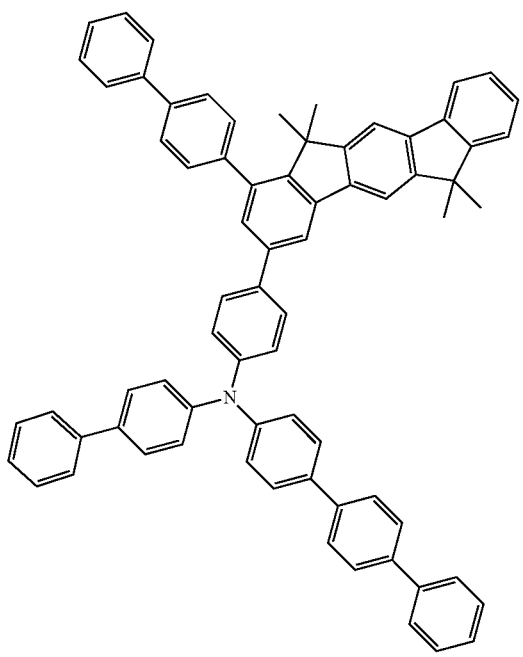 [SMILES: CC1(C)c2ccccc2-c2cc3c(cc21)-c1cc(-c2ccc(N(c4ccc(-c5ccccc5)cc4)c4ccc(-c5ccc(-c6ccccc6)cc5)cc4)cc2)cc(-c2ccc(-c4ccccc4)cc2)c1C3(C)C]
(162)

(163)
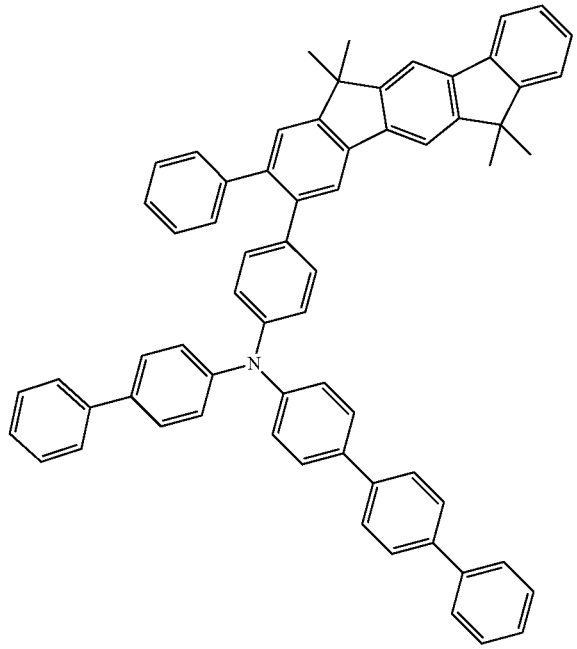 [SMILES: CC1(C)c2ccccc2-c2cc3c(cc21)-c1cc(-c2ccc(N(c4ccc(-c5ccccc5)cc4)c4ccc(-c5ccc(-c6ccccc6)cc5)cc4)cc2)c(-c2ccccc2)cc1C3(C)C]
(164)
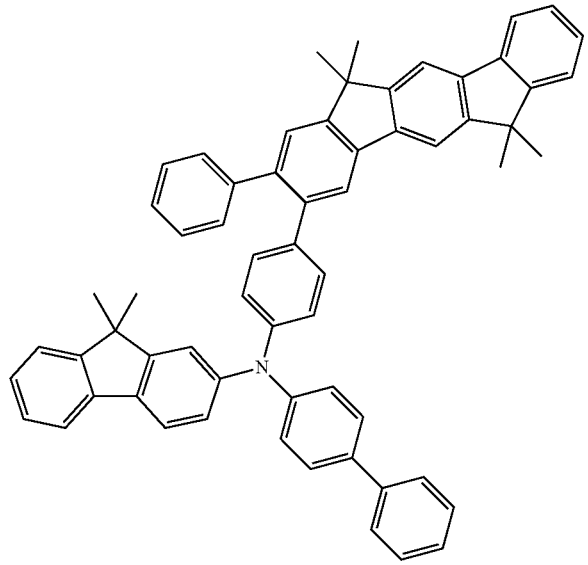 [SMILES: CC1(C)c2ccccc2-c2ccc(N(c3ccc(-c4ccccc4)cc3)c3ccc(-c4cc5c(cc4-c4ccccc4)C(C)(C)c4cc6c(cc4-5)C(C)(C)c4ccccc4-6)cc3)cc21]
(165)
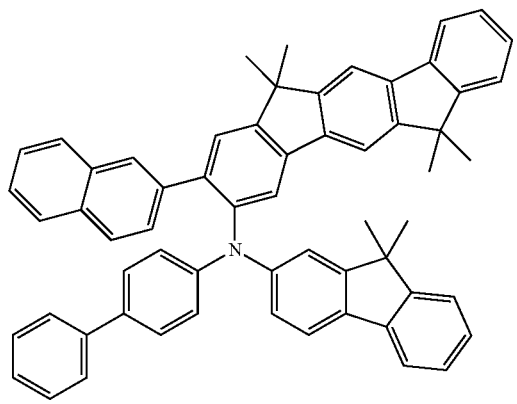 [SMILES: CC1(C)c2ccccc2-c2ccc(N(c3ccc(-c4ccccc4)cc3)c3cc4c(cc3-c3ccc5ccccc5c3)C(C)(C)c3cc5c(cc3-4)C(C)(C)c3ccccc3-5)cc21]

(166)
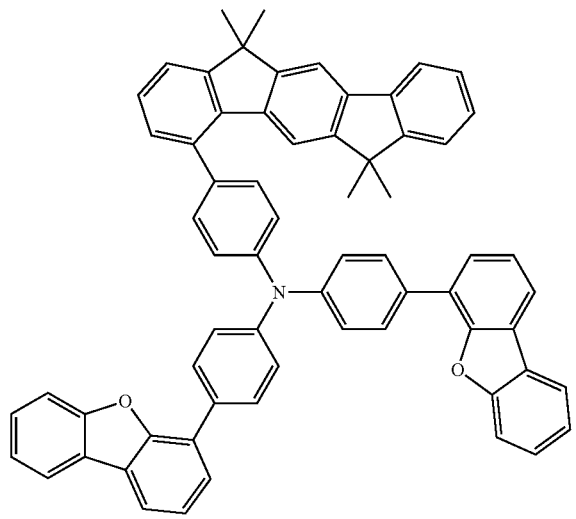 [SMILES: CC1(C)c2ccccc2-c2cc3c(cc21)-c1c(-c2ccc(N(c4ccc(-c5cccc6c5oc5ccccc56)cc4)c4ccc(-c5cccc6c5oc5ccccc56)cc4)cc2)cccc1C3(C)C]
(167)
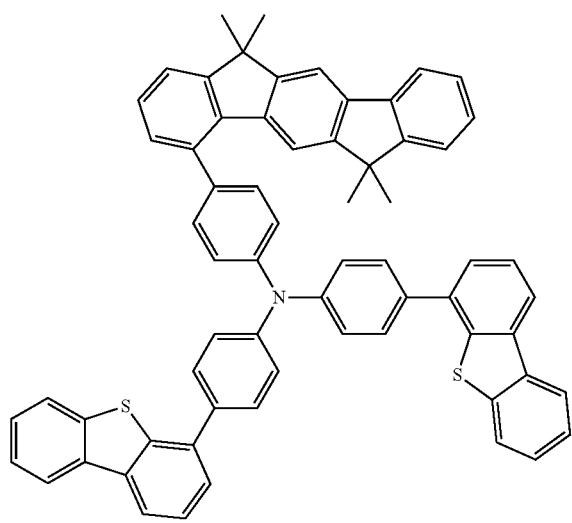 [SMILES: CC1(C)c2ccccc2-c2cc3c(cc21)-c1c(-c2ccc(N(c4ccc(-c5cccc6c5sc5ccccc56)cc4)c4ccc(-c5cccc6c5sc5ccccc56)cc4)cc2)cccc1C3(C)C]
(168)
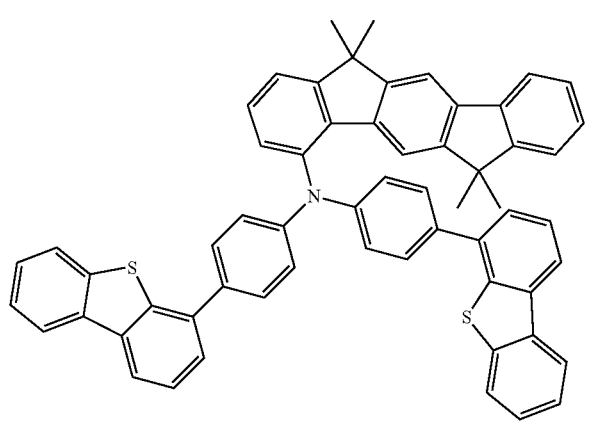

(169)
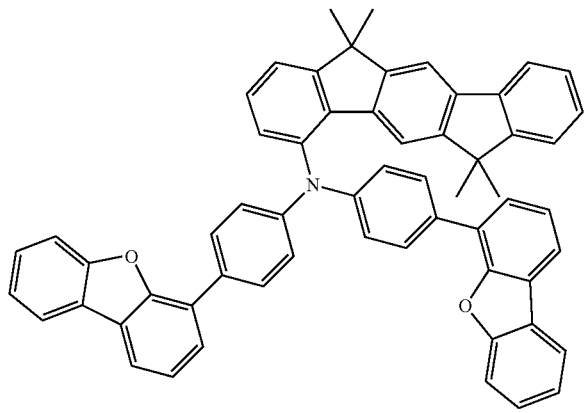 [SMILES: CC1(C)c2ccccc2-c2cc3c(cc21)-c1c(N(c2ccc(-c4cccc5c4oc4ccccc45)cc2)c2ccc(-c4cccc5c4oc4ccccc45)cc2)cccc1C3(C)C]
(170)
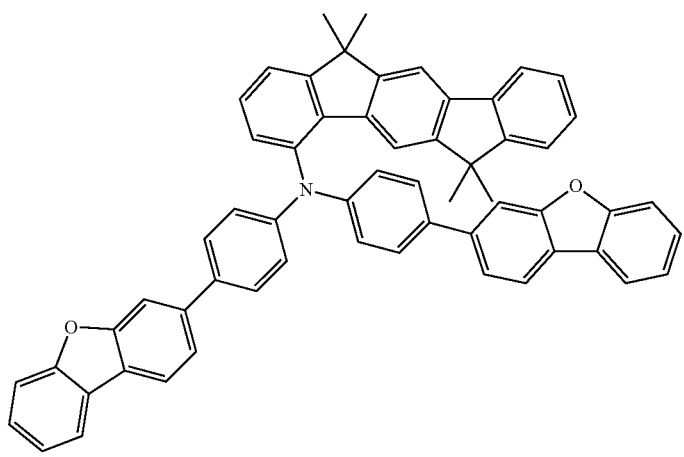 [SMILES: CC1(C)c2ccccc2-c2cc3c(cc21)-c1c(N(c2ccc(-c4ccc5c(c4)oc4ccccc45)cc2)c2ccc(-c4ccc5c(c4)oc4ccccc45)cc2)cccc1C3(C)C]
(171)
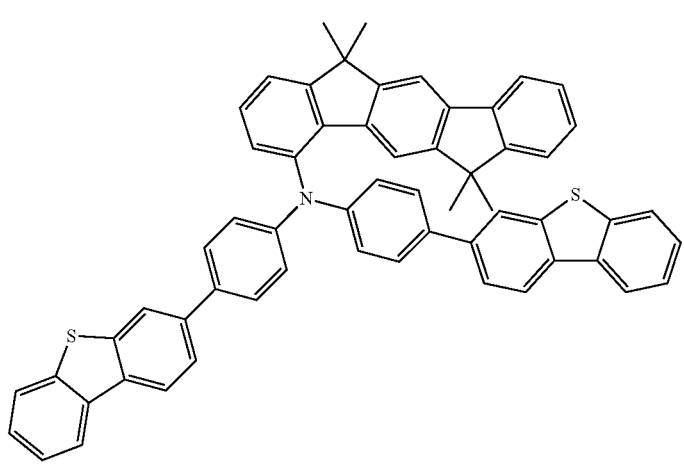

(172)
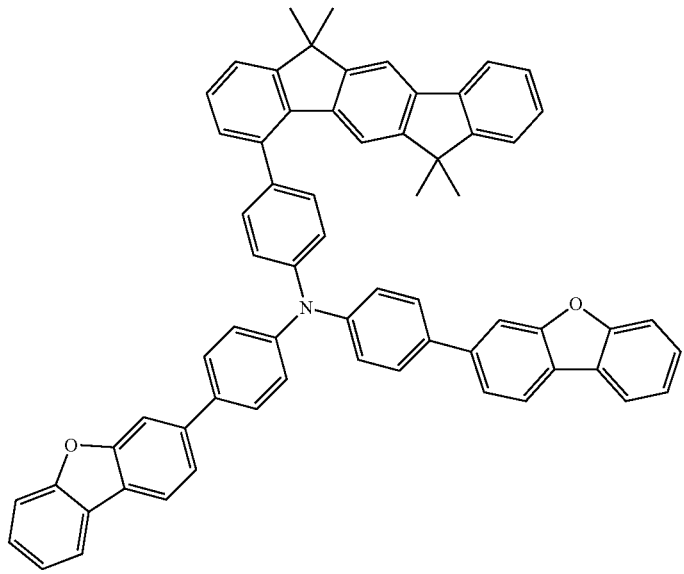 [SMILES: CC1(C)c2ccccc2-c2cc3c(cc21)-c1c(-c2ccc(N(c4ccc(-c5ccc6c(c5)oc5ccccc56)cc4)c4ccc(-c5ccc6c(c5)oc5ccccc56)cc4)cc2)cccc1C3(C)C]
(173)
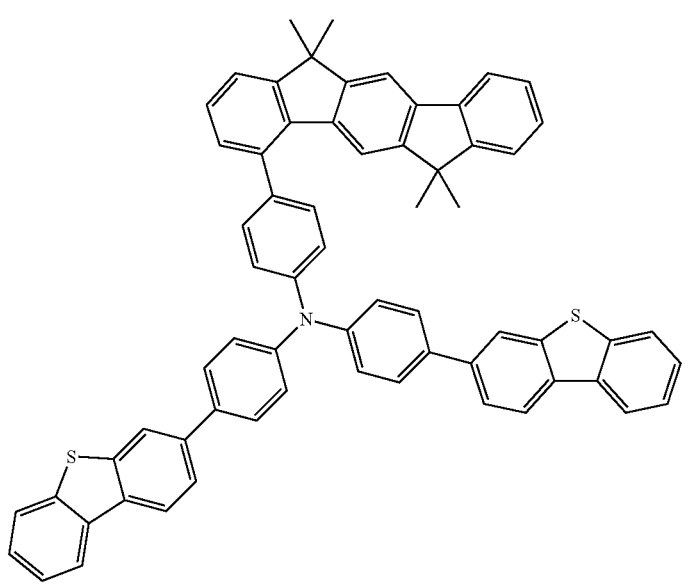
(174)
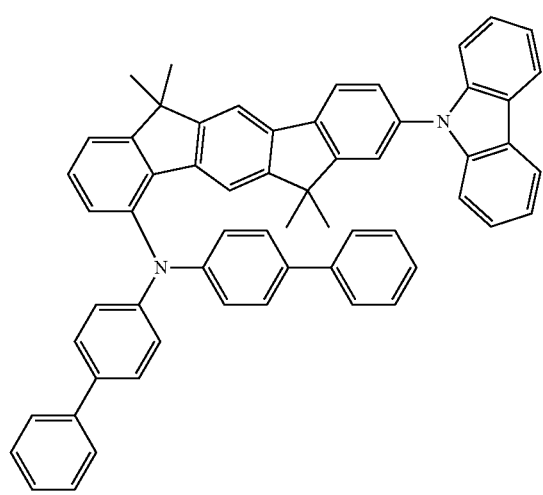 [SMILES: CC1(C)c2cc(-n3c4ccccc4c4ccccc43)ccc2-c2cc3c(cc21)-c1c(N(c2ccc(-c4ccccc4)cc2)c2ccc(-c4ccccc4)cc2)cccc1C3(C)C]

(175)
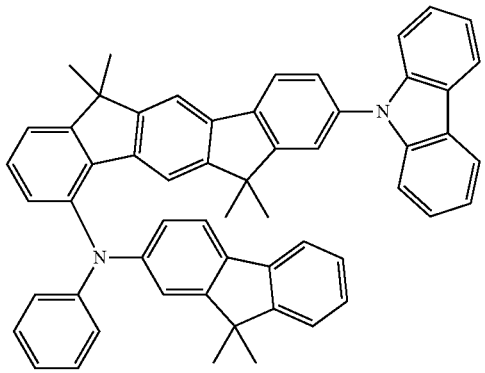 [SMILES: CC1(C)c2ccccc2-c2ccc(N(c3ccccc3)c3cccc4c3-c3cc5c(cc3C4(C)C)-c3ccc(-n4c6ccccc6c6ccccc64)cc3C5(C)C)cc21]
(176)
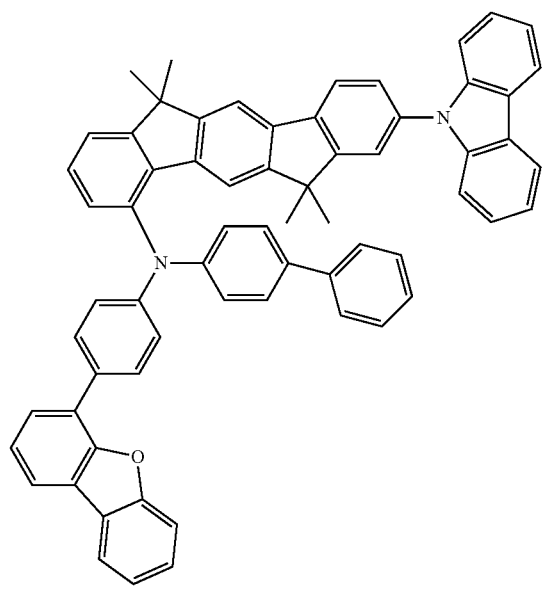 [SMILES: CC1(C)c2cc(-n3c4ccccc4c4ccccc43)ccc2-c2cc3c(cc21)-c1c(N(c2ccc(-c4ccccc4)cc2)c2ccc(-c4cccc5c4oc4ccccc45)cc2)cccc1C3(C)C]
(177)
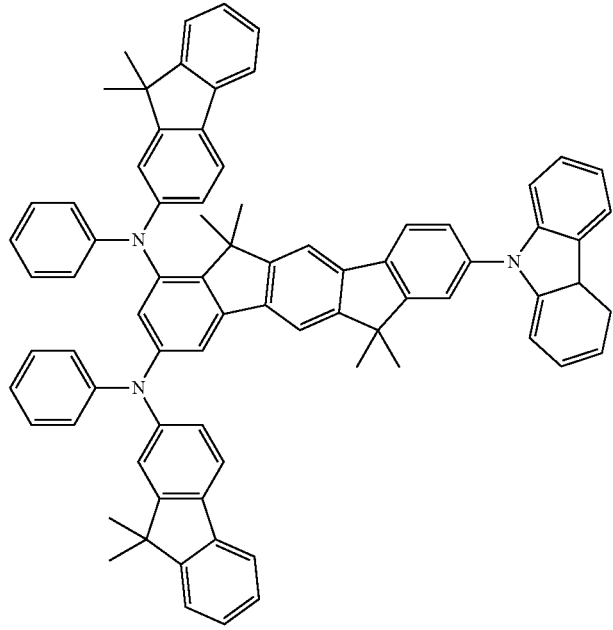 [SMILES: CC1(C)c2ccccc2-c2ccc(N(c3ccccc3)c3cc4c(c(N(c5ccccc5)c5ccc6c(c5)C(C)(C)c5ccccc5-6)c3)C(C)(C)c3cc5c(cc3-4)C(C)(C)c3cc(N4C6=CC=CCC6c6ccccc64)ccc3-5)cc21]

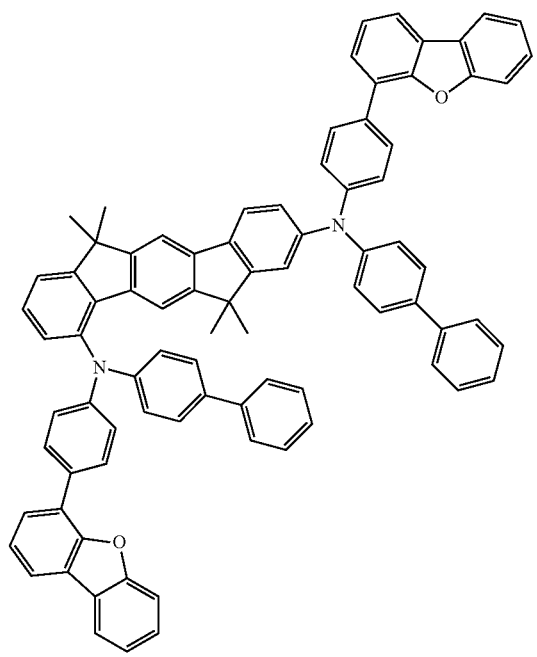 [SMILES: CC1(C)c2cc(N(c3ccc(-c4ccccc4)cc3)c3ccc(-c4cccc5c4oc4ccccc45)cc3)ccc2-c2cc3c(cc21)-c1c(N(c2ccc(-c4ccccc4)cc2)c2ccc(-c4cccc5c4oc4ccccc45)cc2)cccc1C3(C)C]
(178)
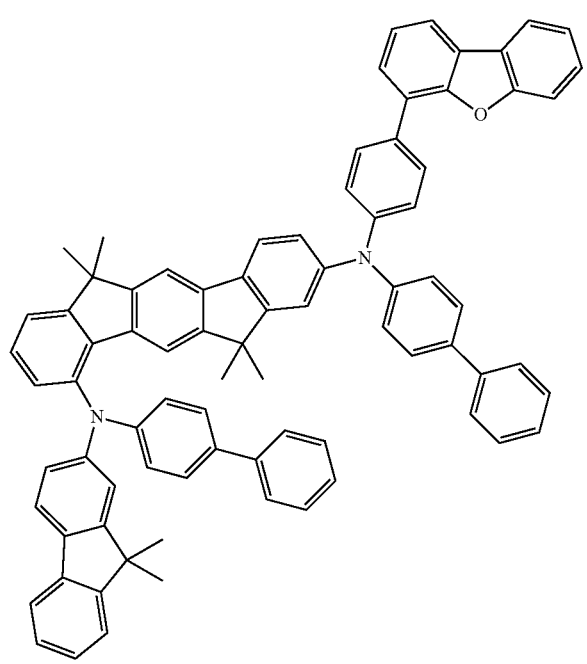 [SMILES: CC1(C)c2ccccc2-c2ccc(N(c3ccc(-c4ccccc4)cc3)c3cccc4c3-c3cc5c(cc3C4(C)C)-c3ccc(N(c4ccc(-c6ccccc6)cc4)c4ccc(-c6cccc7c6oc6ccccc67)cc4)cc3C5(C)C)cc21]
(179)

-continued
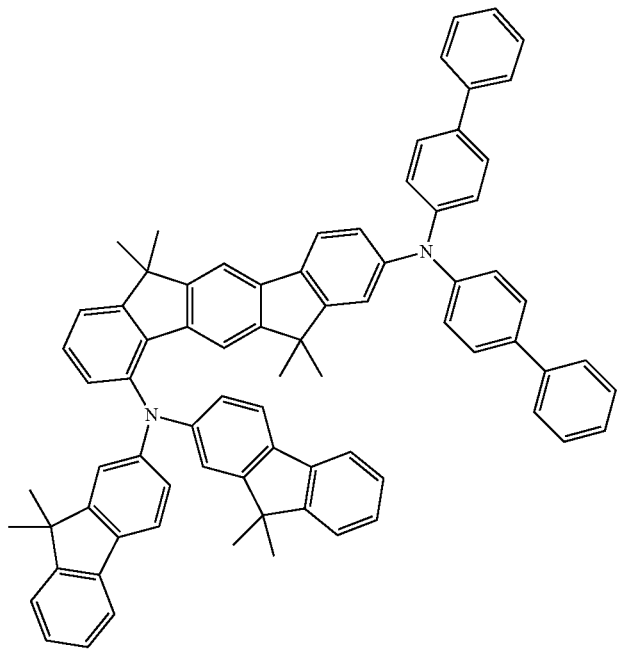 [SMILES: CC1(C)c2ccccc2-c2ccc(N(c3ccc4c(c3)C(C)(C)c3ccccc3-4)c3cccc4c3-c3cc5c(cc3C4(C)C)-c3ccc(N(c4ccc(-c6ccccc6)cc4)c4ccc(-c6ccccc6)cc4)cc3C5(C)C)cc21]
(180)
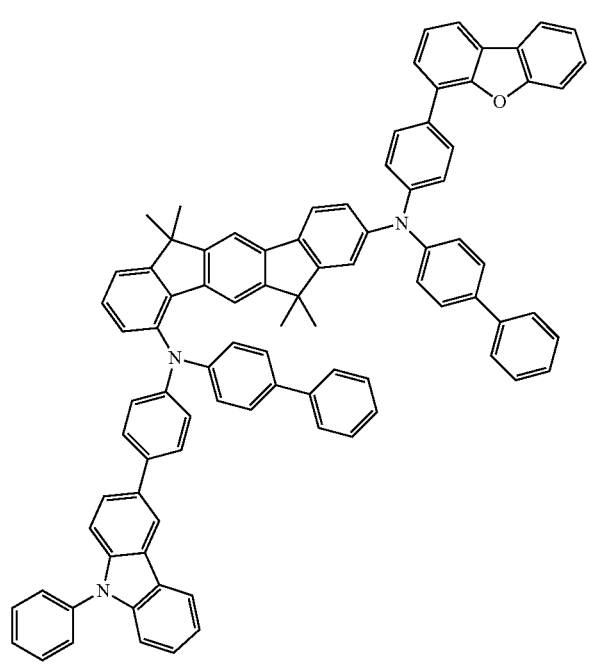 [SMILES: CC1(C)c2cc(N(c3ccc(-c4ccccc4)cc3)c3ccc(-c4cccc5c4oc4ccccc45)cc3)ccc2-c2cc3c(cc21)-c1c(N(c2ccc(-c4ccccc4)cc2)c2ccc(-c4ccc5c(c4)c4ccccc4n5-c4ccccc4)cc2)cccc1C3(C)C]
(181)

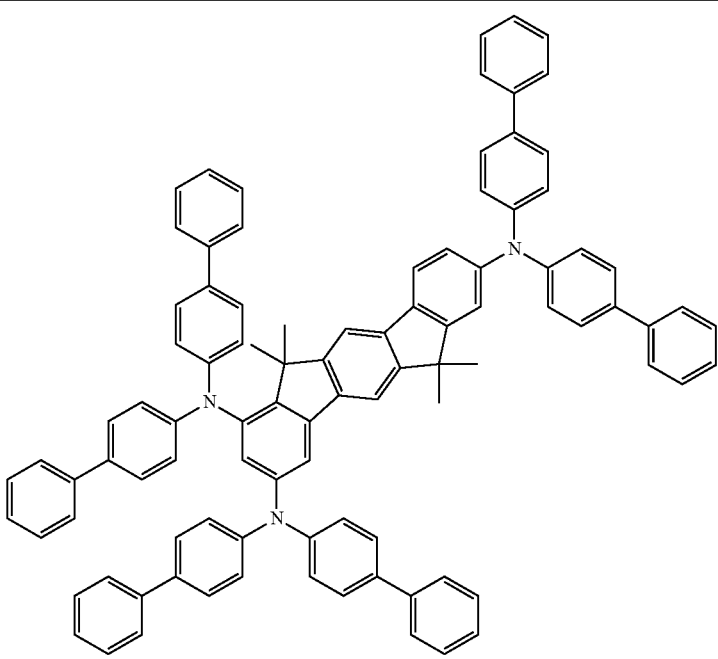

(182)

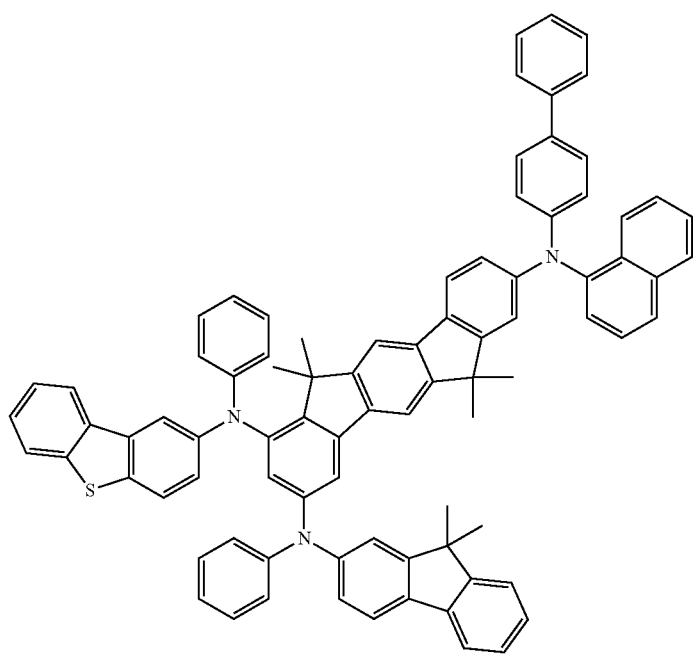 [SMILES: CC1(C)c2ccccc2-c2ccc(N(c3ccccc3)c3cc4c(c(N(c5ccccc5)c5ccc6sc7ccccc7c6c5)c3)C(C)(C)c3cc5c(cc3-4)C(C)(C)c3cc(N(c4ccc(-c6ccccc6)cc4)c4cccc6ccccc46)ccc3-5)cc21]

(183)

The compounds of formula (I) can be prepared by means of known organic reactions, especially by means of Suzuki reactions, Hartwig-Buchwald reactions, and cyclization reactions.

In a preferred process (Scheme 1), proceeding from a benzene compound that bears two reactive X groups and two carboxylic ester groups, via two sequential Suzuki couplings, a compound having a chain of three aryl groups (Ar group and the two phenyl groups) is prepared, where the terminal phenyl group has a reactive X group. The reactive X group is in the ortho or meta position to the bond to the central phenyl group, or in the reacting phenylboronic acid compound is in the ortho or meta position to the boronic acid group.

Subsequently, the carboxylic ester groups of this compound are converted to tertiary alkoxy groups by reaction with a metal alkyl compound, preferably a lithium alkyl compound or a Grignard alkyl compound. These tertiary alkoxy groups cyclize to form rings under the action of acid. Finally, an amino group is introduced via a Buchwald coupling, or a diarylaminoaryl or a diarylaminoheteroaryl group is introduced by Suzuki reaction, such that the compound of the formula (I) is obtained.

Scheme 1

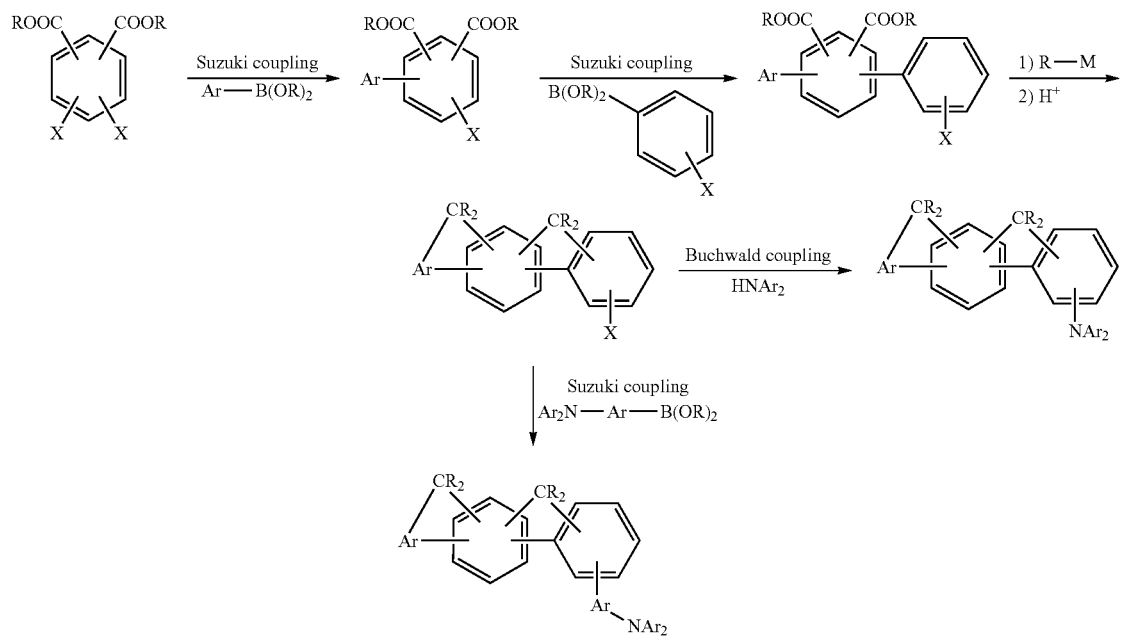

R: organic radical
Ar: Aromatic or heteroaromatic ring system
M: metal or metal halide
X: reactive group, preferably Cl, Br, or I In a modification of the reaction pathway of Scheme 1 (Scheme 2), in one of the Suzuki couplings, a phenyl group that has, rather than the reactive X group, an A group selected from —Ar—NAr₂ and —NAr₂ groups is introduced. The A group in question, like the X group in Scheme 1, is in the ortho or meta position to the boronic acid group. In this synthesis route, there is no need for the Suzuki or Buchwald coupling that takes place in the last step in Scheme 1.

Scheme 2

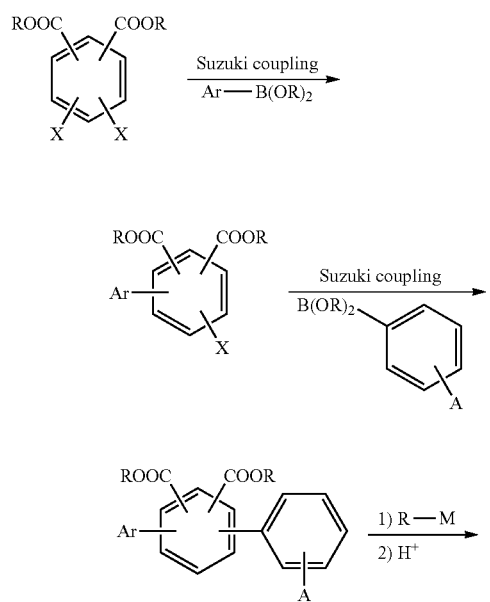

-continued

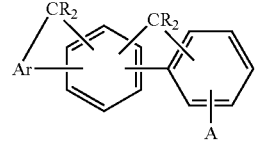

R: organic radical
A: —Ar—NAr₂ or —NAr₂
Ar: Aromatic or heteroaromatic ring system
M: metal or metal halide
X: reactive group, preferably Cl, Br, or I The present application thus further provides a process for preparing a compound of formula (I), characterized in that a benzene compound that bears two carboxylic ester groups, an aromatic or heteroaromatic ring system and a reactive group is reacted in a Suzuki reaction with a benzene compound that contains a boronic acid group and a group selected from reactive groups, diarylamino groups, diarylaminoaryl groups and diarylaminoheteroaryl groups. The boronic acid group and the group selected from reactive groups, diarylamino groups, diarylaminoaryl groups and diarylaminoheteroaryl groups here are in ortho or meta positions to one another on the benzene ring.

The reactive groups here are preferably selected from Cl, Br, I, triflate, mesylate and tosylate.

The above-described compounds of the formula (I), especially compounds substituted by reactive leaving groups, such as bromine, iodine, chlorine, boronic acid or boronic esters, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$, $R^4$ or $R^5$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

It is more preferably an organic electroluminescent device (OLED) comprising anode, cathode and at least one emitting layer, characterized in that at least one organic layer, which may be an emitting layer, a hole-transporting layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present here in a hole transport layer, hole injection layer, electron blocker layer, and/or emitting layer, more preferably in an emitting layer as matrix material, and/or in an electron blocker layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer and/or an emitting layer. More preferably, it is present in an electron blocker layer or in an emitting layer in combination with a phosphorescent emitting compound. In the latter case, the phosphorescent emitting compound is preferably selected from red- or green-phosphorescent emitting compounds. It is most preferably present in an electron blocker layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in the following table:

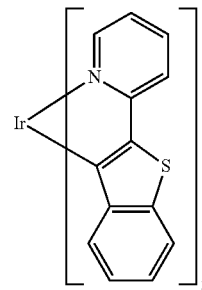

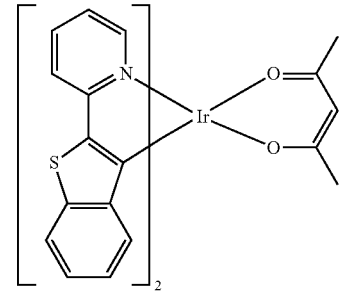

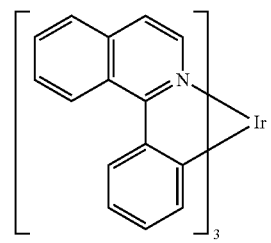

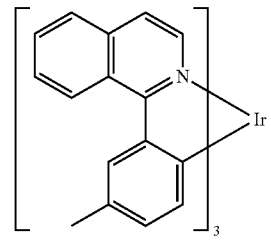

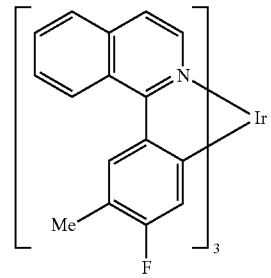

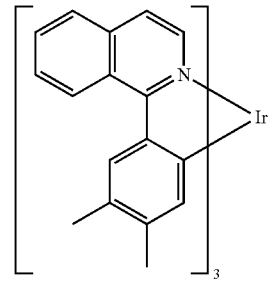

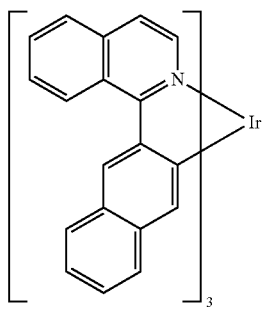
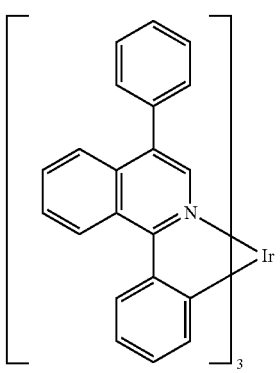
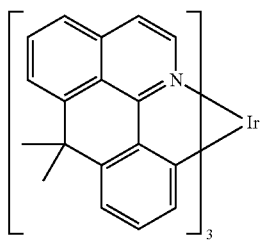
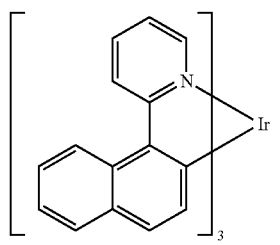
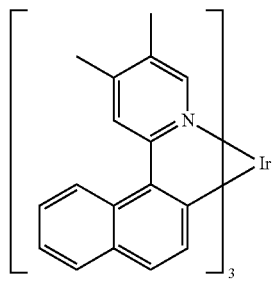
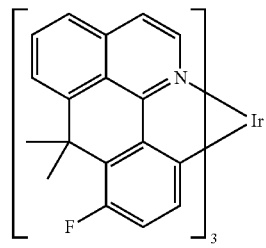
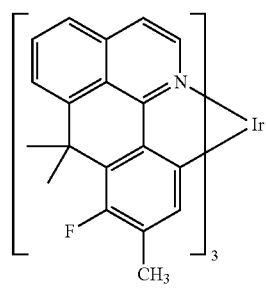
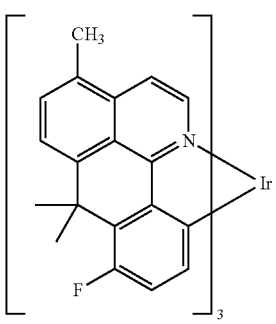
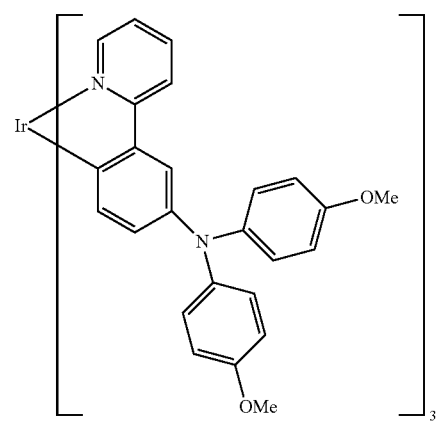
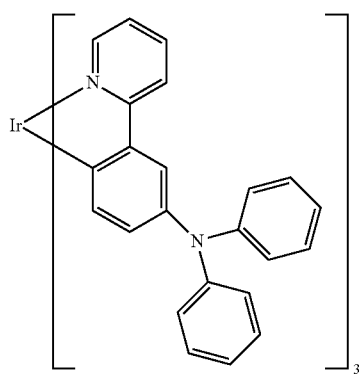

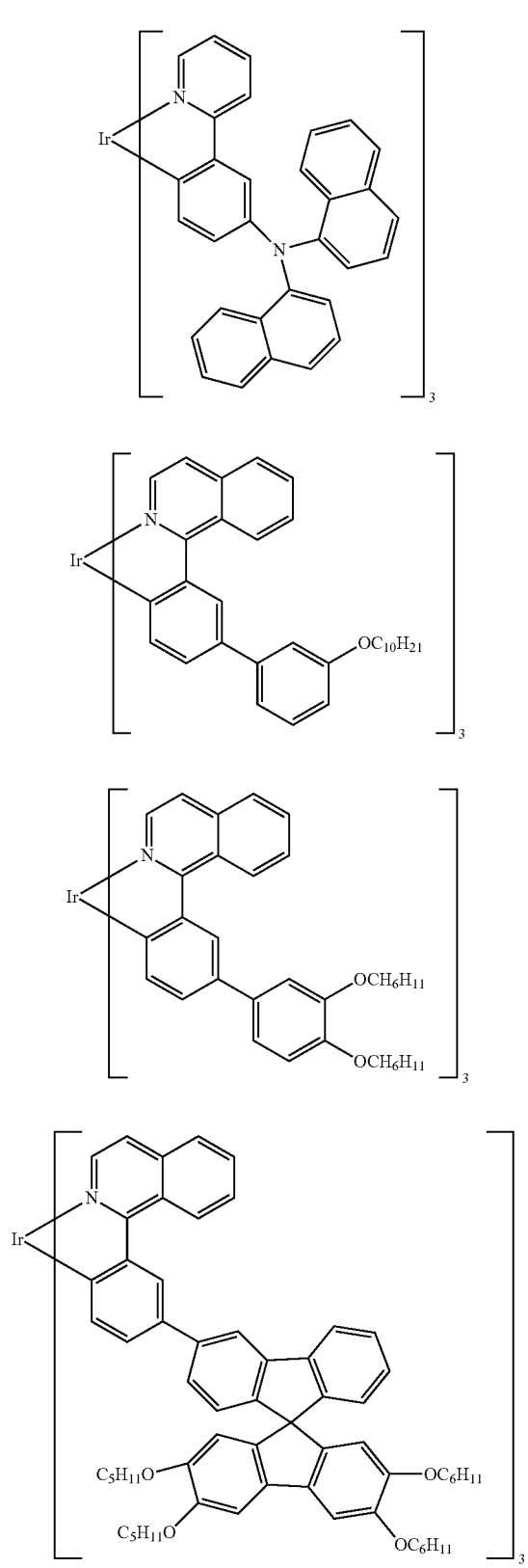
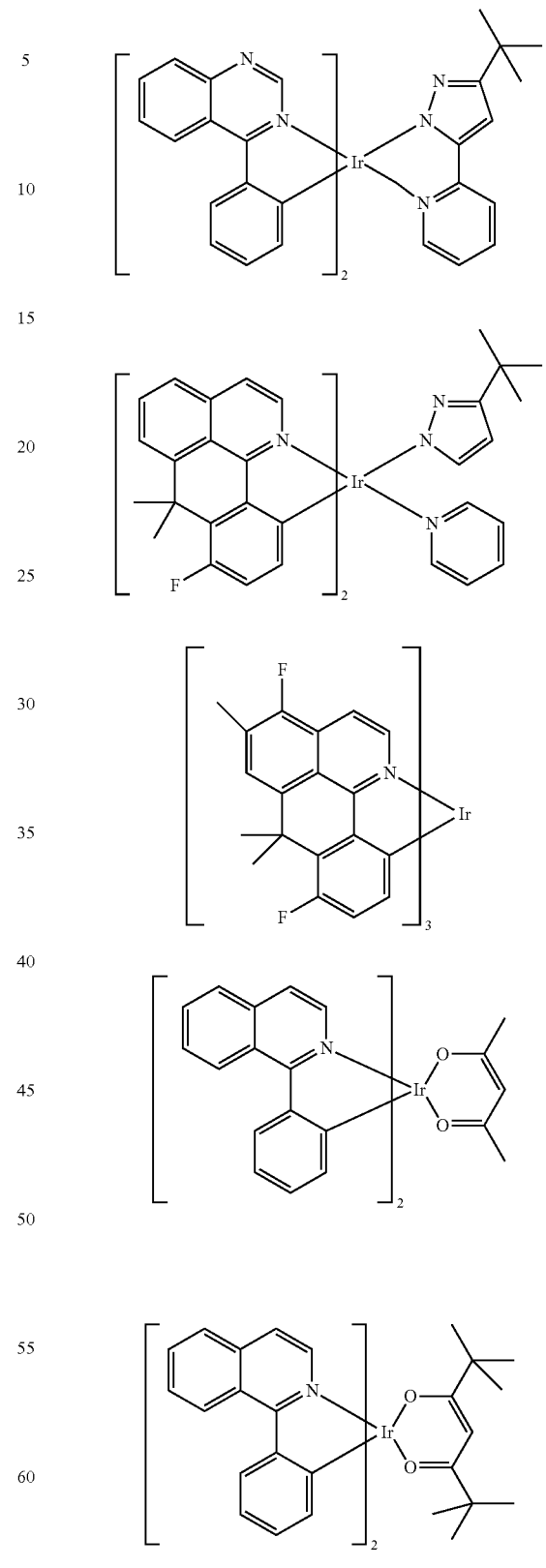

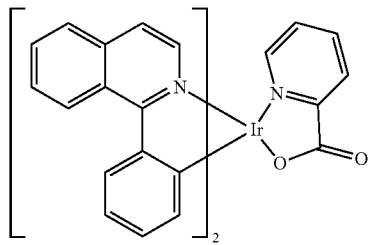
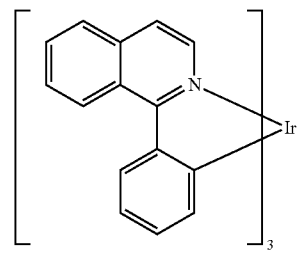
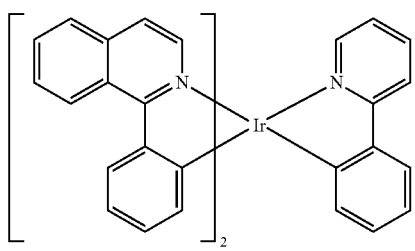
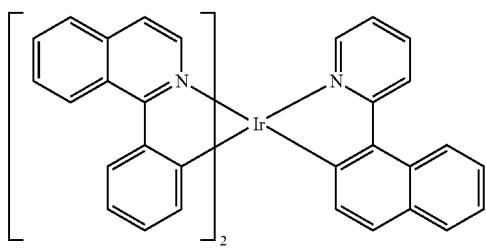
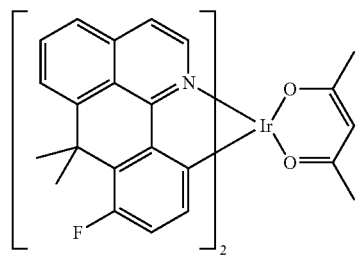
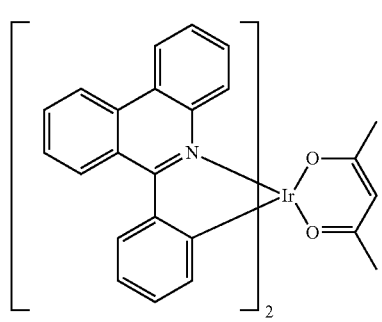
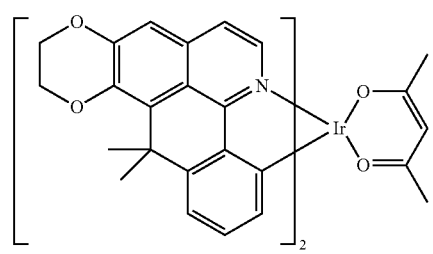
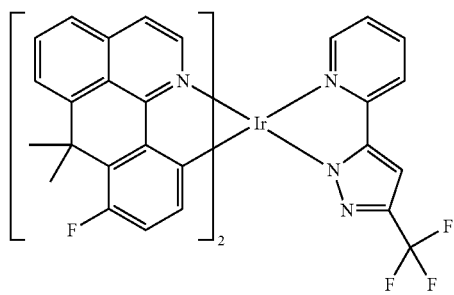
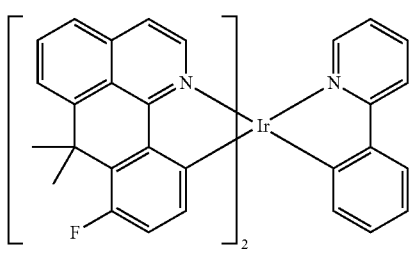
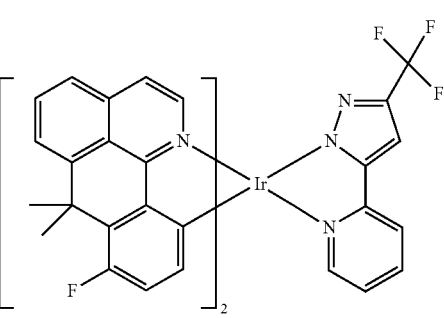
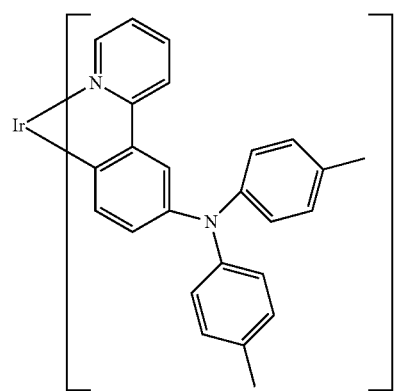

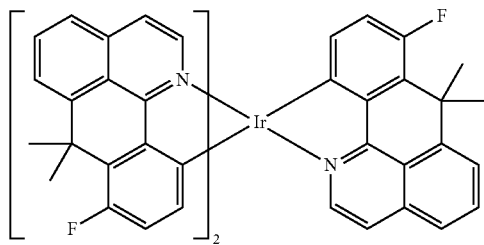
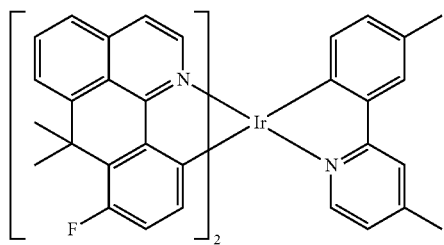
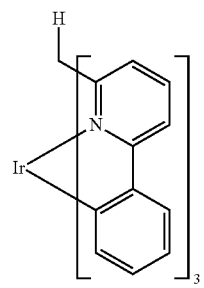
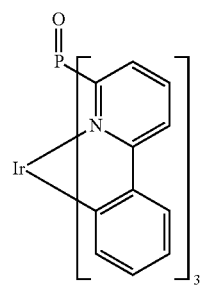
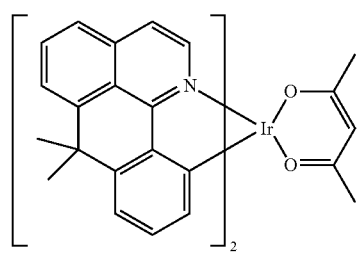
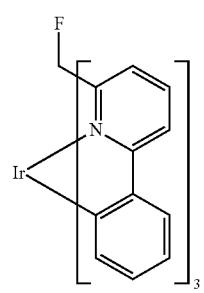
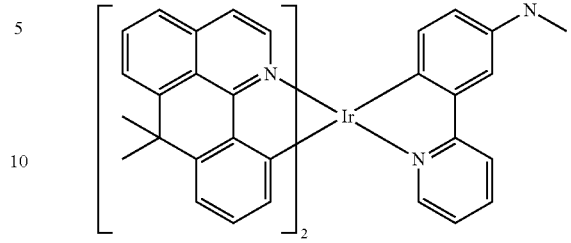
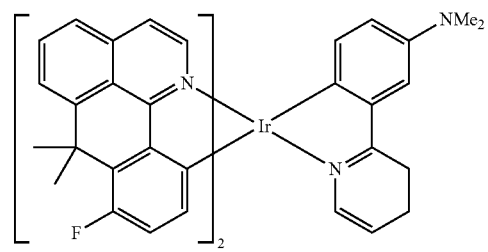
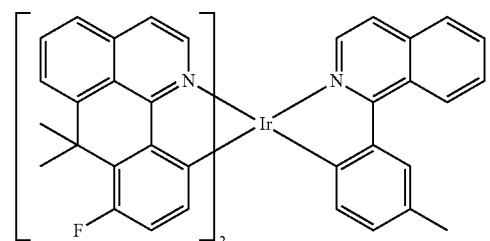
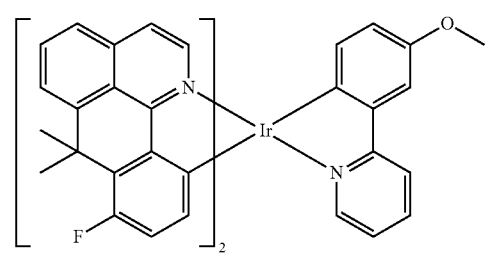
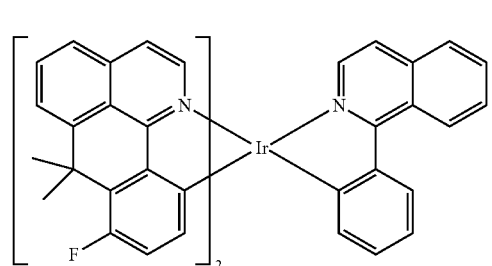
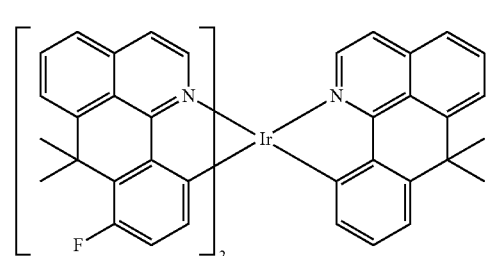

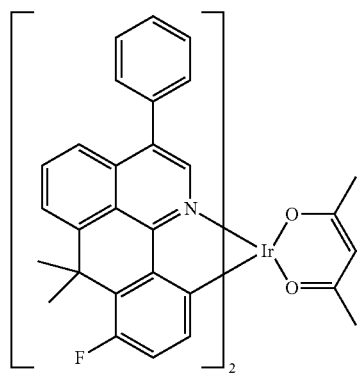
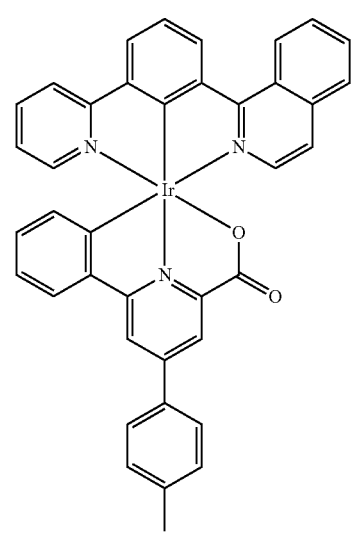
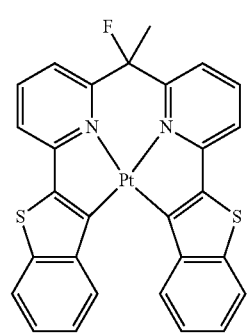
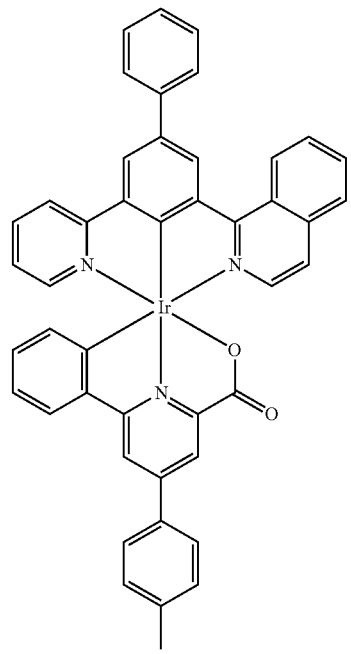
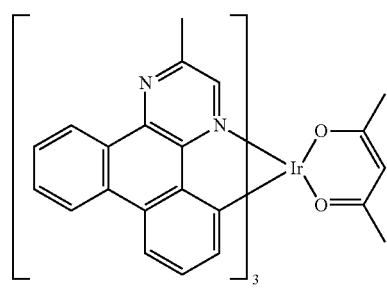
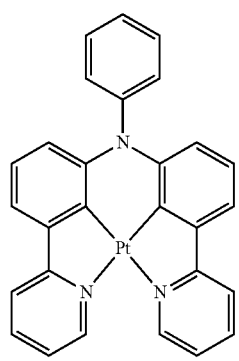
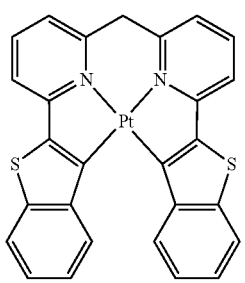

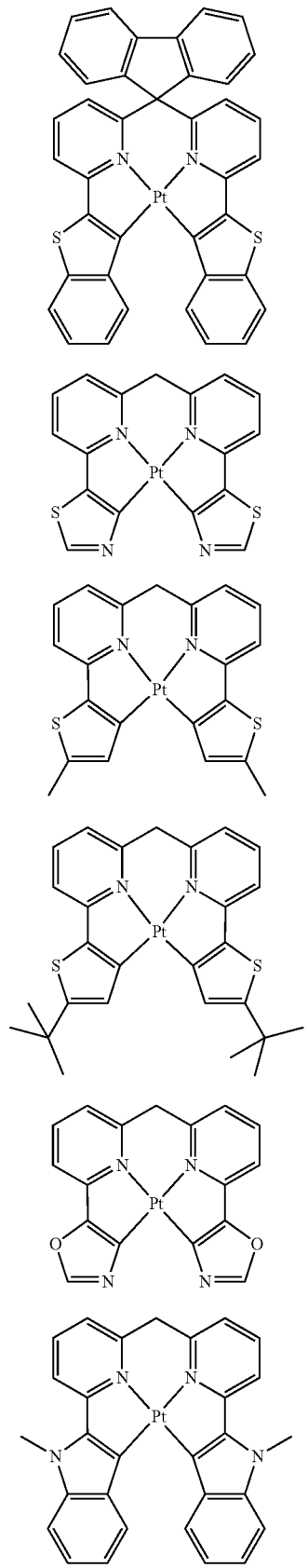
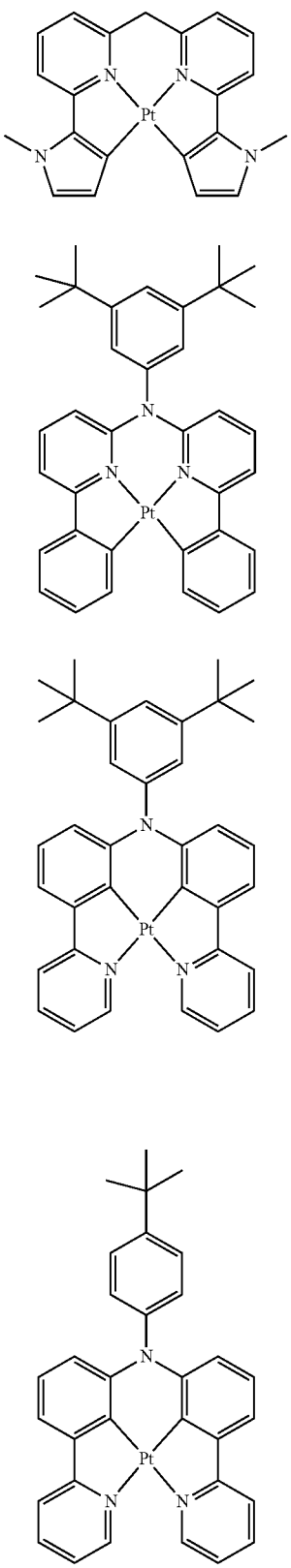

259
-continued
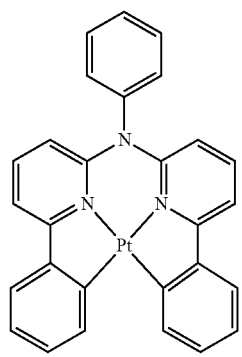
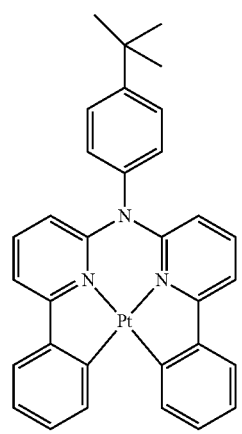
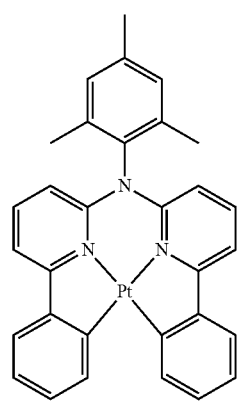
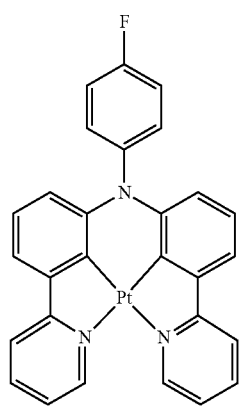
260
-continued
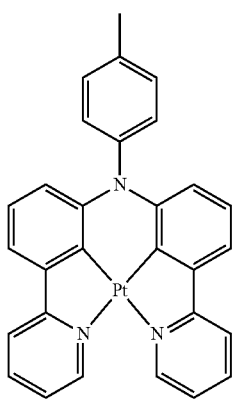
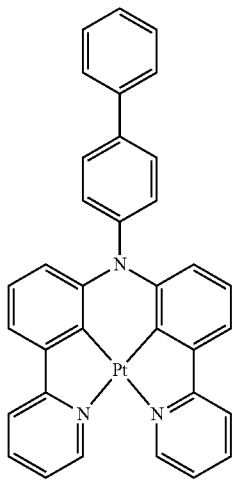
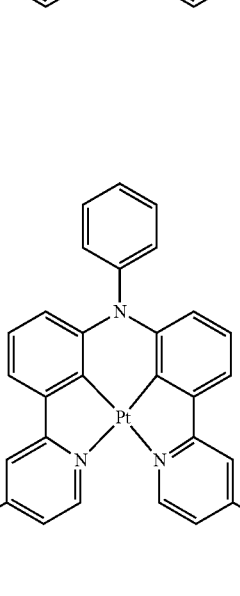

| 261 -continued | 262 -continued |
|---|---|
| 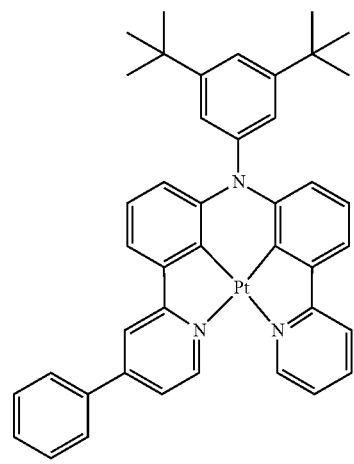 | 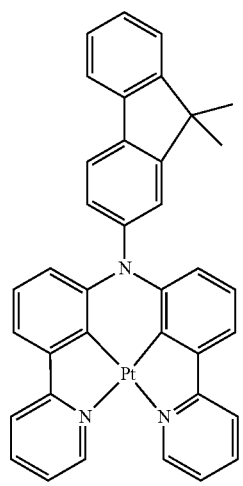 |
| 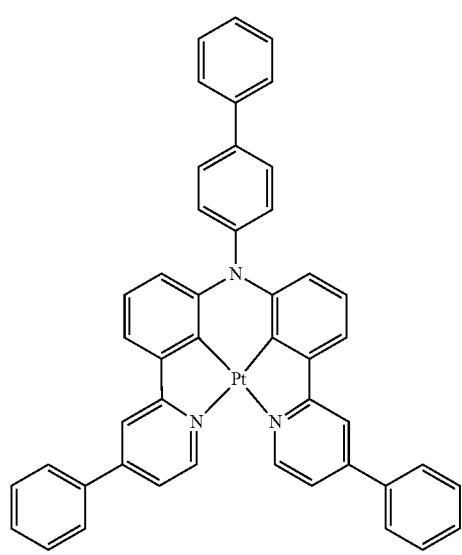 | 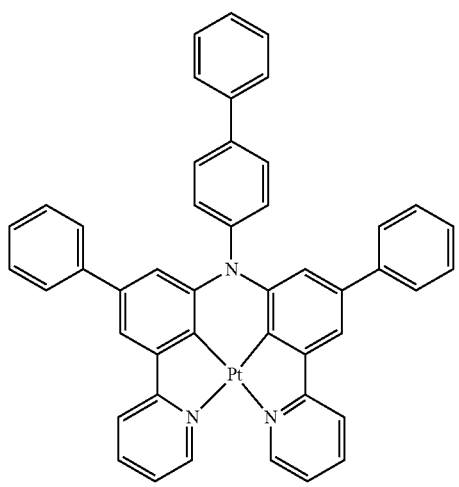 |
| 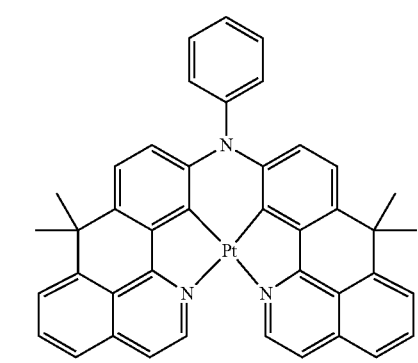 | 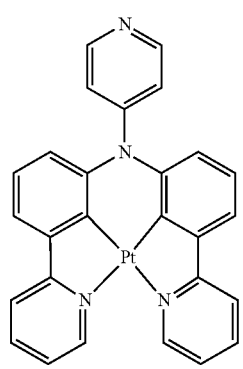 |

263
-continued
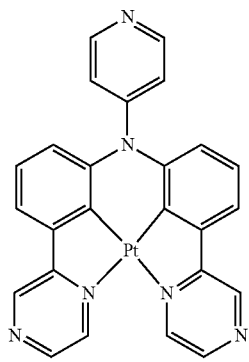
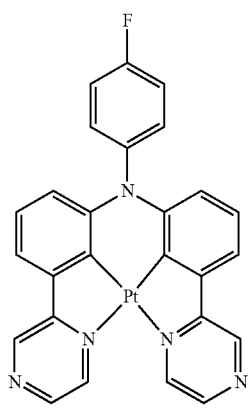
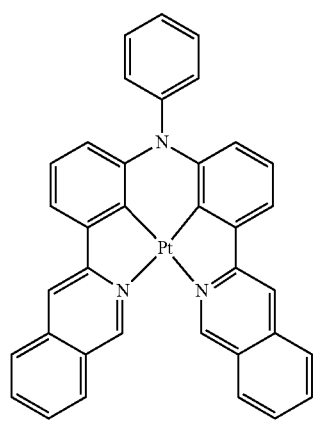
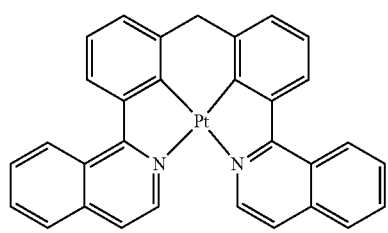
264
-continued
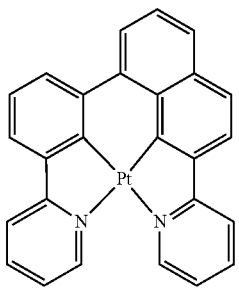
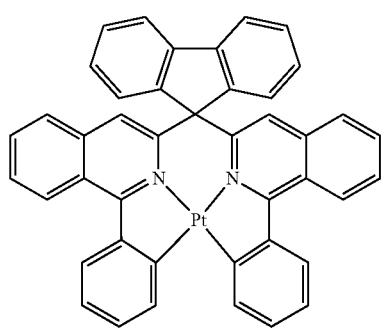
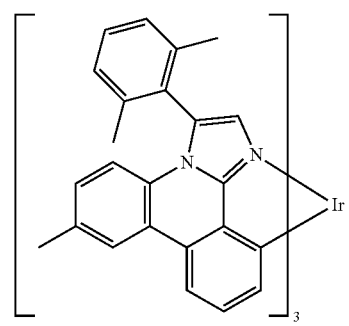
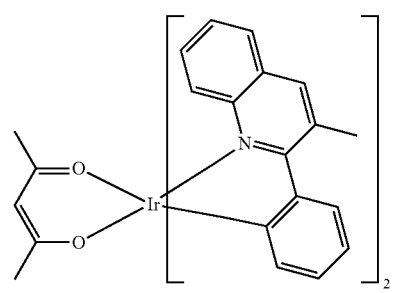
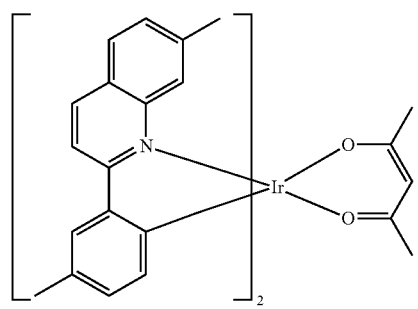

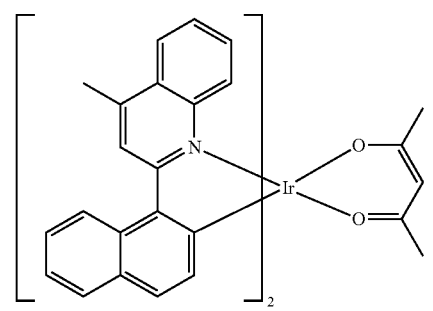
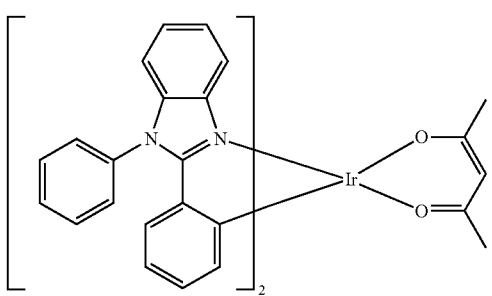
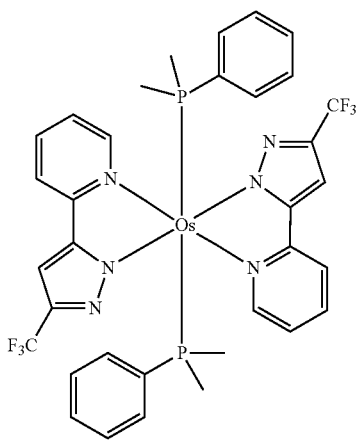
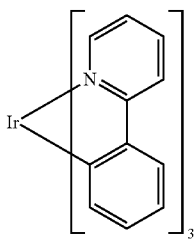
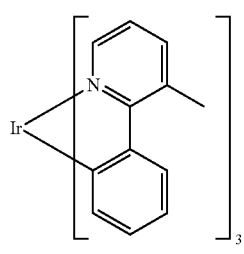
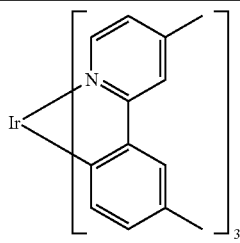
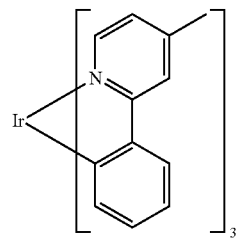
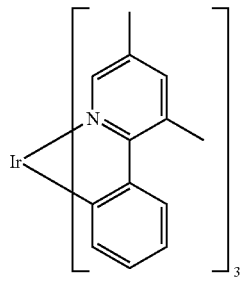
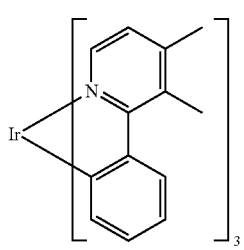
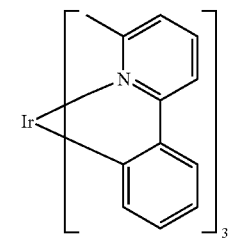
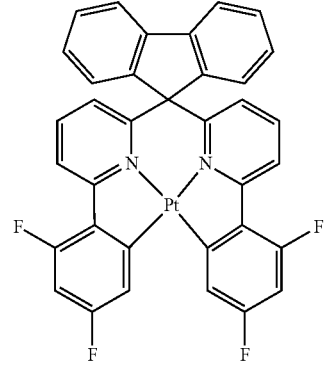

267
-continued
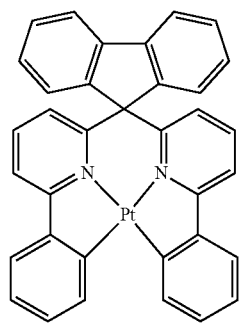
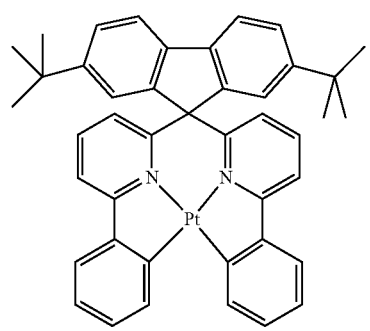
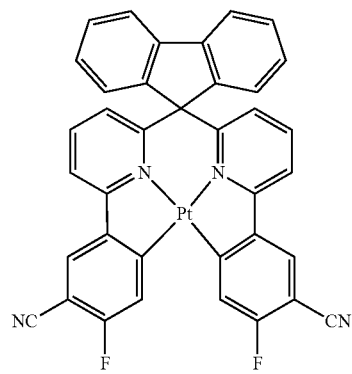
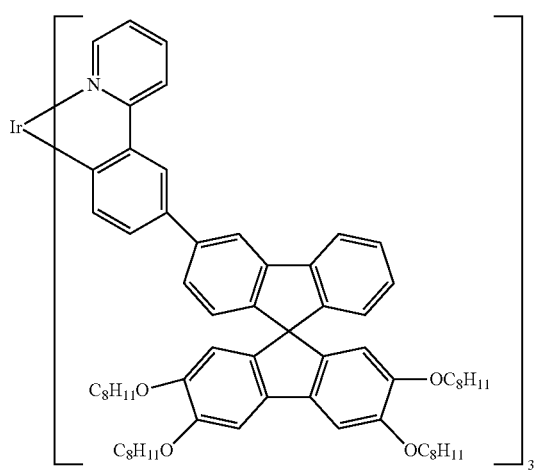
268
-continued
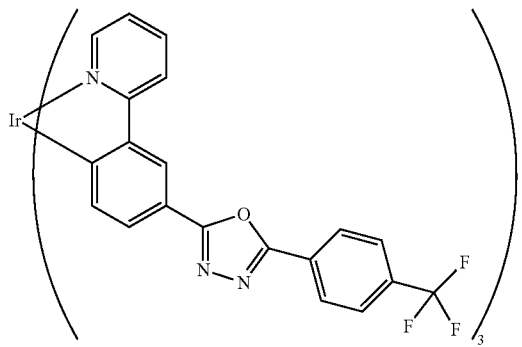
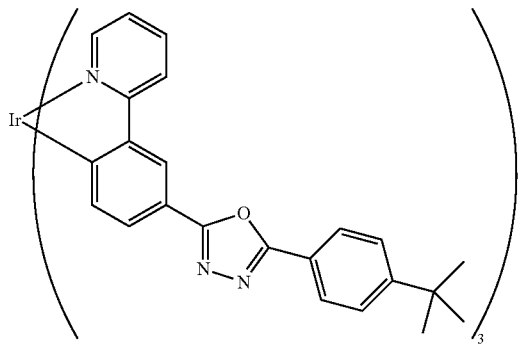
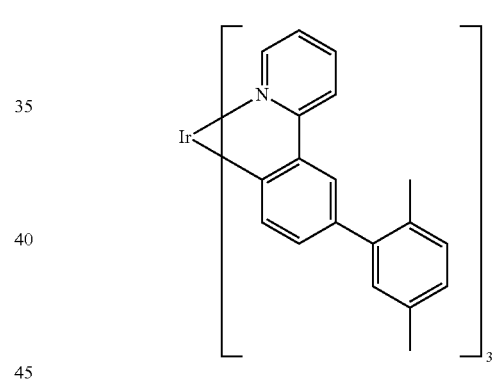
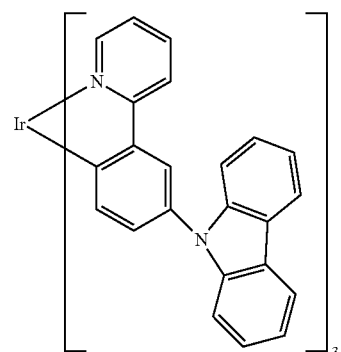

269
-continued
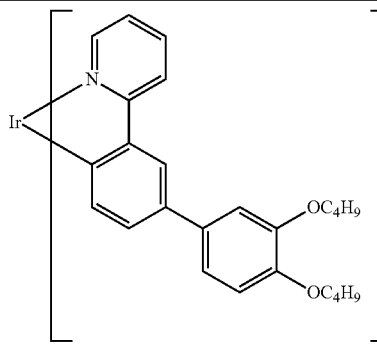
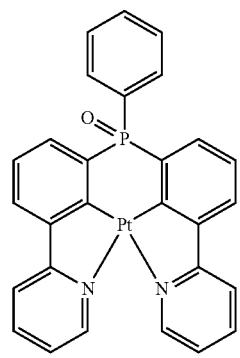
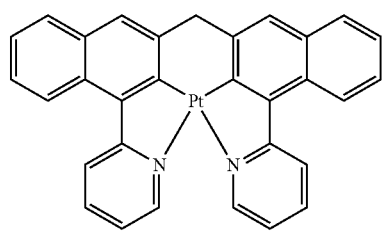
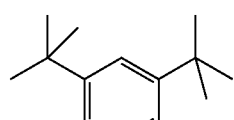
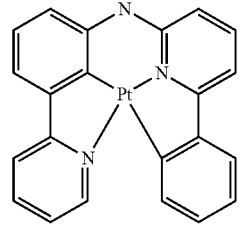
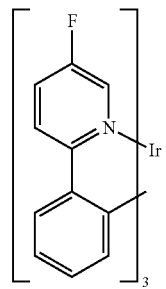
270
-continued
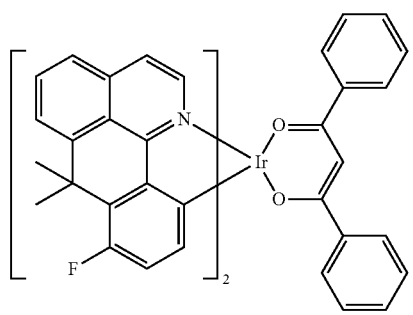
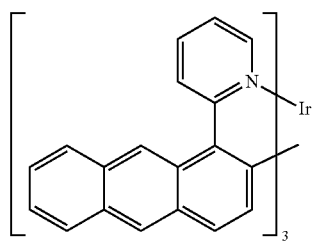
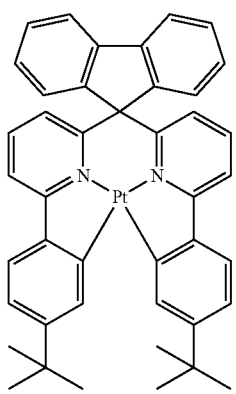
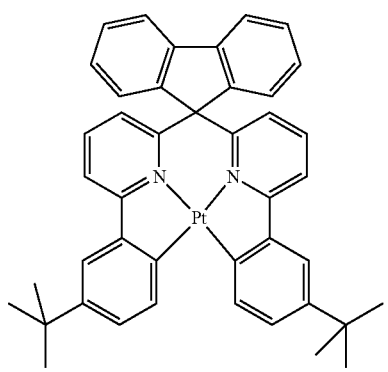

| 271 -continued | 272 -continued |
|---|---|
| 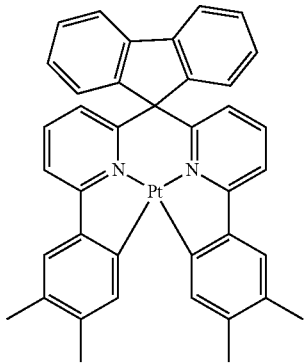 | 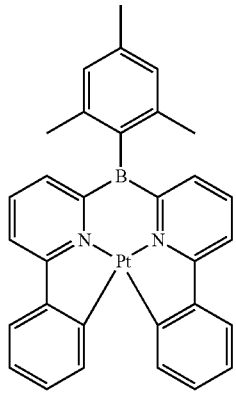 |
| 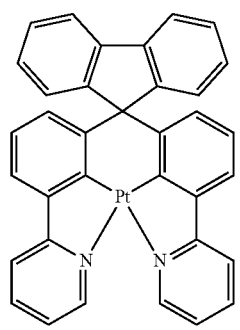 | 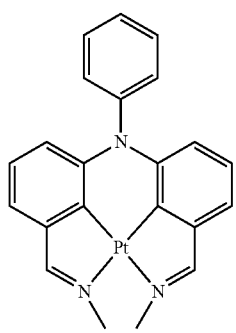 |
| 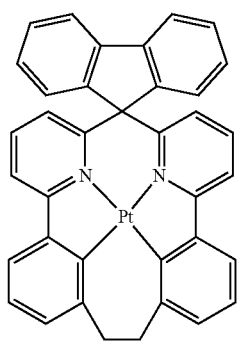 | 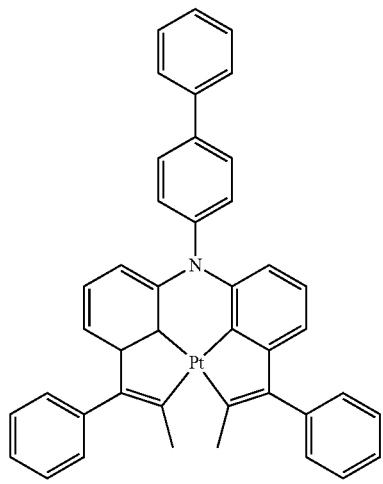 |
| 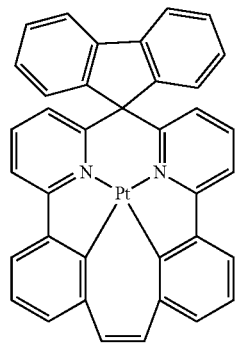 | 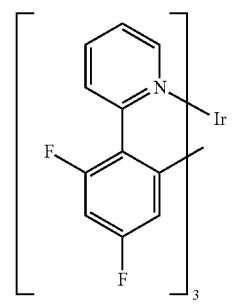 |

| 273 -continued | 274 -continued |
|---|---|
| 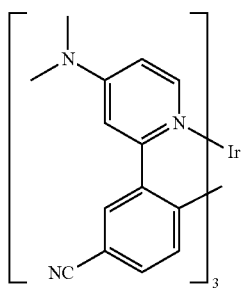 | 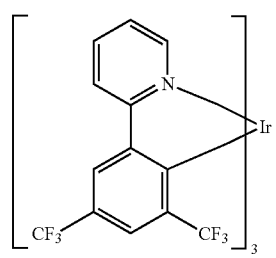 |
| 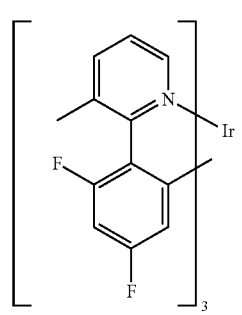 | 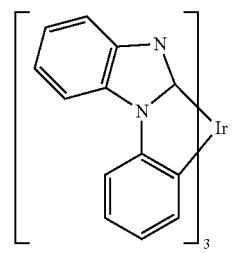 |
| 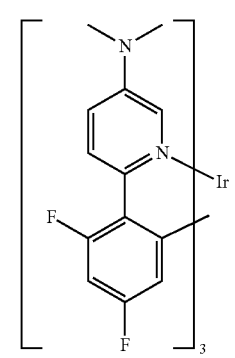 | 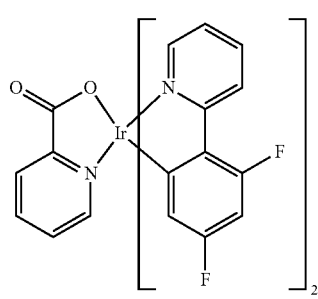 |
| 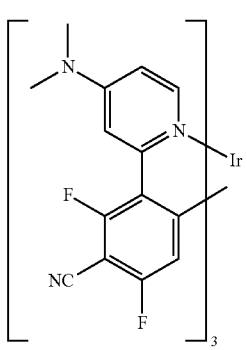 | 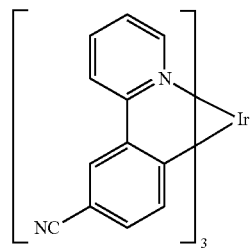 |
| 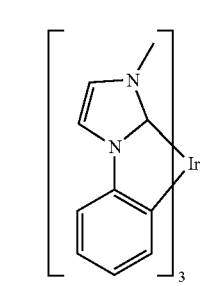 | 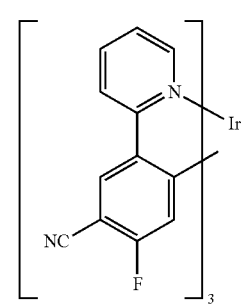 |

275
-continued
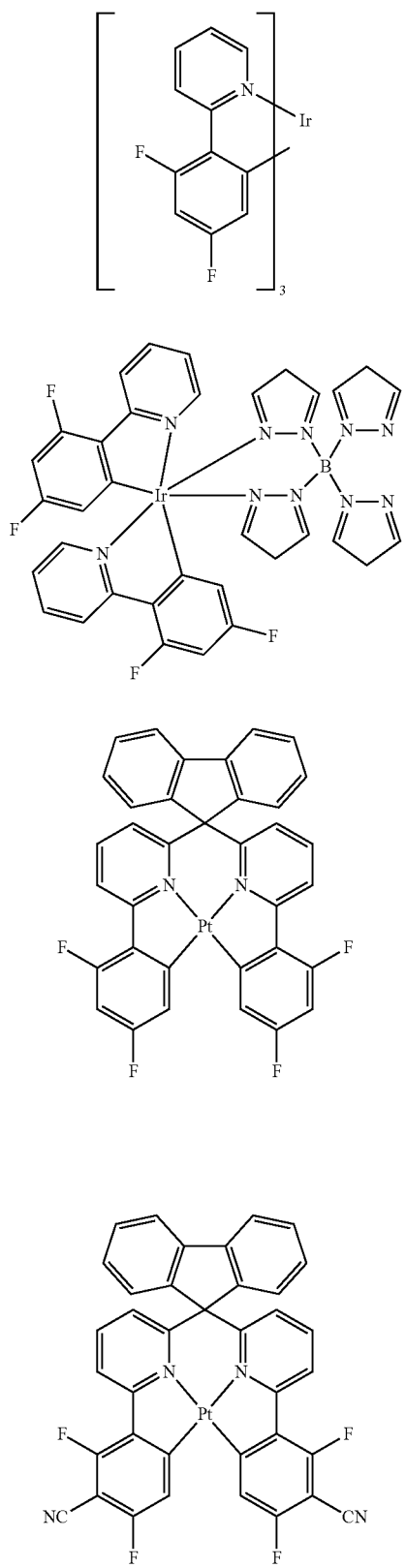
276
-continued
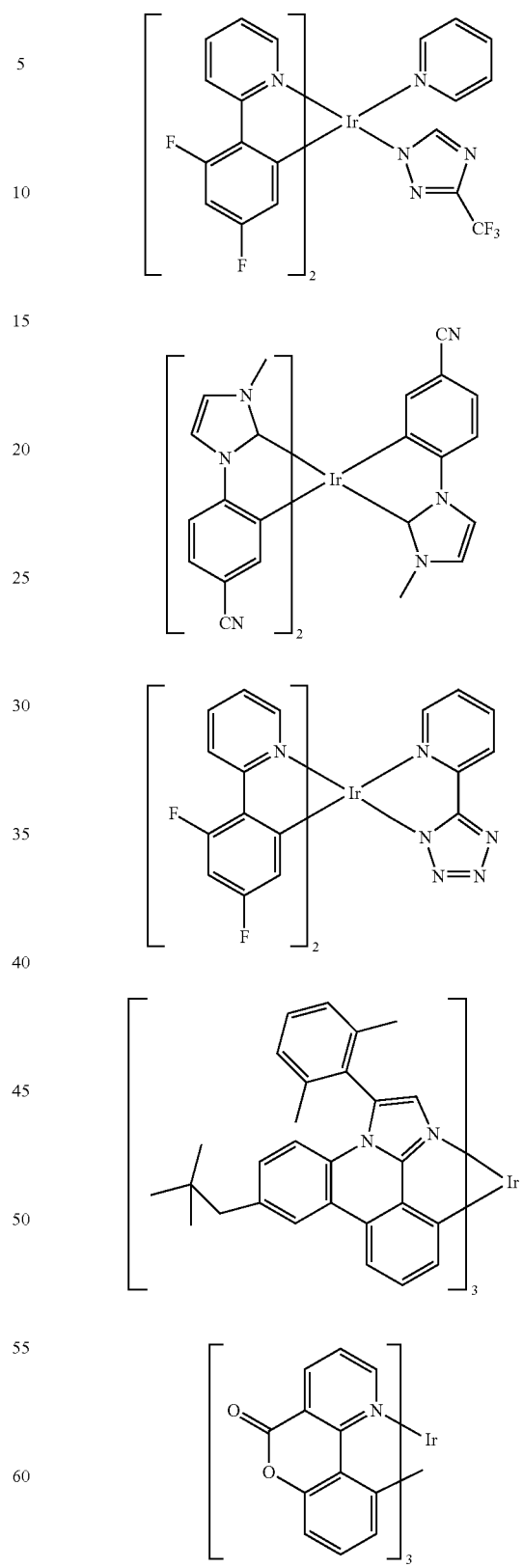

277
-continued
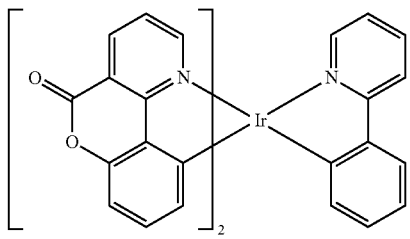
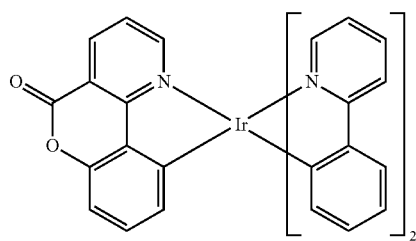
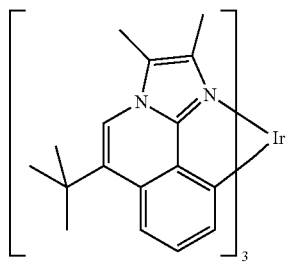
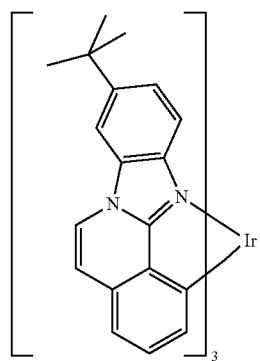
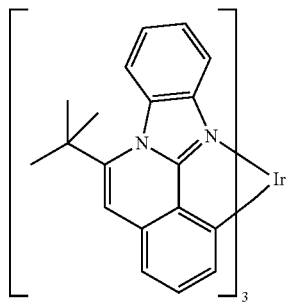
278
-continued
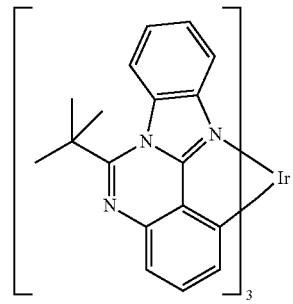
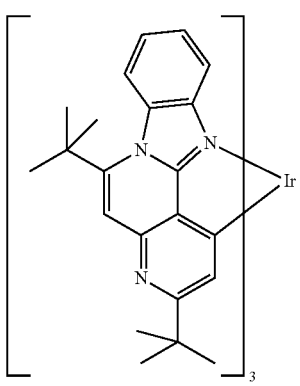
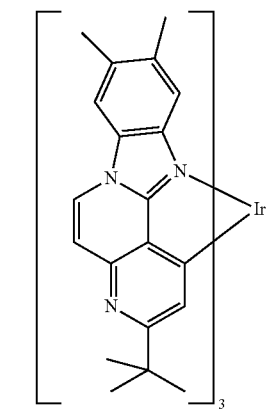
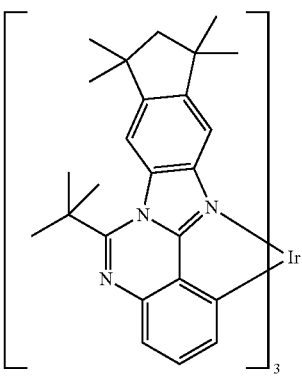

279
-continued
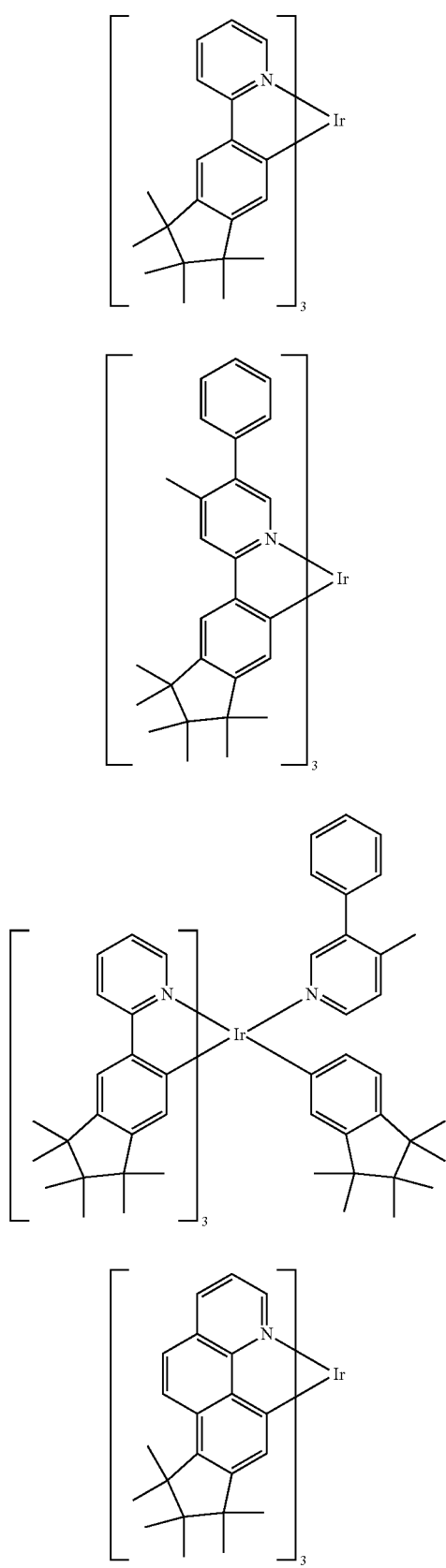
280
-continued
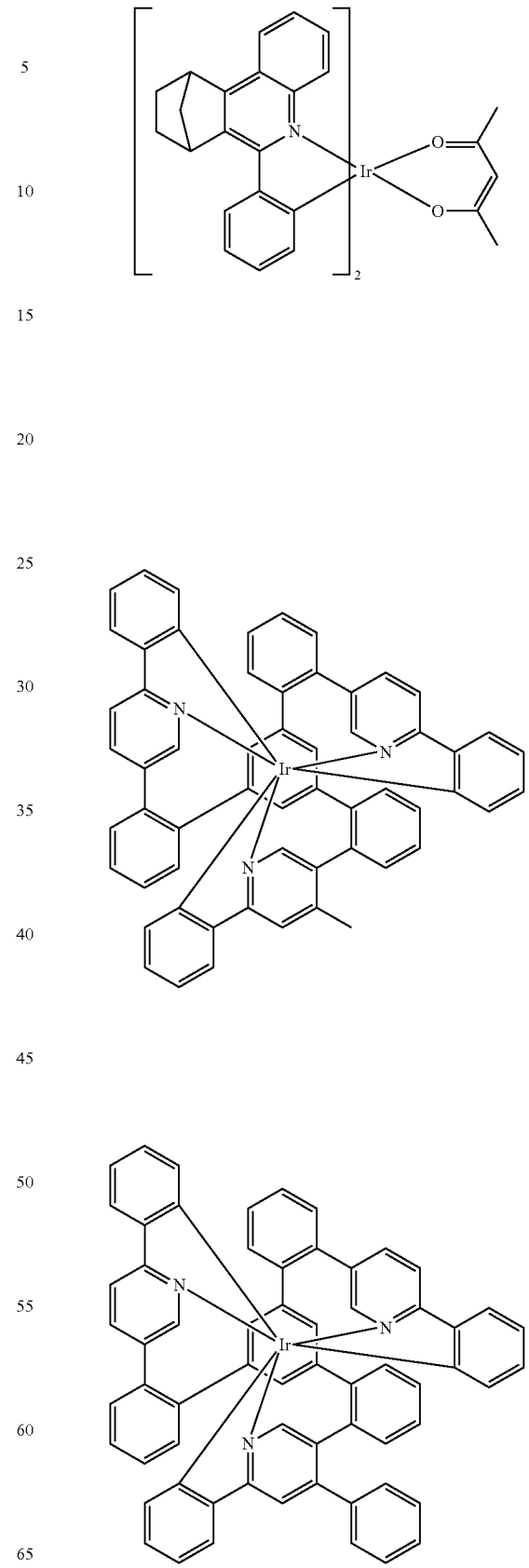

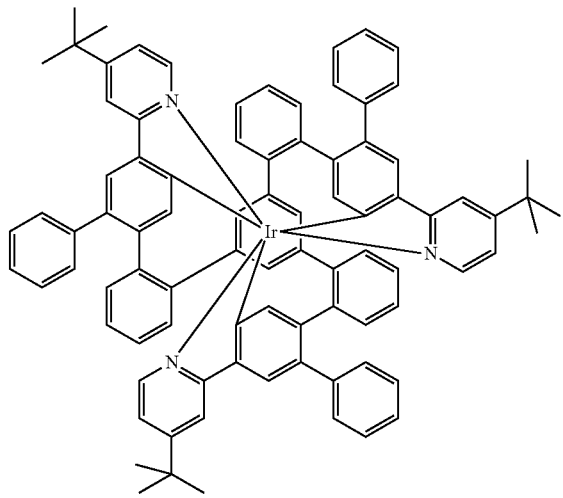

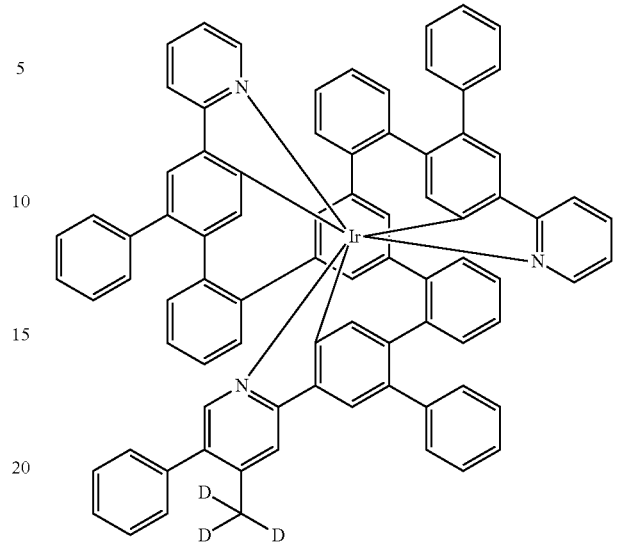

In a preferred embodiment of the invention, the compounds of formula (I) are used as hole-transporting material. The compounds are then preferably in a hole-transporting layer. Preferred embodiments of hole-transporting layers are hole transport layers, electron blocker layers and hole injection layers. When the compound of the formula (I) is present in a hole-transporting layer, the latter is preferably an electron-blocking layer. This preferably directly adjoins the emitting layer on the anode side.

A hole transport layer according to the present application is a layer having a hole-transporting function between the anode and emitting layer. More particularly, it is a hole-transporting layer which is not a hole injection layer and not an electron blocker layer.

Hole injection layers and electron blocker layers are understood in the context of the present application to be specific embodiments of hole-transporting layers. A hole injection layer, in the case of a plurality of hole-transporting layers between the anode and emitting layer, is a hole-transporting layer which directly adjoins the anode or is separated therefrom only by a single coating of the anode. An electron blocker layer, in the case of a plurality of hole-transporting layers between the anode and emitting layer, is that hole-transporting layer which directly adjoins the emitting layer on the anode side. Preferably, the OLED of the invention comprises two, three or four hole-transporting layers between the anode and emitting layer, at least one of which preferably contains a compound of formula (I), and more preferably exactly one or two contain a compound of formula (I).

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I) then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, 12, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:

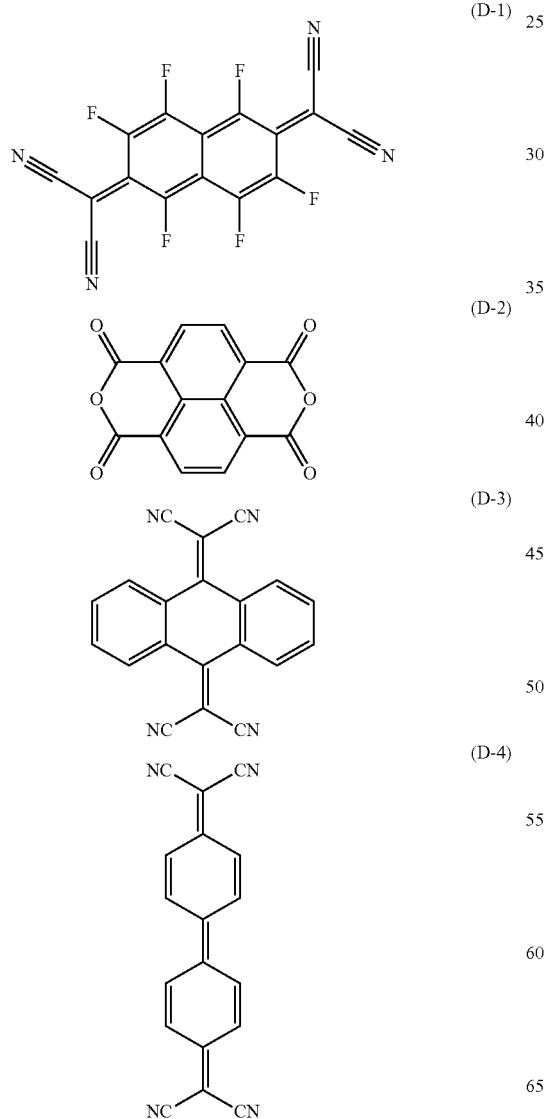

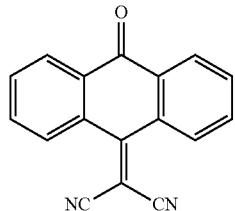

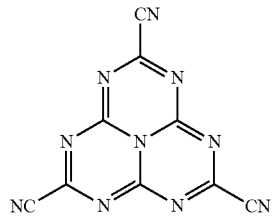

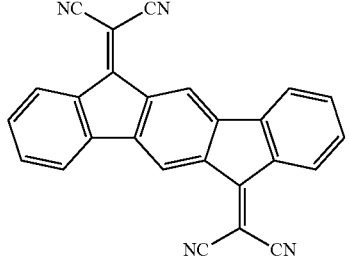

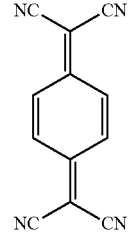

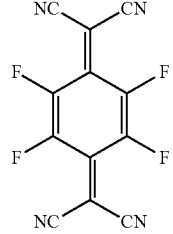

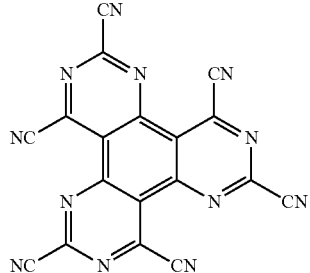

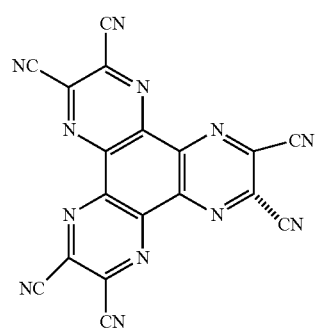

(D-11)

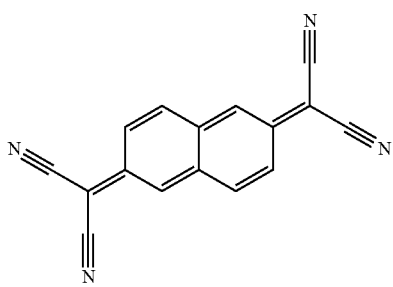

(D-12)

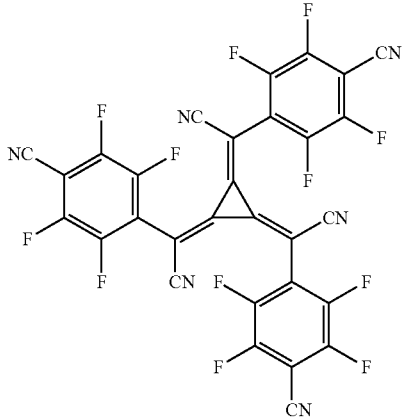

(D-13)

In a further preferred embodiment of the invention, the compound of formula (I) is used as hole transport material in combination with a hexaazatriphenylene derivative as described in US 2007/0092755 in an OLED. Particular preference is given here to using the hexaazatriphenylene derivative in a separate layer.

In a preferred embodiment of the present invention, the compound of the formula (I) is used in an emitting layer as matrix material in combination with one or more emitting compounds, preferably phosphorescent emitting compounds. The phosphorescent emitting compounds here are preferably selected from red-phosphorescent and green-phosphorescent compounds.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also contain systems comprising a plurality of matrix materials (mixed matrix systems) and/or a plurality of emitting compounds. In this case too, the emitting compounds are generally those compounds having the smaller share in the system and the matrix materials are those compounds having the greater share in the system. In individual cases, however, the proportion of a single matrix material in the system may be less than the proportion of a single emitting compound.

It is preferable that the compounds of formula (I) are used as a component of mixed matrix systems, preferably for phosphorescent emitters. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. Correspondingly, when the compound of the formula (I) is used as matrix material for a phosphorescent emitter in the emitting layer of an OLED, a second matrix compound having electron-transporting properties is present in the emitting layer. The two different matrix materials may be present in a ratio of 1:50 to 1:1, preferably 1:20 to 1:1, more preferably 1:10 to 1:1 and most preferably 1:4 to 1:1. More specific details relating to mixed matrix systems are given inter alia in the application WO 2010/108579, the corresponding technical teaching of which is incorporated by reference in this connection.

The desired electron-transporting and hole-transporting properties of the mixed matrix components may, however, also be combined mainly or entirely in a single mixed matrix component, in which case the further mixed matrix component(s) fulfil(s) other functions.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the inventive compounds as matrix components of a mixed matrix system are selected from the preferred matrix materials specified below for phosphorescent emitting compounds, and among these especially from those having electron-transporting properties.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions.

Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyreneary- lamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in WO 2017/036574, the phenoxazines disclosed in WO 2017/028940 and WO 2017/028941, and the fluorene derivatives bonded to furan units or to thiophene units that are disclosed in WO 2016/150544.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573.

Preferred matrix materials for phosphorescent emitting compounds are, as well as the compounds of the formula (I), aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art. Preferred materials for hale-transporting and hole-injecting layers are especially selected from the following materials:

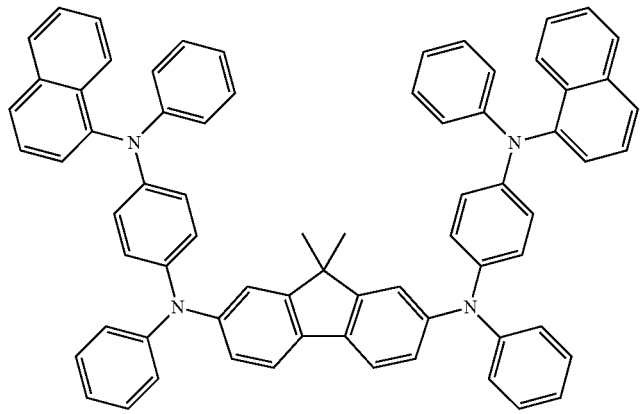

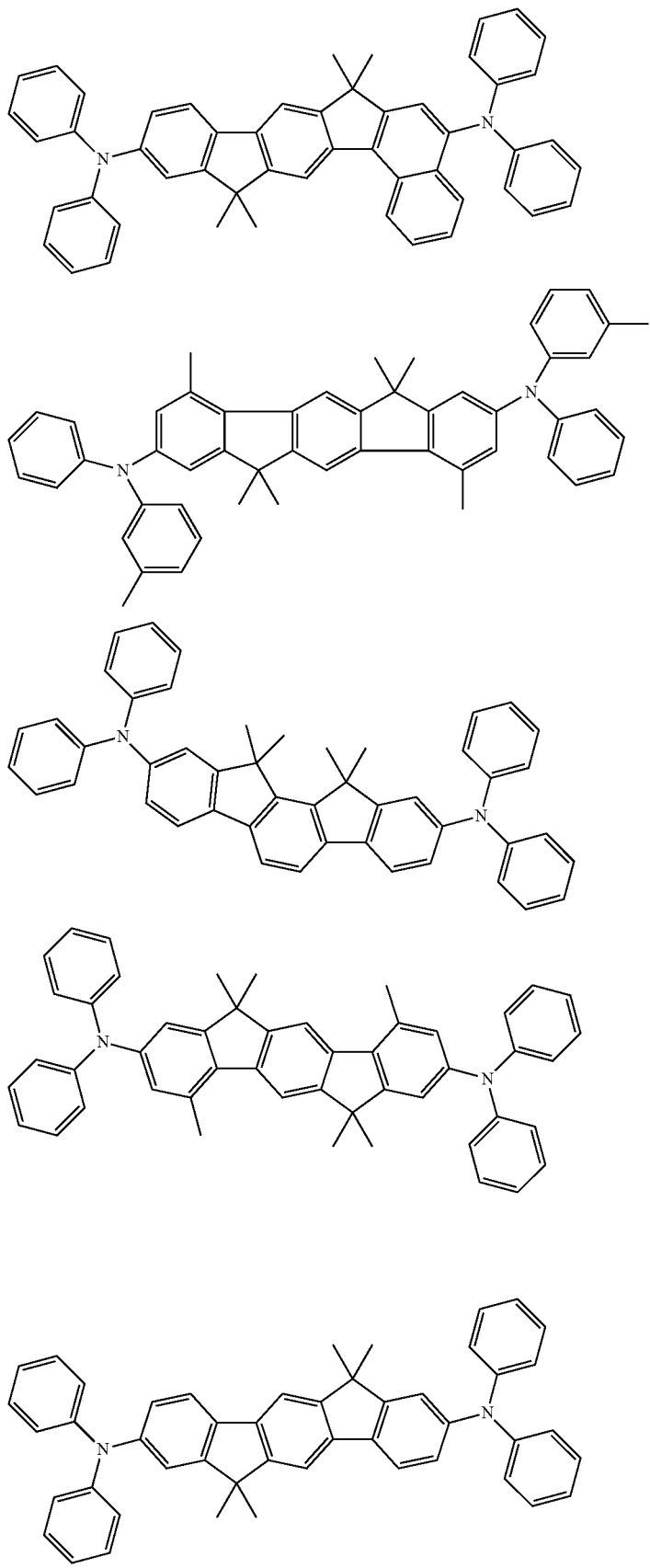

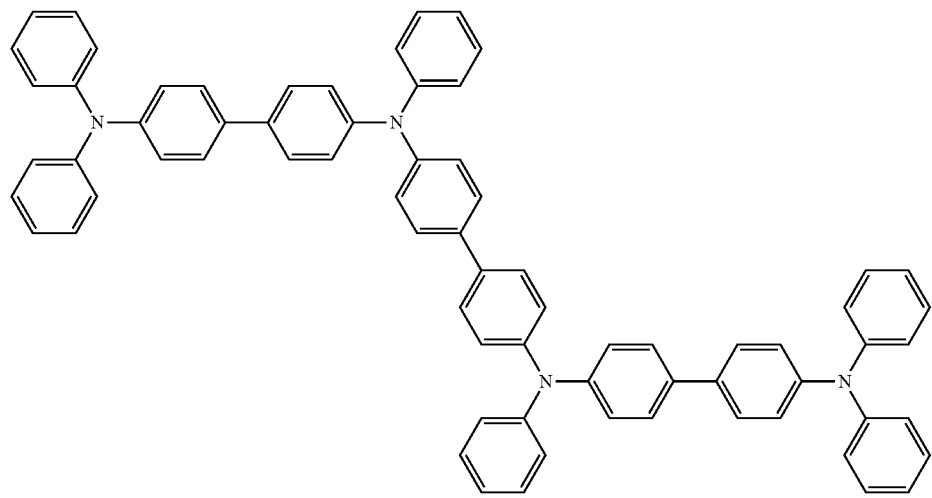
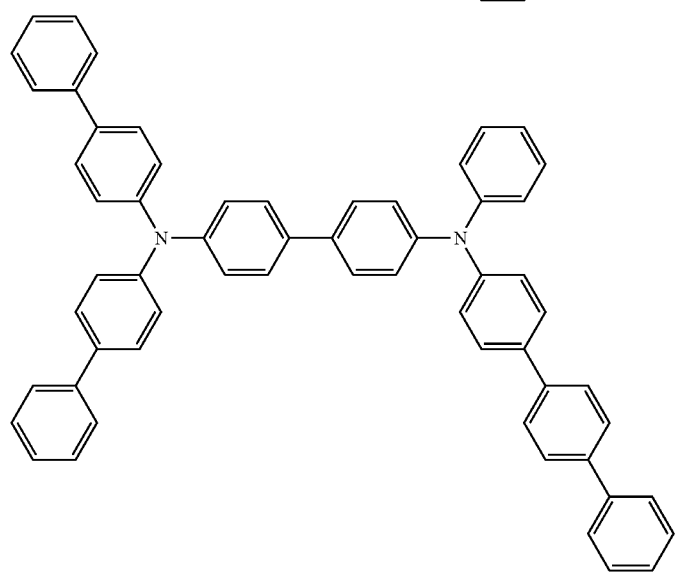
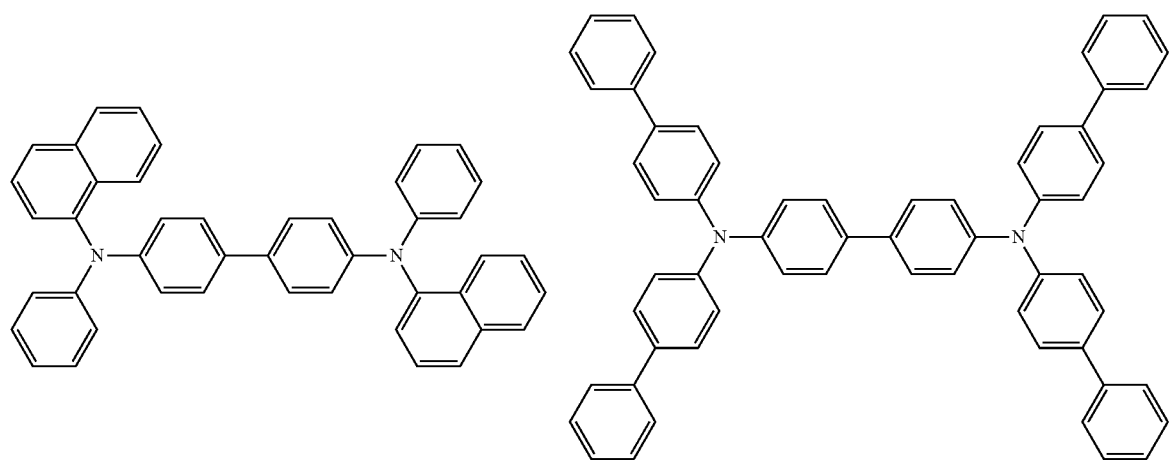

-continued
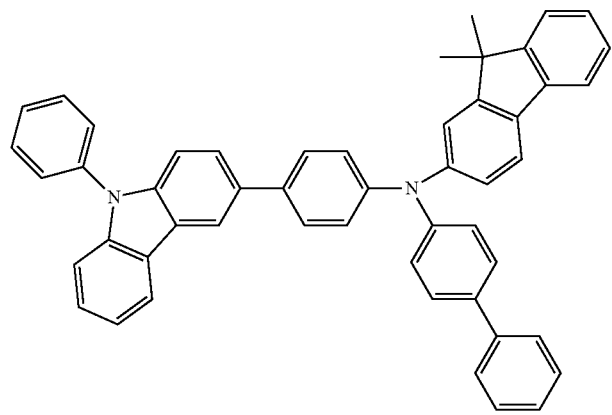
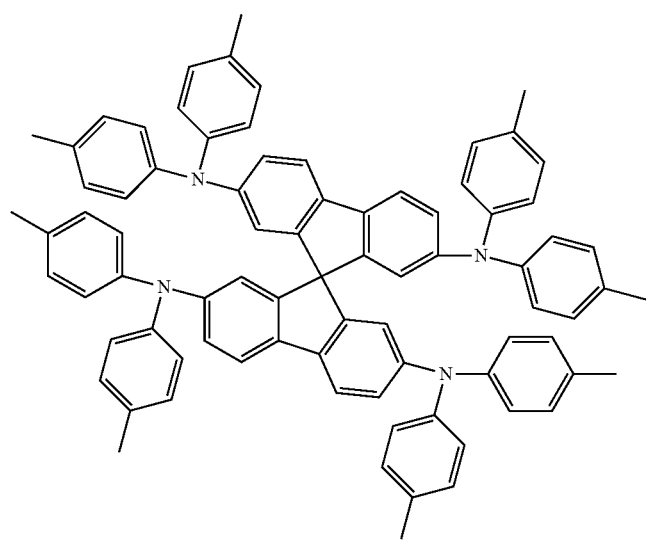
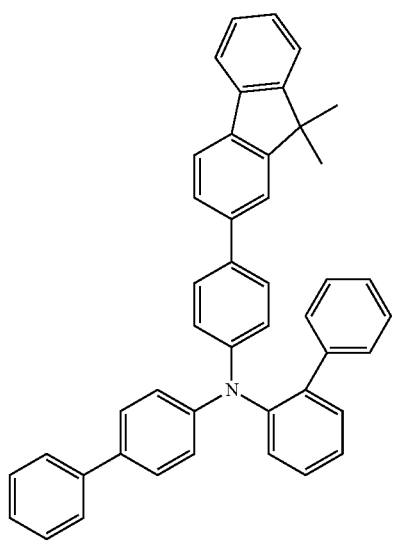
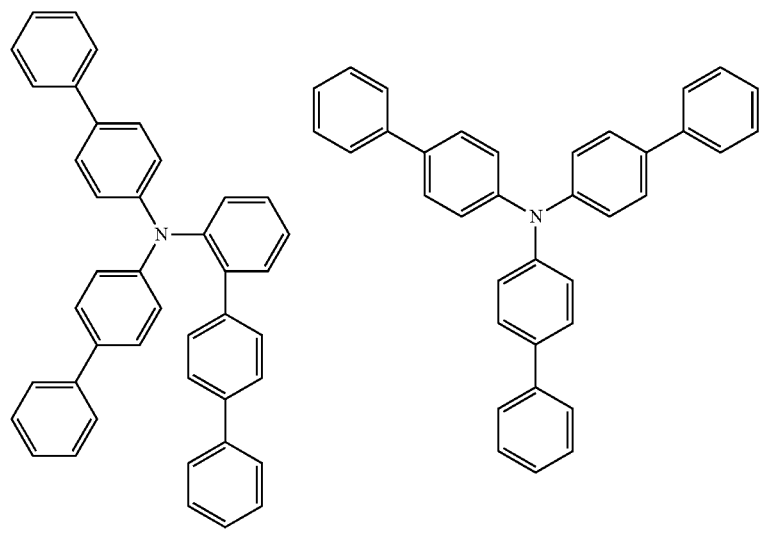

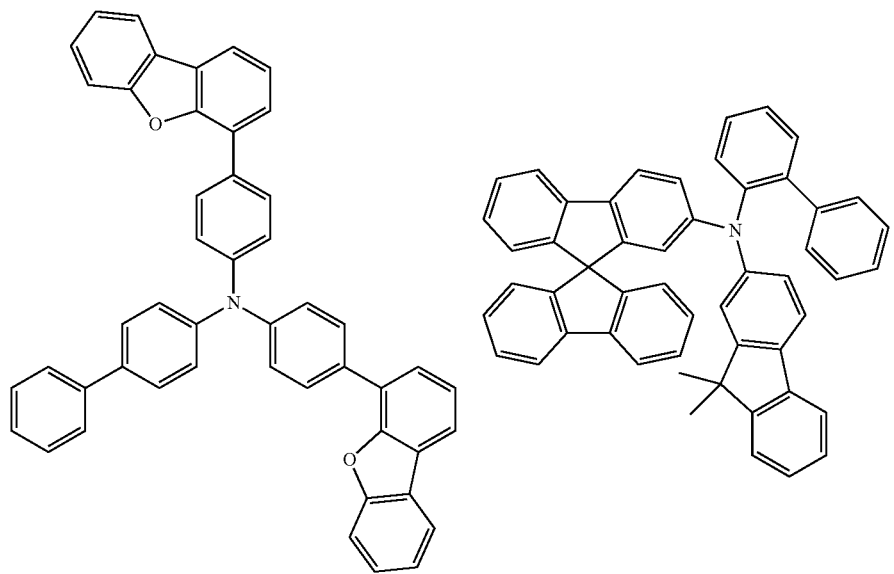
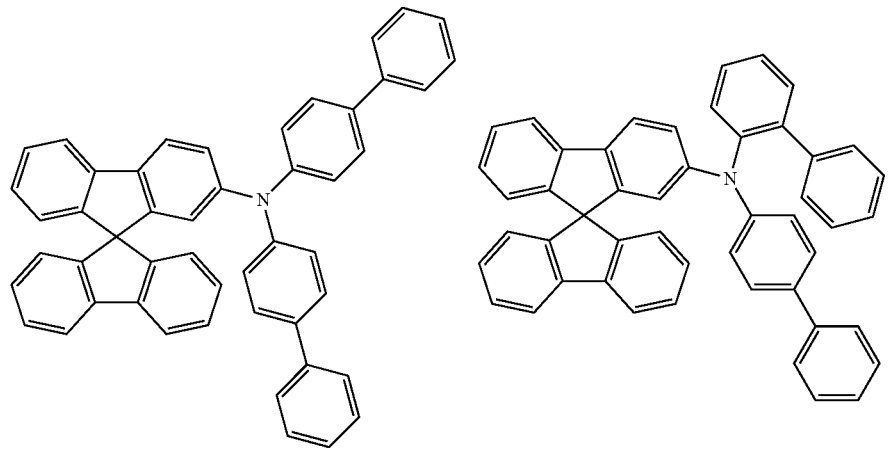
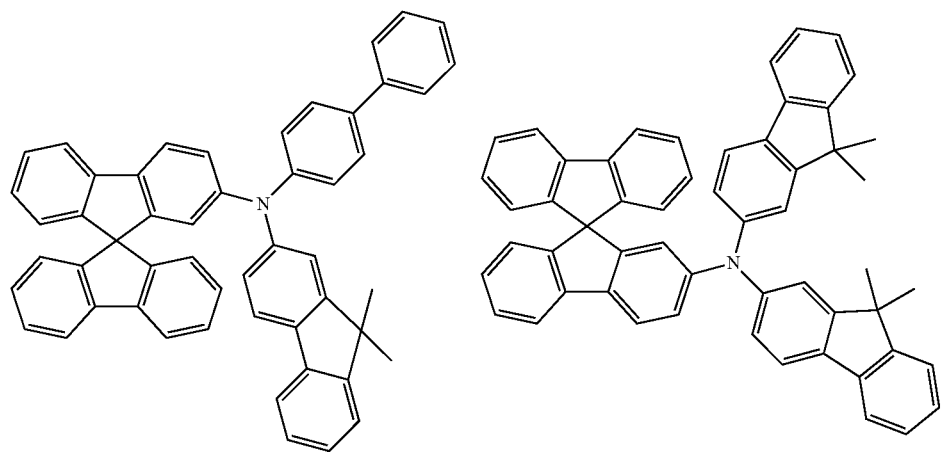

-continued
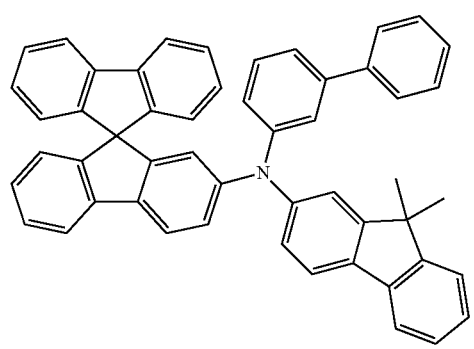
297
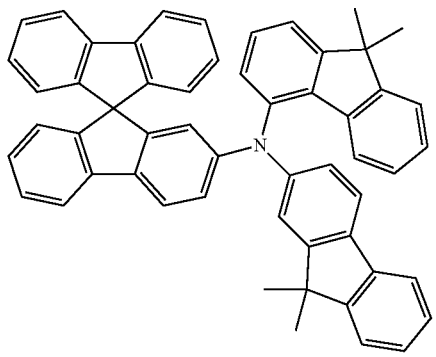
298
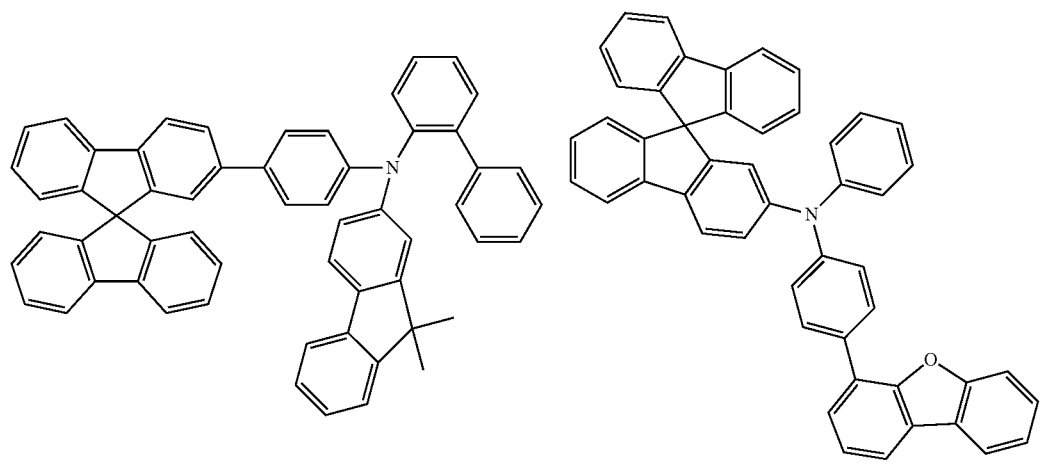
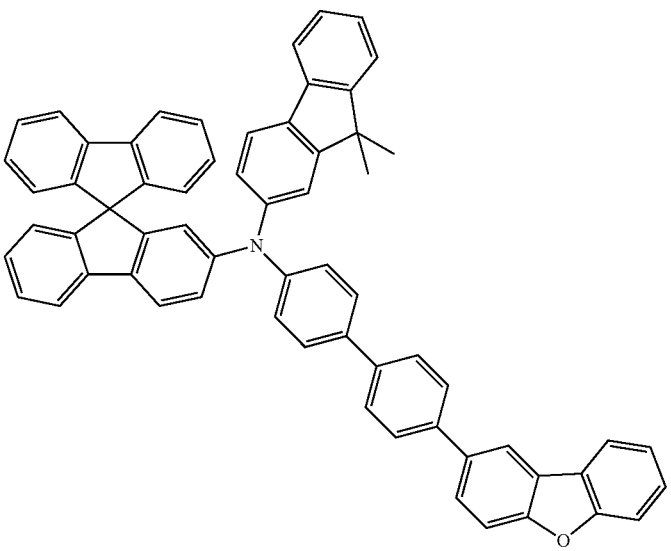

-continued
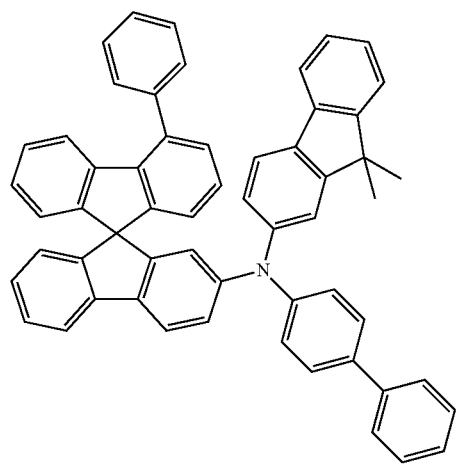
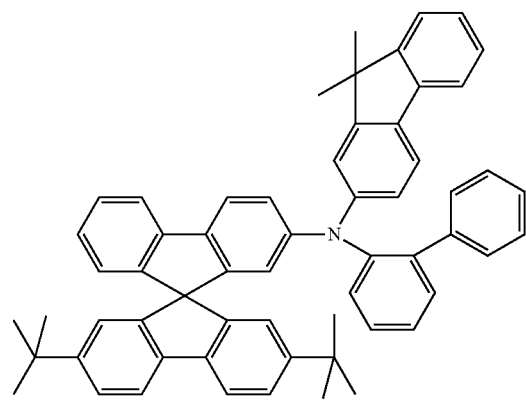
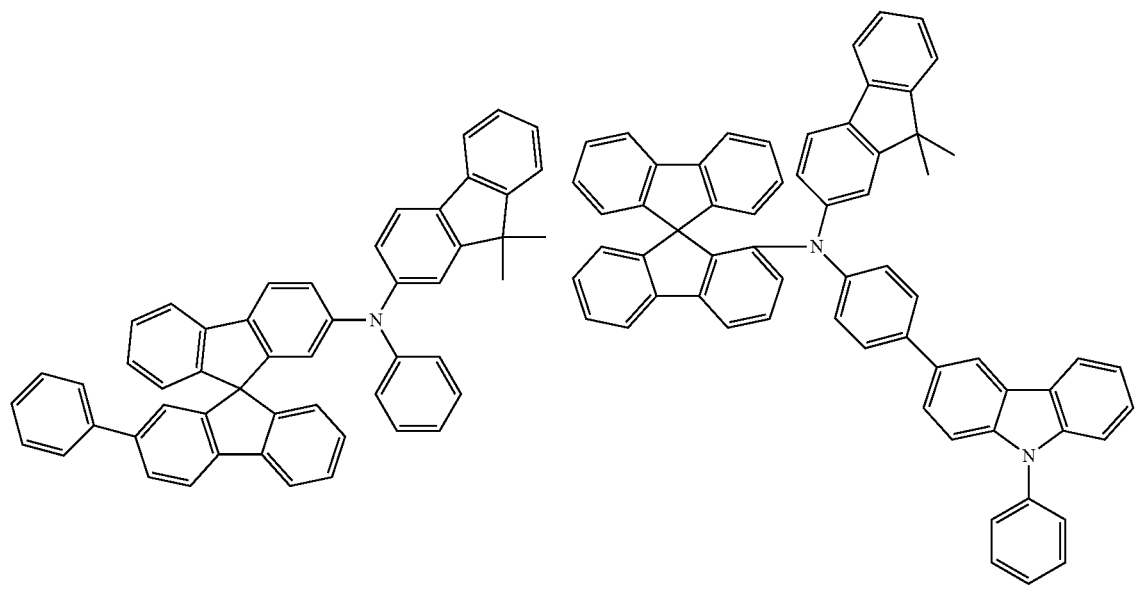
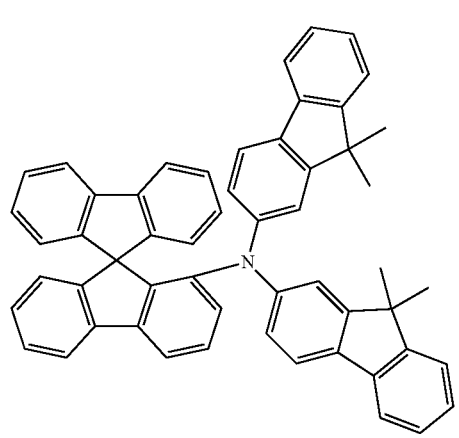
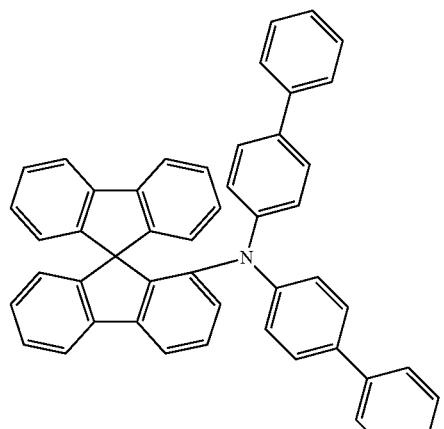

301
302
-continued
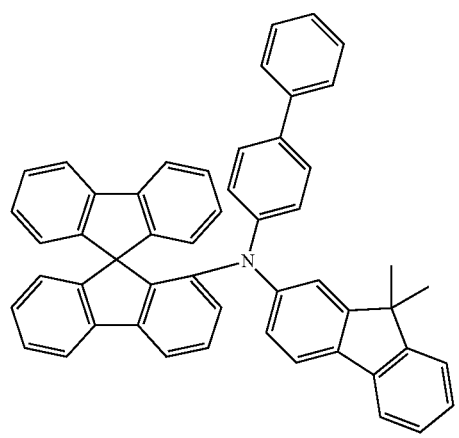
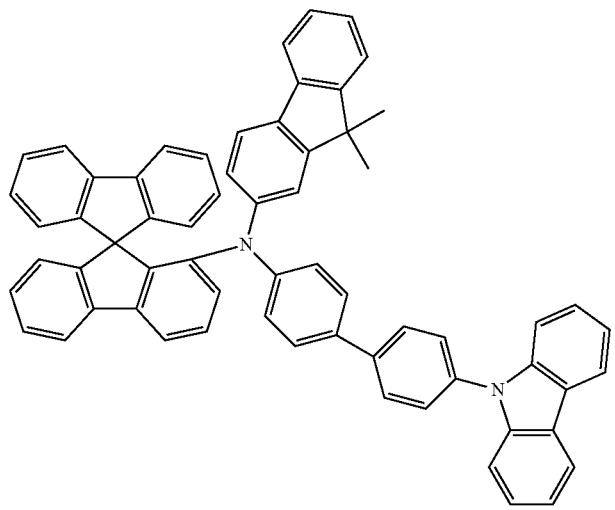
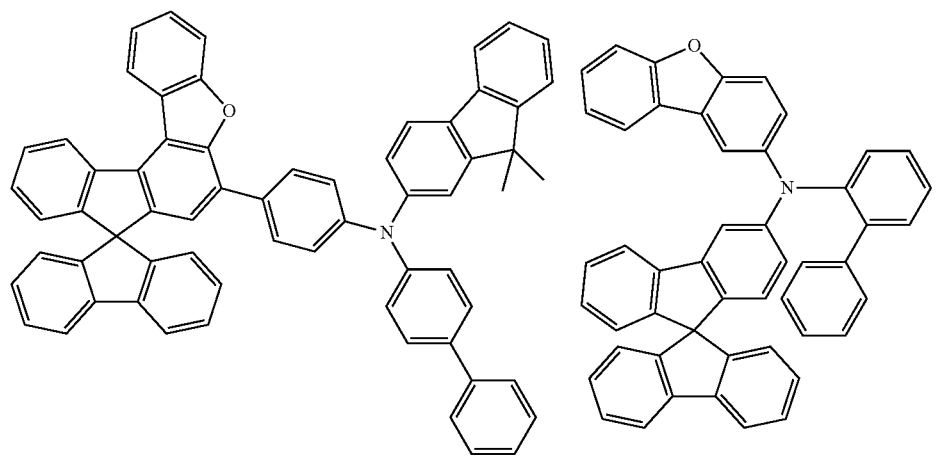
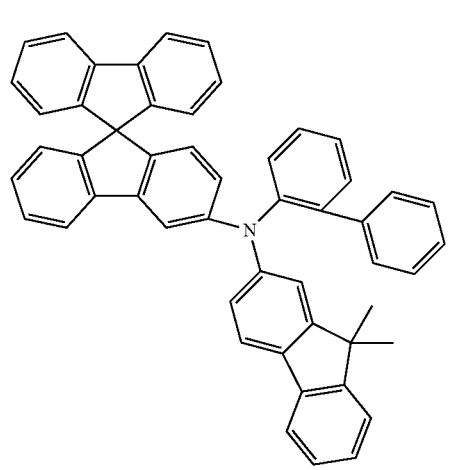
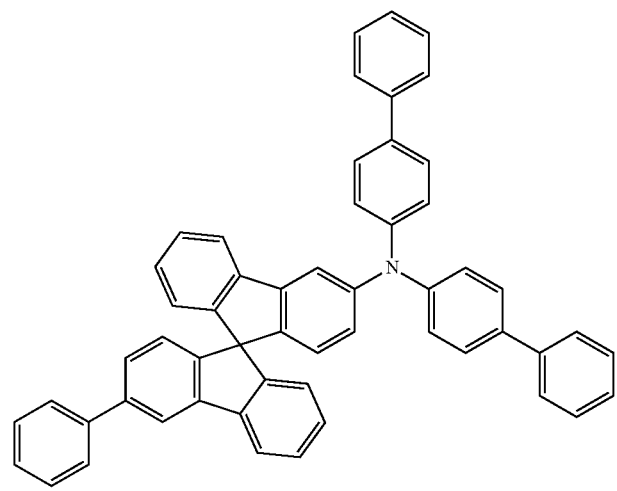

-continued
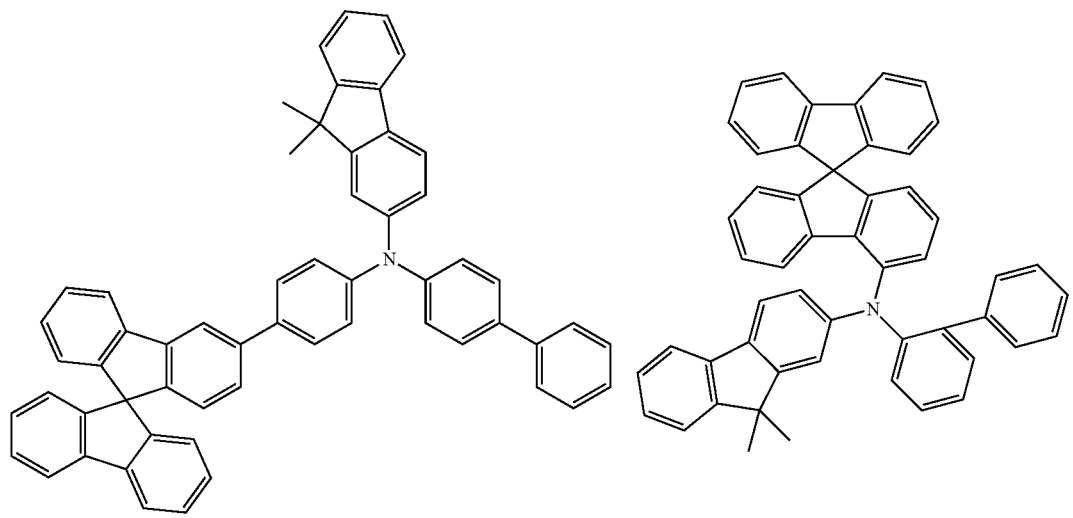
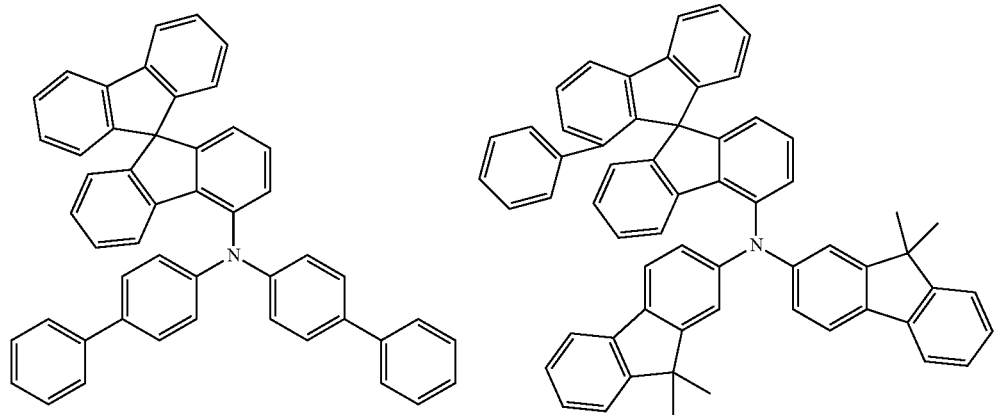
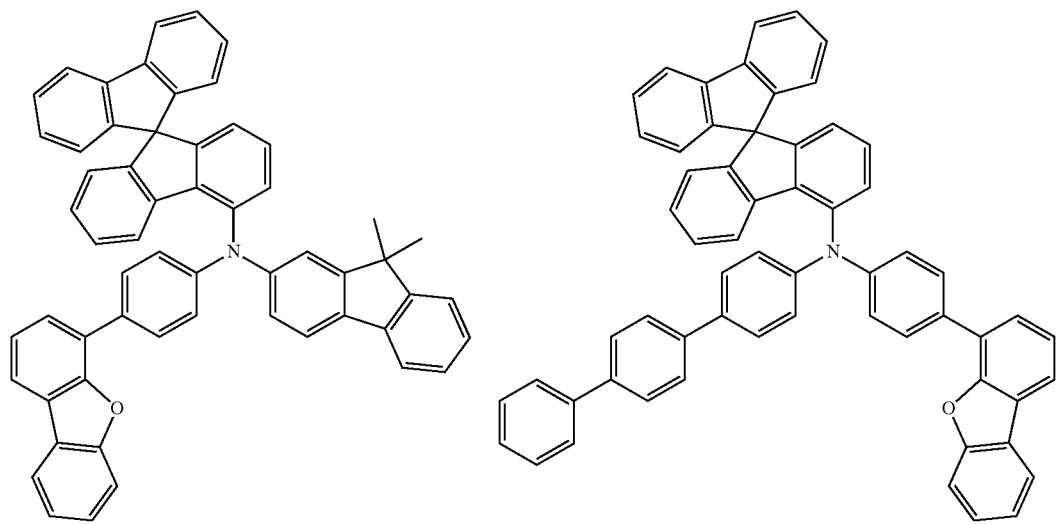

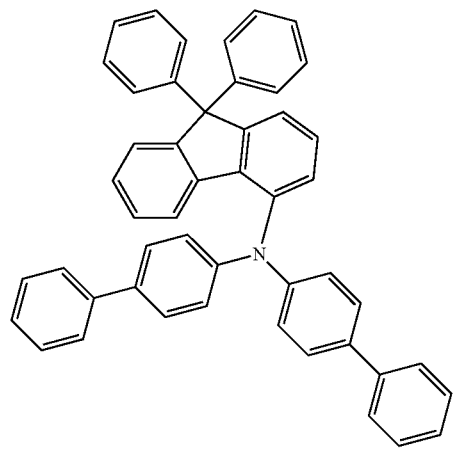
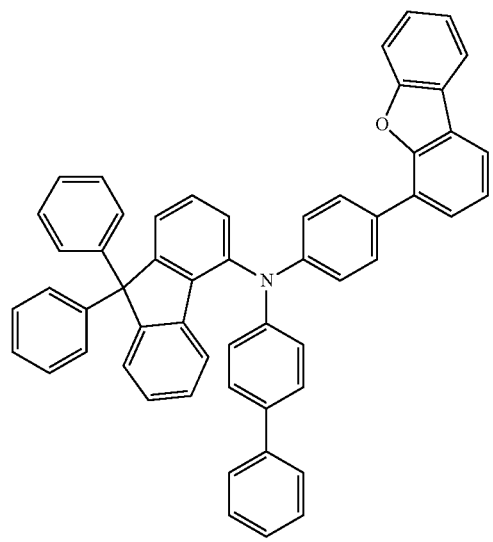
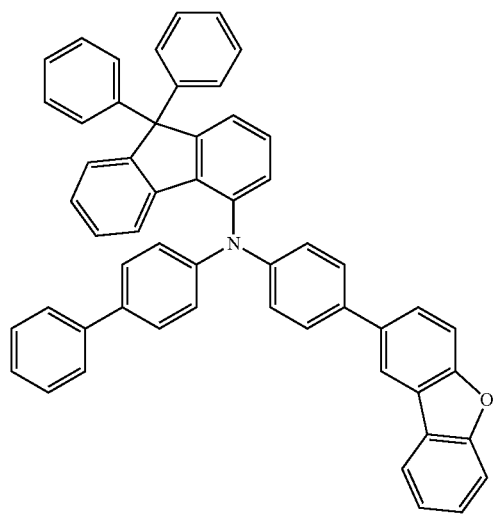
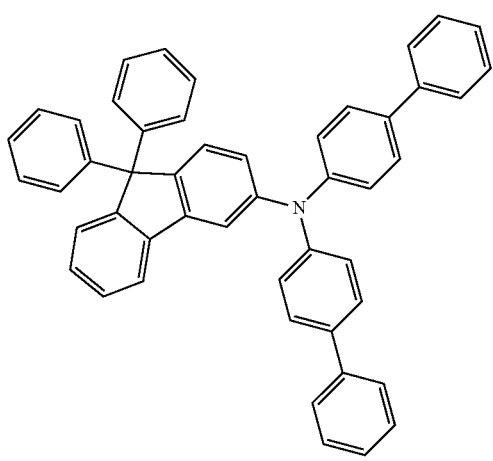
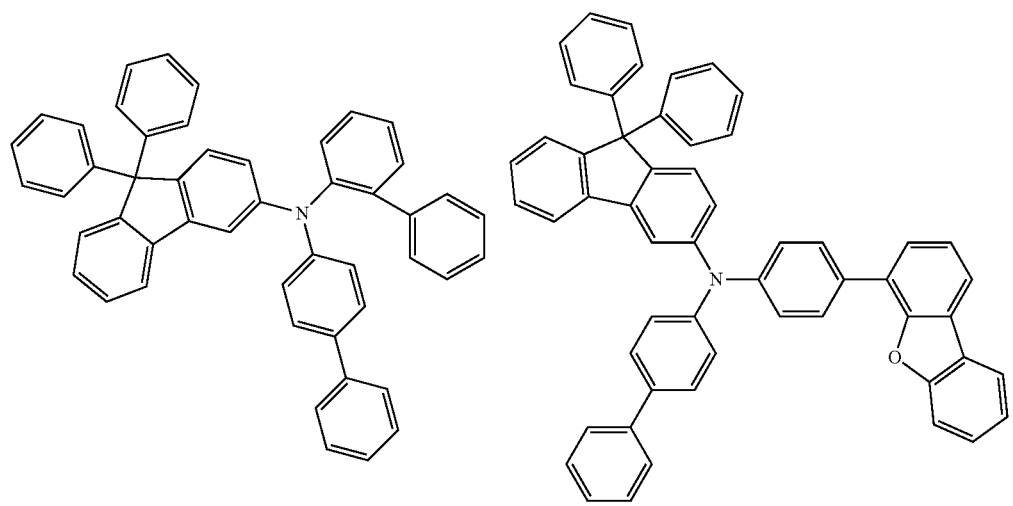

307
308
-continued
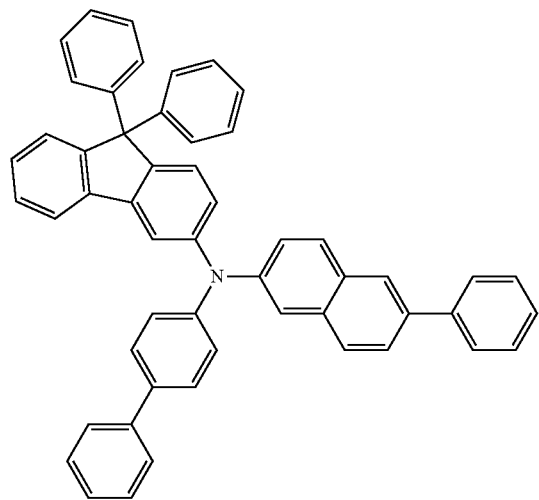
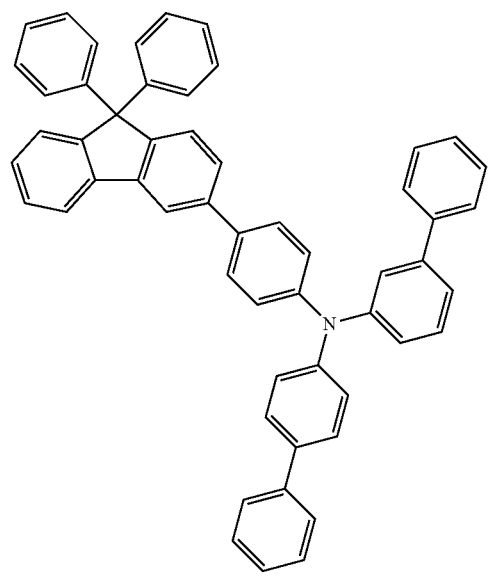
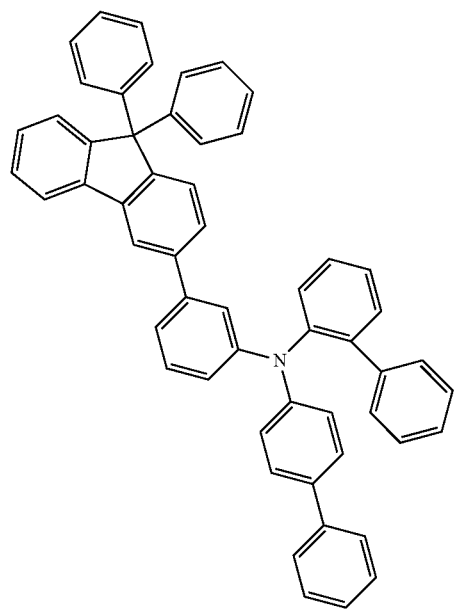
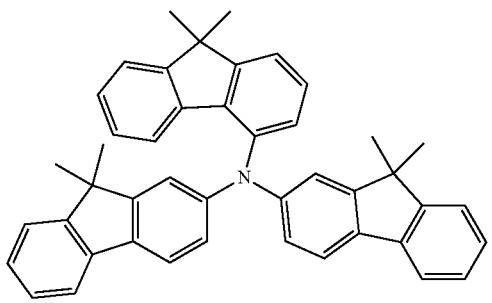
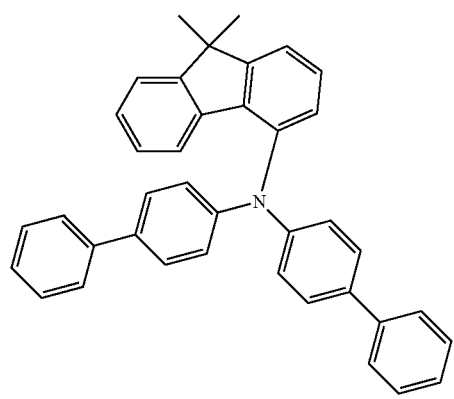
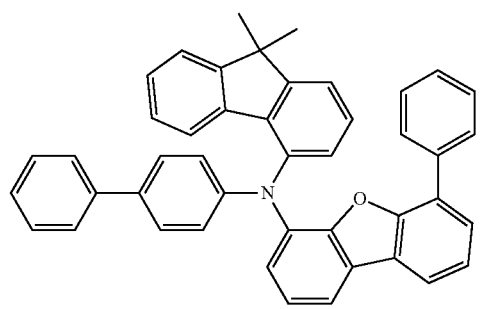

-continued
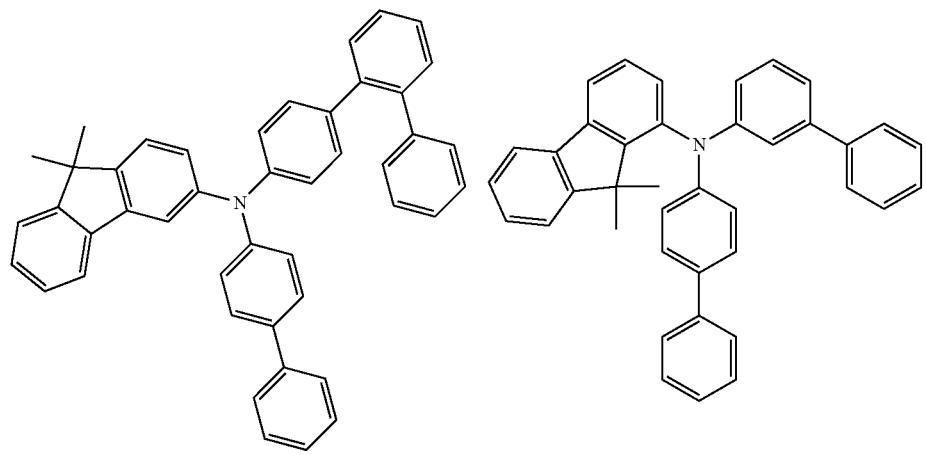
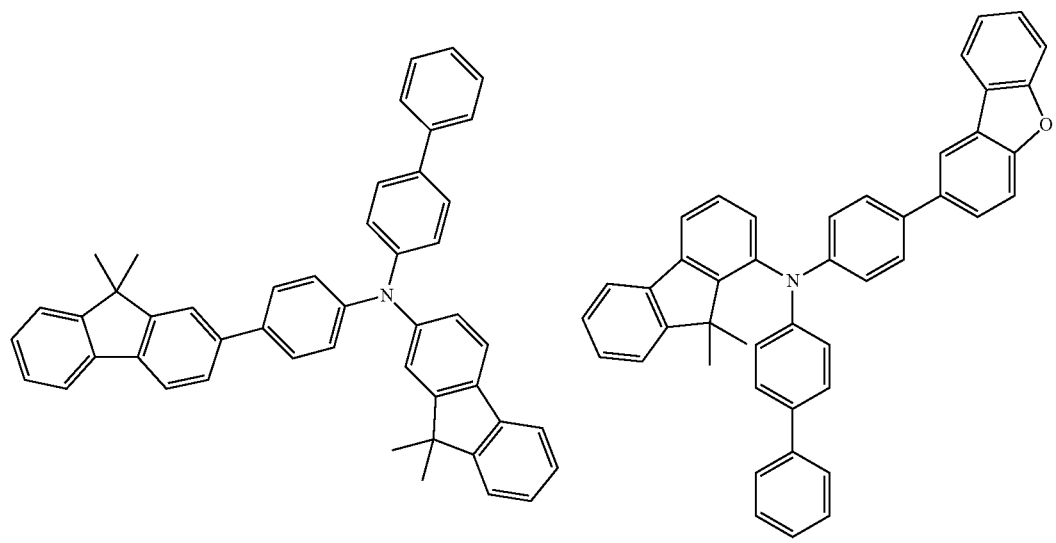
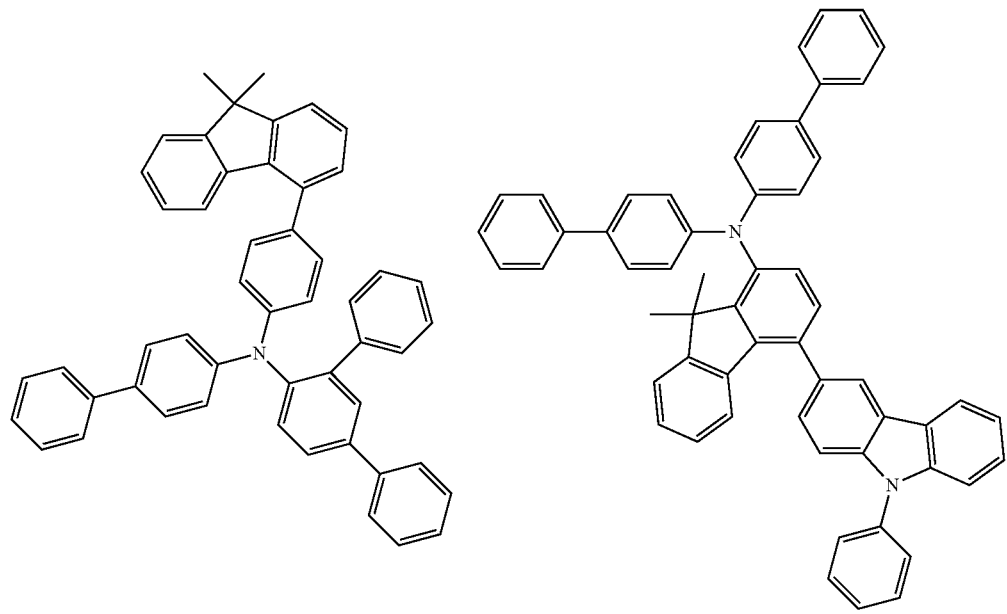

-continued
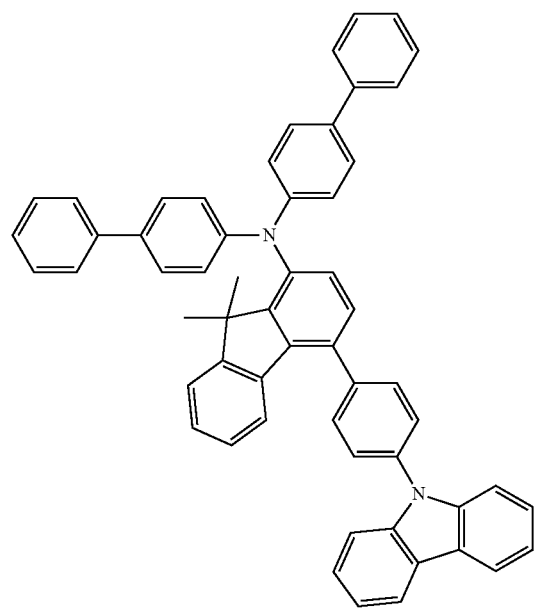
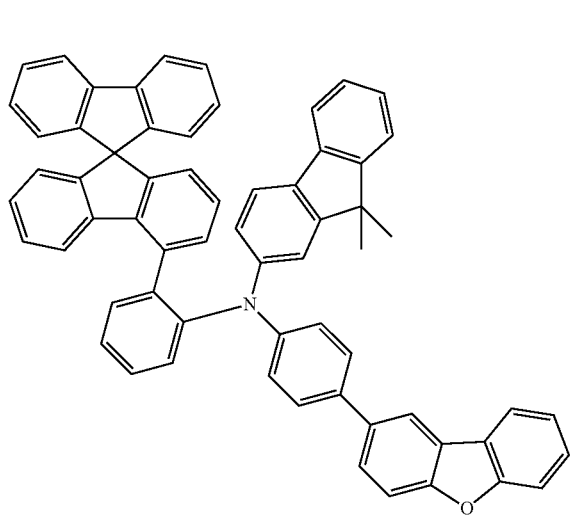
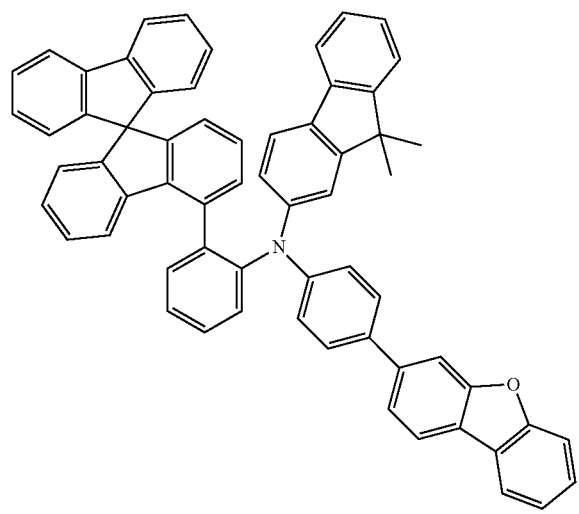
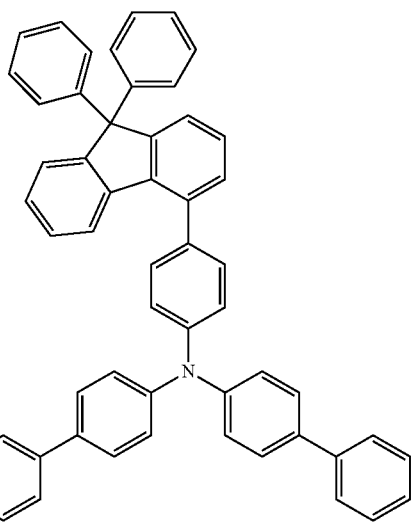
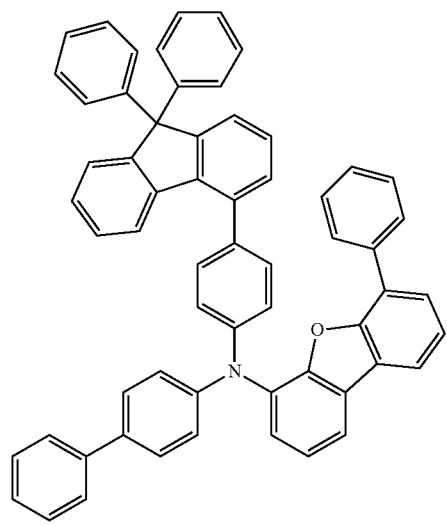
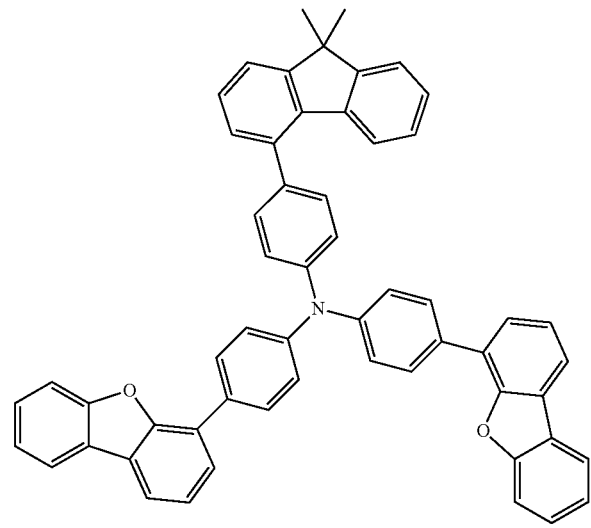

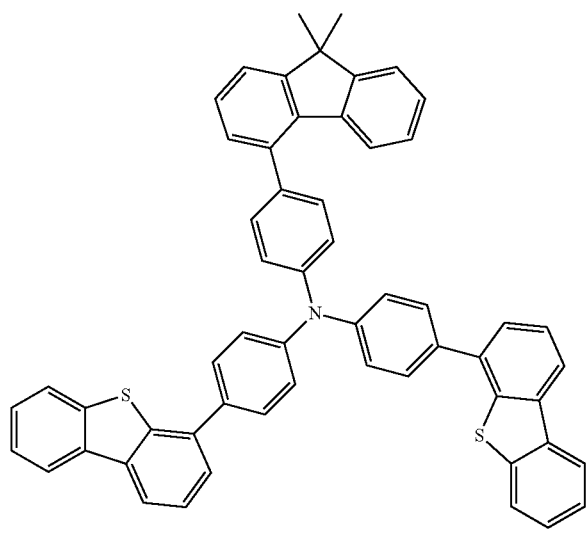
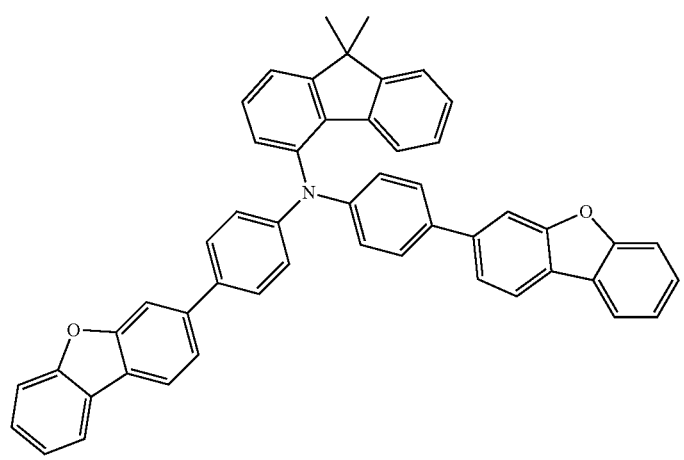
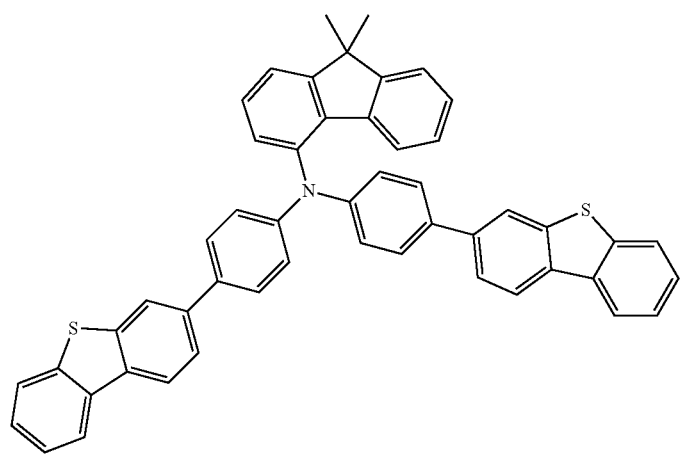

Preferably, the inventive OLE© comprises two or more different hole-transporting layers. The compound of the formula (I) may be used here in one or more of or in all the hole-transporting layers. In a preferred embodiment, the compound of the formula (I) is used in exactly one or exactly two hole-transporting layers, and other compounds, preferably aromatic amine compounds, are used in the further hole-transporting layers present. Further compounds which are used alongside the compounds of the formula (I), preferably in hole-transporting layers of the OLEDs of the invention, are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051, WO 2016/102048 and WO 2016/131521, phenanthrenediarylamines, for example according to WO 2015/131976, spirotribenzotropolones, for example according to WO 2016/087017, spirobifluorenes with meta-phenyldiamine groups, for example according to WO 2016/078738, spirobisacridines, for example according to WO 2015/158411, xanthenediarylamines, for example according to WO 2014/072017, and 9,10-dihydroanthracene Spiro compounds with diarylamino groups according to WO 2015/086108.

Materials used for the electron transport layer may be any materials as used according to the prior art as electron transport materials in the electron transport layer. Especially suitable are aluminium complexes, for example Alq$_3$, zirconium complexes, for example Zrq$_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, Li$_2$O, BaF$_2$, MgO, NaF, CsF, Cs$_2$CO$_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiO$_x$, Al/PtO$_x$) may also be preferred. For some applications, at least one of the electrodes has to be transparent or partly transparent in order to enable either the irradiation of the organic material (organic solar cell) or the emission of light (OLED, 0-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

EXAMPLES

A) Synthesis Examples

Example 1-1: Synthesis of the Inventive Compound 1-1 and Variants

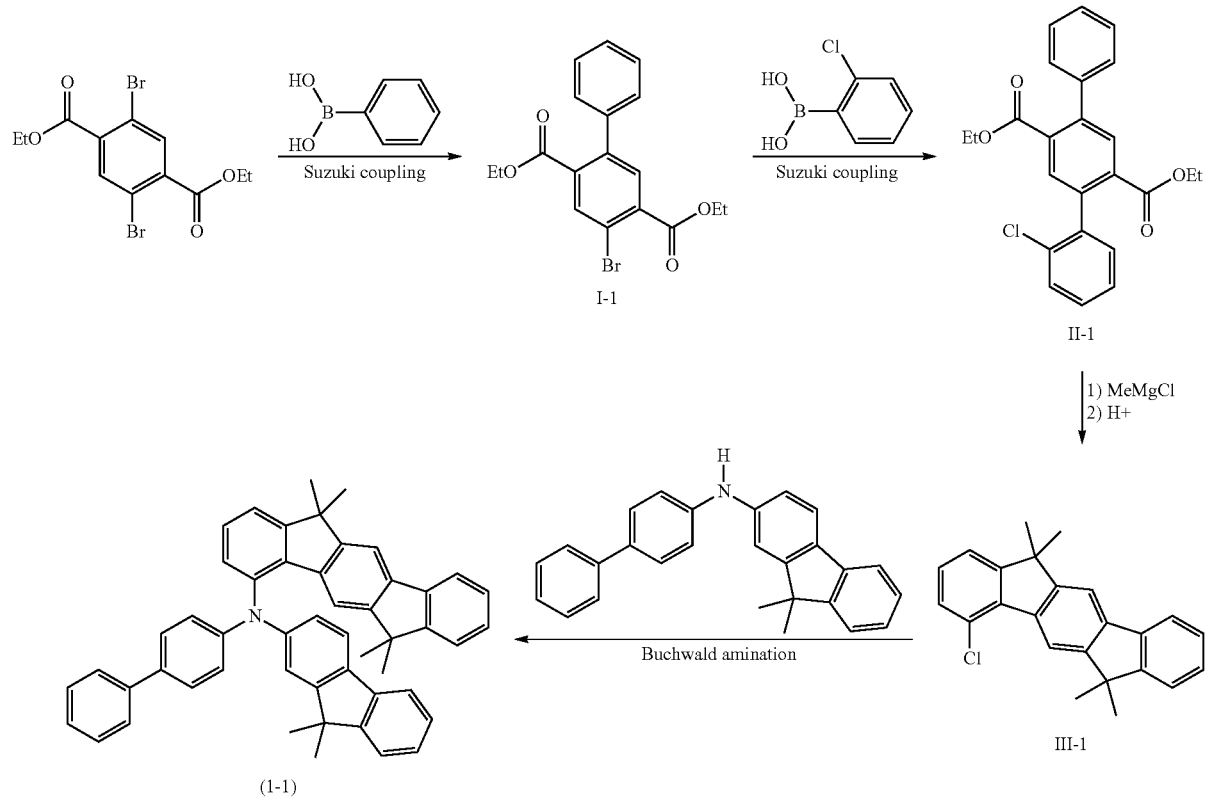

Intermediate I-1

10 g of phenylboronic acid (81 mmol) and 30 g of dibromodicarboxylic ester (CAS No. 18013-97-3) (77 mmol) are suspended in 750 ml of THF. 160 ml of 2 M potassium carbonate solution are slowly added dropwise. The solution is degassed and saturated with $N_2$. Thereafter, 0.89 g (0.8 mmol) of $Pd(Ph_3P)_4$ are added. The reaction mixture is heated to boiling under a protective atmosphere for 16 h. The mixture is subsequently partitioned between toluene and water, and the organic phase is washed three times with water and dried over $Na_2SO_4$ and concentrated by rotary evaporation. The remaining residue is purified by means of column chromatography. The yield is 15.3 g (52% of theory).

Intermediate II-1

7 g of 4-chlorophenylboronic acid (44.6 mmol) and 15.3 g of the bromo derivative I-1 (40.56 mmol) are suspended in 300 ml of THF. 81 ml of 1 M potassium carbonate solution are slowly added dropwise. The solution is degassed and saturated with $N_2$. Thereafter, 0.45 g (0.4 mmol) of $Pd(Ph_3P)_4$ are added. The reaction mixture is heated to boiling under a protective atmosphere for 12 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from MeOH. The yield is 14.5 g (80% of theory).

Analogously, the following compounds are prepared (yield 30-90% of theory):

| Reactant 1 | Boronic acid derivative 1 | Boronic acid derivative 2 | Product |
|---|---|---|---|
| II-2 | phenylboronic acid | 3-chlorophenylboronic acid | |
| II-3 | 2-chlorophenylboronic acid (2 eq.) | | |

| | Reactant 1 | Boronic acid derivative 1 | Boronic acid derivative 2 | Product |
|---|---|---|---|---|
| II-4 | 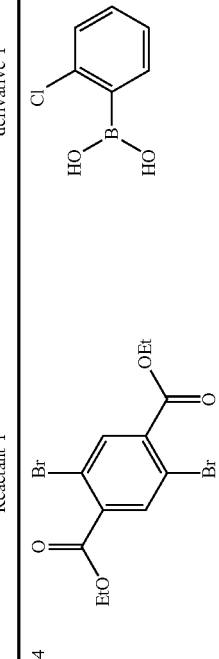 | 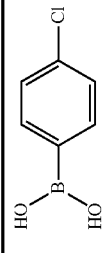 | 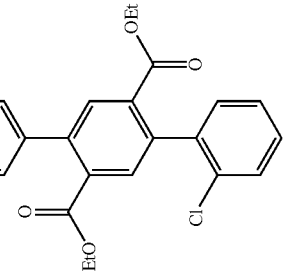 | 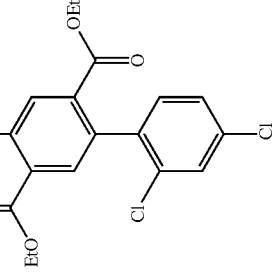 |
| II-5 | 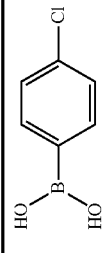 | 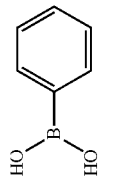 | 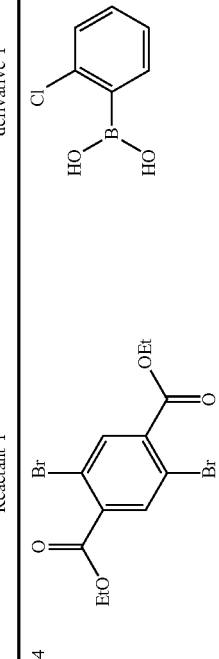 | 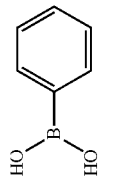 |

| | Reactant 1 | Boronic acid derivative 1 | Boronic acid derivative 2 | Product |
|---|---|---|---|---|
| II-6 | | | | |
| II-7 | | | | |

-continued

| Reactant 1 | Boronic acid derivative 1 | Boronic acid derivative 2 | Product |
|---|---|---|---|
| II-8 | 1-naphthylboronic acid | 2-chlorophenylboronic acid | |
| II-9 | 2-chlorophenylboronic acid | 5-chloronaphthalen-1-ylboronic acid | |

-continued

| | Reactant 1 | Boronic acid derivative 1 | Boronic acid derivative 2 | Product |
|---|---|---|---|---|
| II-10 | | | | |
| II-11 | | | | |

-continued

| Reactant 1 | Boronic acid derivative 1 | Boronic acid derivative 2 | Product |
|---|---|---|---|
| II-12 (340148-60-9) | biphenyl-4-boronic acid | 2-chlorophenylboronic acid | |
| II-13 | 4-methylphenylboronic acid | 2-chlorophenylboronic acid | |

-continued
| | Reactant 1 | Boronic acid derivative 1 | Boronic acid derivative 2 | Product |
|---|---|---|---|---|
| II-14 | 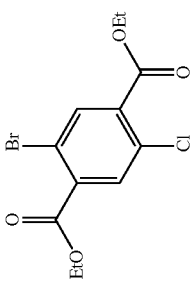 (340148-60-9) |  | 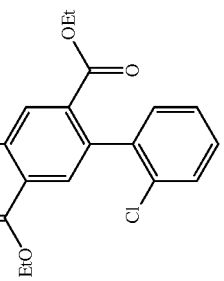 | 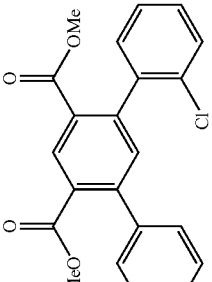 |
| II-15 | 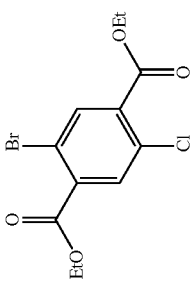 (90766-77-1) |  | 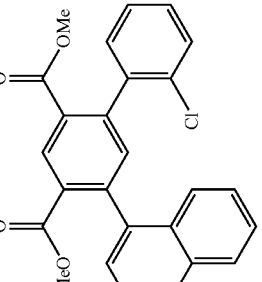 |  |
| II-16 |  | 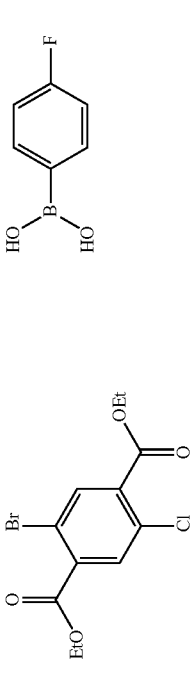 |  |  |

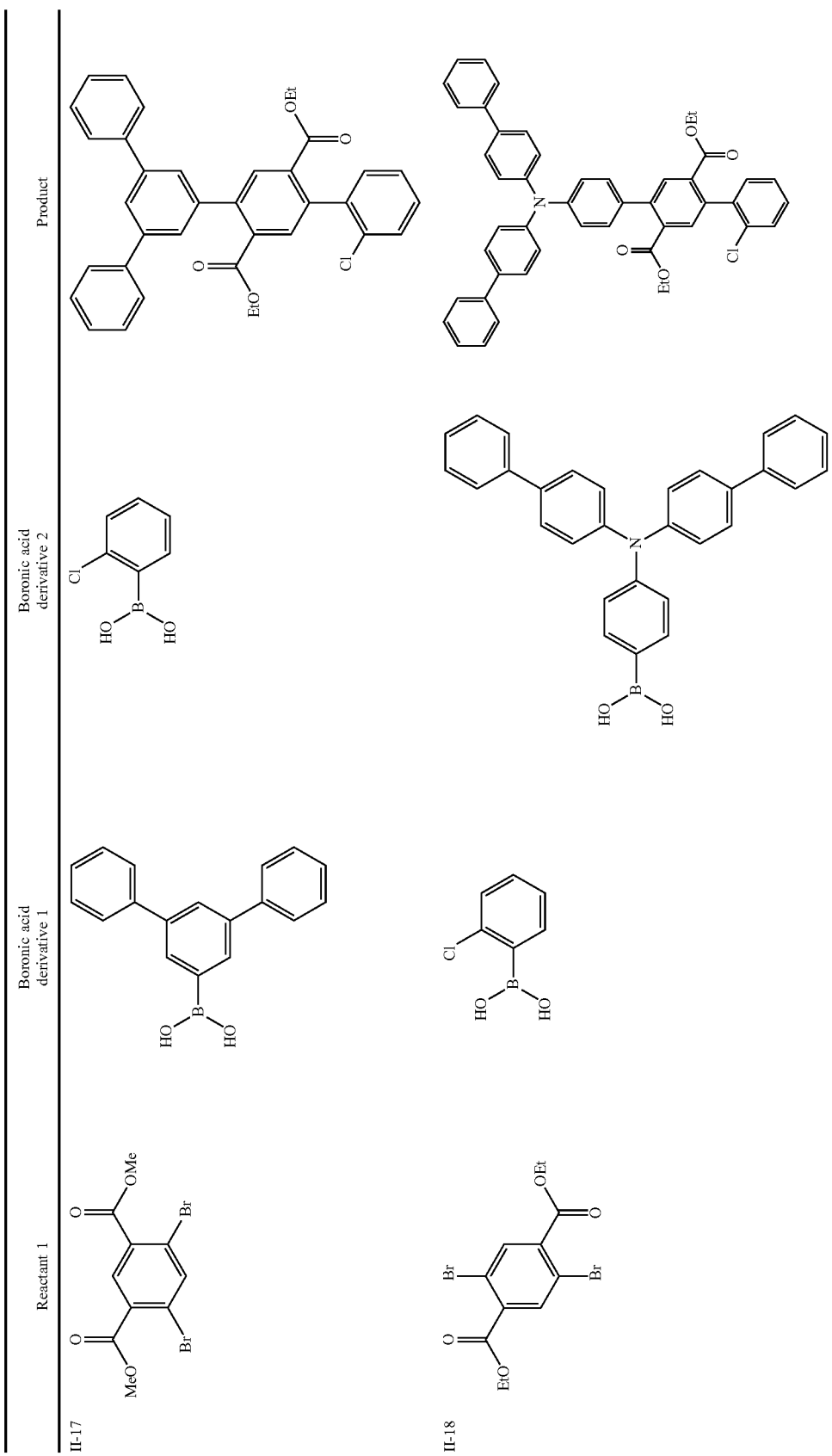

-continued
| Reactant 1 | Boronic acid derivative 1 | Boronic acid derivative 2 | Product |
|---|---|---|---|
| II-19 | | | |
| II-20 | | | |
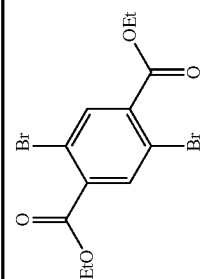

-continued

| | Reactant 1 | Boronic acid derivative 1 | Boronic acid derivative 2 | Product |
|---|---|---|---|---|
| II-21 | 2,5-dibromoterephthalate diethyl ester | naphthalen-2-ylboronic acid | (2-chlorophenyl)boronic acid | |
| II-22 | ethyl 2-bromo-5-chloroterephthalate (340148-60-9) | phenylboronic acid | (2-chlorophenyl)boronic acid | |

-continued

| | Reactant 1 | Boronic acid derivative 1 | Boronic acid derivative 2 | Product |
|---|---|---|---|---|
| II-23 | | | | |
| II-24 | | | | |

-continued

| | Reactant 1 | Boronic acid derivative 1 | Boronic acid derivative 2 | Product |
|---|---|---|---|---|
| II-25 | | | | |
| II-26 | | | | |

Intermediate III-1

14.0 g (34.2 mmol) of intermediate II-1 are dissolved in a baked-out flask in 250 ml of dried THF. The solution is saturated with N₂. The clear solution is cooled down to −5° C. and then 68.5 ml (205 mmol) of a 3M methylmagnesium chloride solution are added. The reaction mixture is gradually warmed to room temperature and then quenched with ammonium chloride. The mixture is subsequently partitioned between ethyl acetate and water, and the organic phase is washed three times with water, dried over Na₂SO₄ and concentrated by rotary evaporation.

The solution that has been concentrated by rotary evaporation is dissolved in toluene, and 6.6 g of Amberlyst 15 are added. The mixture is heated to 110° C. and kept at this temperature for 8 h. During this time, a white solid precipitates out. The mixture is then cooled to room temperature, and the precipitated solid is filtered off with suction and washed with heptane. The residue is dried at 40° C. under reduced pressure. After the crude product has been filtered through silica gel with heptane:ethyl acetate (1:1), 10.2 g (86% of theory) of the product III-1 are obtained.

Analogously, the following compounds are prepared (yields 50-95% of theory):

| | Reactant 1 | Reactant 2 | Product |
|---|---|---|---|
| III-2 | | MeMgBr | |
| III-3 | | MeMgBr | |
| III-4 | | MeMgCl | |

-continued

| | Reactant 1 | Reactant 2 | Product |
|---|---|---|---|
| III-5 | (structure) | MeMgCl | (structure) |
| III-6 | (structure) | MeMgCl | (structure) |
| III-7 | (structure) | MeMgBr | (structure) |
| III-8 | (structure) | MeMgCl | (structure) # |

-continued

| | Reactant 1 | Reactant 2 | Product |
|---|---|---|---|
| III-9 | | MeMgCl | |
| III-10 | | MeLi | |
| III-11 | | MeMgBr | |
| III-12 | | MeMgCl | |

| Reactant 1 | Reactant2 | Product |
| --- | --- | --- |
| III-13 | MeMgCl | |
| III-14 | MeMgCl | |
| III-15 | MeMgCl | |
| III-16 | MeMgBr | |

-continued

| Reactant 1 | Reactant 2 | Product |
|---|---|---|
| III-17 | MeLi | |
| III-18 | MeMgCl | |
| III-19 | EtMgBr | |
| III-20 | i-PrMgBr | |

-continued

| Reactant 1 | Reactant 2 | Product |
|---|---|---|
| III-21 | i-OctMgBr | |
| III-22 | PhLi | |
| III-23 | MeMgBr | (shown as two products with +, second marked #) |

-continued

| Reactant 1 | Reactant2 | Product |
|---|---|---|
| III-24 | MeMgBr | |
| III-25 | MeMgCl | |
| 1-33 | MeMgBr | |

-continued

| | Reactant 1 | Reactant2 | Product |
|---|---|---|---|
| 1-34 | | MeMgBr | |
| 2-18 | | MeMgCl | |
| 2-19 | | MeMgBr | |

: Compounds can be separated by chromatography or by means of recrystallization.

Compound 1-1

14.6 g of 4-biphenyl(9,9-dimethyl-9H-fluoren-2-yl)amine (40.6 mmol) and 14 g of the intermediate III-1 (40.6 mmol) are dissolved in 400 ml of toluene. The solution is degassed and saturated with $N_2$. Thereafter, 0.33 g (0.81 mmol) of S-Phos and 0.46 g (1.75 mmol) of $Pd_2(dba)_3$ are added thereto, and then 5.85 g of sodium tert-butoxide (80.9 mol) are added. The reaction mixture is heated to boiling under a protective atmosphere for 6 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 20 g (75% of theory). Finally, the material is sublimed under high vacuum. The purity is 99.9%.

Analogously, the following compounds are prepared (yields 20-80% of theory):

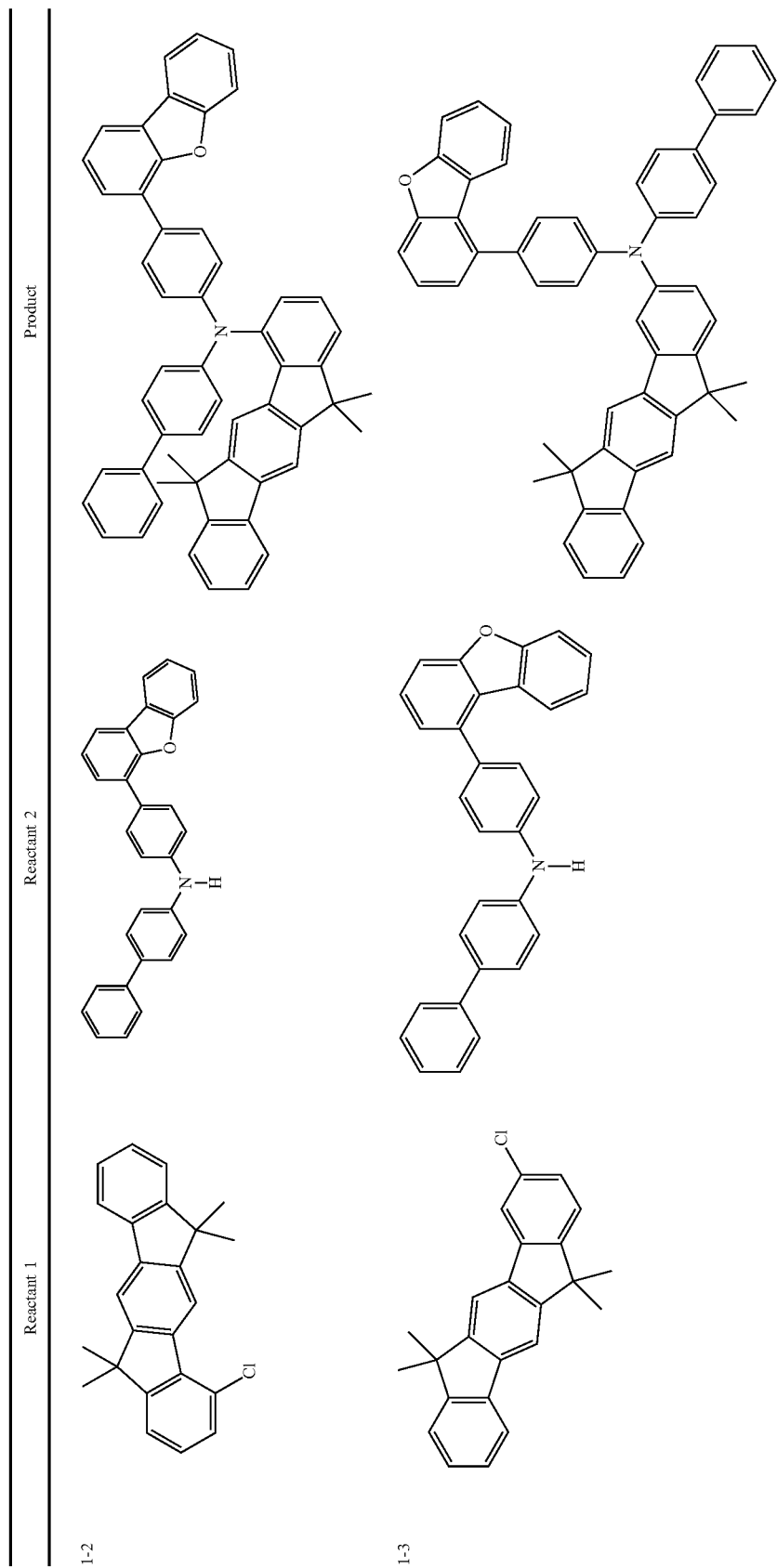

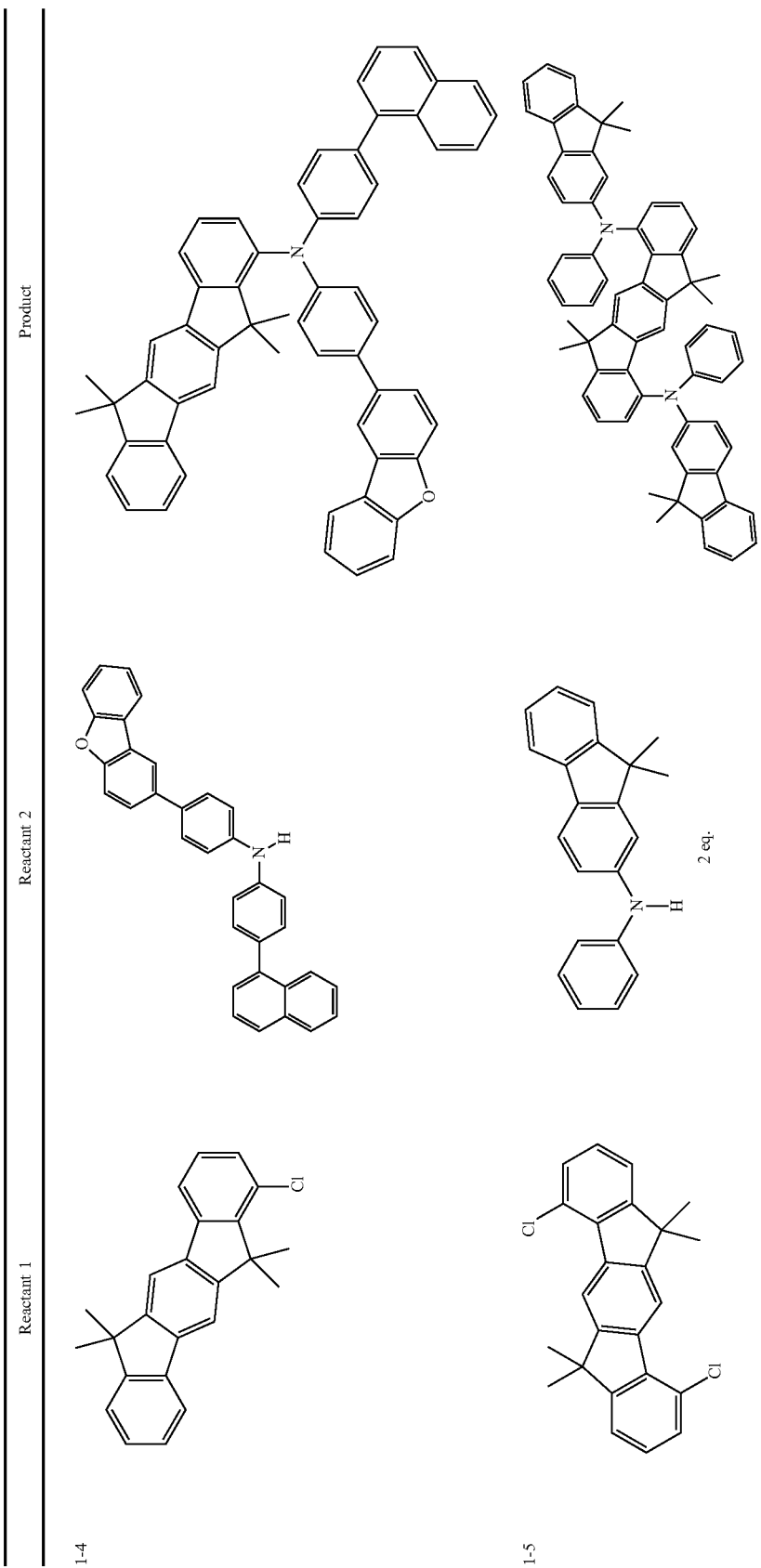

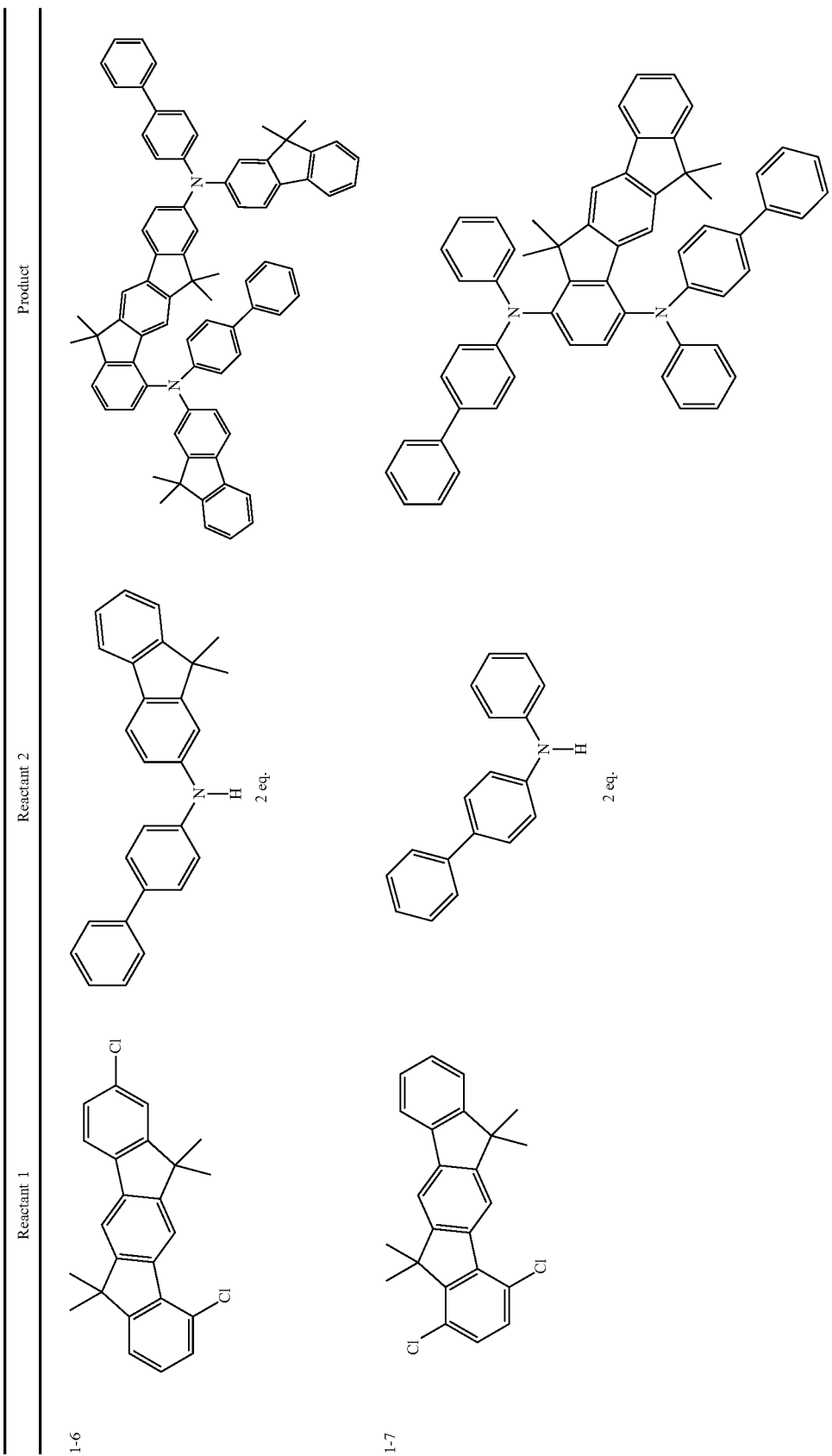

| Reactant 1 | Reactant 2 | Product |
|---|---|---|
| 1-8 | | |
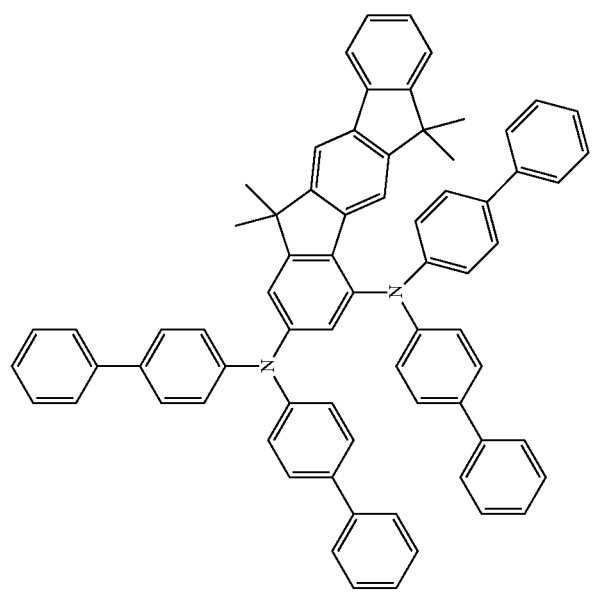

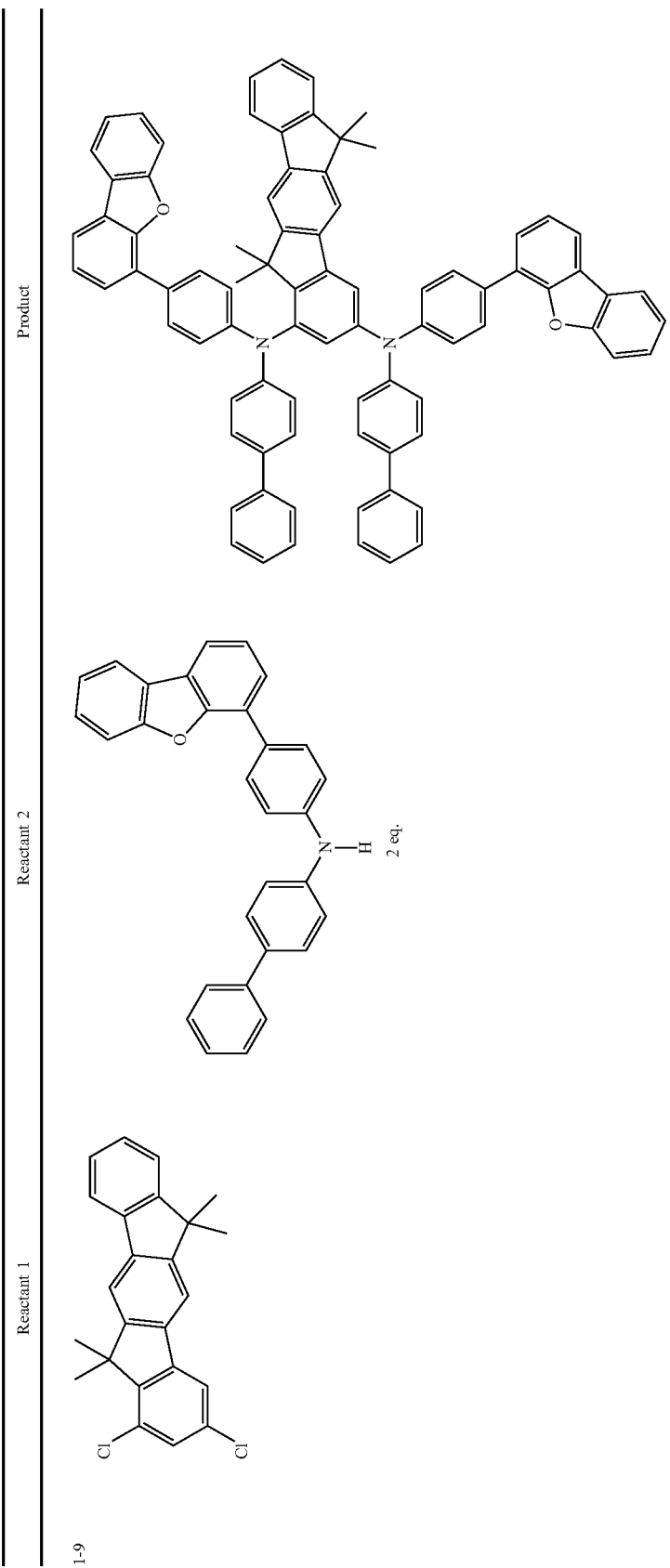

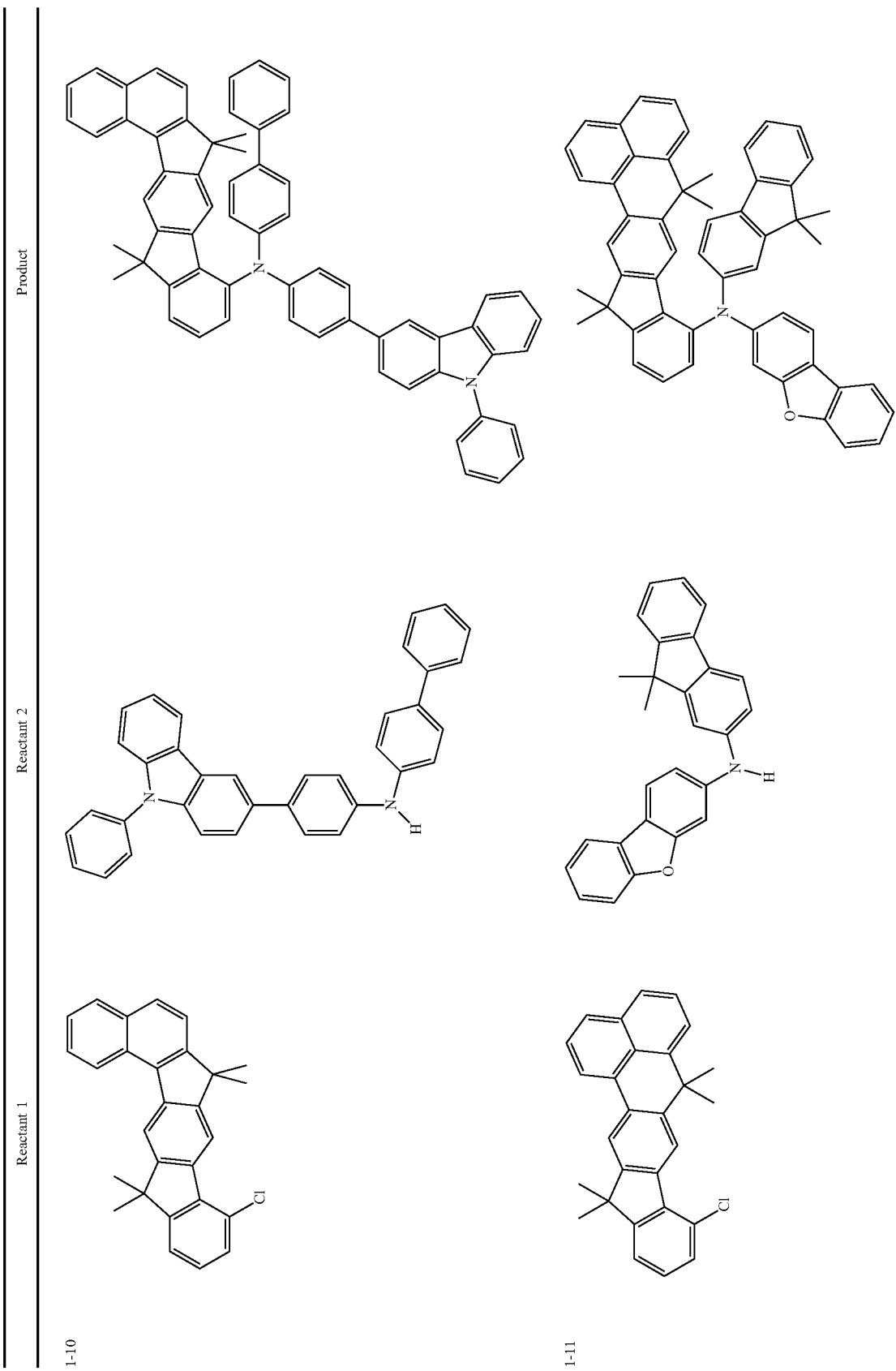

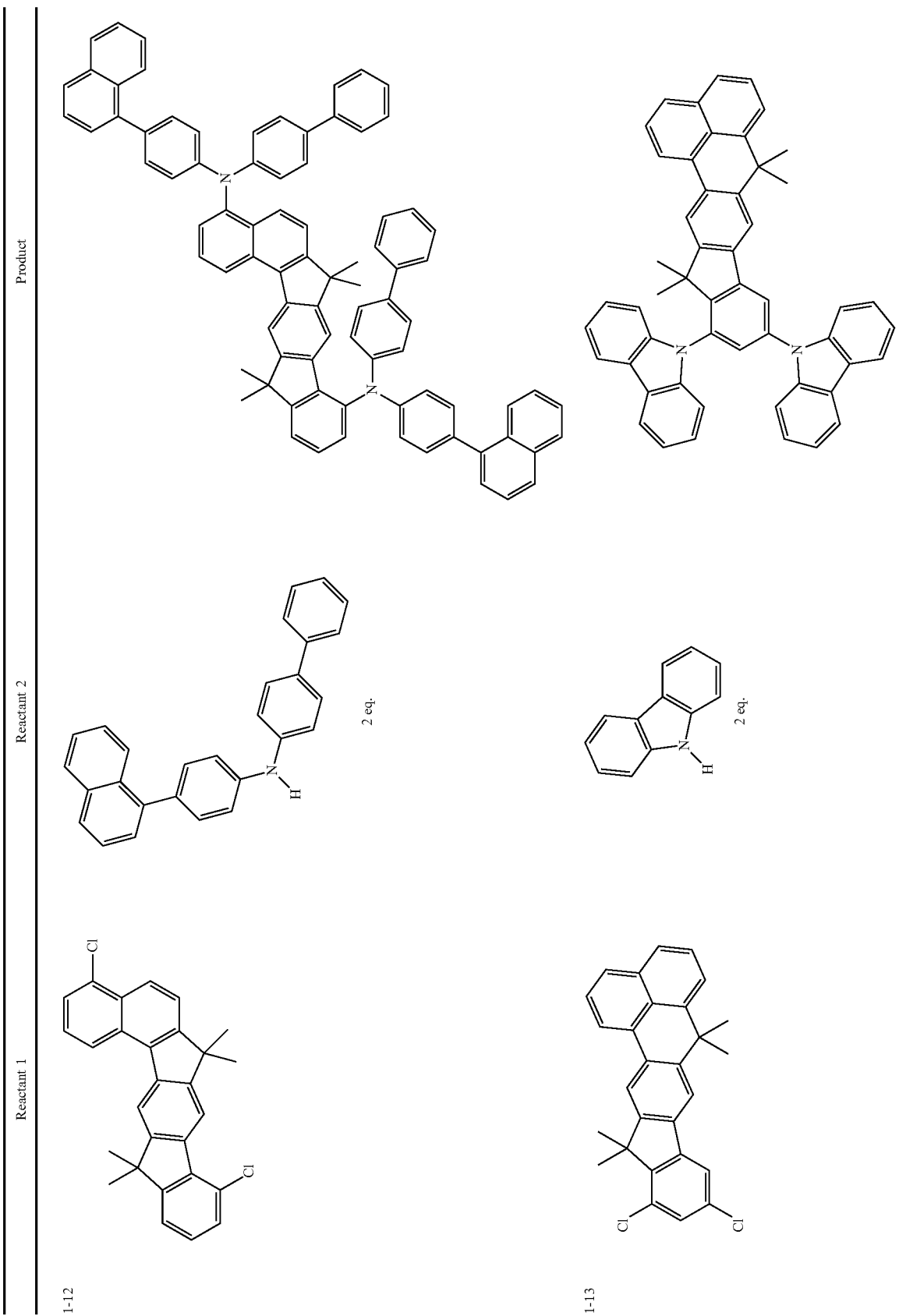

-continued
| Reactant 1 | Reactant 2 | Product |
|---|---|---|
| 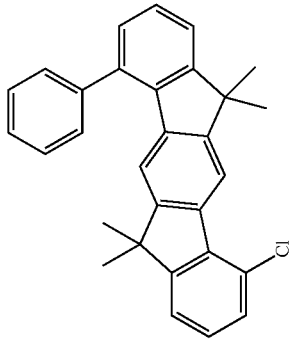 | 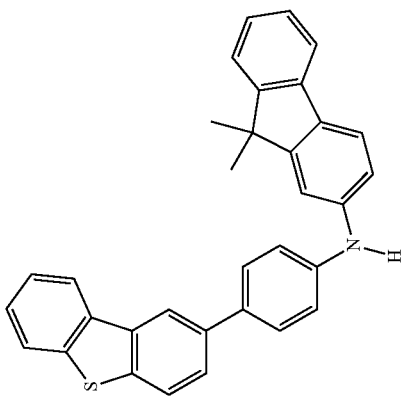 | 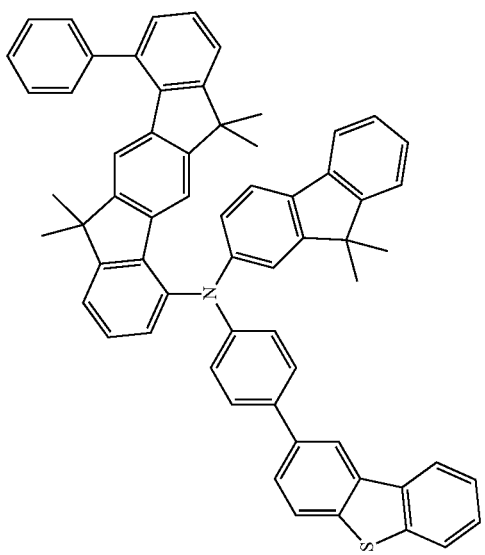 |
| 1-14 | | |
| | | 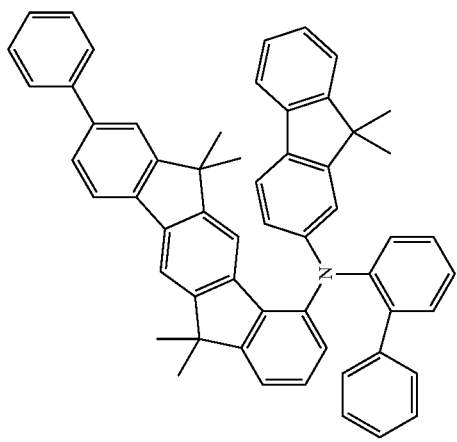 |
| 1-15 | | |

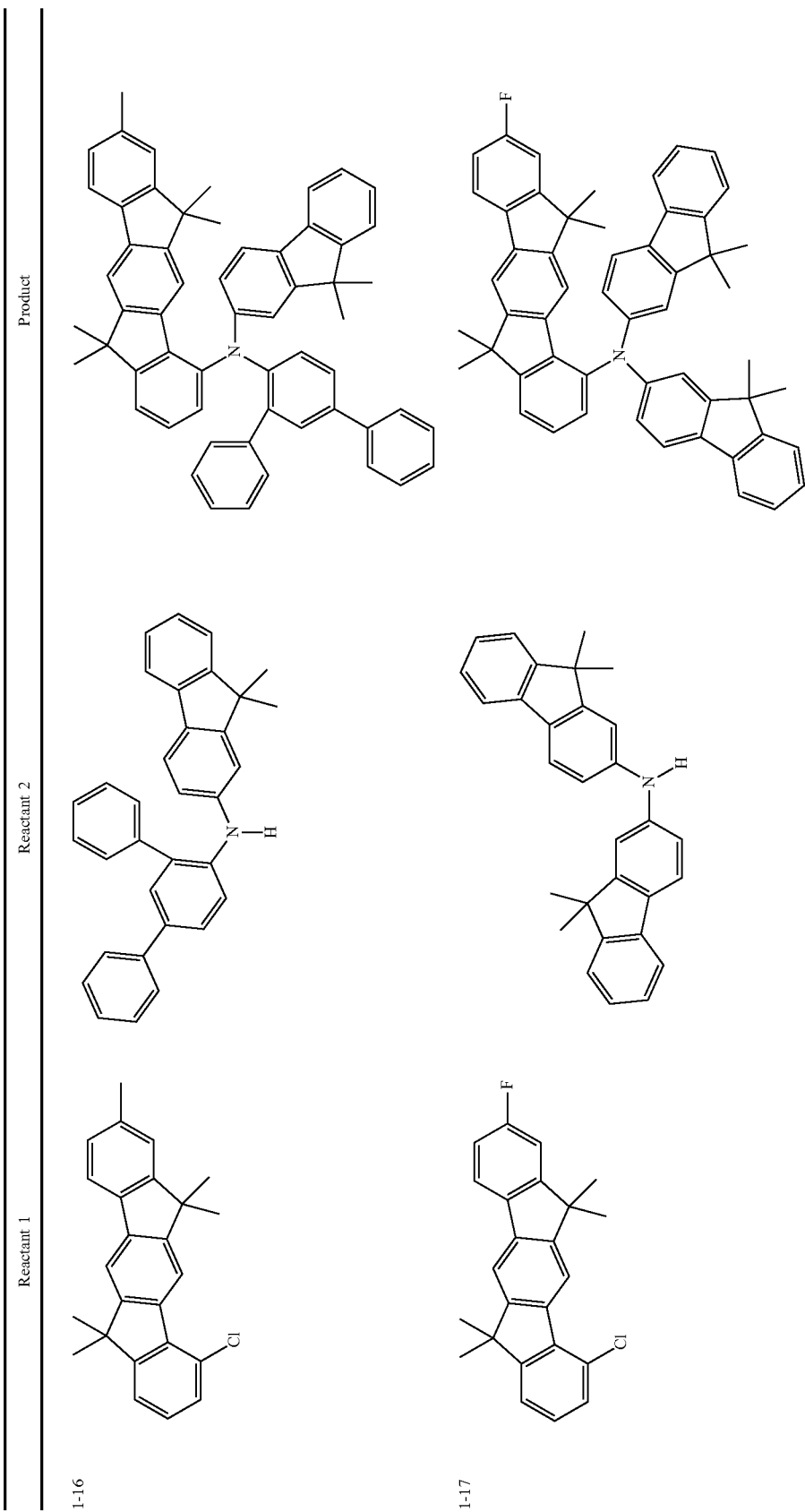

| Reactant 1 | Reactant 2 | Product |
|---|---|---|
| 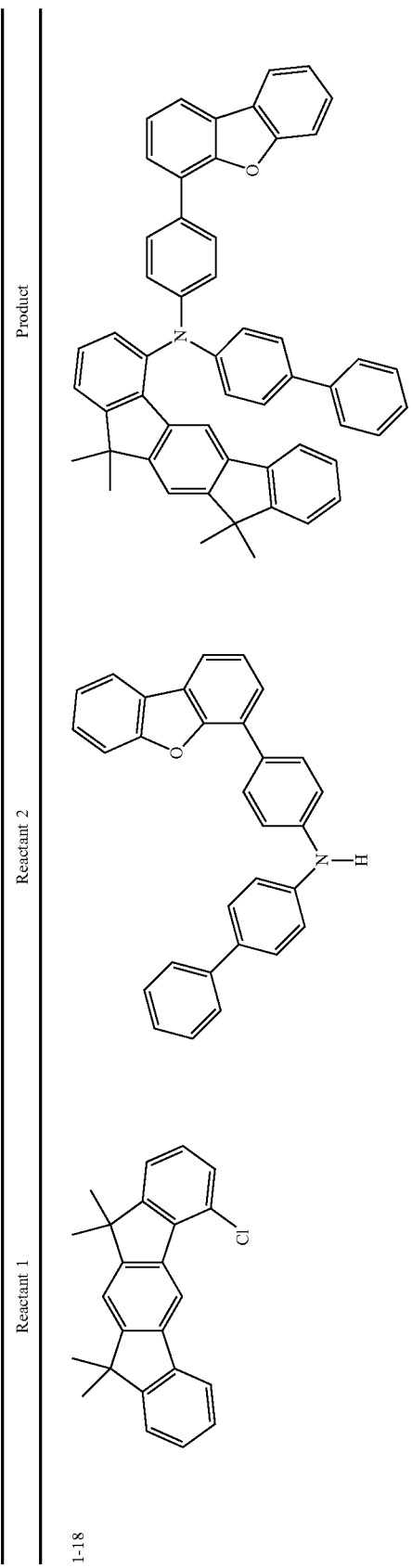 | | |
1-18

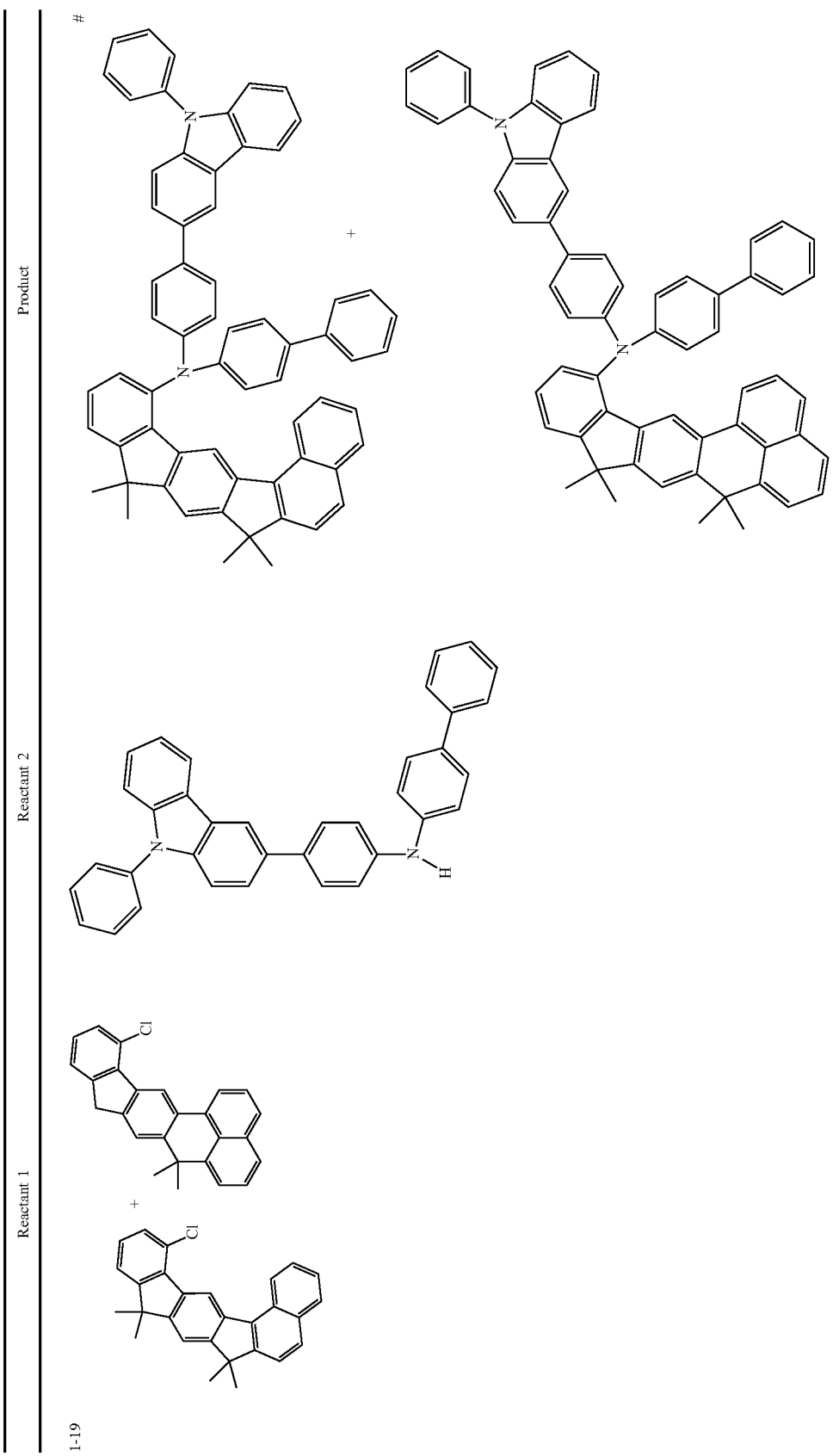

| Reactant 1 | Reactant 2 | Product |
|---|---|---|
| 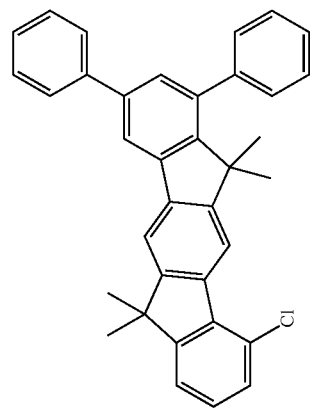 | 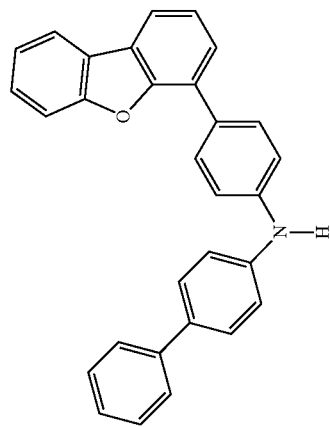 | 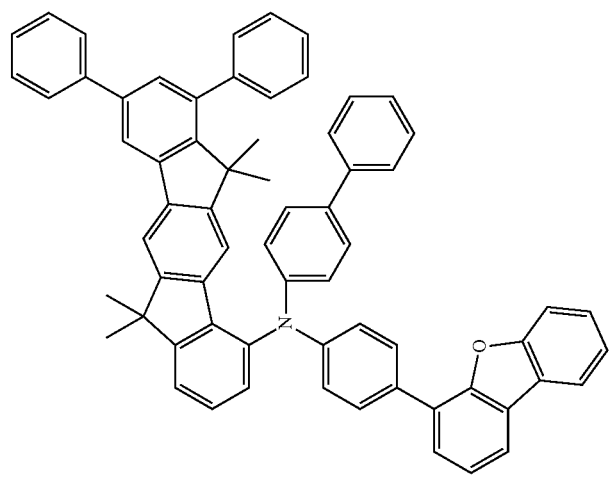 |
1-20

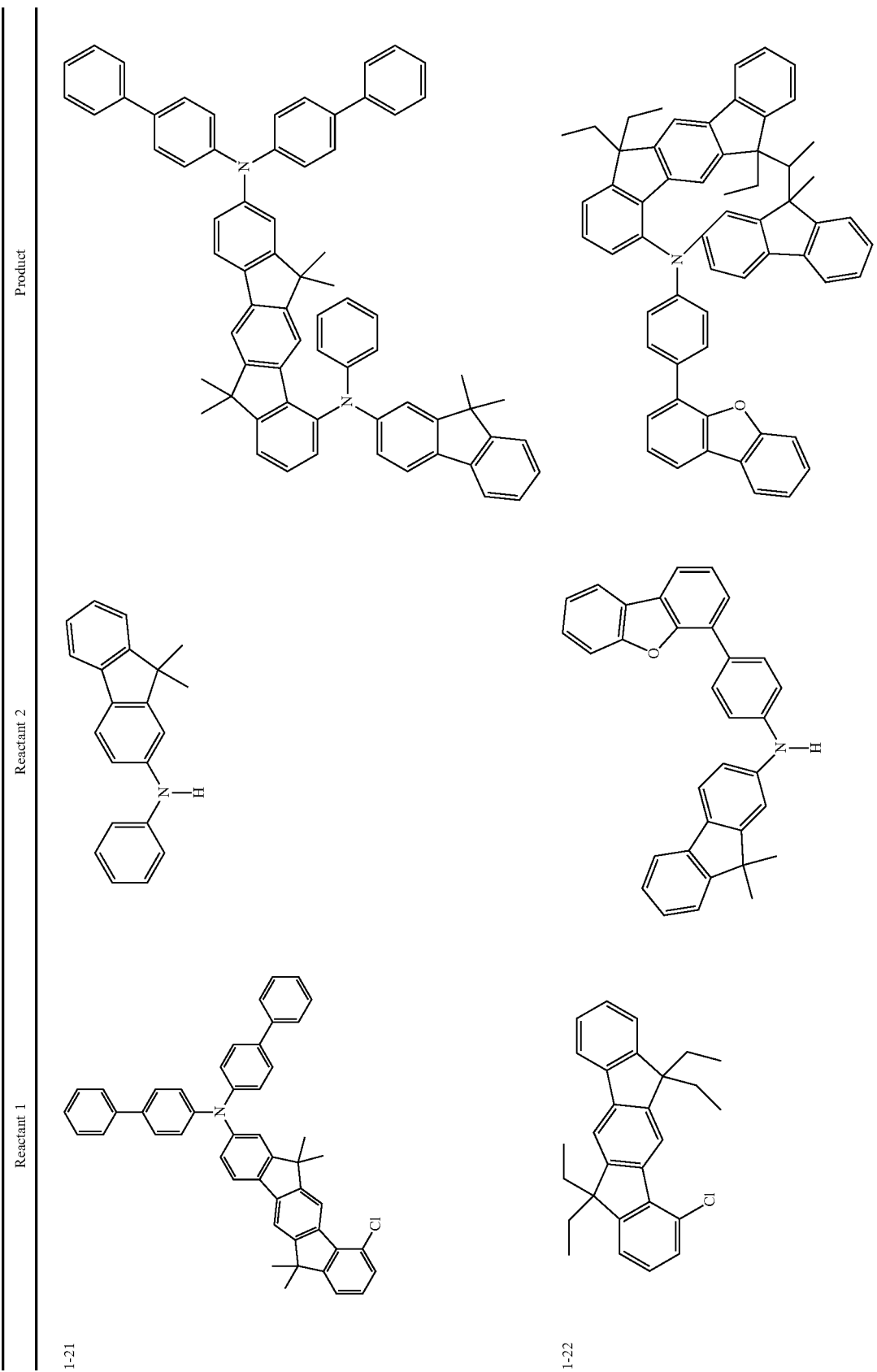

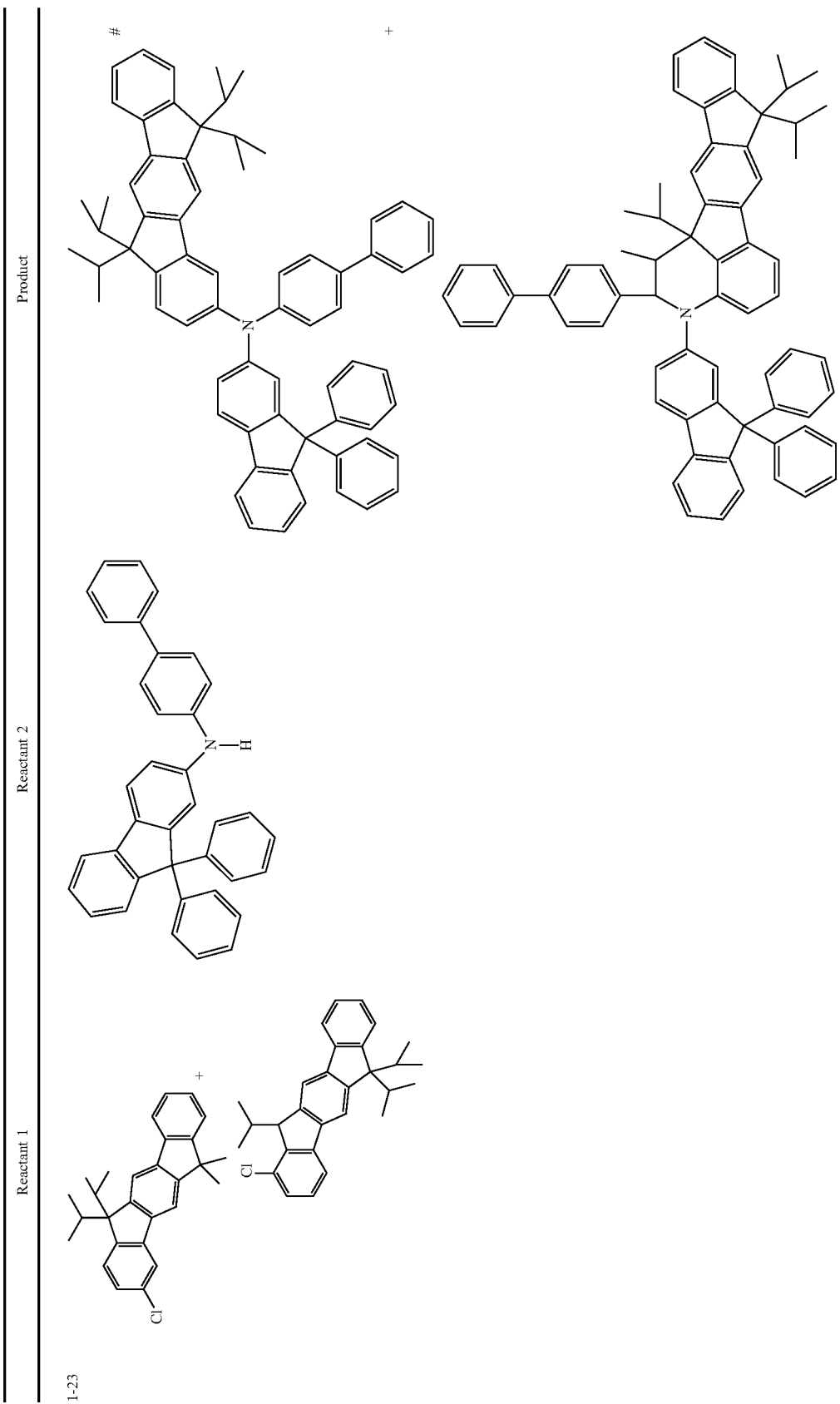

| Reactant 1 | Reactant 2 | Product |
|---|---|---|
| 1-24 | 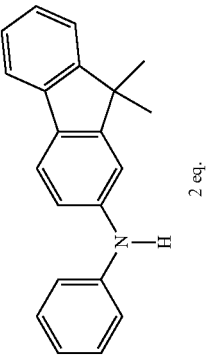 2 eq. | 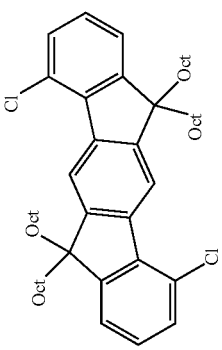 |

-continued
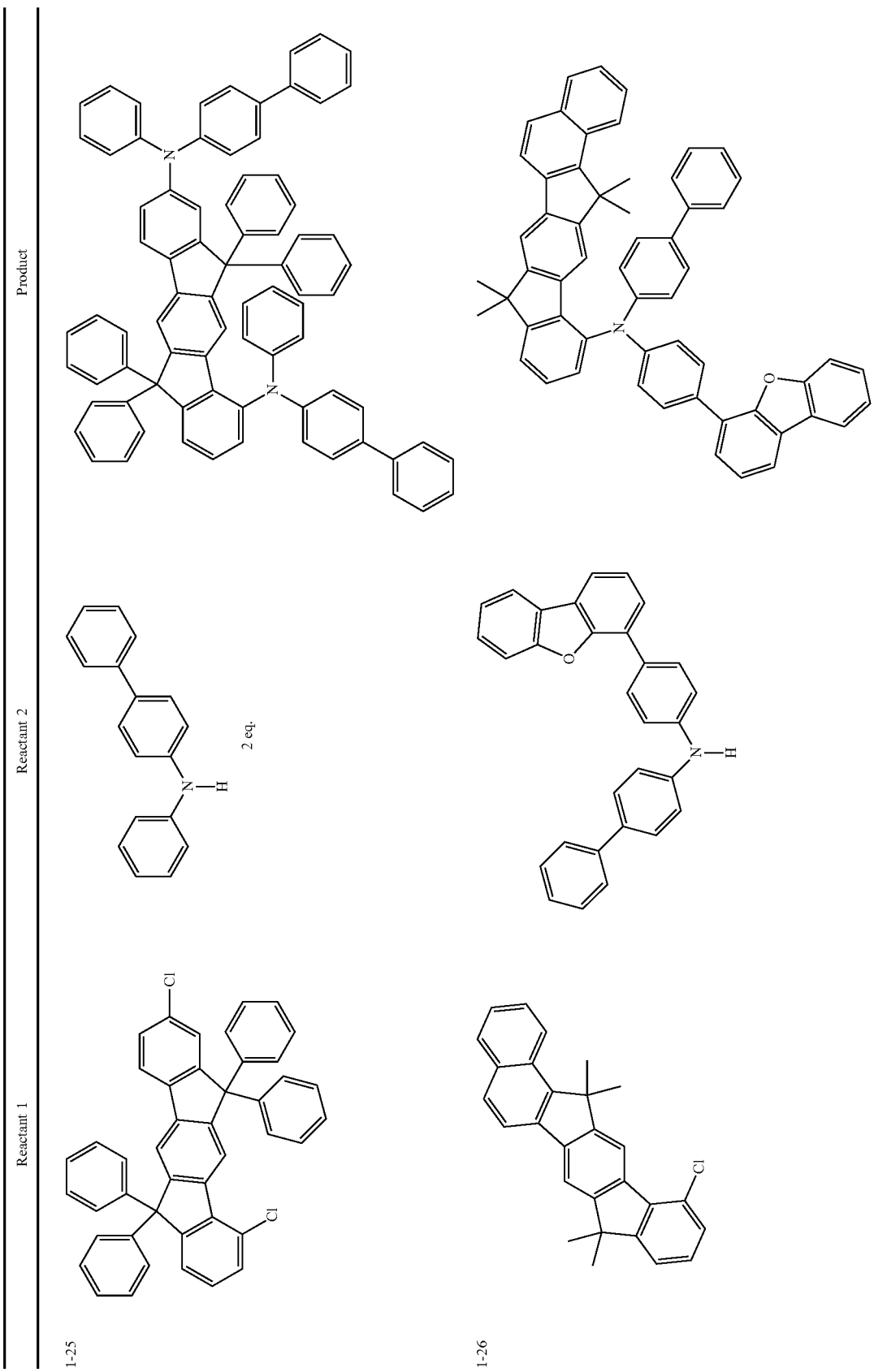

| Reactant 1 | Reactant 2 | Product |
|---|---|---|
| 1-27 | | 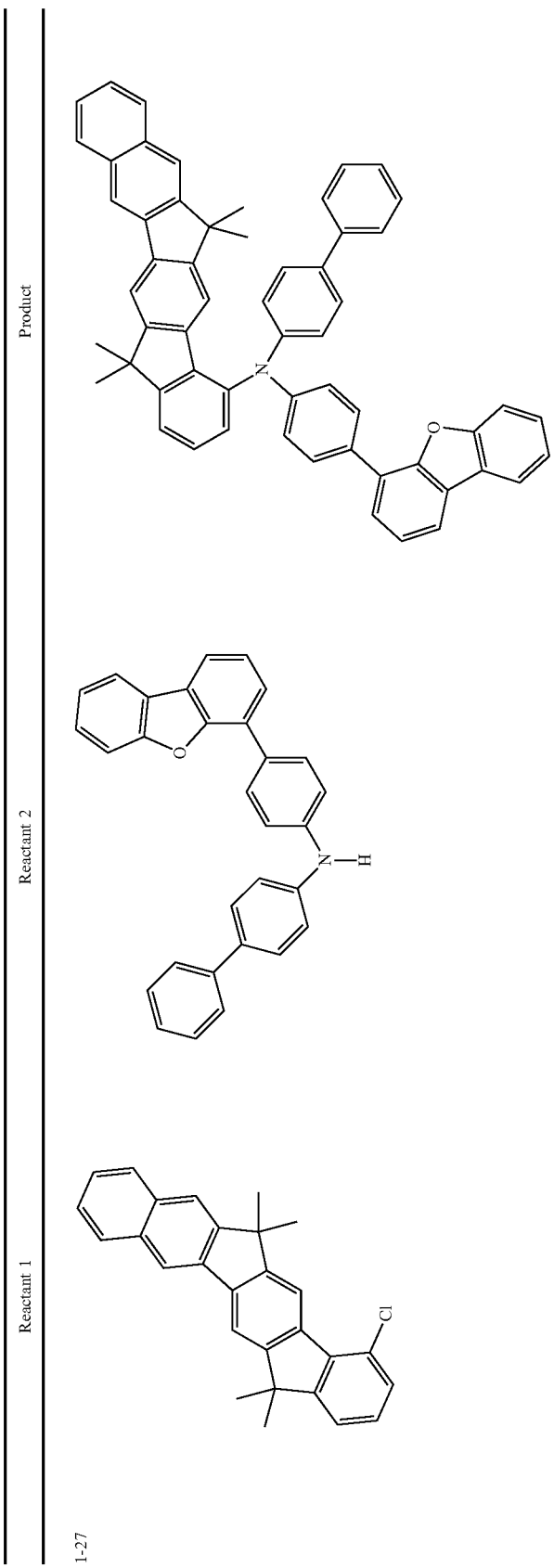 |

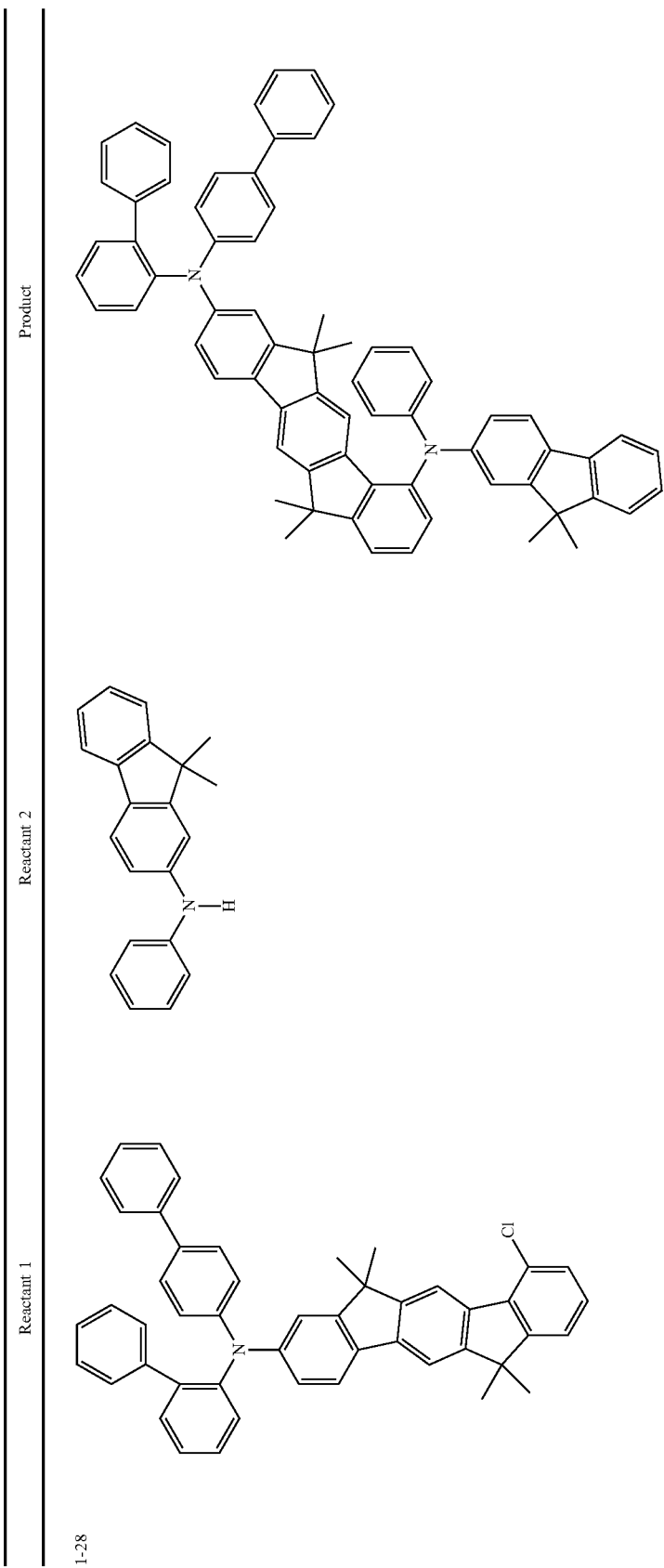

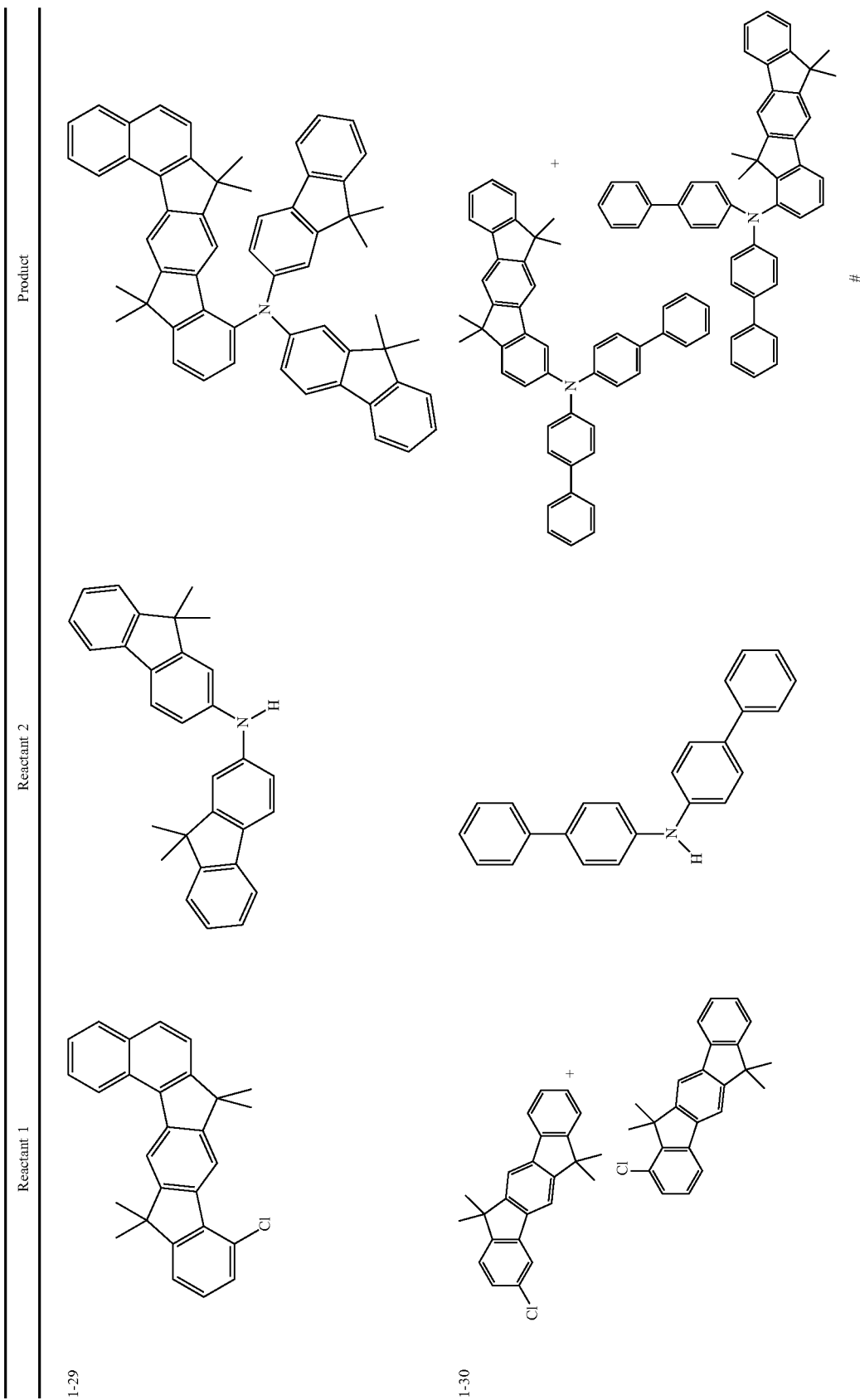

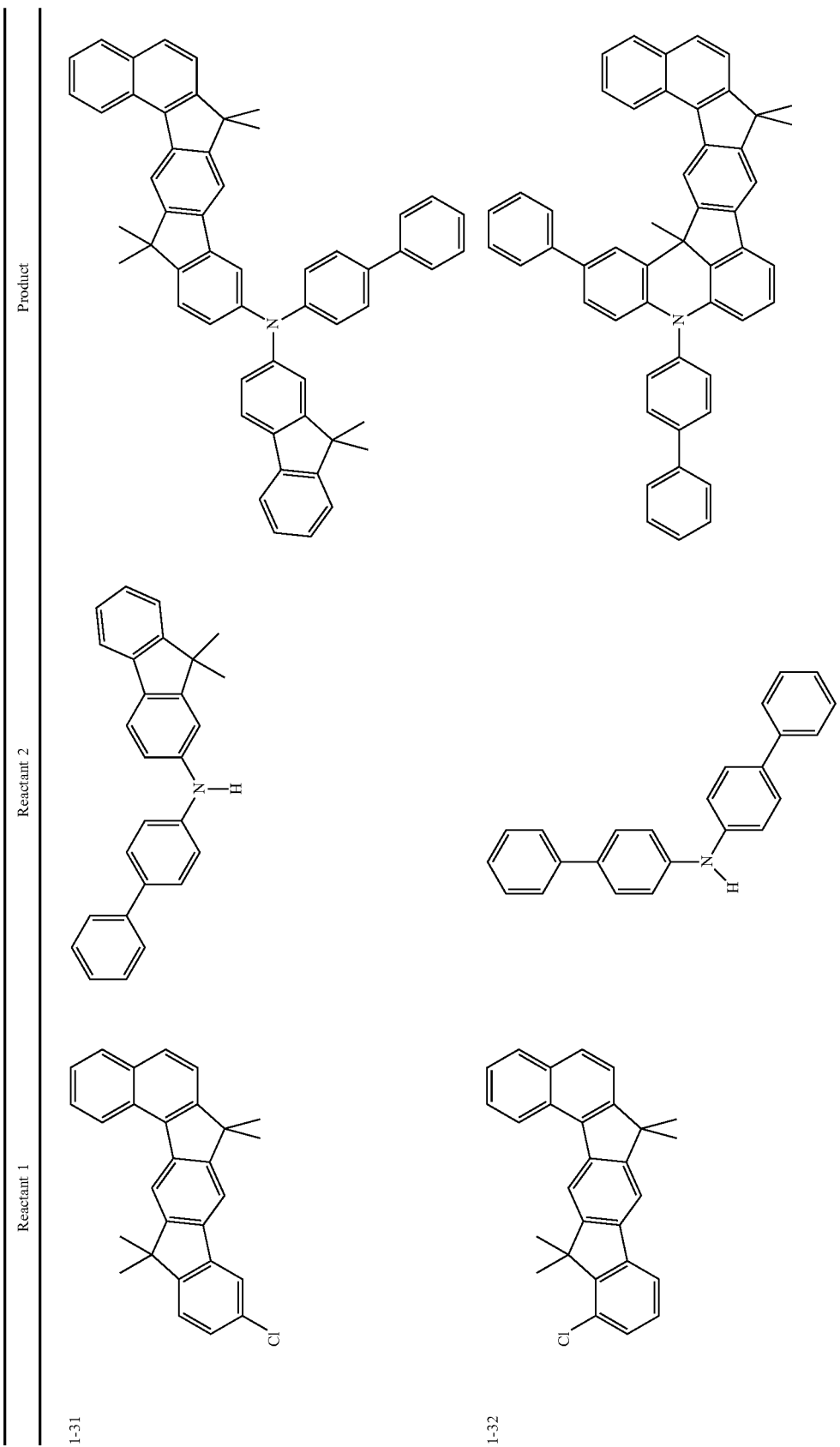

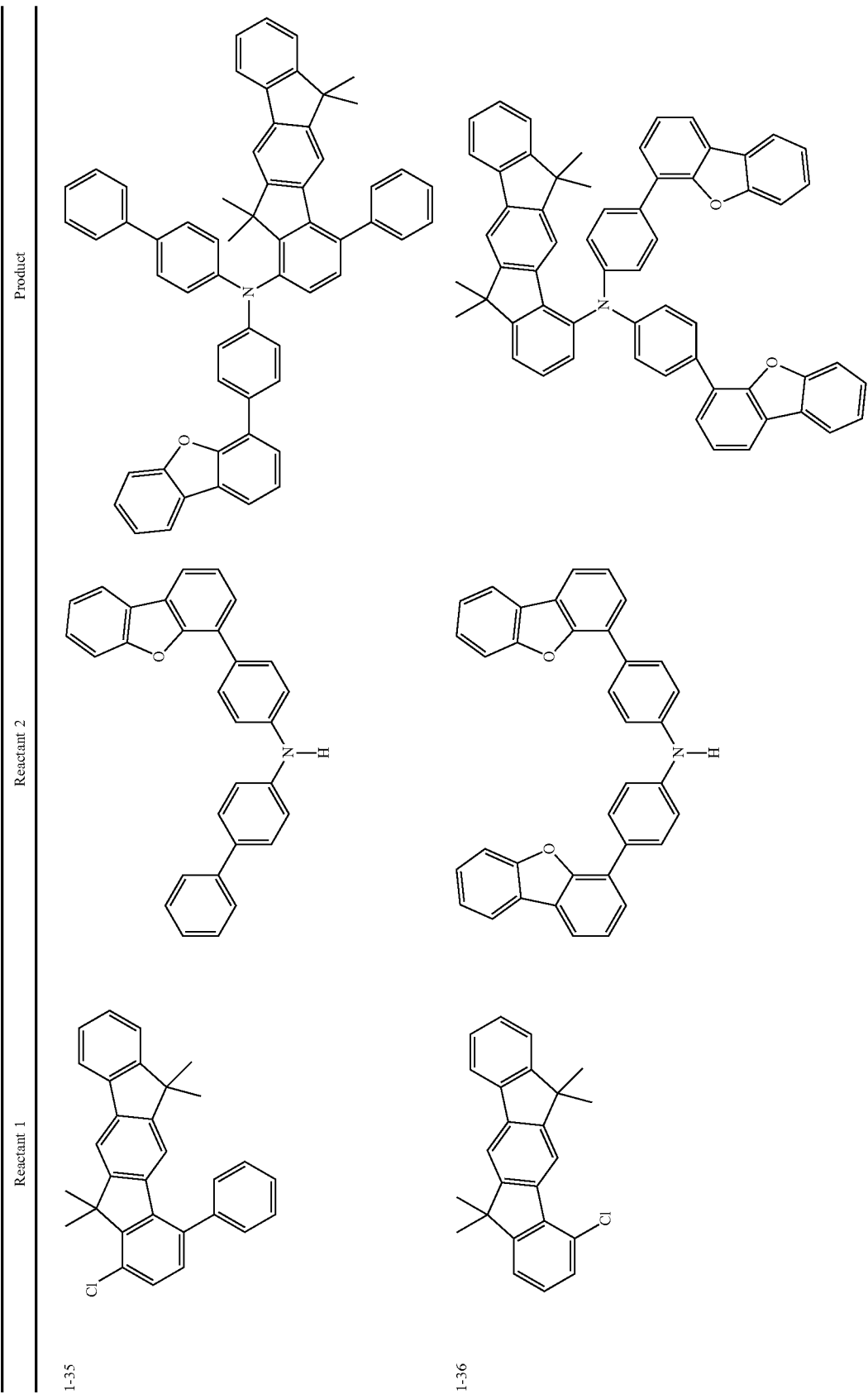

| Reactant 1 | Reactant 2 | Product |
|---|---|---|
| 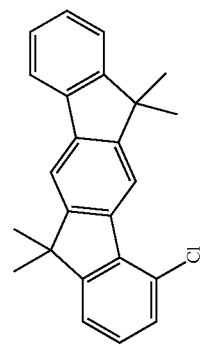 | 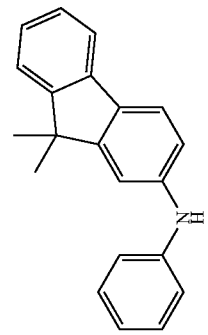 | 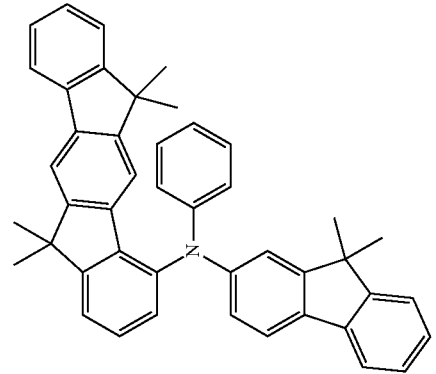 |
1-37

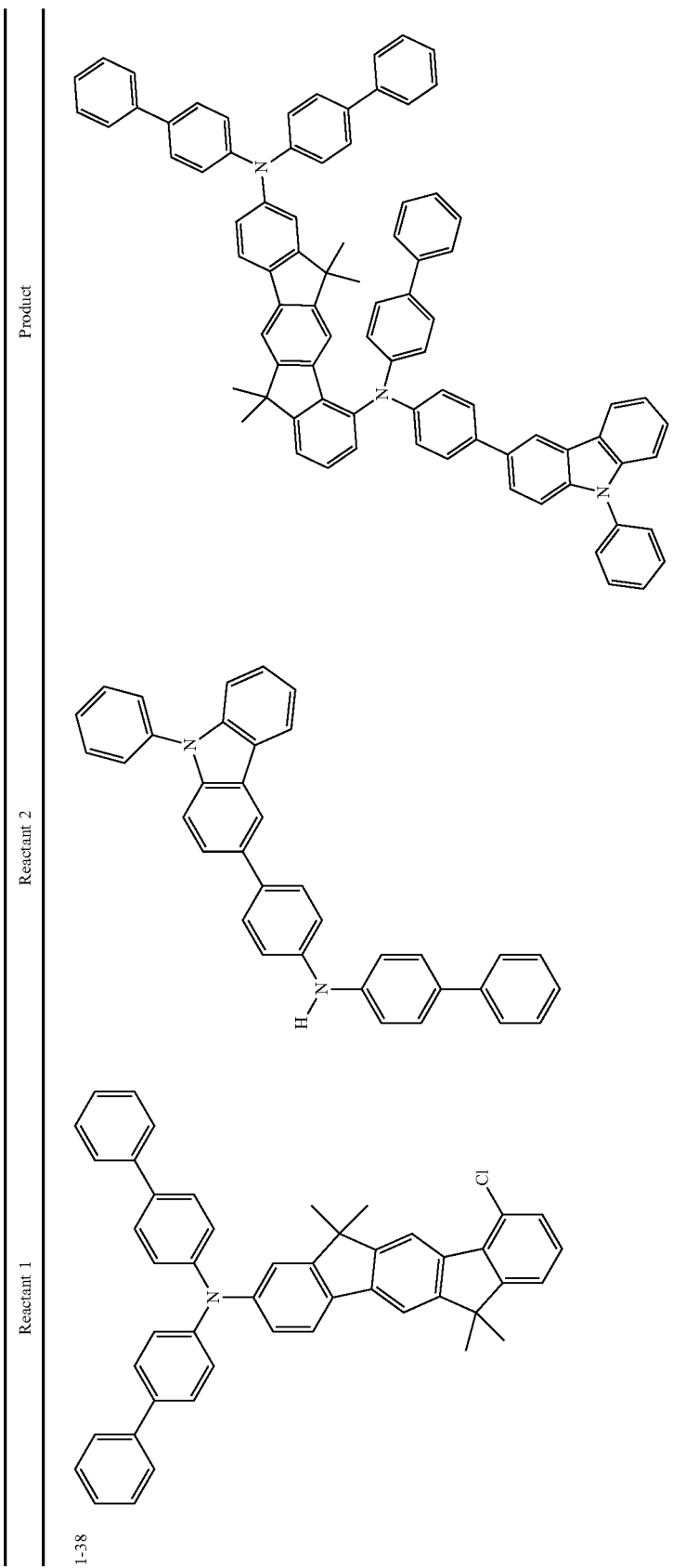

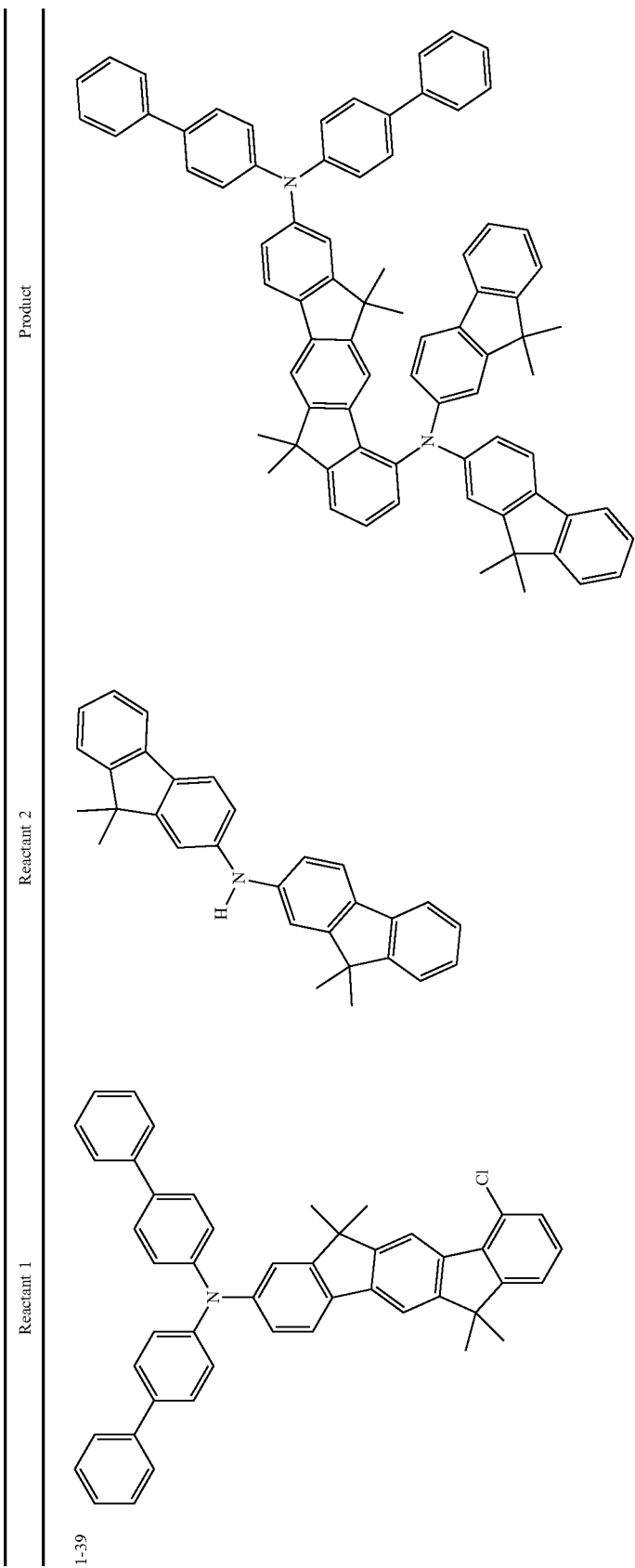

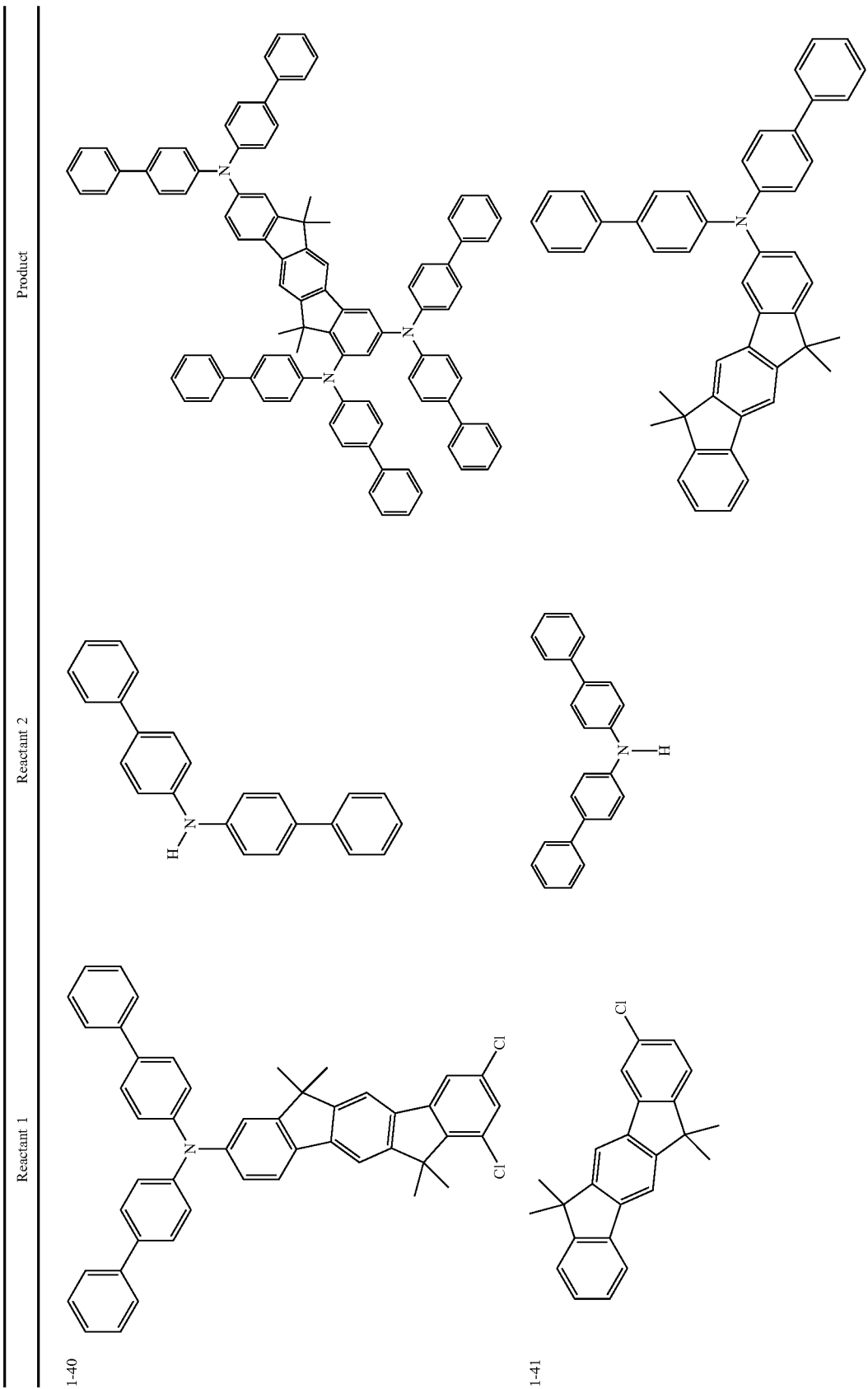

| Reactant 1 | Reactant 2 | Product |
|---|---|---|
| 1-42 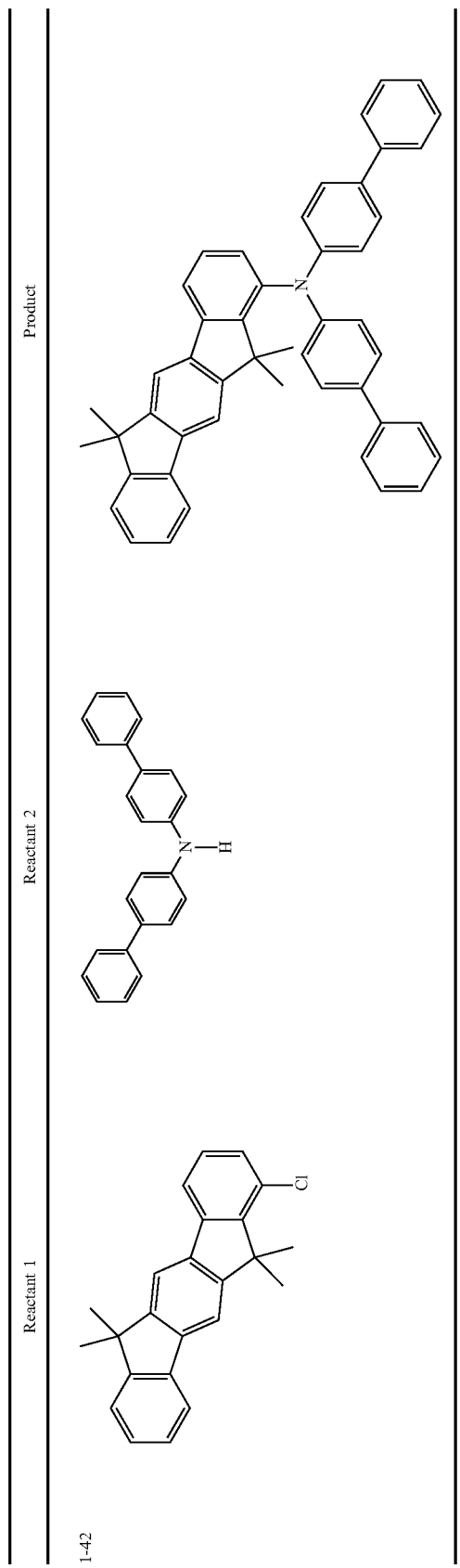 | | |
: Compounds can be separated by chromatography or by means of recrystallization.

Example 2-1

Synthesis of the Inventive Compound 2-1 and Variants

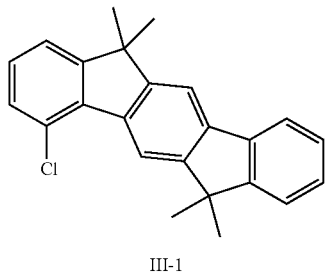

III-1

+

Compound 2-1

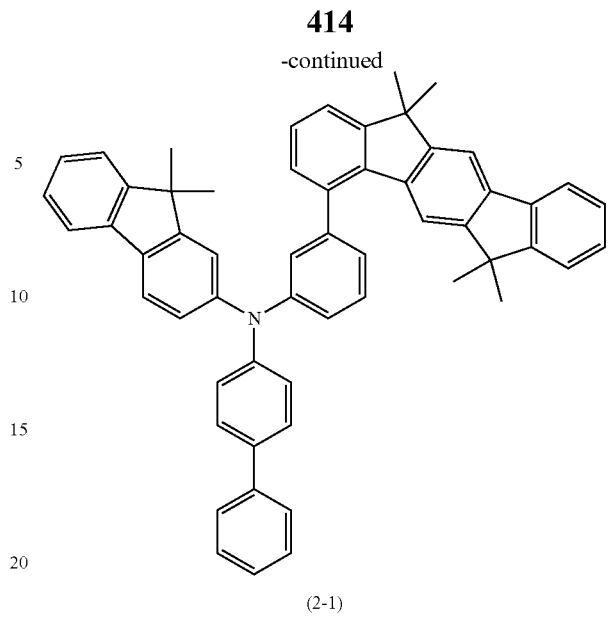

(2-1)

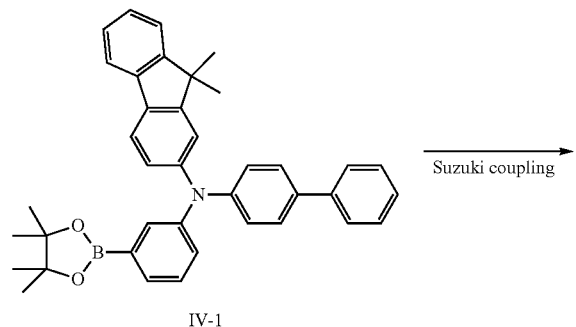

IV-1

→ Suzuki coupling 19.6 g (34.8 mmol) of the pinacolboronic ester derivative (CAS No.: 1616632-73-5) and 12.05 g (45 mmol) of intermediate III-1 are suspended in 350 ml of dioxane and 10.6 g of caesium fluoride (69.9 mmol). 1.02 g (1.39 mmol) of bis(tricyclohexylphosphine)palladium dichloride are added to this suspension, and the reaction mixture is heated under reflux for 18 h. After cooling, the organic phase is removed, filtered through silica gel, washed three times with 80 ml of water and then concentrated to dryness. After the crude product has been filtered through silica gel with toluene, the remaining residue is recrystallized from heptane/toluene. The yield is 20 g (78% of theory). Finally, the material is sublimed under high vacuum. The purity is 99.9%.

Analogously, the following compounds are prepared (yields 60-85% of theory):

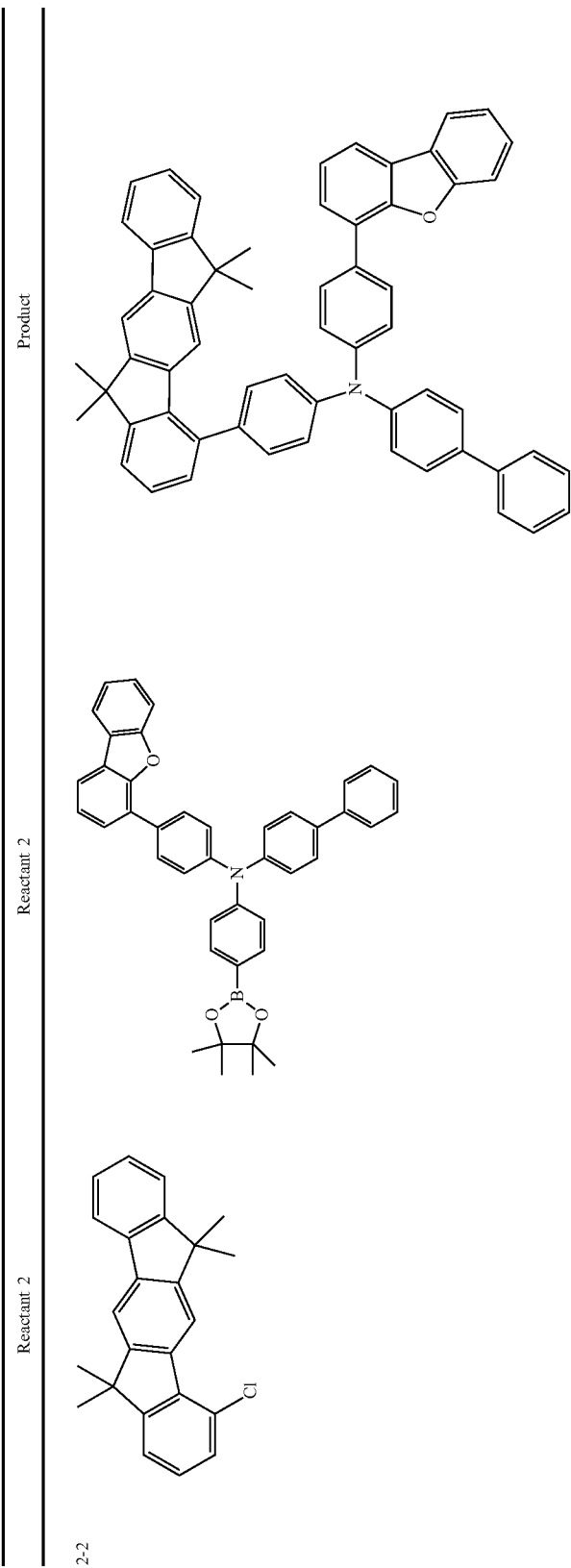

-continued
| | Reactant 2 | Reactant 2 | Product |
|---|---|---|---|
| 2-3 | | | |
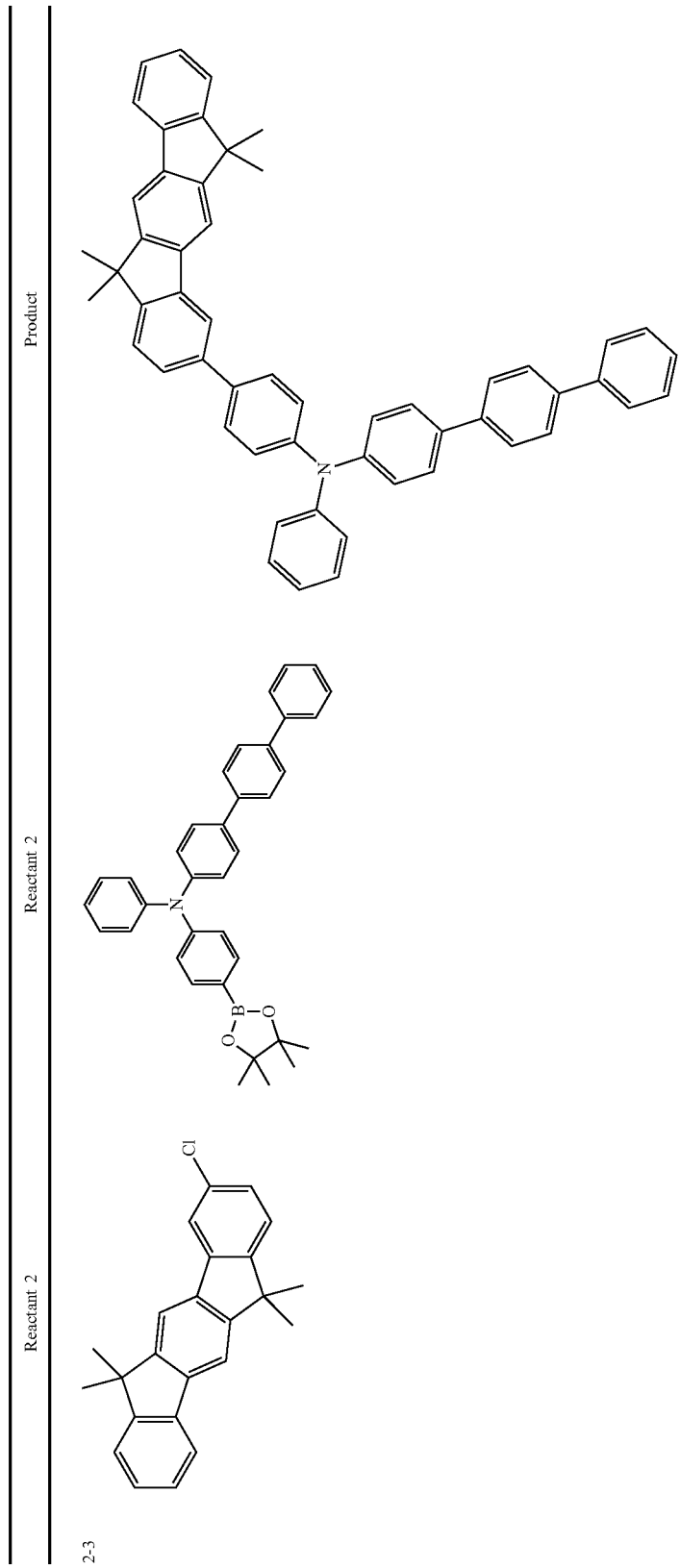

-continued
| | Reactant 2 | Reactant 2 | Product |
|---|---|---|---|
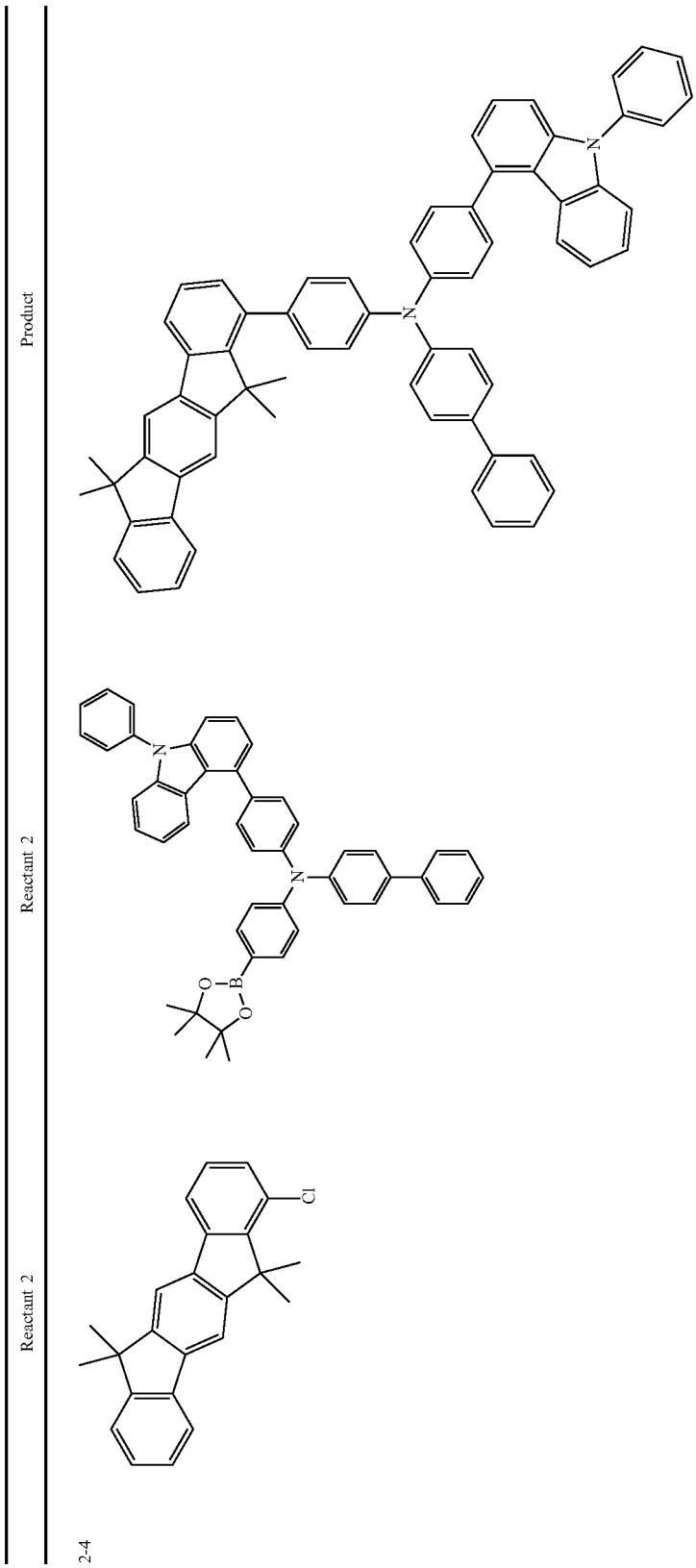
2-4

| | Reactant 2 | Reactant 2 | Product |
|---|---|---|---|
| 2-5 | (9,9,14,14-tetramethyl-dichloro-indenofluorene) | (3-(9H-carbazol-9-yl)phenyl)boronic acid | (product structure) |
| 2-6 | (9,9,14,14-tetramethyl-dichloro-indenofluorene isomer) | (4-(N-phenyl-N-(9,9-dimethylfluoren-2-yl)amino)phenyl pinacol boronate) | (product structure) |

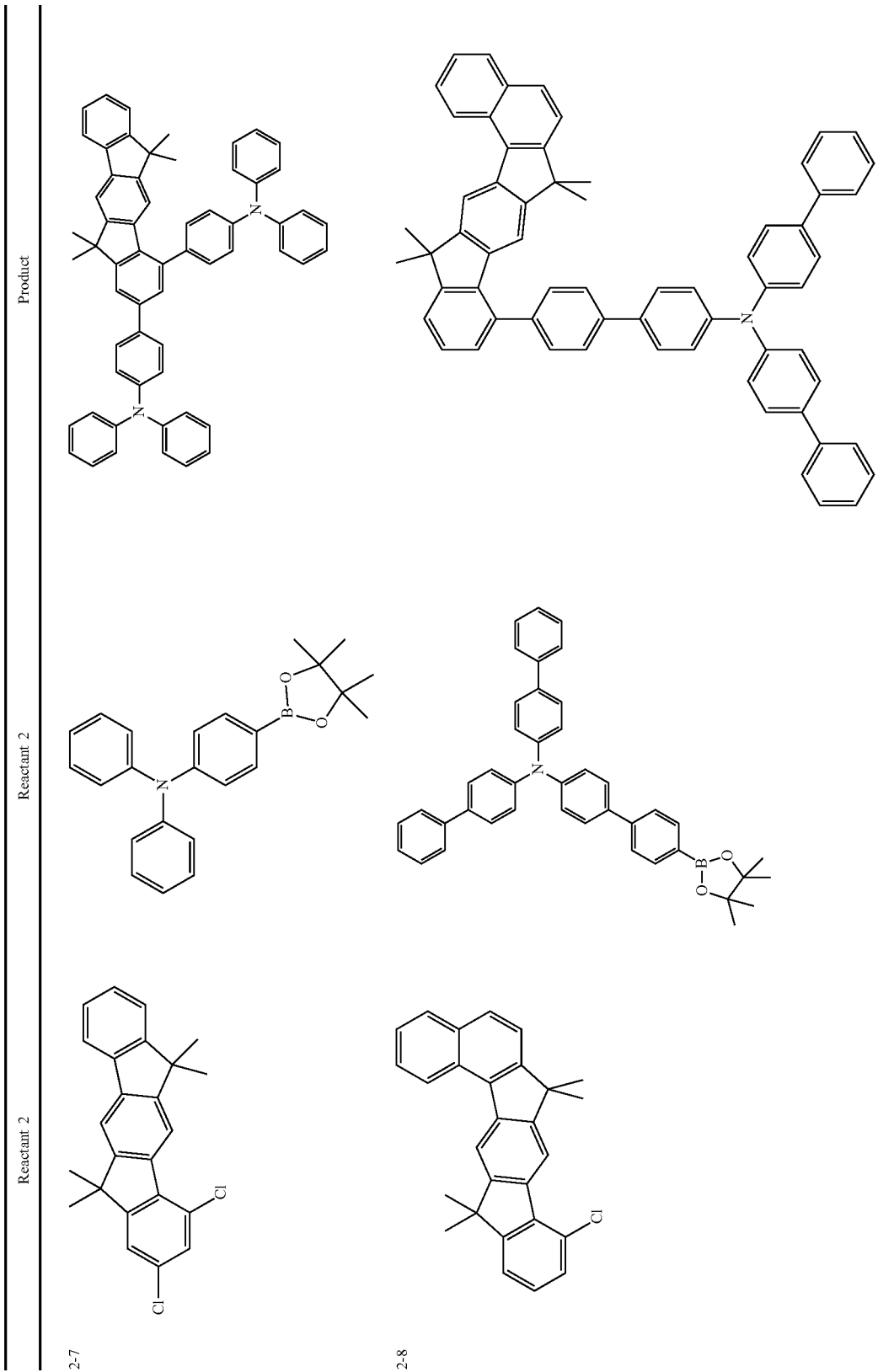

| | Reactant 2 | Reactant 2 | Product |
|---|---|---|---|
| 2-9 | | | |
| 2-10 | | | |

| | Reactant 2 | Reactant 2 | Product |
|---|---|---|---|
| 2-11 | 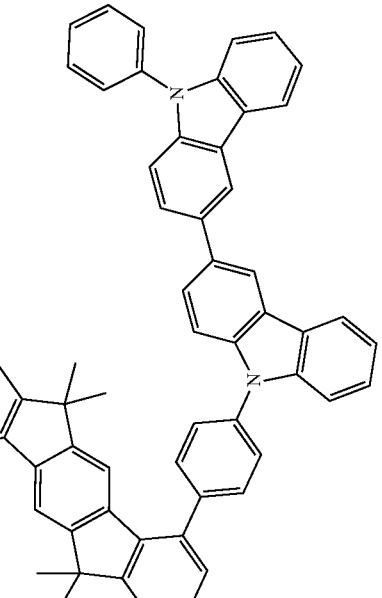 | 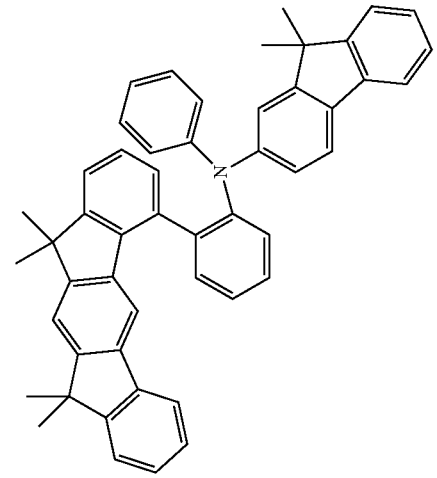 | 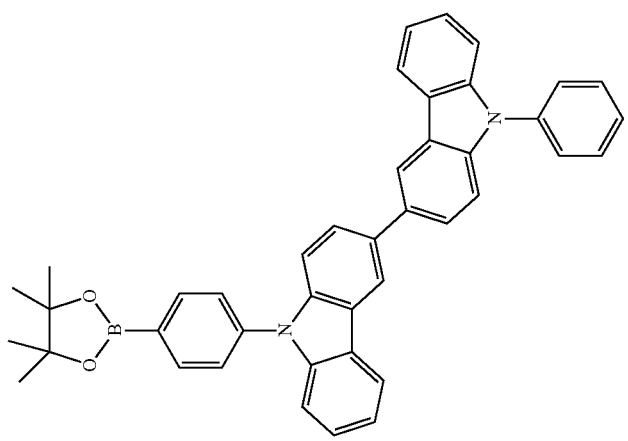 |
| 2-12 | 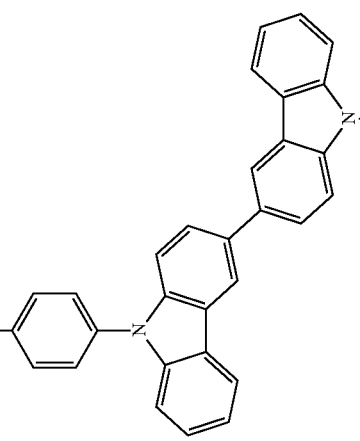 | 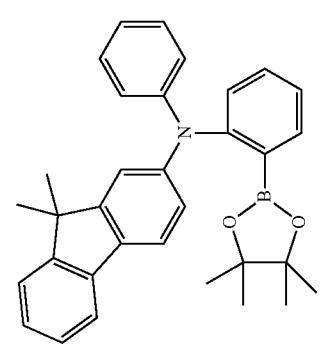 | 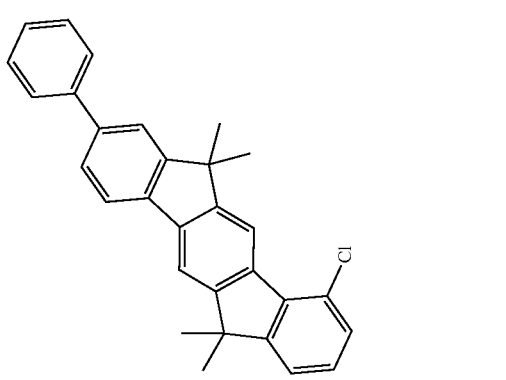 |

| | Reactant 2 | Reactant 2 | Product |
|---|---|---|---|
| 2-13 | 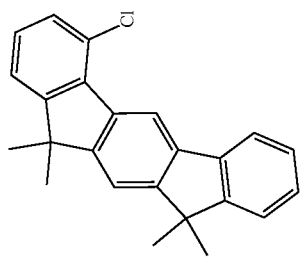 | 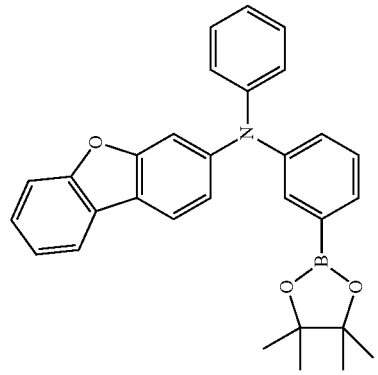 | 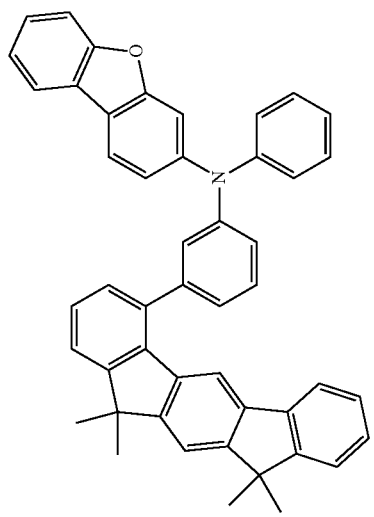 |
| 2-14 | 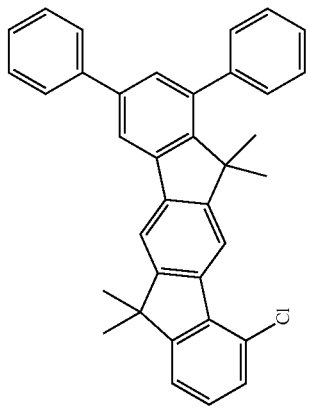 | 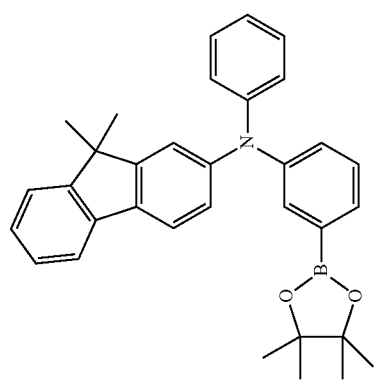 | 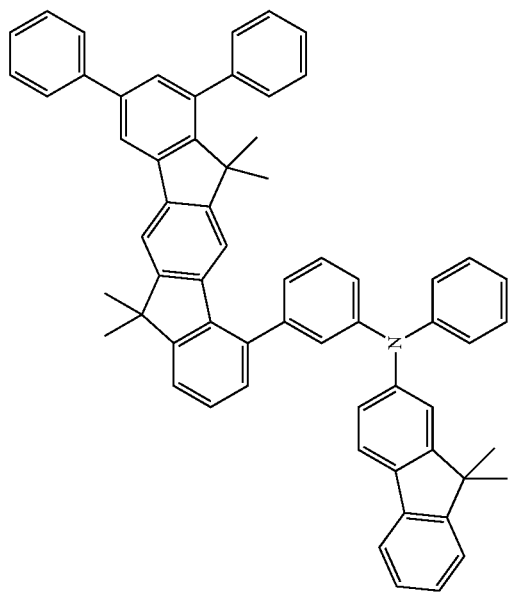 |

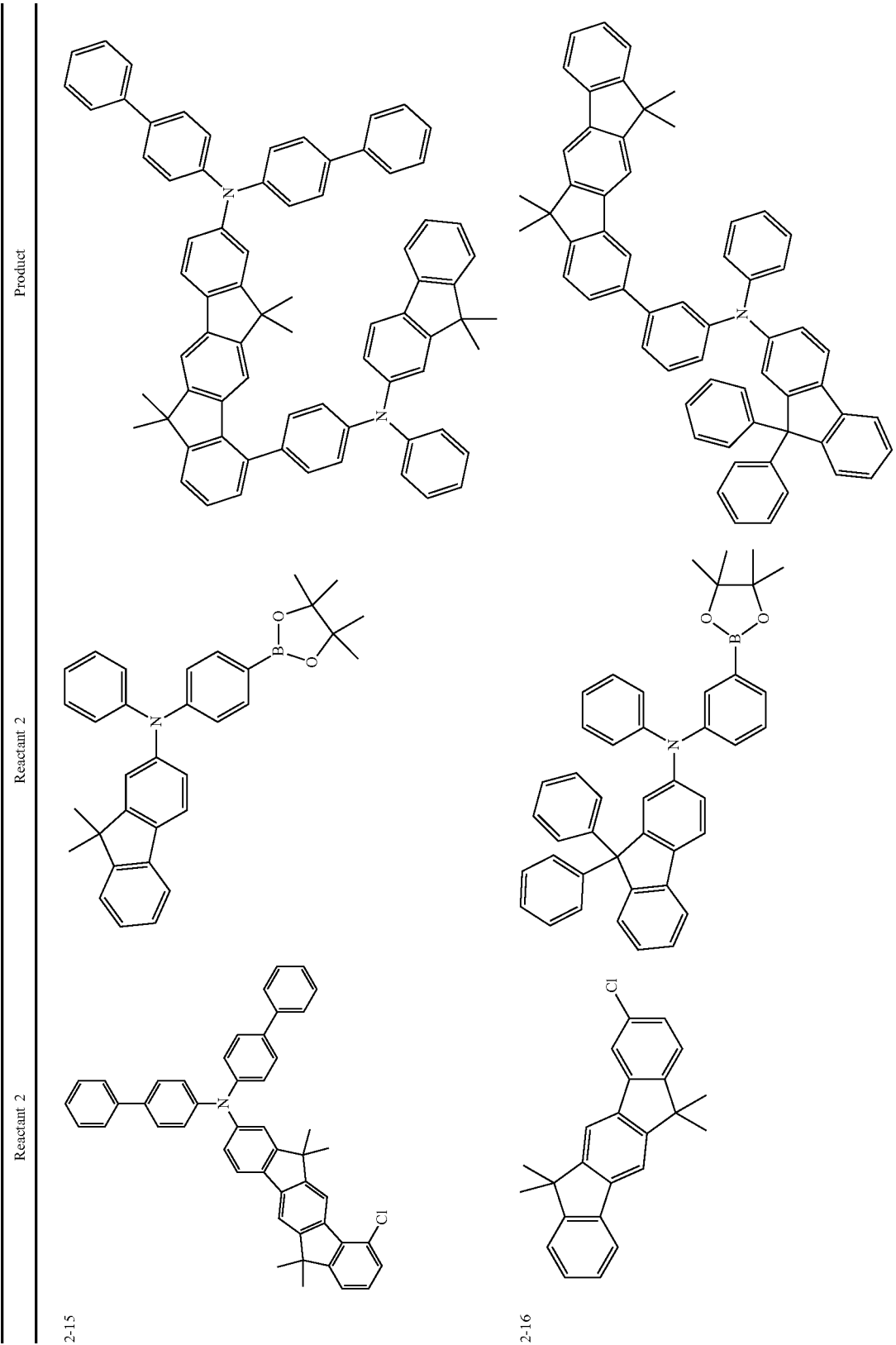

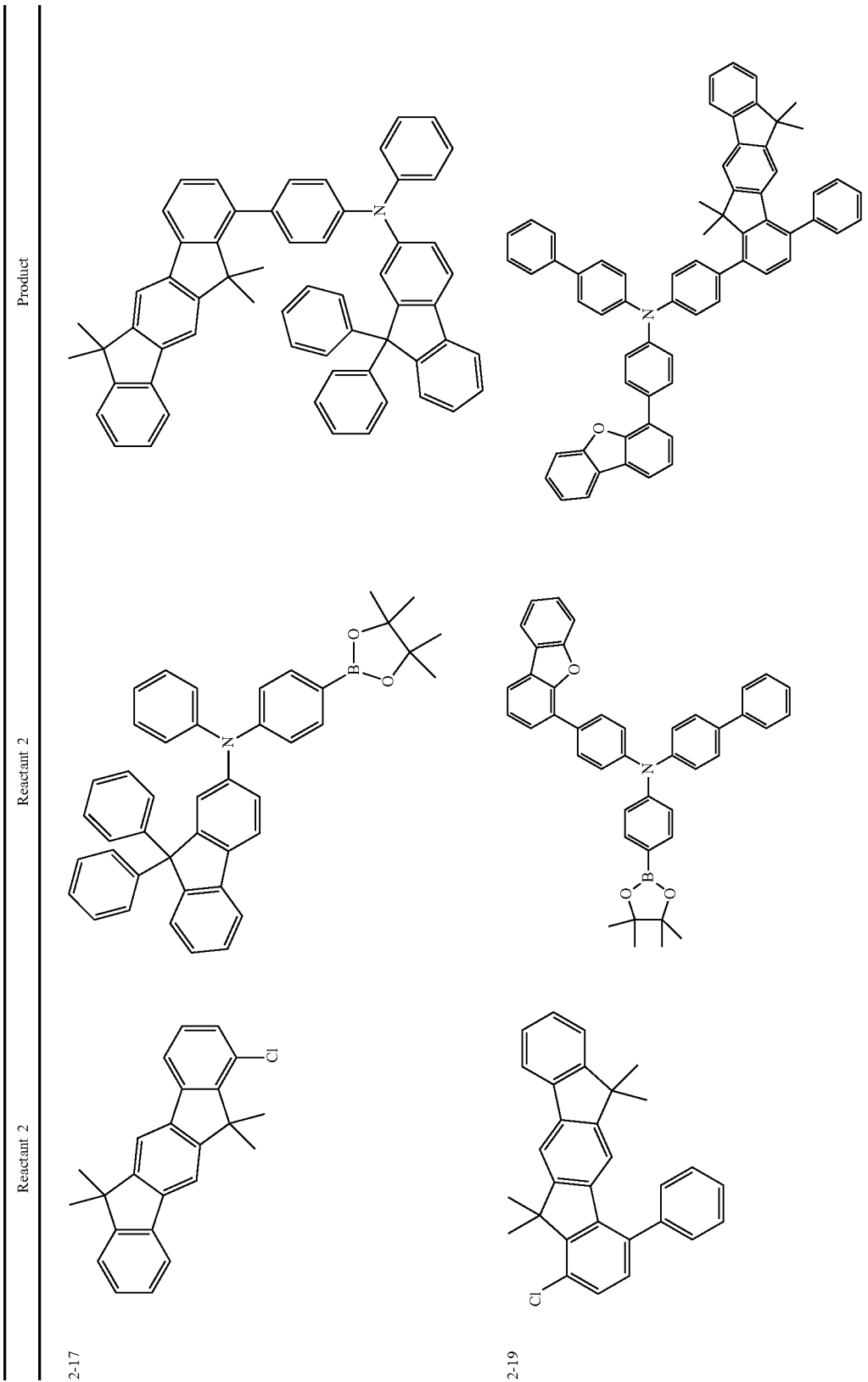

B) Device Examples

Example OLEDs are produced according to the following general method:

The substrates used are glass plaques coated with a 50 nm-thick layer of structured ITO (indium tin oxide). The following layer structure is applied thereto: hole injection layer (HIL)/hole transport layer (HTL)/electron blocker layer (EBL)/emission layer (EML)/electron transport layer (ETL) electron injection layer (EIL)/cathode. The cathode consists of an aluminium layer of thickness 100 nm. The materials that are used in the corresponding layers of the example OLEDs are specified in Table 1, and the chemical structures of these materials are listed in Table 3.

The materials are applied by means of thermal gas phase deposition in a vacuum chamber. The emission layer here always consists of at least one matrix material (host material) and an emitting dopant (emitter) which is added to the matrix material(s) in a particular proportion by volume by coevaporation. The expression TMM:TEG (12%) means here that the TMM material is present in the layer in a proportion by volume of 88%, and that the TEG material is present in a proportion by volume of 12%. The same applies to layers other than the emitting layer. These may likewise correspondingly contain two or more materials.

The OLEDs are characterized in a standard manner. For this purpose, the electroluminescence spectra and the external quantum efficiency (EQE, measured in %), as a function of luminance, calculated from current flow-voltage-luminance characteristics (IUL characteristics), are determined. This is done assuming Lambertian emission characteristics. In addition, the operating voltage is determined (U, in V).

EQE @ 10 mA/cm$^2$ is the external quantum efficiency at an operating current density of 10 mA/cm$^2$. LT80 @ 40 mA/cm$^2$ is the time until the initial luminance of 5000 cd/m$^2$ of an OLED has dropped to 80% of this luminance, i.e. to 4000 cd/m$^2$, without taking account of any acceleration factor.

B-1) Use of the Compounds of the Invention in Green-Fluorescing OLEDs

OLED examples E-0 to E-17 have the layer structure shown in Table 1, with one of the inventive compounds EBL-0 to EBL-17 (Table 3) present in the EBL in each case.

In all cases, the OLEDs of the invention achieve good results with regard to operating voltage, lifetime and EQE (Table 2).

TABLE 1

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| E-0 | HTM:p-dopant (5%) 20 nm | HTM 220 nm | EBL-0 10 nm | TMM-1:TMM-2 (28%):TEG (12%) 30 nm | ETM:LiQ (50%) 30 nm | LiQ 1 nm |
| E-1 | * | * | EBL-1 10 nm | * | * | * |
| E-2 | * | * | EBL-2 10 nm | * | * | * |
| E 3 | * | * | EBL-3 10 nm | * | * | * |
| E-4 | * | * | EBL-4 10 nm | * | * | * |
| E-5 | * | * | EBL-5 10 nm | * | * | * |
| E-6 | * | * | EBL-6 10 nm | * | * | * |
| E-7 | * | * | EBL-7 10 nm | * | * | * |
| E-8 | * | * | EBL-8 10 mil | * | * | * |
| E-9 | * | * | EBL-9 10 nm | * | * | * |
| E-10 | * | * | EBL-10 10 nm | * | * | * |
| E-15 | * | * | EBL-15 10 nm | * | * | * |
| E-16 | * | * | EBL-16 10 nm | * | * | * |
| E-17 | * | * | EBL-17 10 nm | * | * | * |

TABLE 2

Data of the OLEDs

| Example | U [V] | EQE @ 10 mA/cm$^2$ [%] | LT80 @ 40 mA/cm$^2$ [h] |
|---|---|---|---|
| E-0 | 3.9 | >16.5 | >250 |
| E-1 | 3.7 | >16.0 | >300 |
| E-2 | 4.1 | >17.0 | >300 |
| E-3 | 4.1 | >18.0 | >200 |
| E-4 | 4.1 | >16.0 | >250 |
| E-5 | 4.0 | >16.5 | >200 |
| E-6 | 4.0 | >17.0 | >250 |
| E-7 | 3.9 | >15.5 | >250 |
| E-8 | 3.8 | >15.0 | >250 |
| E-9 | 4.1 | >15.5 | >300 |
| E-10 | 4.0 | >17.0 | >250 |
| E-15 | 4.2 | >16.0 | >350 |
| E-16 | 4.1 | >16.0 | >250 |
| E-17 | 4.1 | >14.0 | >300 |

TABLE 3
Materials used
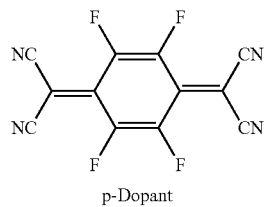 [SMILES: N#CC(C#N)=c1c(F)c(F)c(=C(C#N)C#N)c(F)c1F]
p-Dopant
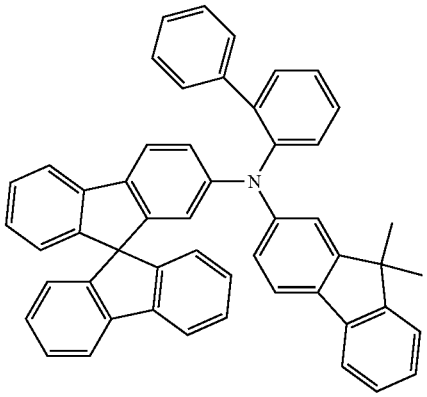
HTM
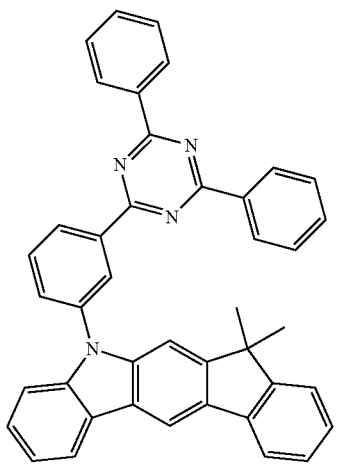
TMM-1
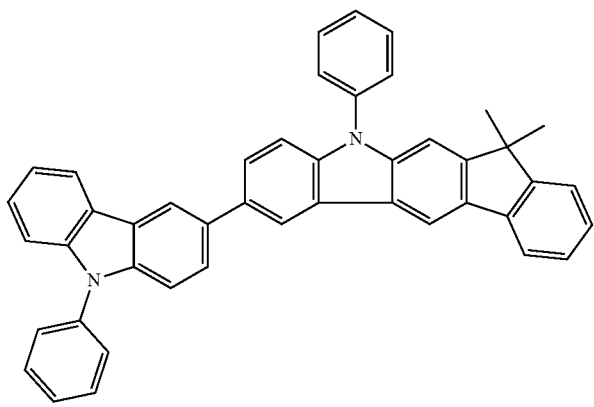
TMM-2

TABLE 3-continued
| Materials used |
|---|
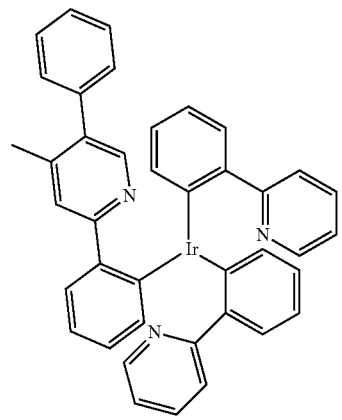
TEG
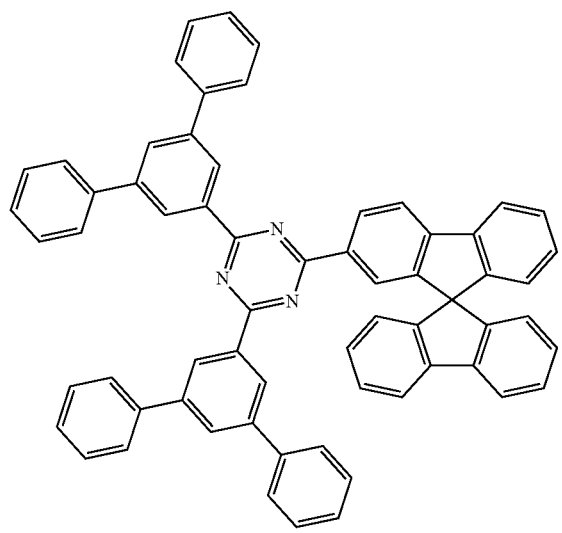
ETM
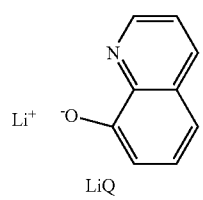
LiQ
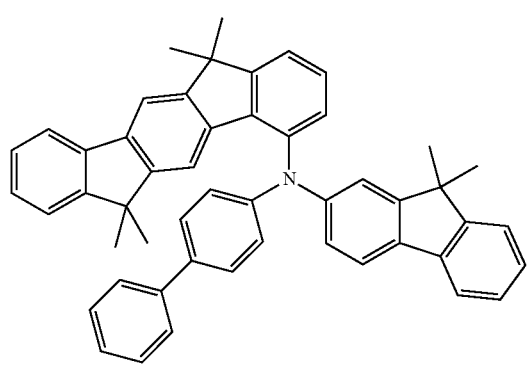
EBL-0

TABLE 3-continued
Materials used
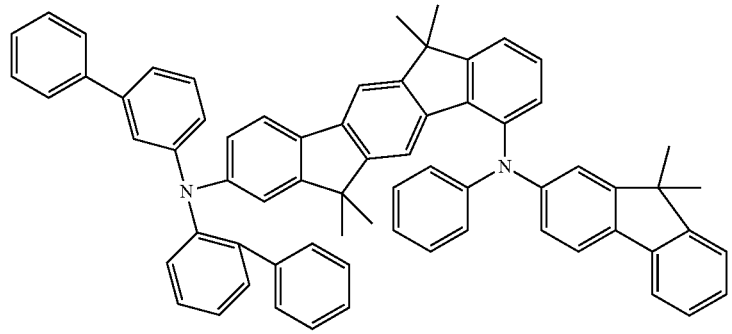
EBL-1
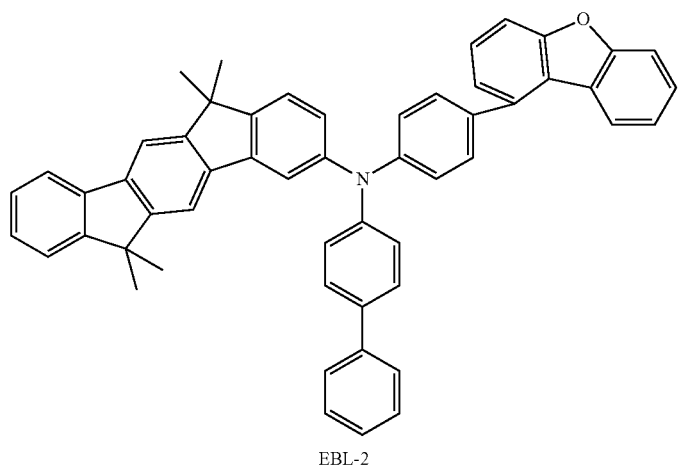 [SMILES: CC1(C)c2ccccc2-c2cc3c(cc21)-c1cc(N(c2ccc(-c4ccccc4)cc2)c2ccc(-c4cccc5oc6ccccc6c45)cc2)ccc1C3(C)C]
EBL-2
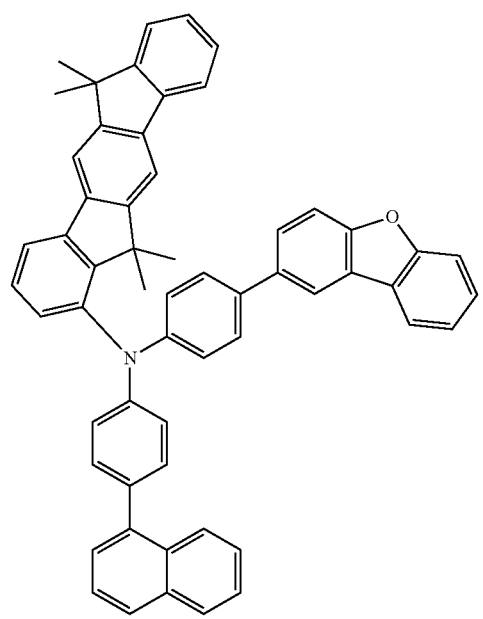
EBL-3

TABLE 3-continued
Materials used
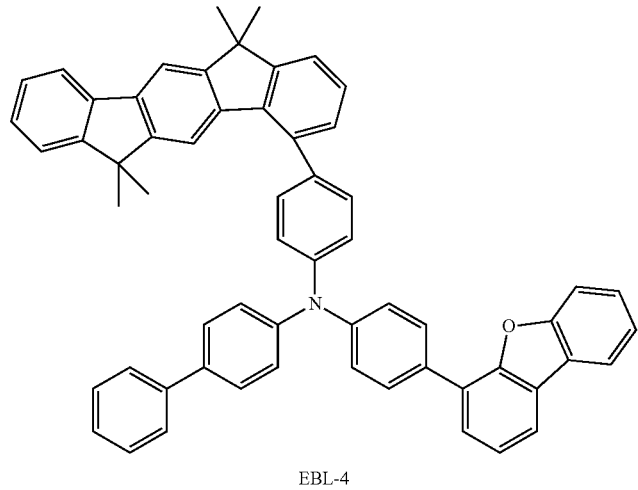 [SMILES: CC1(C)c2ccccc2-c2cc3c(cc21)-c1c(-c2ccc(N(c4ccc(-c5ccccc5)cc4)c4ccc(-c5cccc6c5oc5ccccc56)cc4)cc2)cccc1C3(C)C]
EBL-4
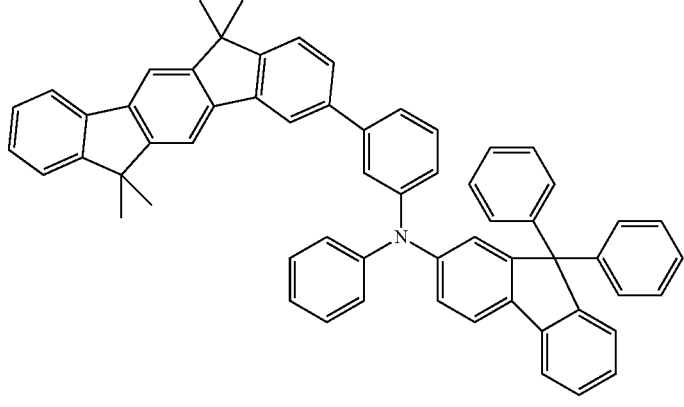
EBL-5
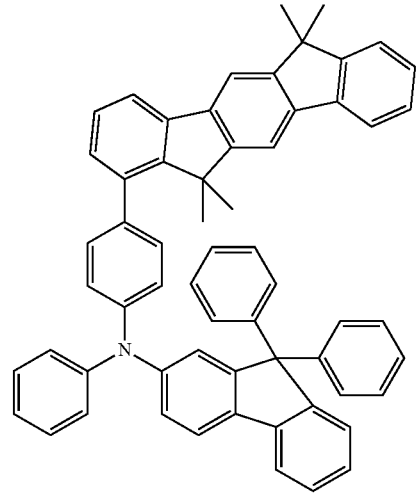
EBL-6

TABLE 3-continued
Materials used
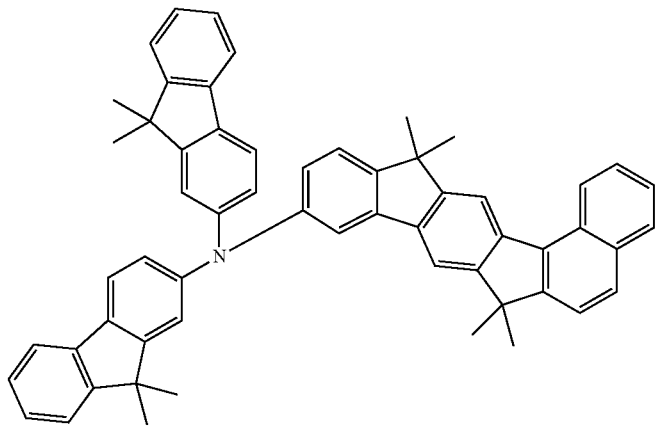
EBL-7
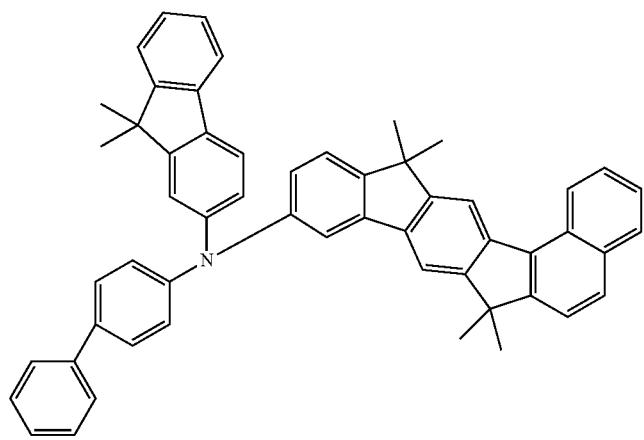
EBL-8
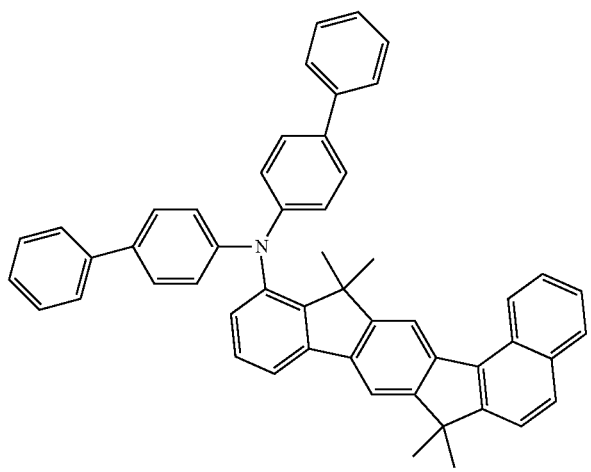
EBL-9

TABLE 3-continued
Materials used
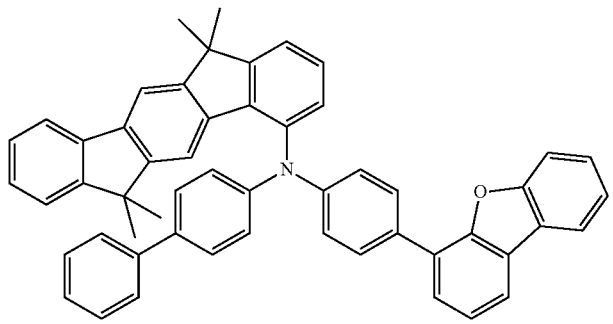
EBL-10
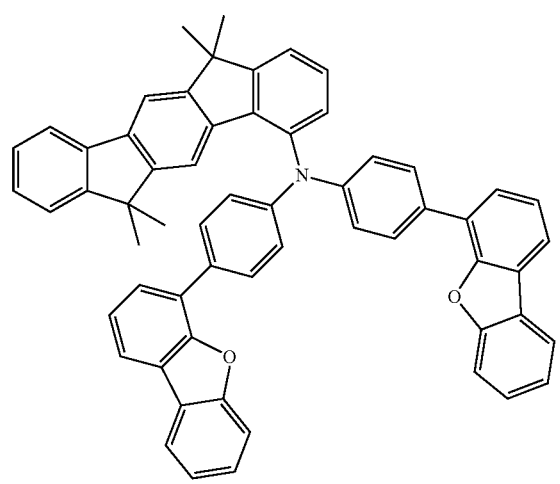
EBL-15
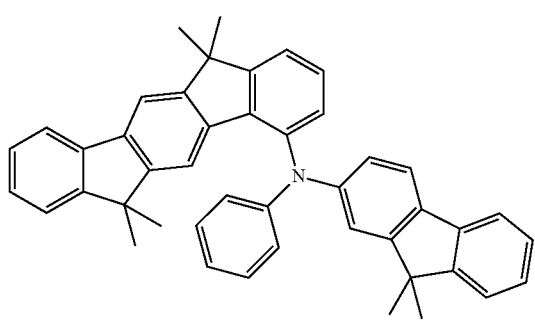
EBL-16

TABLE 3-continued

Materials used

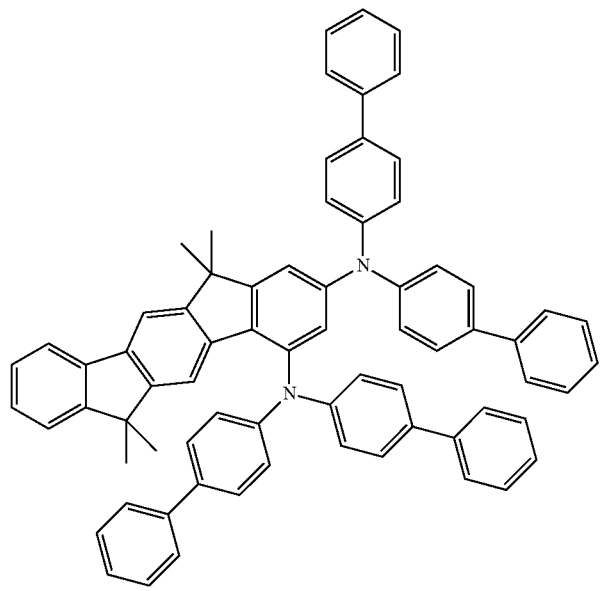

EBL-17

B-2) Comparison of the Inventive Compounds EBL-12, EBL-13 and EBL-14 with Compound EBL-11 According to the Prior Art OLED examples E-12, E-13 and E-14 each contain one of the inventive compounds EBL-12, EBL-13 and EBL-14 in the electron blocker layer. Comparative example OLED E-11 contains the compound EBL-11 in the electron blocker layer. Higher values for EQE are found for the OLEDs E-12, E-13 and E-14 than in the case of the comparative OLED Ell. More particularly, in the case of the inventive OLED E-14, an EQE@ 10 mA/cm$^2$ of more than 16% is obtained, whereas, in the case of comparative example E-11, an EQE@ 10 mA/cm$^2$ of less than 15% is obtained, at a voltage in both cases of 4.1 V.

TABLE 1b

| | Device construction | | | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| E-11 | HTM:p-dopant (5%) 20 nm | HTM 220 nm | EBL-11 10 nm | TMM-1:TMM-2 (28%):TEG (12%) 30 nm | ETM:LiQ (50%) 30 nm | LiQ 1 nm |
| E-12 | * | * | EBL-12 10 nm | * | * | * |
| E-13 | * | * | EBL-13 10 nm | * | * | * |
| E-14 | * | * | EBL-14 10 nm | * | * | * |

TABLE 3b

Materials used

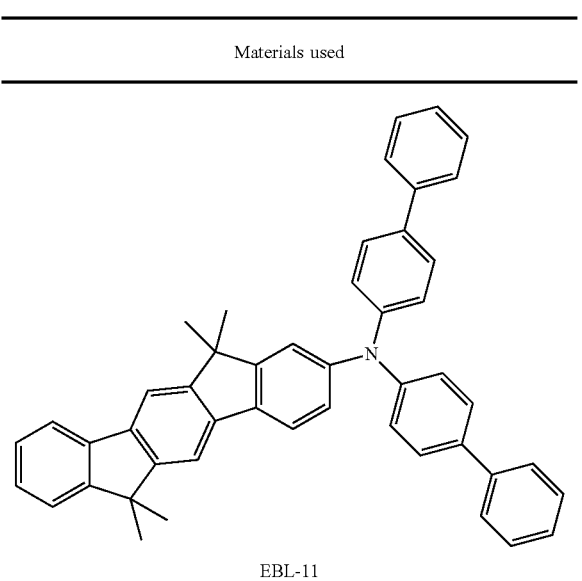

EBL-11

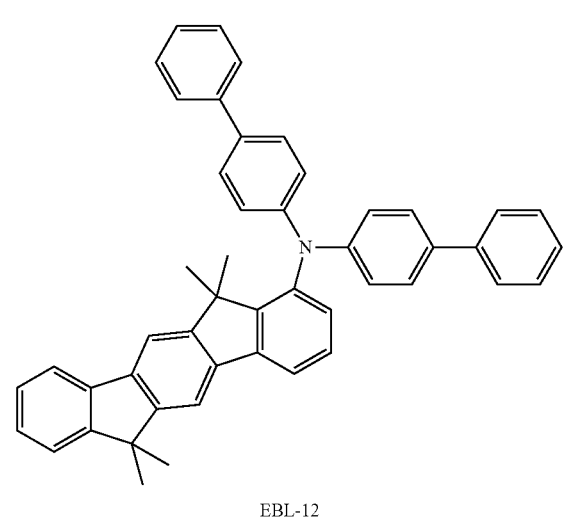 [SMILES: CC1(C)c2ccccc2-c2cc3c(cc21)-c1cccc(N(c2ccc(-c4ccccc4)cc2)c2ccc(-c4ccccc4)cc2)c1C3(C)C]

EBL-12

TABLE 3b-continued

Materials used

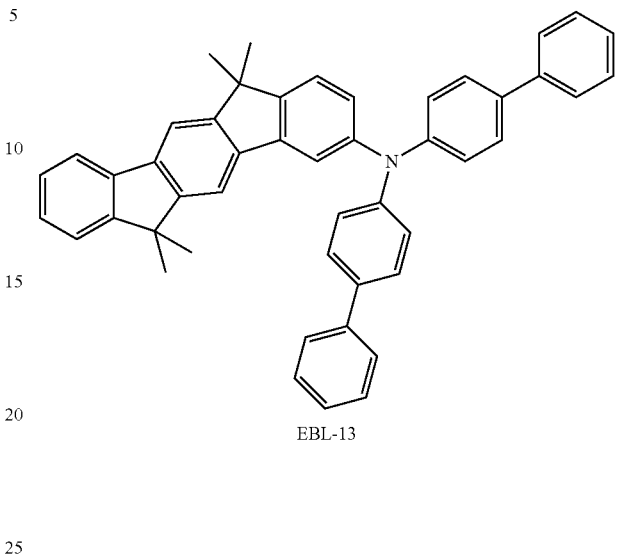

EBL-13

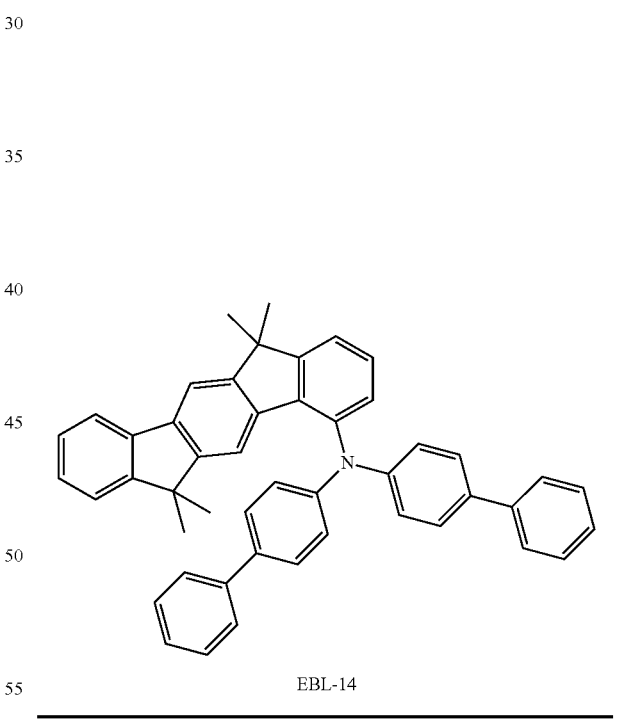

EBL-14

B-3) Use of the Compounds of the Invention in Blue-Fluorescing OLEDs

OLED examples E-19 and E-20 have the layer structure shown in Table 1c, with one of the inventive compounds EBL-15 or EBL-16 (see Table 3c) present in the EBL in each case.

In all cases; the OLEDs of the invention achieve good results with regard to operating voltage, lifetime and EQE (Table 2c).

TABLE 1c

| | | | Device construction | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| E-19 | HTM:p-dopant (5%) 20 nm | HTM 180 nm | EBL-15 10 nm | SMB-1:SEB-1 (5%) 20 nm | ETM:LiQ (50%) 30 nm | LiQ 1 nm |
| E-20 | * | * | EBL-16 10 nm | * | * | * |

TABLE 2c

| | | Data of the OLEDs | |
|---|---|---|---|
| Example | U [V] | EQE @ 10 mA/cm² [%] | LT80 @ 60 mA/cm² [h] |
| E-19 | 4.0 | about 8.5 | about 350 |
| E-20 | 4.0 | about 8.5 | about 350 |

TABLE 3c

Materials used

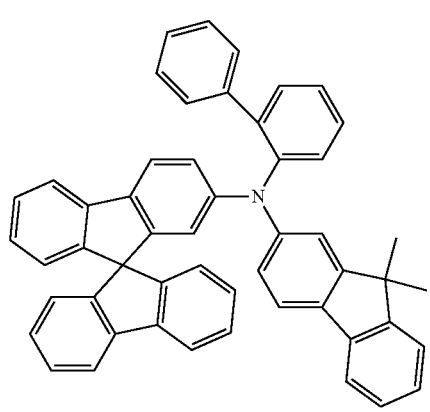

p-Dopant

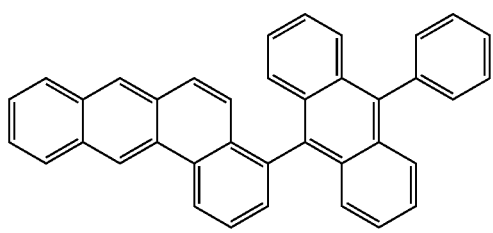

HTM

SMB-1

TABLE 3c-continued

Materials used

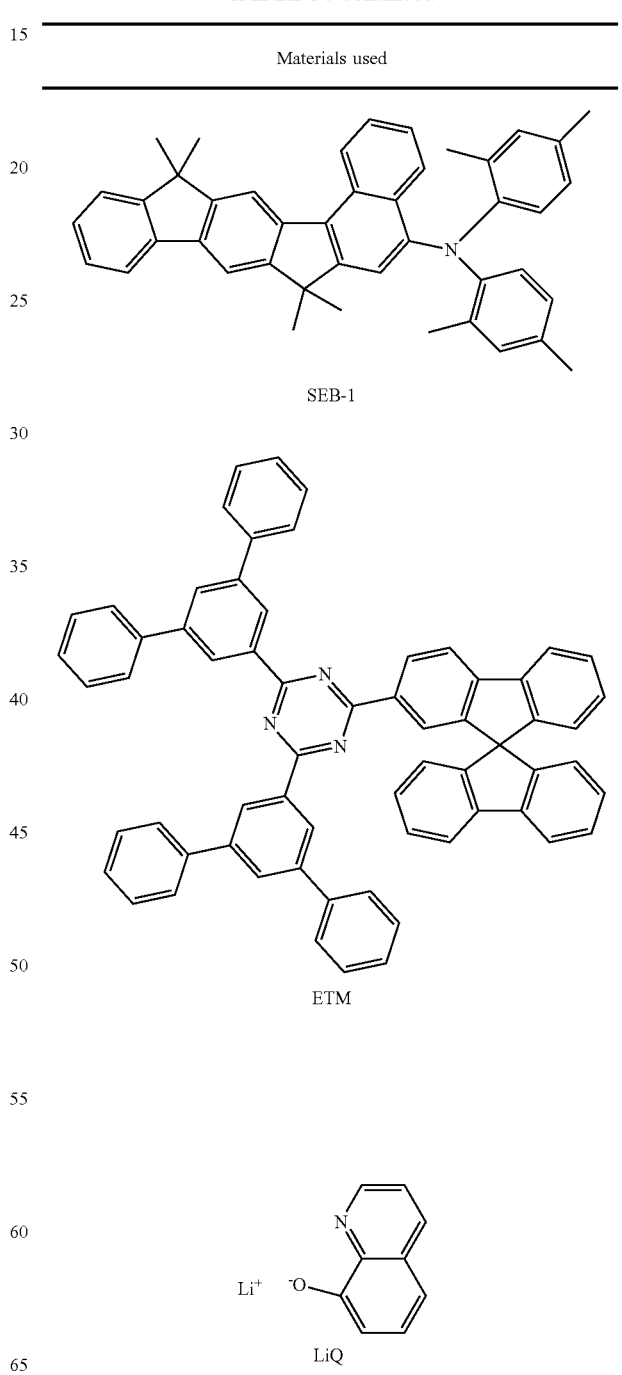

SEB-1

ETM

LiQ

TABLE 3c-continued

Materials used

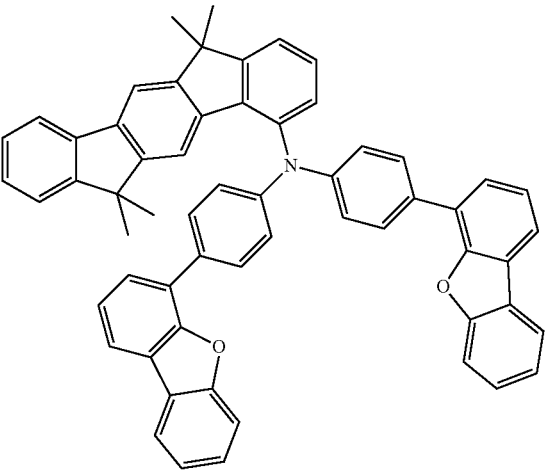

EBL-15

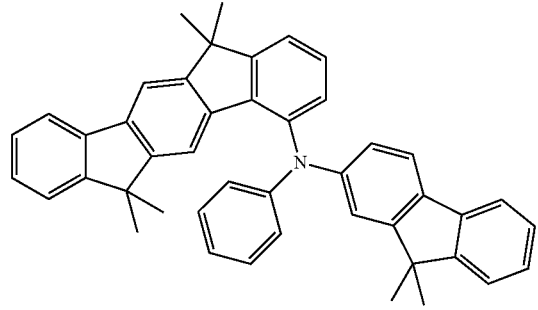

EBL-16

The invention claimed is:

1. A compound of the formula (I-1)

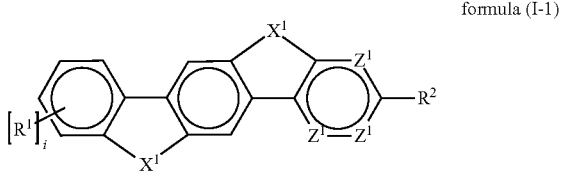

formula (I-1)

where the compounds may each be substituted by an $R^3$ or $R^6$ radical at the unoccupied positions on the aromatic rings, and where the variables that occur are as follows:

$Z^1$ is the same or different at each instance and is selected from $CR^1$ and $CR^3$;

$X^1$ is the same or different at each instance and is a divalent group selected from $-C(R^4)_2-$, $-C(R^4)_2-C(R^4)_2-$, $-CR^4=CR^4-$ and $-Si(R^4)_2-$;

$R^1$ is the same or different at each instance and is a group of the formula (N)

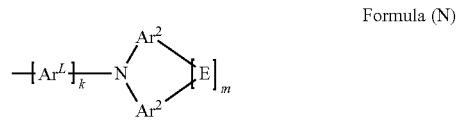

Formula (N)

$Ar^L$ is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

$Ar^2$ is the same or different at each instance and is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

E is a single bond or a divalent group selected from the group consisting of $C(R^5)_2$, $Si(R^5)_2$, $N(R^5)$, O, and S;

$R^2$ is selected from H, and D;

$R^3$ is the same or different at each instance and is selected from H, D, F, CN, $Si(R^7)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^7$ radicals;

$R^5$ is the same or different at each instance and is selected from H, D, F, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by $-R^7C=CR^7-$, $-C\equiv C-$, $Si(R^7)_2$, $C=O$, $C=NR^7$, $-C(=O)O-$, $-C(=O)NR^7-$, $NR^7$, $P(=O)(R^7)$, $-O-$, $-S-$, SO or $SO_2$;

$R^4$ is the same or different at each instance and is selected from H, D, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^7$ radicals;

$R^6$ is the same or different at each instance and is selected from H, D, F, CN, $Si(R^7)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^7$ radicals;

$R^7$ is the same or different at each instance and is selected from H, D, F, CN, Si($R^8$)$_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^8$ radicals;

$R^8$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where the alkyl, alkoxy, alkenyl and alkynyl groups, aromatic ring systems and heteroaromatic ring systems mentioned may be substituted by F or CN;

k is 0 or 1, where, in the case that k=0, the $Ar^L$ group is absent and the nitrogen atom of the group of the formula (N) constitutes the attachment position;

m is 0 or 1, where, in the case that m=0, the E group is absent and the $Ar^2$ groups are not bonded to one another;

i is 0, which means that the $R^1$ group marked with index i is absent; and where there is at least one $Z^1$ group that is $CR^1$.

2. The compound according to claim 1, wherein either
  i) one $Z^1$ group is $CR^1$, and the two other $Z^1$ groups are $CR^3$, or
  ii) two $Z^1$ groups are $CR^1$, and the other $Z^1$ group is $CR^3$.

3. The compound according to claim 1, wherein the $Z^1$ group in the meta position to the bond to $X^1$ is $CR^1$.

4. The compound according to claim 1, wherein the $X^1$ is $C(R^4)_2$.

5. The compound according to claim 1, wherein the group of $Ar^2$ that binds directly to the nitrogen atom is an aromatic ring system.

6. The compound according to claim 1, wherein m=0.

7. The compound according to claim 1, wherein m=1, and the unit

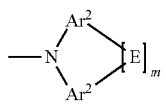

from the group of the formula (N) is selected from the following groups:

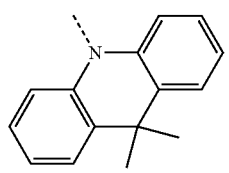

N-1

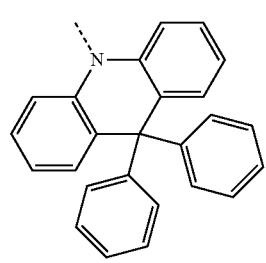

N-2

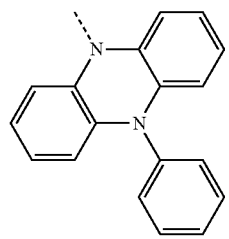

N-3

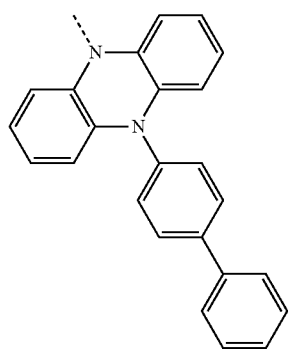

N-4

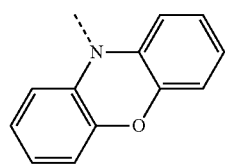

N-5

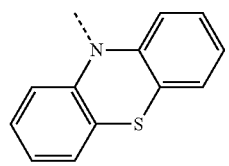

N-6

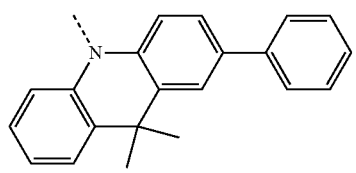

N-7

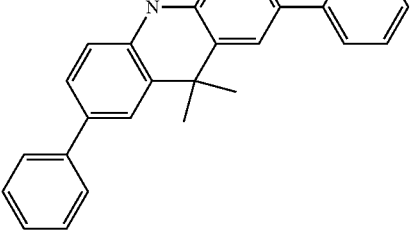

N-8

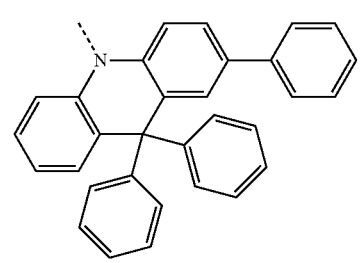

N-9

N-10
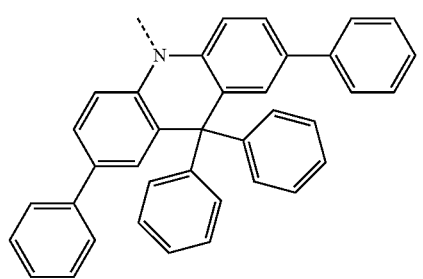
N-11
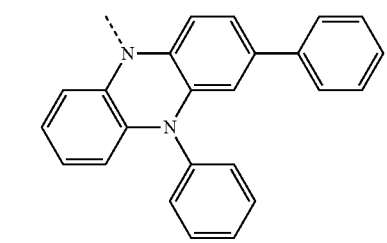
N-12
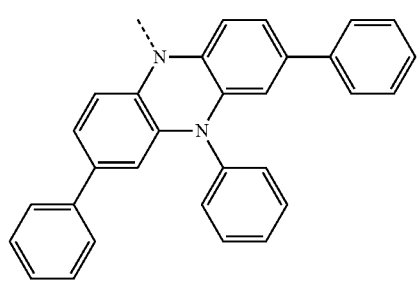
N-13
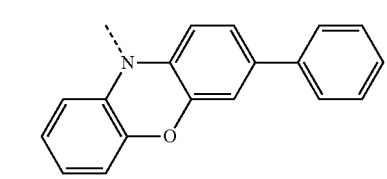
N-14
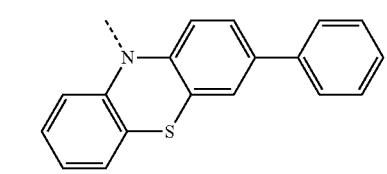
N-15
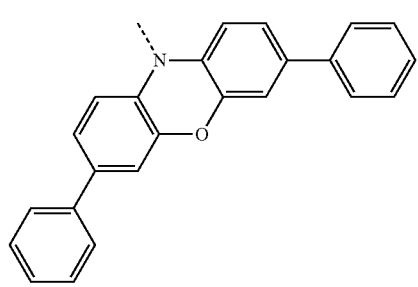
N-16
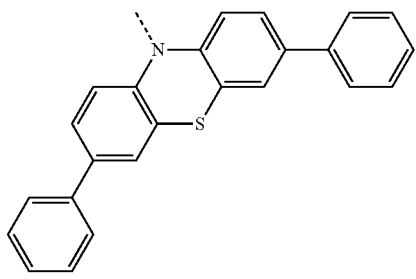
N-17
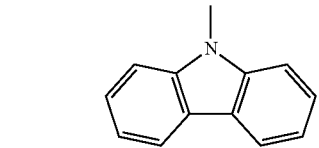
N-18
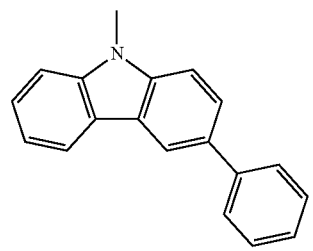
N-19
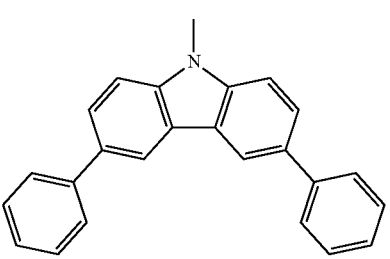
N-20
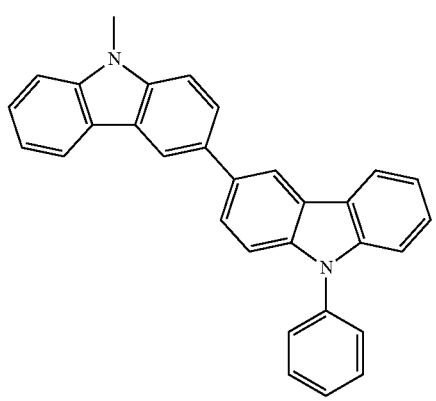
N-21
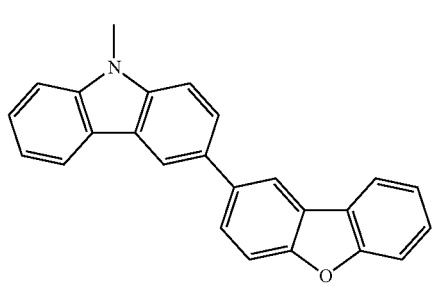

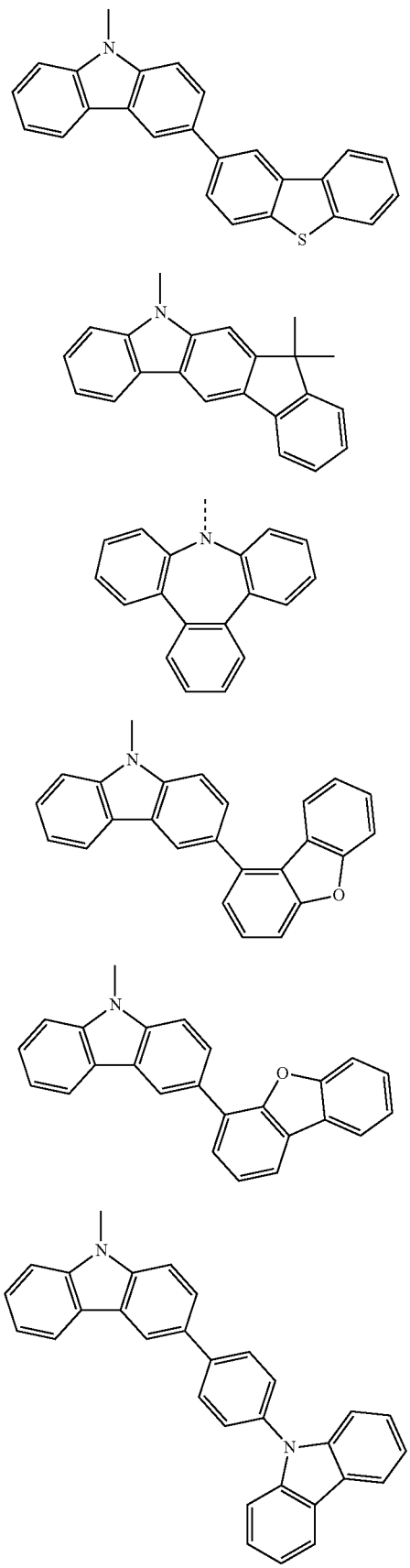
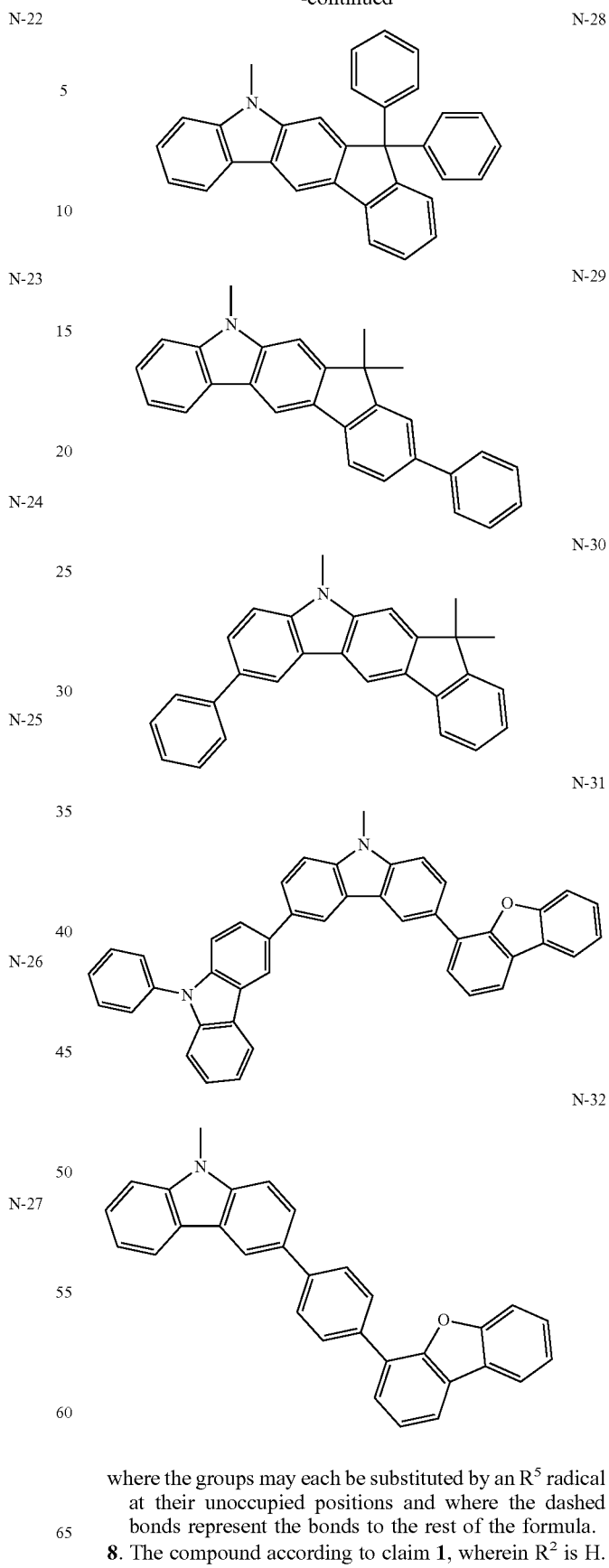
where the groups may each be substituted by an $R^5$ radical at their unoccupied positions and where the dashed bonds represent the bonds to the rest of the formula.
8. The compound according to claim 1, wherein $R^2$ is H.
9. The compound according to claim 1, wherein $R^6$ is H.

10. A process for preparing the compound of formula (I) according to claim 1, which comprises reacting a benzene compound that bears two carboxylic ester groups, an aromatic or heteroaromatic ring system and a reactive group in a Suzuki reaction with a benzene compound that contains a boronic acid group and a group selected from reactive groups, diarylamino groups, diarylaminoaryl groups and diarylaminoheteroaryl groups.

11. An oligomer, polymer or dendrimer containing one or more compounds of formula (I) according to claim 1, wherein the bond(s) to the polymer, oligomer or dendrimer may be localized at any position substituted by $R^1$, $R^2$, $R^3$, $R^4$ or $R^5$ in formula (I).

12. A formulation comprising at least one compound according to claim 1 and at least one solvent.

13. A formulation comprising at the polymer, oligomer or dendrimer according to claim 11 and at least one solvent.

14. An electronic device comprising at least one compound according to claim 1.

15. An electronic device comprising the polymer, oligomer or dendrimer according to claim 11.

16. The electronic device according to claim 14, wherein the electronic device is an organic electroluminescent device comprising anode, cathode and at least one emitting layer, where it is at least one organic layer of the device selected from emitting layers and hole-transporting layers that comprises the at least one compound.

17. The organic electroluminescent device according to claim 16, comprising anode, cathode and at least one emitting layer, characterized in that the at least one compound is present in an electron blocker layer.

18. The compound according to claim 1, wherein
$Ar^L$ is selected from aromatic ring systems which have 6 to 40 aromatic ring atoms and may be substituted by one or more $R^5$ radicals, and
$Ar^2$ is the same or different at each instance and is selected from aromatic ring systems which have 6 to 40 aromatic ring atoms and may be substituted by one or more $R^5$ radicals.

19. The compound according to claim 1, wherein
$R^5$ is the same or different at each instance and is selected from H, D, F, CN, $Si(R^7)_3$, $N(R^7)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^7$ radicals.

20. The compound according to claim 1, wherein:
$X^1$ is a divalent group —$C(R^4)_2$—; and
$Ar^L$ is selected from aromatic ring systems which have 6 to 40 aromatic ring atoms and may be substituted by one or more $R^5$ radicals, and
$Ar^2$ is the same or different at each instance and is selected from aromatic ring systems which have 6 to 40 aromatic ring atoms and may be substituted by one or more $R^5$ radicals, and
$R^3$ and $R^6$ are the same or different at each instance and are selected from H and D;
$R^5$ is the same or different at each instance and is selected from H, D, F, CN, $Si(R^7)_3$, $N(R^7)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^7$ radicals; and
m is 0.

21. The compound according to claim 1, wherein none of $R^4$ radicals can form a ring with another $R^4$ radical.

* * * * *